(12) United States Patent
Rong et al.

(10) Patent No.: US 11,464,849 B2
(45) Date of Patent: Oct. 11, 2022

(54) RECOMBINANT HERPESVIRUS OF TURKEY VECTORS EXPRESSING ANTIGENS OF AVIAN PATHOGENS AND USES THEREOF

(71) Applicant: Zoetis Services LLC, Parsippany, NJ (US)

(72) Inventors: Sing Rong, Kalamazoo, MI (US); Yugang Luo, Kalamazoo, MI (US); Tyler Brown, Kalamazoo, MI (US)

(73) Assignee: Zoetis Services LLC, Parsippany, NJ (US)

( * ) Notice: Subject to any disclaimer, the term of this patent is extended or adjusted under 35 U.S.C. 154(b) by 0 days.

(21) Appl. No.: 17/017,342

(22) Filed: Sep. 10, 2020

(65) Prior Publication Data
US 2021/0196811 A1   Jul. 1, 2021

Related U.S. Application Data

(60) Provisional application No. 62/898,651, filed on Sep. 11, 2019.

(51) Int. Cl.
*A61K 39/12* (2006.01)
*C12N 7/00* (2006.01)
(Continued)

(52) U.S. Cl.
CPC .............. *A61K 39/12* (2013.01); *A61K 39/17* (2013.01); *A61P 31/14* (2018.01); *A61P 31/20* (2018.01); *A61P 37/04* (2018.01); *C12N 7/00* (2013.01); *C12N 15/86* (2013.01); *A61K 2039/53* (2013.01); *A61K 2039/54* (2013.01); *A61K 2039/552* (2013.01);
(Continued)

(58) Field of Classification Search
None
See application file for complete search history.

(56) References Cited

U.S. PATENT DOCUMENTS 5,187,087 A * 2/1993 Sondermeijer ......... A61P 31/12
435/463
5,231,023 A 7/1993 Morgan
(Continued)

FOREIGN PATENT DOCUMENTS

EP        1298139 B1    5/2007
WO    WO 87/04463 A1    7/1987
(Continued)

OTHER PUBLICATIONS

Bublot, M. et al., 2007, "Use of a Vectored Vaccine against Infectious Bursal Disease of Chickens in the Face of High-Titred Maternally Derived Antibody," J. Comp. Path., vol. 137, S81-S84.
(Continued)

*Primary Examiner* — Shanon A. Foley
(74) *Attorney, Agent, or Firm* — Kelly M. Sullivan

(57) ABSTRACT

The invention relates to recombinant viral vectors for the insertion and expression of foreign genes for use in safe immunizations to protect against a variety of pathogens. The invention also relates to multivalent compositions or vaccine comprising one or more recombinant viral vectors for protection against a variety of pathogens. The present invention relates to methods of making an using said recombinant viral vectors.

21 Claims, 35 Drawing Sheets

Specification includes a Sequence Listing.

(51) Int. Cl.
<table>
<tr><td>C12N 15/86</td><td>(2006.01)</td></tr>
<tr><td>A61K 39/17</td><td>(2006.01)</td></tr>
<tr><td>A61P 37/04</td><td>(2006.01)</td></tr>
<tr><td>A61P 31/14</td><td>(2006.01)</td></tr>
<tr><td>A61P 31/20</td><td>(2006.01)</td></tr>
<tr><td>A61K 39/00</td><td>(2006.01)</td></tr>
</table>

(52) U.S. Cl.
CPC .............. C12N 2710/16021 (2013.01); C12N 2710/16034 (2013.01); C12N 2710/16043 (2013.01); C12N 2720/10021 (2013.01); C12N 2720/10034 (2013.01); C12N 2760/18121 (2013.01); C12N 2760/18134 (2013.01); C12N 2830/50 (2013.01)

(56) References Cited

U.S. PATENT DOCUMENTS

<table>
<tr><td>5,650,153 A</td><td></td><td>7/1997</td><td>Ishikawa et al.</td></tr>
<tr><td>5,733,556 A</td><td>*</td><td>3/1998</td><td>Schrier ................ C07K 14/005<br>424/214.1</td></tr>
<tr><td>5,834,305 A</td><td></td><td>11/1998</td><td>Cochran et al.</td></tr>
<tr><td>5,853,733 A</td><td></td><td>12/1998</td><td>Cochran et al.</td></tr>
<tr><td>5,965,138 A</td><td></td><td>10/1999</td><td>Cochran et al.</td></tr>
<tr><td>5,980,906 A</td><td></td><td>11/1999</td><td>Audonnet et al.</td></tr>
<tr><td>6,121,043 A</td><td></td><td>9/2000</td><td>Cochran et al.</td></tr>
<tr><td>6,183,753 B1</td><td></td><td>2/2001</td><td>Cochran et al.</td></tr>
<tr><td>6,299,882 B1</td><td></td><td>10/2001</td><td>Junker</td></tr>
<tr><td>6,406,702 B1</td><td></td><td>6/2002</td><td>Sharma</td></tr>
<tr><td>6,632,664 B1</td><td></td><td>10/2003</td><td>Saitoh et al.</td></tr>
<tr><td>6,866,852 B2</td><td></td><td>3/2005</td><td>Saitoh et al.</td></tr>
<tr><td>7,153,511 B2</td><td></td><td>12/2006</td><td>Sato et al.</td></tr>
<tr><td>7,569,365 B2</td><td></td><td>8/2009</td><td>Sato</td></tr>
<tr><td>10,251,951 B2</td><td></td><td>4/2019</td><td>Fujisawa et al.</td></tr>
<tr><td>10,323,257 B2</td><td></td><td>6/2019</td><td>Bublot et al.</td></tr>
<tr><td>11,058,761 B2</td><td></td><td>7/2021</td><td>Mebatsion et al.</td></tr>
<tr><td>2014/0147465 A1</td><td>*</td><td>5/2014</td><td>Bublot ..................... C12N 7/00<br>424/199.1</td></tr>
</table>

FOREIGN PATENT DOCUMENTS

<table>
<tr><td>WO</td><td>WO 96/05291 A1</td><td>2/1996</td></tr>
<tr><td>WO</td><td>WO 13/057235 A1</td><td>4/2013</td></tr>
<tr><td>WO</td><td>WO 13/057236 A1</td><td>4/2013</td></tr>
<tr><td>WO</td><td>WO 13/082317 A2</td><td>6/2013</td></tr>
<tr><td>WO</td><td>WO 13/082327 A1</td><td>6/2013</td></tr>
<tr><td>WO</td><td>WO 13/144355 A1</td><td>10/2013</td></tr>
<tr><td>WO</td><td>WO 16/102647 A1</td><td>6/2016</td></tr>
<tr><td>WO</td><td>WO 17/216287 A1</td><td>12/2017</td></tr>
<tr><td>WO</td><td>WO 18/075977 A1</td><td>4/2018</td></tr>
<tr><td>WO</td><td>WO 18/112051 A1</td><td>6/2018</td></tr>
<tr><td>WO</td><td>WO 20/127964 A1</td><td>6/2020</td></tr>
</table>

OTHER PUBLICATIONS

Gergen, L. et al., 2019, "A double recombinant herpes virus of turkeys for the protection of chickens against Newcastle, infectious laryngotracheitis and Marek's diseases", Avian Pathology, vol. 48, pp. 45-56.

Jarosinski, K.W. and Osterrieder, N., 2010, "Further Analysis of Marek's Disease Virus Horizontal Transmission Confirms That $U_L44$ (gC) and $U_L13$ Protein Kinase Activity Are Essential, while $U_s2$ Is Nonessential V," Journal of Virology, vol. 84, pp. 7911-7916.

Jarosinski, K.W. et al., 2007, "Horizontal Transmission of Marek's Disease Virus Requires $U_s2$, the $U_L13$ Protein Kinase, and gCV" Journal of Virology, vol. 81, pp. 10575-10587.

Johnson, D.I. et al., 2010, "Protection Against Infectious Laryngotracheitis by In Ovo Vaccination with Commercially Available Viral Vector Recombinant Vaccines," Avian Diseases, vol. 54, pp. 1251-1259.

Morgan, R.W. et al., 1992, "Protection of Chickens from Newcastle and Marek's Diseases with a Recombinant Herpesvirus of Turkeys Vaccine Expressing the Newcastle Disease Virus Fusion Protein," Avian Diseases, vol. 36, pp. 858-870.

Witter, R.L. et al., 1984, "Polyvalent Marek's disease vaccines: Safety, efficacy and protective synergism in chickens with maternal antibodies," Avian Pathology, vol. 13, pp. 75-92.

* cited by examiner

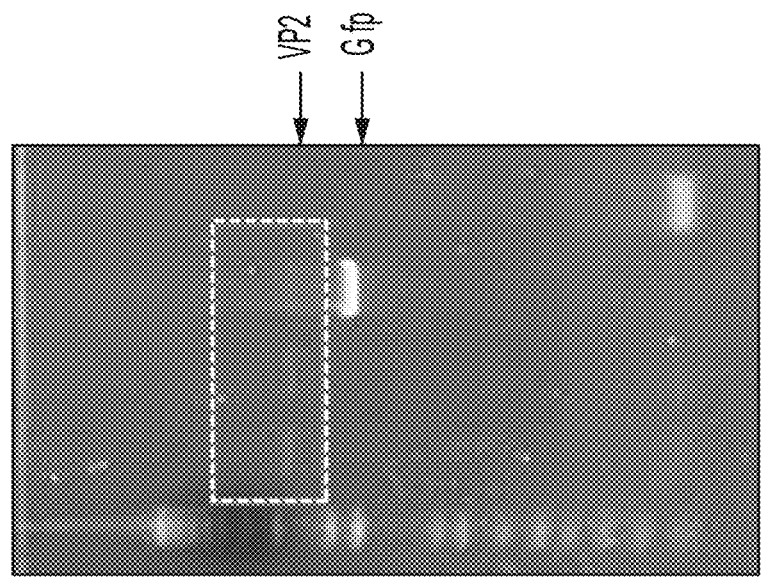
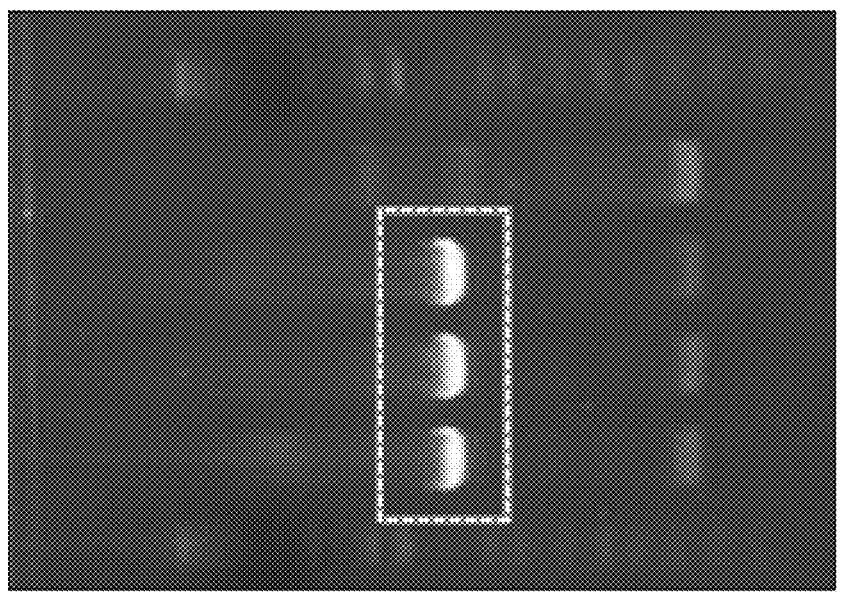
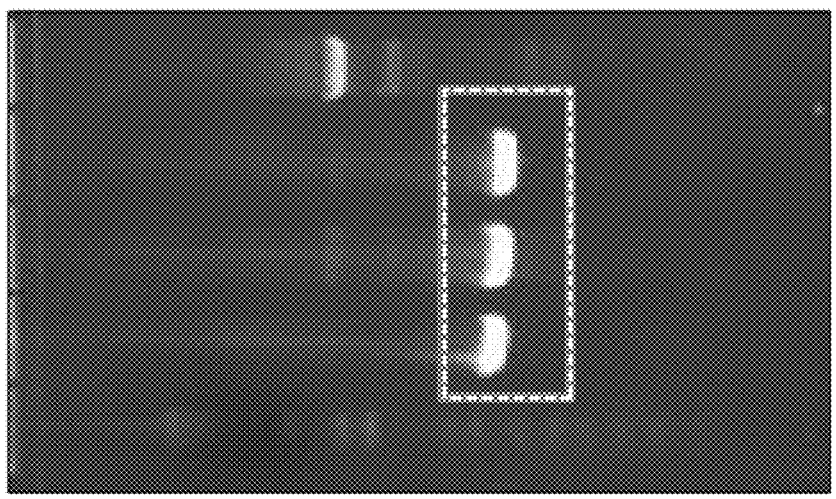
FIG. 12C
FIG. 12B
FIG. 12A

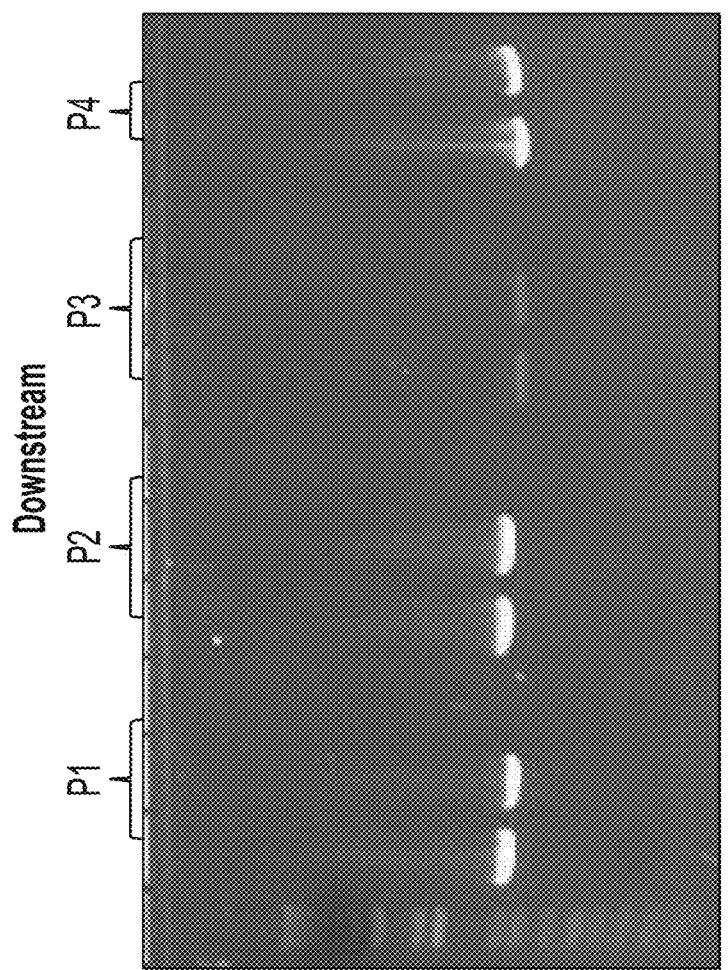
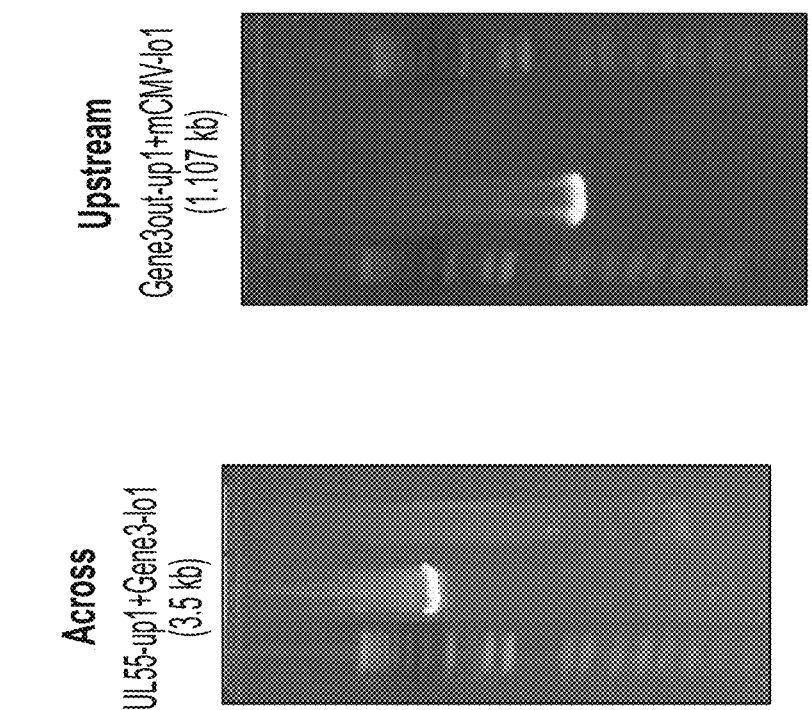
FIG. 20A
FIG. 20B
FIG. 20C

IBDV VP2 Faragher strain F52/70

////// Nonstructureal protein

\\\\\\ Structureal protein

B — VP1 (94 KD) — (2.784 kb)

A — VP2 (62 KD) | VP3 (30 KD) | VP4 (29 KD) | VP5 (17 KD) — (3.092 kb)

Donor gene: IBDV VP2 F52-70

630 bp | PstI | 643 bp | ScaI | 89 bp

Donor gene (IBDV VP2 of Faragher strain F52/70, codon optimized for optimal expression with Gallus gallus) was chemically synthesized as part of the original transfer plasmid pHVT-IBD #30. The IBDV VP2 protein contains 454 amino acids (1362 bp).

FIG. 23

Production of the Intermediate Recombinant HVT-ND #42 (Insertion Site B)

NDV F transfer plasmid pSiteB-#42

HVT genome

UL55-Gene3 Insertion site

- CEF cells were transfected with transfer plasmid pSiteB-#42 and infected with HVT
- 3 days post transfection, the transfected/infected cells were plated onto duplicate 6 well plate and then 96-well plate for screening NDV expressing foci by staining with NDV antiserum.
- Wells corresponding to containing the NDV expression foci were purified 1 time by limiting dilution
- One of the purified viruses was confirmed for target antigen expression by IFA with both NDV and HVT antibodies. It was expanded and frozen stock made. It was designated as "HVT-ND #42".

| Lane | Primer set | Size (bp) |
|---|---|---|
| M | 1 kb Ladder | |
| 1 | B1 | 3625 |
| 2 | B2 | 3594 |
| 3 | B3 | 5730 |
| 4 | B4 | 5951 | anti NDV anti HVT

M 1 2 3 4 M pSiteB-#42 Transfer Plasmid (4945 bp)

800 bp left arm | XhoI PacI KpnI | AvaII SmaI | 800 bp right arm

HVT genome | mCMV (1391 bp) | NDV F (1669 bp) | SV40pA (236 bp) | HVT genome

PCR B1/B2

PCR FL B3/B4

Intermediate Regulated Biological Agent HVT-ND (Insertion Site B)

FIG. 28

Production of the Final Regulated Biological Agent HVT-IBD-ND

IBDV VP2 transfer plasmid pSiteA-#30

HVT-ND (#42) intermediate recombinant

UL35-UL36 (Insertion site A)

UL66-Gene3 (Insertion site B with NDV F expression cassette)

- CEF cells were transfected with transfer plasmid pSiteA-#30 and infected with HVT-ND #42 intermediate recombinant
- 3 days post transfection, the transfected/infected cells were plated onto duplicate 6 well plate and then 96-well plate for screening IBDV expressing foci by staining with IBDV antiserum.
- Wells corresponding to containing the IBDV expression foci were purified 3 times by limiting dilution
- One of the purified viruses was confirmed for target antigen expression by IFA with both IBDV and HVT antibodies. It was expanded and frozen stock made. It was designated as "HVT-IBD-ND (#42-#30 LP C2)".

| Lane | Primer set | Size (bp) |
|---|---|---|
| M | 1 kb Ladder | |
| 1 | A1 | 2570 |
| 2 | A2 | 2608 |
| 3 | A3 | 4982 |
| 4 | A4 | 4937 | anti IBDV | anti HVT

M 1 2 3 4 M pSiteA-#30 Transfer Plasmid (4092 bp)

900 bp left arm | SpeI | HindIII | PstI | AvaI | ScaI | 900 bp right arm

HVT genome | hCMV (687 bp) | IBDV VP2 (1359 bp) | BGHpA (225 bp) | HVT genome

PCR A1/A2

PCR FL A3/A4

Final Regulated Biological Agent HVT-IBD-ND (Showing Insertion Site A only)

FIG. 29

HVT-IBD-ND (Insertion Site A)
Construct Characterization based on PCR & Restriction Endonuclease Digestion

| Lanes | Enzymes | Fragments (bp) |
|---|---|---|
| M | 1 Kb ladder | |
| 1 | AvaI | 1608, 962 |
| 2 | BcfI | 1602, 968 |
| 3 | BstYI | 983, 1587 |
| 4 | HindWI | 776, 1794 |
| 5 | NcoI | 475, 2095 |
| 6 | PstI | 1420, 1150 |
| 7 | ScaI | 2063, 507 |
| 8 | SpeI | 114, 2456 |
| 9 | XcmI | 1309, 1261 |
| 10 | Uncut PCR fragment (2570 bp) | |

1.2% Agarose gel

FIG. 30

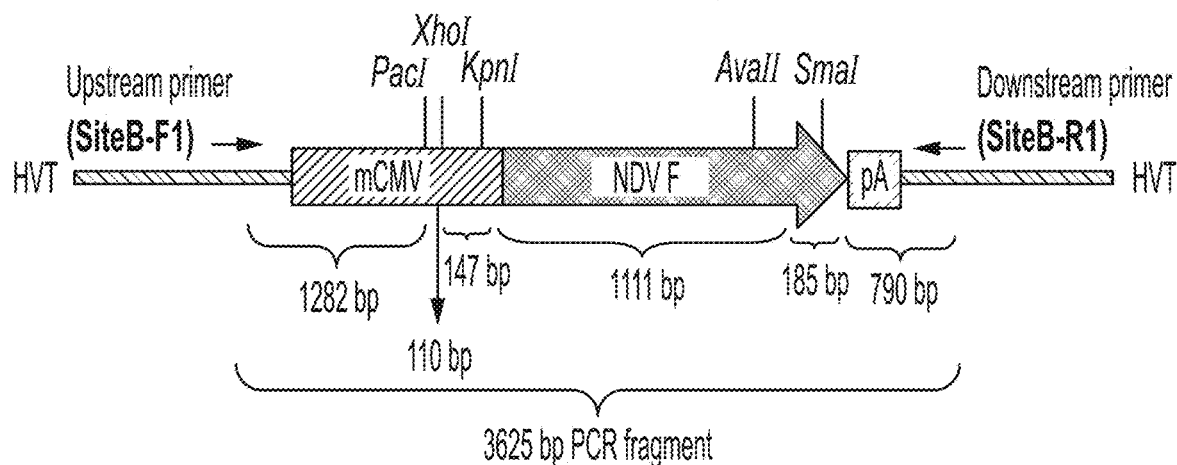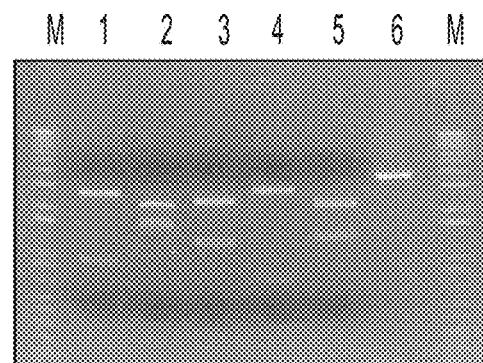
FIG. 31

Western Blot Analysis of HVT-IBD-ND Target Protein Expression
(Donor Gene 2 at Insertion Site B: NDV F)

| Lane | Samples |
|------|---------|
| M | MW Marker |
| 1 | HVT Control |
| 2 | HVT-IBD-ND MSV |
| 3 | HVT-IBD-ND n+5 |
| 4 | Vectormune ND control |

← NDV F (61 KD)

Samples: ~4x10$^5$ cells lysed in sample buffer and loaded per lane
Primary antibody: NDV antiserum 1:1000 dilution
Secondary antibody: Peroxidase-conjugated anti-chicken IgY (Jackson Lab) at 1:1000 dilution

FIG. 33

SEQUENCE LISTING

<160> NUMBER OF SEQ ID NOS: 158

<210> SEQ ID NO 1
<211> LENGTH: 687
<212> TYPE: DNA
<213> ORGANISM: Artificial Sequence
<220> FEATURE:
<223> OTHER INFORMATION: DNA sequence of human CMV (hCMV) promoter

<400> SEQUENCE: 1

```
ttgacattga ttattgacta gttattaata gtaatcaatt acggggtcat tagttcatag      60
cccatatatg gagttccgcg ttacataact tacggtaaat ggcccgcctg gctgaccgcc     120
caacgacccc cgcccattga cgtcaataat gacgtatgtt cccatagtaa cgccaatagg     180
gactttccat tgacgtcaat gggtggagta tttacggtaa actgcccact tggcagtaca     240
tcaagtgtat catatgccaa gtacgccccc tattgacgtc aatgacggta aatggcccgc     300
ctggcattat gcccagtaca tgaccttatg gactttcct acttggcagt acatctacgt      360
attagtcatc gctattacca tggtgatgcg gttttggcag tacatcaatg ggcgtggata     420
gcggtttgac tcacggggat ttccaagtct ccaccccatt gacgtcaatg ggagtttgtt     480
ttggcaccaa aatcaacggg actttccaaa atgtcgtaac aactccgccc cattgacgca     540
aatgggcggt aggcgtgtac ggtgggaggt ctatataagc agagctctct ggctaactag     600
agaacccact gcttactggc ttatcgaaat taatacgact cactataggg agacccaagc     660
tggctagcgt ttaaacttaa gcttacc                                         687
```

<210> SEQ ID NO 2
<211> LENGTH: 1391
<212> TYPE: DNA
<213> ORGANISM: Artificial Sequence
<220> FEATURE:
<223> OTHER INFORMATION: DNA sequence of mouse CMV (mCMV) promoter

<400> SEQUENCE: 2

```
aactccgccc gttttatgac tagaaccaat agtttttaat gccaaatgca ctgaaatccc     60
ctaatttgca aagccaaacg ccccctatgt gagtaatacg gggacttttt acccaatttc    120
ccaagcggaa agccccctaa tacactcata tggcatatga atcagcacgg tcatgcactc    180
taatggcggc ccatagggac tttccacata gggggcgttc accatttccc agcatagggg    240
tggtgactca atggccttta cccaagtaca ttgggtcaat gggaggtaag ccaatgggtt    300
tttcccatta ctggcaagca cactgagtca aatgggactt tccactgggt tttgcccaag    360
tacattgggt caatgggagg tgagccaatg ggaaaaaccc attgctgcca agtacactga    420
ctcaataggg actttccaat gggtttttcc attgttggca agcatataag gtcaatgtgg    480
gtgagtcaat agggactttc cattgtattc tgcccagtac ataaggtcaa taggggtga    540
atcaacagga aagtcccatt ggagccaagt acactgcgtc aatagggact ttccattggg    600
ttttgcccag tacataaggt caatagggga tgagtcaatg ggaaaaaccc attggagcca    660
agtacactga ctcaataggg actttccatt gggttttgcc cagtacataa ggtcaatagg    720
gggtgagtca acaggaaagt cccattggag ccaagtacat tgagtcaata gggactttcc    780
aatgggtttt gcccagtaca taaggtcaat gggaggtaag ccaatgggtt tttcccatta    840
ctggcacgta tactgagtca ttagggactt tccaatgggt tttgcccagt acataaggtc    900
aataggggtg aatcaacagg aaagtcccat tggagccaag tacactgagt caatagggac    960
tttccattgg gttttgccca gtacaaaagg tcaatagggg gtgagtcaat gggtttttcc   1020
cattattggc acgtacataa ggtcaatagg ggtgagtcat tgggtttttc cagccaattt   1080
aattaaaacg ccatgtactt tcccaccatt gacgtcaatg ggctattgaa actaatgcaa   1140
cgtgaccttt aaacggtact ttcccatagc tgattaatgg gaaagtaccg ttctcgagcc   1200
aatacacgtc aatgggaagt gaaagggcag ccaaaacgta acaccgcccc ggttttcccc   1260
tggaaattcc atattggcac gcattctatt ggctgagctg cgttctacgt gggtataaga   1320
ggcgcgacca gcgtcggtac cgtcgcagtc ttcggtctga ccaccgtaga acgcagagct   1380
cctcgctgca g                                                        1391
```

<210> SEQ ID NO 3
<211> LENGTH: 1662
<212> TYPE: DNA
<213> ORGANISM: Artificial Sequence
<220> FEATURE:
<223> OTHER INFORMATION: DNA sequence of strain D26-76 NDV F protein

<400> SEQUENCE: 3

```
atgggctcca gatcttctac caggatccca gtacctctga tgctgaccgt ccgaatcatg     60
ttggcactga gttgcgtctg tccgaccagc tcccttgatg gcaggcctct tgcagctgca    120
gggattgtgg taacaggaga caaagcagtc aacatataca cctcatctca gacagggtca    180
atcataatca agttactccc aaatatgccc aaggataaag aggcgtgtgc aaaagcccca    240
ttggaagcat acaacaggac attgactact ttgctcaccc cccttggtga ttctatccgt    300
aggatacaag agtctgtgac cacatccgga ggagggaaac agggacgtct tataggcgcc    360
```

```
attatcggtg gtgtagctct cggggttgca accgctgcac agataacagc agcctcggct    420
ctgatacaag ccaatcaaaa tgctgccaac atcctccggc tcaaagagag cattgctgca    480
accaatgagg ctgtgcacga ggtcactgac ggattatcac aactagcagt ggcagttggg    540
aagatgcagc aatttgttaa tgaccagttt aataaaacag ctcaggaatt ggactgtata    600
aaaattacac agcaggttgg tgtagaactc aacctgtacc taactgaatt gactacagta    660
ttcgggccac aaatcacttc ccctgcctta actcagctga ctatccaggc gctttacaat    720
ctagctggtg ggaatatgga ttacttgttg actaagttag gtgtaggaaa caaccaactc    780
agctcattaa ttggtagtgg cctgattacc ggcaacccta tcctgtacga ctcacagact    840
caactcttgg gtatacaggt caccctaccc tcagtcggga atctaaataa tatgcgtgcc    900
acctacctgg aaaccttgtc tgtaagtaca accaaaggat ttgcctcagc acttgtccca    960
aaagtagtga cacaggttgg ttccgtgata gaagagcttg acacctcgta ctgtatcgag   1020
accgatttgg acctatattg tacaagaata gtgacattcc ctatgtctcc tggtatttat   1080
tcctgtttga gtggcaatac atctgcttgc atgtattcaa agactgaagg cgcactcact   1140
acgccgtata tgaccctcaa aggctcagtt attgccaact gtaagatgac aacatgtaga   1200
tgtgcagacc ccccgggtat catatcgcag aattatggag aagctgtgtc tctaatagat   1260
aggcaatcat gcaatatctt atccttagac gggataactt tgaggctcag tggggaattt   1320
gatgcaactt atcaaaagaa tatctcaata caagattctc aagtaatagt tacaggcaat   1380
cttgacatct cgactgagct tgggaatgtc aacaactcga taagtaatgc tttggataag   1440
ttagaggaaa gcaacagcaa actagacaag gtcaatgtta aactgaccag cacatccgct   1500
cttattacct atatcgtttt aactgtcata tctcttgtat gtggtatact agcctggtt   1560 ctagcatgct acctgatgta caagcaaaag gcgcaacaga gaccttgtt gtggcttggg   1620 aataataccc tagaccagat gagggccact acaaaaatgt ag                      1662
```

<210> SEQ ID NO 4
<211> LENGTH: 553
<212> TYPE: PRT
<213> ORGANISM: Artificial Sequence
<220> FEATURE:
<223> OTHER INFORMATION: Amino acid sequence of strain D26-76 NDV F
      protein

<400> SEQUENCE: 4

```
Met Gly Ser Arg Ser Ser Thr Arg Ile Pro Val Pro Leu Met Leu Thr
1               5                   10                  15

Val Arg Ile Met Leu Ala Leu Ser Cys Val Cys Pro Thr Ser Ser Leu
            20                  25                  30

Asp Gly Arg Pro Leu Ala Ala Ala Gly Ile Val Val Thr Gly Asp Lys
        35                  40                  45

Ala Val Asn Ile Tyr Thr Ser Ser Gln Thr Gly Ser Ile Ile Ile Lys
    50                  55                  60

Leu Leu Pro Asn Met Pro Lys Asp Lys Glu Ala Cys Ala Lys Ala Pro
65                  70                  75                  80

Leu Glu Ala Tyr Asn Arg Thr Leu Thr Thr Leu Leu Thr Pro Leu Gly
                85                  90                  95

Asp Ser Ile Arg Arg Ile Gln Glu Ser Val Thr Thr Ser Gly Gly Gly
            100                 105                 110

Lys Gln Gly Arg Leu Ile Gly Ala Ile Ile Gly Gly Val Ala Leu Gly
        115                 120                 125
```

```
Val Ala Thr Ala Ala Gln Ile Thr Ala Ala Ser Ala Leu Ile Gln Ala
    130                 135                 140

Asn Gln Asn Ala Ala Asn Ile Leu Arg Leu Lys Glu Ser Ile Ala Ala
145                 150                 155                 160

Thr Asn Glu Ala Val His Glu Val Thr Asp Gly Leu Ser Gln Leu Ala
                165                 170                 175

Val Ala Val Gly Lys Met Gln Gln Phe Val Asn Asp Gln Phe Asn Lys
                180                 185                 190

Thr Ala Gln Glu Leu Asp Cys Ile Lys Ile Thr Gln Gln Val Gly Val
            195                 200                 205

Glu Leu Asn Leu Tyr Leu Thr Glu Leu Thr Thr Val Phe Gly Pro Gln
210                 215                 220

Ile Thr Ser Pro Ala Leu Thr Gln Leu Thr Ile Gln Ala Leu Tyr Asn
225                 230                 235                 240

Leu Ala Gly Gly Asn Met Asp Tyr Leu Leu Thr Lys Leu Gly Val Gly
                245                 250                 255

Asn Asn Gln Leu Ser Ser Leu Ile Gly Ser Gly Leu Ile Thr Gly Asn
                260                 265                 270

Pro Ile Leu Tyr Asp Ser Gln Thr Gln Leu Leu Gly Ile Gln Val Thr
    275                 280                 285

Leu Pro Ser Val Gly Asn Leu Asn Asn Met Arg Ala Thr Tyr Leu Glu
    290                 295                 300

Thr Leu Ser Val Ser Thr Thr Lys Gly Phe Ala Ser Ala Leu Val Pro
305                 310                 315                 320

Lys Val Val Thr Gln Val Gly Ser Val Ile Glu Glu Leu Asp Thr Ser
                325                 330                 335

Tyr Cys Ile Glu Thr Asp Leu Asp Leu Tyr Cys Thr Arg Ile Val Thr
                340                 345                 350

Phe Pro Met Ser Pro Gly Ile Tyr Ser Cys Leu Ser Gly Asn Thr Ser
                355                 360                 365

Ala Cys Met Tyr Ser Lys Thr Glu Gly Ala Leu Thr Thr Pro Tyr Met
            370                 375                 380

Thr Leu Lys Gly Ser Val Ile Ala Asn Cys Lys Met Thr Thr Cys Arg
385                 390                 395                 400

Cys Ala Asp Pro Pro Gly Ile Ile Ser Gln Asn Tyr Gly Glu Ala Val
                405                 410                 415

Ser Leu Ile Asp Arg Gln Ser Cys Asn Ile Leu Ser Leu Asp Gly Ile
            420                 425                 430

Thr Leu Arg Leu Ser Gly Glu Phe Asp Ala Thr Tyr Gln Lys Asn Ile
            435                 440                 445

Ser Ile Gln Asp Ser Gln Val Ile Val Thr Gly Asn Leu Asp Ile Ser
    450                 455                 460

Thr Glu Leu Gly Asn Val Asn Asn Ser Ile Ser Asn Ala Leu Asp Lys
465                 470                 475                 480

Leu Glu Glu Ser Asn Ser Lys Leu Asp Lys Val Asn Val Lys Leu Thr
                485                 490                 495

Ser Thr Ser Ala Leu Ile Thr Tyr Ile Val Leu Thr Val Ile Ser Leu
            500                 505                 510

Val Cys Gly Ile Leu Ser Leu Val Leu Ala Cys Tyr Leu Met Tyr Lys
            515                 520                 525

Gln Lys Ala Gln Gln Lys Thr Leu Leu Trp Leu Gly Asn Asn Thr Leu
    530                 535                 540

Asp Gln Met Arg Ala Thr Thr Lys Met
```

<210> SEQ ID NO 5
<211> LENGTH: 1362
<212> TYPE: DNA
<213> ORGANISM: Artificial Sequence
<220> FEATURE:
<223> OTHER INFORMATION: DNA Sequence of vIBDV (F52/70) VP2

<400> SEQUENCE: 5

| | | | | | |
|---|---|---|---|---|---|
| atgaccaatc | tccaggacca | gacccagcag | attgtgcctt | ttattaggag | tctcttgatg | 60 |
| cctacaaccg | ccccgccag | catcccggac | gacacactgg | aaaaacatac | actgagaagc | 120 |
| gagacatcta | catacaattt | gaccgtgggc | gataccggct | ccgggcttat | cgtgttcttc | 180 |
| ccaggttttc | ccggatctat | cgtaggagc | cactacaccc | tccaaagtaa | cggcaattac | 240 |
| aaattcgacc | agatgctcct | gacagcccag | aaccttcctg | cttcttacaa | ttactgtaga | 300 |
| cttgtgtcca | ggtccctgac | tgtgcggagt | agcacgcttc | caggaggcgt | atacgccctg | 360 |
| aacggaacta | taaacgccgt | caccttccag | ggctccttgt | ccgaacttac | cgacgtgtcc | 420 |
| tacaatggcc | tcatgagcgc | aacggccaac | ataaacgata | gatcggcaa | tgttcttgtg | 480 |
| ggcgaggggg | ttacagtcct | ttctctgcca | accagttatg | atctgggata | cgtgcggctt | 540 |
| ggcgatccca | ttcccgctat | cggtctcgac | cctaaaatgg | tggctacttg | cgactcatct | 600 |
| gaccgcccaa | gggtctatac | aattactgca | gccgatgact | atcagttttc | cagccaatac | 660 |
| cagccagggg | gtgtgacaat | cacacttttc | agcgccaata | ttgacgctat | cacatccctc | 720 |
| tcaatcggag | tgagcttgt | gttccagact | tctgttcagg | gcttggtatt | gggcgccact | 780 |
| atttacttga | tcgggttcga | cgggaccgca | gtgatcactc | gggcagtggc | tgcggataac | 840 |
| ggactcactg | ccggaactga | caaccttatg | ccttttaatc | tggtcatccc | cactaacgag | 900 |
| atcacccagc | ctattaccctc | cataaagctc | gaaattgtga | ccagcaagag | cggagggcag | 960 |
| gcaggcgacc | aaatgagttg | gtctgcaagc | gggtccctcg | ccgtgaccat | ccacggtggc | 1020 |
| aactatcctg | gggcgctcag | acccgtcacc | ctggtagcct | acgaaagggt | tgccacaggc | 1080 |
| tcagttgtca | cggtggctgg | agtaagcaat | ttcgagctca | tcccgaatcc | tgagctcgct | 1140 |
| aaaaatcttg | tgaccgagta | tggaaggttc | gaccctggcg | caatgaatta | cacaaagctg | 1200 |
| attctgtccg | aacgggatag | gctgggtatc | aagacagttt | ggcccacgcg | cgaatacaca | 1260 |
| gatttcaggg | agtactttat | ggaggtcgca | gatttgaata | gcccacttaa | gatcgctgga | 1320 |
| gcatttggct | ttaaggatat | tatccgcgca | atcagaaggt | ag | | 1362 |

<210> SEQ ID NO 6
<211> LENGTH: 225
<212> TYPE: DNA
<213> ORGANISM: Artificial Sequence
<220> FEATURE:
<223> OTHER INFORMATION: DNA sequence of Bovine Growth Hormone Poly A

<400> SEQUENCE: 6

| | | | | | |
|---|---|---|---|---|---|
| tgtgccttct | agttgccagc | catctgttgt | ttgcccctcc | cccgtgcctt | ccttgaccct | 60 |
| ggaaggtgcc | actcccactg | tcctttccta | ataaaatgag | gaaattgcat | cgcattgtct | 120 |
| gagtaggtgt | cattctattc | tggggggtgg | ggtggggcag | gacagcaagg | gggaggattg | 180 |
| ggaagacaat | agcaggcatg | ctggggatgc | ggtgggctct | atggt | | 225 |

<210> SEQ ID NO 7
<211> LENGTH: 580

<212> TYPE: DNA
<213> ORGANISM: Artificial Sequence
<220> FEATURE:
<223> OTHER INFORMATION: DNA Sequence of HVT UL55 Flanking

<400> SEQUENCE: 7

```
atggcagcga gcatgggata ttcatcctcg tcatcgttaa catctctacg ggttcagaat    60
gtttggcatg tcgtcgatcc tttgcccatc gttgcaaatt acaagtccga tcgccatgac   120
cgcgataagc ctgtaccatg tggcattagg gtgacatctc gatcatacat tataagacca   180
acgtgcgagt cttccaaaga cctgcacgcc ttcttcttcg gattgtcaac gggttcttca   240
gaatctatgc ccatatctgg cgttgagacc attgtgcgtt taatgaacaa taaagcggca   300
tgccatggaa aggagggctg cagatctcca ttttctcacg ccactatcct ggacgctgta   360
gacgataatt ataccatgaa atagaggggg tatgtttcc actgccactg tgatgataag    420
ttttctccag attgttggat atctgcattt tctgctgccg aacaaacttc atcgctatgc   480
aaagagatgc gtgtgtacac gcgccgttga gtatacggga aactaaatgt tcatagaggt   540
ctttgggcta tatgttatta aataaaataa ttgaccagtg                         580
```

<210> SEQ ID NO 8
<211> LENGTH: 678
<212> TYPE: DNA
<213> ORGANISM: Artificial Sequence
<220> FEATURE:
<223> OTHER INFORMATION: DNA Sequence of HVT Gene 3 Flanking

<400> SEQUENCE: 8

```
gtttaatgtt agtttattca atgcattggt tgcaaatatt cattacttct ccaatcccag    60
gtcattcttt agcgagatga tgttatgaca ttgctgtgaa attactaca ggatatattt    120
ttaagatgca ggagtaacaa tgtgcatagt aggcgtagtt atcgcagacg tgcaacgctt   180
cgcatttgag ttaccgaagt gcccaacagt gctgcggtta tggtttatgc gcacagaatc   240
catgcatgtc ctaattgaac catccgattt ttctttaat cgcgatcgtt gtttgggcaa    300
ctgcgttatt tcagatctaa aaaatttacc ctttatgacc atcacatctc tctggctcat   360
accccgcttg gataagatat catgtagatt ccgccctaag aaatgcaaac taacattatt   420
gtcggttcca tatacacttc catcttgtcc ttcgaaaata acaaactcgc gcaatagacc   480
gtccgtacat gcatggccga tgtgtgtcaa catcattggt ctgctagatc ccgatgggac   540
gaatcgtaca gtcgtcgctc cagcattggc aaaaatcccc agataccctc catgcggcaa   600
atctaaattg cgaccccgaa gagactgcac caaagtctta tcgacgcacg ctgattttt    660
tgaacagcgg gagcccat                                                 678
```

<210> SEQ ID NO 9
<211> LENGTH: 561
<212> TYPE: DNA
<213> ORGANISM: Artificial Sequence
<220> FEATURE:
<223> OTHER INFORMATION: DNA Sequence of Pec Promoter

<400> SEQUENCE: 9

```
agttattaat agtaatcaat tacggggtca ttagttcata gcccatatat ggagttccgc    60
gttacataac ttacggtaaa tggcccgccg gctgaccgcc caacgacccc cgcccattga   120
cgtcaataat gacgtatgtt cccatagtaa cgccaatagg gactttccat tgacgtcaat   180
gggtggagta tttacggtaa actgcccatt ggcagtacat caagtgtatc atatgccaag   240
```

```
tacgcccct  attgacgtca  atgacggtaa  atggatgcag  tattttgtgc  agcgatgggg    300 gcggggggg  ggggggcgcg  cgccaggcgg  ggcggggcgg  ggcgagggc  ggggcggggc    360 gaggcggaga  ggtgcggcgg  cagccaatca  gagcggcgcg  ctccgaaagt  ttccttttat   420
ggcgaggcgg  cggcggcggc  ggccctataa  aaagcgaagc  gcgcggcggg  cgggagtcgc   480
tgcgcgctgc  cttcgccccg  tgccccgctc  cgccgccgcc  tcgcgccgcc  cgccccggct   540
ctgactgacc  gcgtctagag  g                                                561
```

<210> SEQ ID NO 10
<211> LENGTH: 1362
<212> TYPE: DNA
<213> ORGANISM: Artificial Sequence
<220> FEATURE:
<223> OTHER INFORMATION: DNA Sequence of vvIBDV VP2

<400> SEQUENCE: 10

```
atgacaaatc  ttcaggatca  gacccagcag  atagttccct  ttattaggtc  ccttctgatg    60
ccaaccacag  ggcccgctag  cattccggac  gataccctgg  agaaacacac  tttgcggagt   120
gagacaagca  cttacaatct  gacggtggga  gataccggct  caggtcttat  cgtgttttt   180 cccggctttc  ctggatccat  tgttggcgcg  cattacacgc  tgcagagcaa  cggcaactat   240
aaattcgatc  agatgctcct  gacggctcag  aatctccccg  ccagttacaa  ttactgccgc   300
cttgtaagta  ggtccttgac  tgttagaagc  tcaacgctgc  caggcggagt  atatgccctg   360
aatggaacca  ttaatgctgt  aacattccaa  ggatcactgt  ccgagctcac  cgatgtgtct   420
tacaatggat  tgatgtctgc  cacggctaac  attaacgaca  gatcgggaa   tgtgctcgtg   480 ggcgagggag  tgaccgtttt  gagcctgccg  acaagctacg  acctcggcta  cgtaaggctc   540
ggggatccaa  tccccgcgat  cggcttggat  cccaaaatgg  ttgctacgtg  cgacagcagc   600
gatagaccca  gggtctatac  catcaccgct  gccgatgatt  accagtttag  ctcccagtac   660
caggcgggag  gggtcacgat  cacccttttt  agcgccaaca  tcgacgccat  aacctcactt   720 tctataggg   gcgagttggt  ttttcagacc  agtgtccagg  ggctcatcct  cggtgcgaca   780
atctatctga  tcggctttga  cggaacagct  gtcatcacga  gggccgtagc  tgcagataat   840
ggcctgactg  ctgggacaga  taatctgatg  ccgttcaaca  tagtgatccc  caccagtgag   900
attacgcaac  ccatcacgag  catcaaactg  gagatcgtga  cgtcaaaatc  cggcggtcag   960
gcaggtgacc  agatgtcttg  gtccgcaagc  ggaagtttgg  ccgtgacaat  tcacgggggg  1020 aattacccccg  gcgcactcag  gcccgtgacc  ctcgtcgcct  acgaaagagt  tgcaacggga  1080
agtgtagtga  cagtcgctgg  agtgagtaac  ttcgaactca  tccctaatcc  cgagctcgcc  1140
aaaaatctcg  tcacggagta  tgggaggttt  gatcccggcg  ccatgaacta  cacaaaactg  1200
atattgtccg  aaagggatag  gttgggcatt  aaaaccgtgt  ggcctactag  ggaatacacc  1260
gatttccgcg  aatattttat  ggaggtcgcg  gatctgaact  ctcccctgaa  gatagcaggc  1320
gcttttgggt  tcaaggatat  tatccgggcg  ttgcggcggt  ag                      1362
```

<210> SEQ ID NO 11
<211> LENGTH: 197
<212> TYPE: DNA
<213> ORGANISM: Artificial Sequence
<220> FEATURE:
<223> OTHER INFORMATION: DNA Sequence SV40 promoter

<400> SEQUENCE: 11

```
tgcatctcaa  ttagtcagca  accatagtcc  cgcccctaac  tccgcccatc  cgcccctaa     60
```

```
ctccgcccag ttccgcccat tctccgcccc atcgctgact aatttttttt atttatgcag    120
aggccgaggc cgcctcggcc tctgagctat tccagaagta gtgaggaggc ttttttggag    180
gcctaggctt ttgcaaa                                                   197
```

```
<210> SEQ ID NO 12
<211> LENGTH: 122
<212> TYPE: DNA
<213> ORGANISM: Artificial Sequence
<220> FEATURE:
<223> OTHER INFORMATION: DNA Sequence SV40 polyA sequence

<400> SEQUENCE: 12
```

```
taagatacat tgatgagttt ggacaaacca caactagaat gcagtgaaaa aaatgcttta     60
tttgtgaaat ttgtgatgct attgctttat ttgtaaccat tataagctgc aataaacaag    120
tt                                                                   122
```

```
<210> SEQ ID NO 13
<211> LENGTH: 531
<212> TYPE: DNA
<213> ORGANISM: Artificial Sequence
<220> FEATURE:
<223> OTHER INFORMATION: DNA Sequence of HVT UL35 Flanking

<400> SEQUENCE: 13
```

```
gccactgtat gggccattta tgtttatcga gtctaaaagt cgtggaagcg cctggccatc     60
gccagtctcg acctgccact gctgagttcg gcttcaattc cagcatccca gaaatgtcgc    120
agtcaccatc acgccgtgca tcgcttccta cgaggccttt tgacgcttct gatttgggca    180
catacaccct ggacatactc caccgctatt cgctcgtaga tttagtacaa ctactgaatg    240
acttgccgcg taacattacc tccacgcccg cttctaatgt agaaaccatg gcaaaaatta    300
atgttttaag ggccatttgc gtaggatttg ccgaggtccg tcgccacaac gacgcgcgaa    360
ctttacagcg aacggcaatg tttgccgccg acgacgtcgc atcacggatc agaccatcca    420
ttggattaaa gcgcacctac ccaccgggta tattttccac agctattacc gtatctaatt    480
ccgaggatga agagcgaaat tcgtgatcgt aaaaataaaa aatacaagat a             531
```

```
<210> SEQ ID NO 14
<211> LENGTH: 700
<212> TYPE: DNA
<213> ORGANISM: Artificial Sequence
<220> FEATURE:
<223> OTHER INFORMATION: DNA Sequence of HVT UL36 Flanking

<400> SEQUENCE: 14
```

```
gtacataatt cttatttatc tttaatccat gaggagcatt tttattttaa aaatgtcagc     60
cgccagccct ataaccctag atcgcaactg atccctagtc tgcgttattt gtcttgcaat    120
cttttcgcac gcctttgtga gtgcatacaa tgcccccctg ctcgcttttc tgaaatcgcg    180
tcgggtcatt aatgtgtcgg ctatcacaat gcgagatgta ctcgacatgt ccgtgtctgt    240
actattggga ttgtaaatag tcgaccgcga atcatcagag tcggaatctg taaaggatac    300
agattccgac tctgagcgct tatgaatggg atccactcgg acgttgttga acttccgttc    360
ggattctgct tcagtcaaca ccggcccccg atagctacta aggttggggg gtttgtgggt    420
tgtttgtgaa actgctttgc ggtgtgcatt accacggggg gtgtgggaa gtatctgttt    480 ccacgatgcg ataacgttcg gtggcggagg gggcgattca ttctctagtg tacgcgtttc    540
```

| | | |
|---|---|---|
| aacttcagga acgtgattat ttctttcagg acactctttc caatttcctt cttccttcac | 600 | |
| ttcgggtaca ggtatattct taatgtttac atacatgtcg tctgctcgtc tcaactgcgg | 660 | |
| ggttatgatg ggtggtggtg acagtctctc cgaatgatcg | 700 | |

<210> SEQ ID NO 15
<211> LENGTH: 1278
<212> TYPE: DNA
<213> ORGANISM: Artificial Sequence
<220> FEATURE:
<223> OTHER INFORMATION: DNA Sequence of Chicken Beta-actin Promoter

<400> SEQUENCE: 15

| | |
|---|---|
| tcgaggtgag ccccacgttc tgcttcactc tccccatctc ccccccctcc ccaccccaa | 60 |
| ttttgtattt atttattttt taattatttt gtgcagcgat gggggcgggg ggggggggg | 120 |
| cgcgcgccag gcggggcggg gcgggcgag gggcggggcg gggcgaggcg gagaggtgcg | 180 |
| gcggcagcca atcagagcgg cgcgctccga aagtttcctt ttatggcgag gcggcggcgg | 240 |
| cggcggccct ataaaaagcg aagcgcgcgg cgggcggag tcgctgcgtt gccttcgccc | 300 |
| cgtgccccgc tccgcgccgc ctcgcgccgc ccgcccggc tctgactgac cgcgttactc | 360 |
| ccacaggtga gcgggcggga cggcccttct cctccgggct gtaattagcg cttggtttaa | 420 |
| tgacggctcg tttcttttct gtggctgcgt gaaagcctta aagggctccg ggagggccct | 480 |
| ttgtgcgggg gggagcggct cggggggtgc gtgcgtgtgt gtgtgcgtgg ggagcgccgc | 540 |
| gtgcggcccg cgctgcccgg cggctgtgag cgctgcgggc gcggcgcggg gctttgtgcg | 600 |
| ctccgcgtgt gcgcgagggg agcgcggccg ggggcggtgc cccgcggtgc ggggggctg | 660 |
| cgagggggaac aaaggctgcg tgcggggtgt gtgcgtgggg gggtgagcag ggggtgtggg | 720 |
| cgcggcggtc gggctgtaac cccccctgc accccctcc ccgagttgct gagcacggcc | 780 |
| cggcttcggg tgcggggctc cgtgcggggc gtggcgcggg gctcgccgtg ccgggcgggg | 840 |
| ggtggcggca ggtgggggtg ccgggcgggg cggggccgcc tcgggccggg gagggctcgg | 900 |
| gggagggggcg cggcggcccc ggagcgccgg cggctgtcga ggcgcggcga ccgcagcca | 960 |
| ttgcctttta tggtaatcgt gcgagagggc gcagggactt cctttgtccc aaatctggcg | 1020 |
| gagccgaaat ctgggaggcg ccgccgcacc ccctctagcg ggcgcgggcg aagcggtgcg | 1080 |
| gcgccggcag gaaggaaatg ggcggggagg gccttcgtgc gtcgccgcgc cgccgtcccc | 1140 |
| ttctccatct ccagcctcgg ggctgccgca ggggacggc tgccttcggg ggggacgggg | 1200 |
| cagggcgggg ttcggcttct ggcgtgtgac cggcggggtt tatatcttcc cttctctgtt | 1260 |
| cctccgcagc cagccatg | 1278 |

<210> SEQ ID NO 16
<211> LENGTH: 2882
<212> TYPE: DNA
<213> ORGANISM: Artificial Sequence
<220> FEATURE:
<223> OTHER INFORMATION: DNA Sequence of Modified transfer plasmid for
    HVT-gfp-A #14*

<400> SEQUENCE: 16

| | |
|---|---|
| gccactgtat gggccatttta tgtttatcga gtctaaaagt cgtggaagcg cctggccatc | 60 |
| gccagtctcg acctgccact gctgagttcg cttcaattc cagcatccca gaaatgtcgc | 120 |
| agtcaccatc acgccgtgca tcgcttccta cgaggccttt tgacgcttct gatttgggca | 180 |
| catacaccct ggacatactc caccgctatt cgctcgtaga tttagtacaa ctactgaatg | 240 |

```
acttgccgcg taacattacc tccacgcccg cttctaatgt agaaaccatg gcaaaaatta      300
atgttttaag ggccatttgc gtaggatttg ccgaggtccg tcgccacaac gacgcgcgaa      360
ctttacagcg aacggcaatg tttgccgccg acgacgtcgc atcacggatc agaccatcca      420
ttggattaaa gcgcacctac ccaccgggta tattttccac agctattacc gtatctaatt      480
ccgaggatga agagcgaaat tcgtgatcgt aaaaataaaa aatacaagat attgacattg      540
attattgact agttattaat agtaatcaat tacggggtca ttagttcata gcccatatat      600
ggagttccgc gttacataac ttacggtaaa tggcccgcct ggctgaccgc ccaacgaccc      660
ccgcccattg acgtcaataa tgacgtatgt tcccatagta acgccaatag ggactttcca      720
ttgacgtcaa tgggtggagt atttacggta aactgcccac ttggcagtac atcaagtgta      780
tcatatgcca gtacgccccc tattgacgtc aatgacggt aaatggcccg cctggcatta       840
tgcccagtac atgaccttat gggactttcc tacttggcag tacatctacg tattagtcat      900
cgctattacc atggtgatgc ggttttggca gtacatcaat gggcgtggat agcggtttga      960
ctcacgggga tttccaagtc tccacccat tgacgtcaat gggagtttgt tttggcacca      1020
aaatcaacgg gactttccaa aatgtcgtaa caactccgcc ccattgacgc aaatgggcgg      1080
taggcgtgta cggtgggagg tctatataag cagagctctc tggctaacta gagaacccac      1140
tgcttactgg cttatcgaaa ttaatacgac tcactatagg gagacccaag ctggctagcg      1200
tttaaactta agcttacctg caggccacca tggtgagcaa gggcgccgag ctgttcaccg      1260
gcatcgtgcc catcctgatc gagctgaatg gcgatgtgaa tggccacaag ttcagcgtga      1320
gcggcgaggg cgagggcgat gccacctacg gcaagctgac cctgaagttc atctgcacca      1380
ccggcaagct gcctgtgccc tggcccaccc tggtgaccac cctgagctac ggcgtgcagt      1440
gcttctcacg ctaccccgat cacatgaagc agcacgactt cttcaagagc gccatgcctg      1500
agggctacat ccaggagcgc accatcttct tcgaggatga cggcaactac aagtcgcgcg      1560
ccgaggtgaa gttcgagggc gatacccgg tgaatcgcat cgagctgacc ggcaccgatt       1620
tcaaggagga tggcaacatc ctgggcaata agatggagta caactacaac gcccacaatg      1680
tgtacatcat gaccgacaag gccaagaatg gcatcaaggt gaacttcaag atccgccaca      1740
acatcgagga tggcagcgtg cagctggccg accactacca gcagaatacc cccatcggcg      1800
atggccctgt gctgctgccc gataaccact acctgtccac ccagagcgcc ctgtccaagg      1860
accccaacga gaagcgcgat cacatgatct acttcggctt cgtgaccgcc gccgccatca      1920
cccacggcat ggatgagctg tacaagtgac ctgcaggtgt gccttctagt tgccagccat      1980
ctgttgtttg ccctccccc gtgccttcct tgaccctgga aggtgccact cccactgtcc       2040
tttcctaata aaatgaggaa attgcatcgc attgtctgag taggtgtcat tctattctgg      2100
ggggtggggt ggggcaggac agcaagggg aggattggga agacaatagc aggcatgctg       2160
gggatgcggt gggctctatg gtgtacataa ttcttattta tctttaatcc atgaggagca      2220 ttttttatttt aaaaatgtca gccgccagcc ctataaccct agatcgcaac tgatccctag     2280
tctgcgttat ttgtcttgca atcttttcgc acgcctttgt gagtgcatac aatgccccc       2340 tgctcgcttt tctgaaatcg cgtcgggtca ttaatgtgtc ggctatcaca atgcgagatg      2400
tactcgacat gtccgtgtct gtactattgg gattgtaaat agtcgaccgc gaatcatcag      2460
agtcggaatc tgtaaaggat acagattccg actctgagcg cttatgaatg ggatccactc      2520
ggacgttgtt gaacttccgt tcggattctg cttcagtcaa caccggcccc cgatagctac      2580
taaggttggg gggtttgtgg gttgtttgtg aaactgcttt gcggtgtgca ttaccacggg      2640
```

```
gggtgtgggg aagtatctgt ttccacgatg cgataacgtt cggtggcgga gggggcgatt    2700
cattctctag tgtacgcgtt tcaacttcag gaacgtgatt atttctttca ggacactctt    2760
tccaatttcc ttcttccttc acttcgggta caggtatatt cttaatgttt acatacatgt    2820
cgtctgctcg tctcaactgc ggggttatga tgggtggtgg tgacagtctc tccgaatgat    2880
cg                                                                   2882
```

<210> SEQ ID NO 17
<211> LENGTH: 2869
<212> TYPE: DNA
<213> ORGANISM: Artificial Sequence
<220> FEATURE:
<223> OTHER INFORMATION: DNA sequence Original transfer plasmid for HVT-gfp-A #14

<400> SEQUENCE: 17

```
gccactgtat gggccattta tgtttatcga gtctaaaagt cgtggaagcg cctggccatc      60
gccagtctcg acctgccact gctgagttcg gcttcaattc cagcatccca gaaatgtcgc     120
agtcaccatc acgccgtgca tcgcttccta cgaggccttt tgacgcttct gatttgggca     180
catacaccct ggacatactc caccgctatt cgctcgtaga tttagtacaa ctactgaatg     240
acttgccgcg taacattacc tccacgcccg cttctaatgt agaaaccatg gcaaaaatta     300
atgttttaag ggccatttgc gtaggatttg ccgaggtccg tcgccacaac gacgcgcgaa     360 cttttacagcg aacggcaatg tttgccgccg acgacgtcgc atcacggatc agaccatcca     420
ttggattaaa gcgcacctac ccaccgggta tattttccac agctattacc gtatctaatt     480
ccgaggatga agagcgaaat tcgtgatcgt aaaaataaaa aatacaagat attgacattg     540
attattgact agttattaat agtaatcaat acgggtca ttagttcata gcccatatat     600
ggagttccgc gttacataac ttacggtaaa tggcccgcct ggctgaccgc ccaacgaccc     660
ccgcccattg acgtcaataa tgacgtatgt tcccatagta acgccaatag ggactttcca     720
ttgacgtcaa tgggtggagt atttacggta aactgcccac ttggcagtac atcaagtgta     780
tcatatgcca gtacgccccc ctattgacgt caatgacggt aaatggcccg cctggcatta     840
tgcccagtac atgaccttat gggactttcc tacttggcag tacatctacg tattagtcat     900
cgctattacc atggtgatgc ggttttggca gtacatcaat gggcgtggat agcggtttga     960
ctcacgggga tttccaagtc tccaccccat tgacgtcaat gggagtttgt tttggcacca    1020
aaatcaacgg gactttccaa aatgtcgtaa caactccgcc ccattgacgc aaatgggcgg    1080
taggcgtgta cggtgggagg tctatataag cagagctctc tggctaacta gagaacccac    1140
tgcttactgg cttatcgaaa ttaatacgac tcactatagg gagacccaag ctggctagcg    1200
tttaaactta agcttaccgc caccatggtg agcaagggcg ccgagctgtt caccggcatc    1260
gtgcccatcc tgatcgagct gaatggcgat gtgaatggcc acaagttcag cgtgagcggc    1320
gagggcgagg gcgatgccac ctacggcaag ctgaccctga gttcatctg caccaccggc    1380 aagctgcctg tgccctggcc caccctggtg accaccctga gctacggcgt gcagtgcttc    1440
tcacgctacc ccgatcacat gaagcagcac gacttcttca gagcgccat gcctgagggc    1500 tacatccagg agcgcaccat cttcttcgag gatgacggca actacaagtc gcgcgccgag    1560
gtgaagttcg agggcgatac cctggtgaat cgcatcgagc tgaccggcac cgatttcaag    1620
gaggatggca acatcctggg caataagatg gagtacaact acaacgccca caatgtgtac    1680
atcatgaccg acaaggccaa gaatggcatc aaggtgaact tcaagatccg ccacaacatc    1740
```

```
gaggatggca gcgtgcagct ggccgaccac taccagcaga ataccccat cggcgatggc      1800 cctgtgctgc tgcccgataa ccactacctg tccacccaga gcgccctgtc caaggacccc      1860
aacgagaagc gcgatcacat gatctacttc ggcttcgtga ccgccgccgc catcacccac      1920
ggcatggatg agctgtacaa gtgatgtgcc ttctagttgc cagccatctg ttgtttgccc      1980 ctccccgtg ccttccttga ccctggaagg tgccactccc actgtccttt cctaataaaa      2040
tgaggaaatt gcatcgcatt gtctgagtag gtgtcattct attctggggg gtggggtggg      2100
gcaggacagc aagggggagg attgggaaga caatagcagg catgctgggg atgcggtggg      2160
ctctatggtg tacataattc ttatttatct ttaatccatg aggagcattt ttattttaaa      2220
aatgtcagcc gccagcccta taccctaga tcgcaactga tccctagtct gcgttatttg      2280
tcttgcaatc ttttcgcacg cctttgtgag tgcatacaat gccccctgc tcgcttttct      2340 gaaatcgcgt cgggtcatta atgtgtcggc tatcacaatg cgagatgtac tcgacatgtc      2400
cgtgtctgta ctattgggat tgtaaatagt cgaccgcgaa tcatcagagt cggaatctgt      2460
aaaggataca gattccgact ctgagcgctt atgaatggga tccactcgga cgttgttgaa      2520
cttccgttcg gattctgctt cagtcaacac cggcccccga tagctactaa ggttgggggg      2580
tttgtgggtt gtttgtgaaa ctgctttgcg gtgtgcatta ccacgggggg tgtggggaag      2640
tatctgtttc cacgatgcga taacgttcgg tggcggaggg ggcgattcat tctctagtgt      2700
acgcgtttca acttcaggaa cgtgattatt tctttcagga cactcttttcc aatttccttc      2760 ttccttcact tcgggtacag gtatattctt aatgtttaca tacatgtcgt ctgctcgtct      2820
caactgcggg gttatgatgg gtggtggtga cagtctctcc gaatgatcg                   2869

<210> SEQ ID NO 18
<211> LENGTH: 2895
<212> TYPE: DNA
<213> ORGANISM: Artificial Sequence
<220> FEATURE:
<223> OTHER INFORMATION: DNA Sequence Transfer plasmid for HVT-gfp-B #13

<400> SEQUENCE: 18
atggcagcga gcatgggata ttcatcctcg tcatcgttaa catctctacg ggttcagaat        60
gtttggcatg tcgtcgatcc tttgcccatc gttgcaaatt acaagtccga tcgccatgac       120
cgcgataagc ctgtaccatg tggcattagg gtgacatctc gatcatacat tataagacca       180
acgtgcgagt cttccaaaga cctgcacgcc ttcttcttcg gattgtcaac gggttcttca       240
gaatctatgc ccatatctgg cgttgagacc attgtgcgtt taatgaacaa taaagcggca       300
tgccatggaa aggagggctg cagatctcca ttttctcacg ccactatcct ggacgctgta       360
gacgataatt ataccatgaa tatagagggg gtatgtttcc actgccactg tgatgataag       420
ttttctccag attgttggat atctgcattt tctgctgccg aacaaacttc atcgctatgc       480
aaagagatgc gtgtgtacac gcgccgttga gtatacggga aactaaatgt tcatagaggt       540
ctttgggcta tatgttatta ataaaaataa ttgaccagtg ttgacattga ttattgacta       600
gttattaata gtaatcaatt acggggtcat tagttcatag cccatatatg gagttccgcg       660
ttacataact tacggtaaat ggcccgcctg gctgaccgcc caacgacccc cgcccattga       720
cgtcaataat gacgtatgtt cccatagtaa cgccaatagg gactttccat tgacgtcaat       780
gggtggagta tttacggtaa actgcccact tggcagtaca tcaagtgtat catatgccaa       840
gtacgccccc tattgacgtc aatgacggta aatggcccgc ctggcattat gcccagtaca       900
```

```
tgaccttatg ggactttcct acttggcagt acatctacgt attagtcatc gctattacca        960
tggtgatgcg gttttggcag tacatcaatg ggcgtggata gcggtttgac tcacggggat       1020
ttccaagtct ccaccccatt gacgtcaatg ggagtttgtt ttggcaccaa atcaacggg        1080
actttccaaa atgtcgtaac aactccgccc cattgacgca aatgggcggt aggcgtgtac       1140
ggtgggaggt ctatataagc agagctctct ggctaactag agaacccact gcttactggc       1200
ttatcgaaat taatacgact cactataggg agacccaagc tggctagcgt ttaaacttaa       1260
gcttaccgcc accatggtga gcaagggcgc cgagctgttc accggcatcg tgcccatcct       1320
gatcgagctg aatggcgatg tgaatggcca aagttcagc gtgagcggcg agggcgaggg        1380
cgatgccacc tacggcaagc tgaccctgaa gttcatctgc accaccggca agctgcctgt       1440
gccctggccc accctggtga ccaccctgag ctacggcgtg cagtgcttct cacgctaccc       1500
cgatcacatg aagcagcacg acttcttcaa gagcgccatg cctgagggct acatccagga       1560
gcgcaccatc ttcttcgagg atgacggcaa ctacaagtcg cgcgccgagg tgaagttcga       1620
gggcgatacc ctggtgaatc gcatcgagct gaccggcacc gatttcaagg aggatggcaa       1680
catcctgggc aataagatgg agtacaacta caacgcccac aatgtgtaca tcatgaccga       1740
caaggccaag aatggcatca aggtgaactt caagatccgc cacaacatcg aggatggcag       1800
cgtgcagctg gccgaccact accagcagaa taccccatc ggcgatggcc ctgtgctgct        1860
gcccgataac cactacctgt ccacccgagg cgccctgtcc aaggaccca acgagaagcg        1920
cgatcacatg atctacttcg gcttcgtgac cgccgccgcc atcacccacg gcatggatga       1980
gctgtacaag tgatgtgcct tctagttgcc agccatctgt tgtttgcccc tccccgtgc        2040
cttccttgac cctggaaggt gccactccca ctgtcctttc ctaataaaat gaggaaattg       2100
catcgcattg tctgagtagg tgtcattcta ttctgggggg tggggtgggg caggacagca       2160
agggggagga ttgggaagac aatagcaggc atgctgggga tgcggtgggc tctatggttt       2220
taatgttagt ttattcaatg cattggttgc aaatattcat tacttctcca atcccaggtc       2280
attctttagc gagatgatgt tatgacattg ctgtgaaaat tactacagga tatattttta       2340
agatgcagga gtaacaatgt gcatagtagg cgtagttatc gcagacgtgc aacgcttcgc       2400
atttgagtta ccgaagtgcc caacagtgct gcggttatgg tttatgcgca cagaatccat       2460
gcatgtccta attgaaccat ccgatttttc ttttaatcgc gatcgttgtt tgggcaactg       2520
cgttatttca gatctaaaaa atttacccttt tatgaccatc acatctctct ggctcatacc       2580
ccgcttggat aagatatcat gtagattccg ccctaagaaa tgcaaactaa cattattgtc       2640
ggttccatat acacttccat cttgtccttc gaaaataaca aactcgcgca atagaccgtc       2700
cgtacatgca tggccgatgt gtgtcaacat cattggtctg ctagatcccg atgggacgaa       2760
tcgtacagtc gtcgctccag cattggcaaa aatccccaga taccctccat gcggcaaatc       2820
taaattgcga ccccgaagag actgcaccaa agtcttatcg acgcacgctg attttttga        2880
acagcgggag cccat                                                        2895
```

<210> SEQ ID NO 19
<211> LENGTH: 2908
<212> TYPE: DNA
<213> ORGANISM: Artificial Sequence
<220> FEATURE:
<223> OTHER INFORMATION: DNA sequence Transfer plasmid for HVT-gfp-B
      #13a

<400> SEQUENCE: 19

-continued

```
atggcagcga gcatgggata ttcatcctcg tcatcgttaa catctctacg ggttcagaat    60
gtttggcatg tcgtcgatcc tttgcccatc gttgcaaatt acaagtccga tcgccatgac   120
cgcgataagc ctgtaccatg tggcattagg gtgacatctc gatcatacat tataagacca   180
acgtgcgagt cttccaaaga cctgcacgcc ttcttcttcg gattgtcaac gggttcttca   240
gaatctatgc ccatatctgg cgttgagacc attgtgcgtt taatgaacaa taaagcggca   300
tgccatggaa aggagggctg cagatctcca tttctcacg ccactatcct ggacgctgta   360
gacgataatt ataccatgaa tatagagggg gtatgtttcc actgccactg tgatgataag   420
ttttctccag attgttggat atctgcattt tctgctgccg aacaaacttc atcgctatgc   480
aaagagatgc gtgtgtacac gcgccgttga gtatacggga aactaaatgt tcatagaggt   540
ctttgggcta tatgttatta aataaaataa ttgaccagtg ttgacattga ttattgacta   600
gttattaata gtaatcaatt acgggtcat tagttcatag cccatatatg gagttccgcg   660
ttacataact tacggtaaat ggcccgcctg gctgaccgcc caacgacccc cgcccattga   720
cgtcaataat gacgtatgtt cccatagtaa cgccaatagg gactttccat tgacgtcaat   780
gggtggagta tttacggtaa actgcccact tggcagtaca tcaagtgtat catatgccaa   840
gtacgccccc tattgacgtc aatgacggta aatggcccgc ctggcattat gcccagtaca   900
tgaccttatg ggactttcct acttggcagt acatctacgt attagtcatc gctattacca   960
tggtgatgcg gttttggcag tacatcaatg ggcgtggata gcggtttgac tcacggggat  1020
ttccaagtct ccaccccatt gacgtcaatg ggagtttgtt ttggcaccaa aatcaacggg  1080
actttccaaa atgtcgtaac aactccgccc cattgacgca aatgggcggt aggcgtgtac  1140
ggtgggaggt ctatataagc agagctctct ggctaactag agaacccact gcttactggc  1200
ttatcgaaat taatacgact cactataggg agacccaagc tggctagcgt ttaaacttaa  1260
gcttacctgc aggccaccat ggtgagcaag ggcgccgagc tgttcaccgg catcgtgccc  1320
atcctgatcg agctgaatgg cgatgtgaat ggccacaagt tcagcgtgag cggcgagggc  1380
gagggcgatg ccacctacgg caagctgacc ctgaagttca tctgcaccac cggcaagctg  1440
cctgtgccct ggcccaccct ggtgaccacc ctgagctacg gcgtgcagtg cttctcacgc  1500
taccccgatc acatgaagca gcacgacttc ttcaagagcg ccatgcctga gggctacatc  1560
caggagcgca ccatcttctt cgaggatgac ggcaactaca gtcgcgcgc cgaggtgaag  1620
ttcgagggcg ataccctggt gaatcgcatc gagctgaccg gcaccgattt caaggaggat  1680
ggcaacatcc tgggcaataa gatggagtac aactacaacg cccacaatgt gtacatcatg  1740
accgacaagg ccaagaatgg catcaaggtg aacttcaaga tccgccacaa catcgaggat  1800
ggcagcgtgc agctggccga ccactaccag cagaataccc catcggcga tggccctgtg  1860
ctgctgcccg ataaccacta cctgtccacc cagagcgccc tgtccaagga ccccaacgag  1920
aagcgcgatc acatgatcta cttcggcttc gtgaccgccg ccgccatcac ccacggcatg  1980
gatgagctgt acaagtgacc tgcaggtgtg ccttctagtt gccagccatc tgttgtttgc  2040
ccctcccccg tgccttcctt gaccctggaa ggtgccactc ccactgtcct ttcctaataa  2100
aatgaggaaa ttgcatcgca ttgtctgagt aggtgtcatt ctattctggg ggtgggtg  2160
gggcaggaca gcaaggggga ggattgggaa gacaatagca ggcatgctgg ggatgcggtg  2220
ggctctatgg ttttaatgtt agtttattca atgcattggt tgcaaatatt cattacttct  2280
ccaatcccag gtcattcttt agcgagatga tgttatgaca ttgctgtgaa aattactaca  2340
ggatatattt ttaagatgca ggagtaacaa tgtgcatagt aggcgtagtt atcgcagacg  2400
```

```
tgcaacgctt cgcatttgag ttaccgaagt gcccaacagt gctgcggtta tggtttatgc    2460
gcacagaatc catgcatgtc ctaattgaac catccgattt ttcttttaat cgcgatcgtt    2520
gtttgggcaa ctgcgttatt tcagatctaa aaaatttacc ctttatgacc atcacatctc    2580
tctggctcat accccgcttg gataagatat catgtagatt ccgccctaag aaatgcaaac    2640
taacattatt gtcggttcca tatacacttc catcttgtcc ttcgaaaata acaaactcgc    2700
gcaatagacc gtccgtacat gcatggccga tgtgtgtcaa catcattggt ctgctagatc    2760
ccgatgggac gaatcgtaca gtcgtcgctc cagcattggc aaaaatcccc agataccctc    2820
catgcggcaa atctaaattg cgaccccgaa gagactgcac caaagtctta tcgacgcacg    2880 ctgattttttt tgaacagcgg gagcccat    2908
```

<210> SEQ ID NO 20
<211> LENGTH: 3538
<212> TYPE: DNA
<213> ORGANISM: Artificial Sequence
<220> FEATURE:
<223> OTHER INFORMATION: DNA sequence Transfer plasmid for HVT-IBD #1

<400> SEQUENCE: 20

```
atggcagcga gcatgggata ttcatcctcg tcatcgttaa catctctacg ggttcagaat      60
gtttggcatg tcgtcgatcc tttgcccatc gttgcaaatt acaagtccga tcgccatgac     120
cgcgataagc ctgtaccatg tggcattagg gtgacatctc gatcatacat tataagacca     180
acgtgcgagt cttccaaaga cctgcacgcc ttcttcttcg gattgtcaac gggttcttca     240
gaatctatgc ccatatctgg cgttgagacc attgtgcgtt aatgaacaa taaagcggca     300 tgccatggaa aggagggctg cagatctcca ttttctcacg ccactatcct ggacgctgta     360
gacgataatt ataccatgaa tatagagggg gtatgtttcc actgccactg tgatgataag    420
ttttctccag attgttggat atctgcattt tctgctgccg aacaaacttc atcgctatgc     480
aaagagatgc gtgtgtacac gcgccgttga gtatacggga aactaaatgt tcatagaggt    540 cttttgggcta tatgttatta aataaaataa ttgaccagtg ttgacattga ttattgacta    600
gttattaata gtaatcaatt acgggtcat tagttcatag cccatatatg gagttccgcg    660
ttacataact tacggtaaat ggcccgcctg gctgaccgcc caacgacccc cgcccattga    720
cgtcaataat gacgtatgtt cccatagtaa cgccaatagg gactttccat tgacgtcaat    780
gggtggagta tttacggtaa actgcccact tggcagtaca tcaagtgtat catatgccaa    840
gtacgccccc tattgacgtc aatgacggta aatggcccgc ctggcattat gcccagtaca    900
tgaccttatg ggactttcct acttggcagt acatctacgt attagtcatc gctattacca    960
tggtgatgcg gttttggcag tacatcaatg ggcgtggata gcggtttgac tcacggggat   1020
ttccaagtct ccaccccatt gacgtcaatg ggagtttgtt ttggcaccaa aatcaacggg   1080
actttccaaa atgtcgtaac aactccgccc cattgacgca aatgggcggt aggcgtgtac   1140
ggtgggaggt ctatataagc agagctctct ggctaactag agaacccact gcttactggc   1200
ttatcgaaat taatacgact cactataggg agacccaagc tggctagcgt ttaaacttaa   1260
gcttaccgcc accatgacaa atcttcagga tcagacccag cagatagttc cctttattag   1320
gtcccttctg atgccaacca cagggcccgc tagcattccg gacgatatccc tggagaaaca   1380 cactttgcgg agtgagacaa gcacttacaa tctgacggtg ggagataccg gctcaggtct   1440
tatcgtgttt tttcccggct ttcctggatc cattgttggc gcgcattaca cgctgcagag   1500
```

```
caacggcaac tataaattcg atcagatgct cctgacggct cagaatctcc ccgccagtta    1560
caattactgc cgccttgtaa gtaggtcctt gactgttaga agctcaacgc tgccaggcgg    1620
agtatatgcc ctgaatggaa ccattaatgc tgtaacattc caaggatcac tgtccgagct    1680
caccgatgtg tcttacaatg gattgatgtc tgccacggct aacattaacg acaagatcgg    1740
gaatgtgctc gtgggcgagg gagtgaccgt tttgagcctg ccgacaagct acgacctcgg    1800
ctacgtaagg ctcggggatc caatccccgc gatcggcttg gatcccaaaa tggttgctac    1860
gtgcgacagc agcgatagac ccagggtcta taccatcacc gctgccgatg attaccagtt    1920
tagctcccag taccaggcgg gagggtcac gatcacccctt tttagcgcca acatcgacgc    1980
cataacctca ctttctatag ggggcgagtt ggttttttcag accagtgtcc aggggctcat    2040
cctcggtgcg acaatctatc tgatcggctt tgacggaaca gctgtcatca cgagggccgt    2100
agctgcagat aatggcctga ctgctgggac agataatctg atgccgttca acatagtgat    2160
ccccaccagt gagattacgc aacccatcac gagcatcaaa ctggagatcg tgacgtcaaa    2220
atccggcggt caggcaggtg accagatgtc ttggtccgca agcggaagtt tggccgtgac    2280
aattcacggg gggaattacc ccggcgcact caggcccgtg accctcgtcg cctacgaaag    2340
agttgcaacg ggaagtgtag tgacagtcgc tggagtgagt aacttcgaac tcatccctaa    2400
tcccgagctc gccaaaaatc tcgtcacgga gtatgggagg tttgatcccg cgccatgaa    2460 ctacacaaaa ctgatattgt ccgaaaggga taggttgggc attaaaaccg tgtggcctac    2520
tagggaatac accgatttcc gcgaatattt tatggaggtc gcggatctga actctcccct    2580
gaagatagca ggcgcttttg ggttcaagga tattatccgg gcgttgcggc ggtagtgtgc    2640
cttctagttg ccagccatct gttgtttgcc cctcccccgt gccttccttg accctggaag    2700
gtgccactcc cactgtcctt tcctaataaa atgaggaaat tgcatcgcat tgtctgagta    2760
ggtgtcattc tattctgggg ggtggggtgg ggcaggacag caaggggag gattgggaag    2820 acaatagcag gcatgctggg gatgcggtgg gctctatggt gtttaatgtt agtttattca    2880
atgcattggt tgcaaatatt cattacttct ccaatcccag gtcattcttt agcgagatga    2940
tgttatgaca ttgctgtgaa aattactaca ggatatattt ttaagatgca ggagtaacaa    3000
tgtgcatagt aggcgtagtt atcgcagacg tgcaacgctt cgcatttgag ttaccgaagt    3060
gcccaacagt gctgcggtta tggtttatgc gcacagaatc catgcatgtc ctaattgaac    3120
catccgattt ttcttttaat cgcgatcgtt gtttgggcaa ctgcgttatt tcagatctaa    3180
aaaatttacc ctttatgacc atcacatctc tctggctcat accccgcttg gataagtat    3240 catgtagatt ccgccctaag aaatgcaaac taacattatt gtcggttcca tatacacttc    3300
catcttgtcc ttcgaaaata acaaactcgc gcaatagacc gtccgtacat gcatggccga    3360
tgtgtgtcaa catcattggt ctgctagatc ccgatgggac gaatcgtaca gtcgtcgctc    3420
cagcattggc aaaatccccc agatacccctc catgcggcaa atctaaattg cgaccccgaa    3480
gagactgcac caaagtctta tcgacgcacg ctgatttttt tgaacagcgg gagcccat    3538
```

<210> SEQ ID NO 21
<211> LENGTH: 3511
<212> TYPE: DNA
<213> ORGANISM: Artificial Sequence
<220> FEATURE:
<223> OTHER INFORMATION: DNA sequence Transfer plasmid for HVT-IBD #5

<400> SEQUENCE: 21

```
gccactgtat gggccattta tgtttatcga gtctaaaagt cgtggaagcg cctggccatc     60
```

```
gccagtctcg acctgccact gctgagttcg gcttcaattc cagcatccca gaaatgtcgc    120
agtcaccatc acgccgtgca tcgcttccta cgaggccttt tgacgcttct gatttgggca    180
catacaccct ggacatactc caccgctatt cgctcgtaga tttagtacaa ctactgaatg    240
acttgccgcg taacattacc tccacgcccg cttctaatgt agaaaccatg gcaaaaatta    300
atgttttaag ggccatttgc gtaggatttg ccgaggtccg tcgccacaac gacgcgcgaa    360
ctttacagcg aacggcaatg tttgccgccg acgacgtcgc atcacggatc agaccatcca    420
ttggattaaa gcgcacctac ccaccgggta tattttccac agctattacc gtatctaatt    480
ccgaggatga gagcgaaat tcgtgatcgt aaaaataaaa aatacaagat attgacattg     540
attattgact agttattaat agtaatcaat tacggggtca ttagttcata gcccatatat    600
ggagttccgc gttacataac ttacggtaaa tggcccgcct ggctgaccgc ccaacgaccc    660
ccgcccattg acgtcaataa tgacgtatgt tcccatagta acgccaatag ggactttcca    720
ttgacgtcaa tgggtggagt atttacggta aactgcccac ttggcagtac atcaagtgta    780
tcatatgcca agtacgcccc ctattgacgt caatgacggt aaatggcccg cctggcatta    840
tgcccagtac atgaccttat gggactttcc tacttggcag tacatctacg tattagtcat    900
cgctattacc atggtgatgc ggttttggca gtacatcaat gggcgtggat agcggtttga    960
ctcacgggga tttccaagtc tccaccccat tgacgtcaat gggagtttgt tttggcacca   1020
aaatcaacgg gactttccaa aatgtcgtaa caactccgcc ccattgacgc aaatgggcgg   1080
taggcgtgta cggtgggagg tctatataag cagagctctc tggctaacta gagaacccac   1140
tgcttactgg cttatcgaaa ttaatacgac tcactatagg gagacccaag ctggctagcg   1200
tttaaactta agcttaccgc caccatgaca aatcttcagg atcagaccca gcagatagtt   1260
ccctttatta ggtcccttct gatgccaacc acagggcccg ctagcattcc ggacgatacc   1320
ctggagaaac acactttgcg gagtgagaca agcacttaca atctgacggt gggagatacc   1380
ggctcaggtc ttatcgtgtt tttcccggc tttcctggat ccattgttgg cgcgcattac    1440
acgctgcaga gcaacggcaa ctataaattc gatcagatgc tcctgacggc tcagaatctc   1500
cccgccagtt acaattactg ccgccttgta agtaggtcct tgactgttag aagctcaacg   1560
ctgccaggcg gagtatatgc cctgaatgga accattaatg ctgtaacatt ccaaggatca   1620
ctgtccgagc tcaccgatgt gtcttacaat ggattgatgt ctgccacggc taacattaac   1680
gacaagatcg ggaatgtgct cgtgggcgag ggagtgaccg ttttgagcct gccgacaagc   1740
tacgacctcg gctacgtaag gctcggggat ccaatccccg cgatcggctt ggatcccaaa   1800
atggttgcta cgtgcgacag cagcgataga cccagggtct ataccatcac cgctgccgat   1860
gattaccagt ttagctccca gtaccaggcg ggaggggtca cgatcaccct ttttagcgcc   1920
aacatcgacg ccataacctc actttctata ggggcgagt tggttttca gaccagtgtc     1980 caggggctca tcctcggtgc gacaatctat ctgatcggct ttgacggaac agctgtcatc   2040
acgagggccg tagctgcaga taatggcctg actgctggga cagataatct gatgccgttc   2100
aacatagtga tccccaccag tgagattacg caacccatca cgagcatcaa actggagatc   2160
gtgacgtcaa aatccggcgg tcaggcaggt gaccagatgt cttggtccgc aagcggaagt   2220
ttggccgtga caattcacgg ggggaattac cccggcgcac tcaggcccgt gaccctcgtc   2280
gcctacgaaa gagttgcaac gggaagtgta gtgacagtcg ctggagtgag taacttcgaa   2340
ctcatcccta atcccgagct cgccaaaaat ctcgtcacgg agtatgggag gtttgatccc   2400
```

```
ggcgccatga actacacaaa actgatattg tccgaaaggg ataggttggg cattaaaacc      2460
gtgtggccta ctagggaata caccgatttc cgcgaatatt ttatggaggt cgcggatctg      2520
aactctcccc tgaagatagc aggcgctttt gggttcaagg atattatccg ggcgttgcgg      2580
cggtagtgtg ccttctagtt gccagccatc tgttgtttgc ccctcccccg tgccttcctt      2640
gaccctggaa ggtgccactc ccactgtcct ttcctaataa aatgaggaaa ttgcatcgca      2700
ttgtctgagt aggtgtcatt ctattctggg gggtggggtg gggcaggaca gcaaggggga      2760
ggattgggaa gacaatagca ggcatgctgg ggatgcggtg ggctctatgg tgtacataat      2820
tcttatttat ctttaatcca tgaggagcat ttttatttta aaaatgtcag ccgccagccc      2880
tataacccta gatcgcaact gatccctagt ctgcgttatt tgtcttgcaa tcttttcgca      2940
cgcctttgtg agtgcataca atgccccct gctcgctttt ctgaaatcgc gtcgggtcat      3000
taatgtgtcg gctatcacaa tgcgagatgt actcgacatg tccgtgtctg tactattggg      3060 attgtaaaata gtcgaccgcg aatcatcaga gtcggaatct gtaaaggata cagattccga      3120
ctctgagcgc ttatgaatgg gatccactcg gacgttgttg aacttccgtt cggattctgc      3180
ttcagtcaac accggccccc gatagctact aaggttgggg ggtttgtggg ttgtttgtga      3240
aactgctttg cggtgtgcat taccacgggg ggtgtgggga agtatctgtt ccacgatgc      3300 gataacgttc ggtggcggag ggggcgattc attctctagt gtacgcgttt caacttcagg      3360
aacgtgatta tttctttcag gacactcttt ccaatttcct tcttccttca cttcgggtac      3420
aggtatattc ttaatgttta catacatgtc gtctgctcgt ctcaactgcg gggttatgat      3480
gggtggtggt gacagtctct ccgaatgatc g                                     3511

<210> SEQ ID NO 22
<211> LENGTH: 3385
<212> TYPE: DNA
<213> ORGANISM: Artificial Sequence
<220> FEATURE:
<223> OTHER INFORMATION: DNA Sequence Transfer plasmid for HVT-IBD #6a

<400> SEQUENCE: 22
gccactgtat gggccattta tgtttatcga gtctaaaagt cgtggaagcg cctggccatc        60
gccagtctcg acctgccact gctgagttcg gcttcaattc cagcatccca gaaatgtcgc       120
agtcaccatc acgccgtgca tcgcttccta cgaggccttt tgacgcttct gatttgggca       180
catacaccct ggacatactc caccgctatt cgctcgtaga tttagtacaa ctactgaatg       240
acttgccgcg taacattacc tccacgcccc cttctaatgt agaaaccatg gcaaaaatta       300
atgttttaag ggccatttgc gtaggatttg ccgaggtccg tcgccacaac gacgcgcgaa       360
ctttacagcg aacggcaatg tttgccgccg acgacgtcgc atcacggatc agaccatcca       420
ttggattaaa gcgcacctac ccaccgggta tattttccac agctattacc gtatctaatt       480
ccgaggatga gagcgaaat tcgtgatcgt aaaaataaaa aatacaagat aagttattaa       540
tagtaatcaa ttacggggtc attagttcat agcccatata tggagttccg cgttacataa       600
cttacggtaa atggcccgcc ggctgaccgc ccaacgaccc ccgcccattg acgtcaataa       660
tgacgtatgt tcccatagta acgccaatag ggactttcca ttgacgtcaa tgggtggagt       720
atttacggta aactgcccat tgcagtaca tcaagtgtat catatgccaa gtacgccccc       780
tattgacgtc aatgacggta aatggatgca gtatttgtg cagcgatggg ggcgggggggg       840 gggggggcgc gcgccaggcg gggcggggcg gggcgagggg cgggcgggg cgaggcggag       900 aggtgcggcg gcagccaatc agagcggcgc gctccgaaag tttcctttta tggcgaggcg       960
```

```
gcggcggcgg cggccctata aaaagcgaag cgcgcggcgg gcgggagtcg ctgcgcgctg    1020
ccttcgcccc gtgccccgct ccgccgccgc ctcgcgccgc ccgccccggc tctgactgac    1080
cgcgtctaga gggccaccat gacaaatctt caggatcaga cccagcagat agttcccttt    1140
attaggtccc ttctgatgcc aaccacaggg cccgctagca ttccggacga taccctggag    1200
aaacacactt tgcggagtga gacaagcact tacaatctga cggtgggaga taccggctca    1260
ggtcttatcg tgttttttcc cggctttcct ggatccattg ttggcgcgca ttacacgctg    1320
cagagcaacg gcaactataa attcgatcag atgctcctga cggctcagaa tctccccgcc    1380
agttacaatt actgccgcct tgtaagtagg tccttgactg ttagaagctc aacgctgcca    1440
ggcggagtat atgccctgaa tggaaccatt aatgctgtaa cattccaagg atcactgtcc    1500
gagctcaccg atgtgtctta caatggattg atgtctgcca cggctaacat taacgacaag    1560
atcgggaatg tgctcgtggg cgagggagtg accgttttga gcctgccgac aagctacgac    1620
ctcggctacg taaggctcgg ggatccaatc ccgcgatcg gcttggatcc caaaatggtt    1680
gctacgtgcg acagcagcga tagacccagg gtctatacca tcaccgctgc cgatgattac    1740
cagtttagct cccagtacca ggcgggaggg gtcacgatca ccctttttag cgccaacatc    1800
gacgccataa cctcactttc tataggggc gagttggttt ttcagaccag tgtccagggg    1860
ctcatcctcg gtcgacaat ctatctgatc ggctttgacg aacagctgt catcacgagg    1920 gccgtagctg cagataatgg cctgactgct gggacagata atctgatgcc gttcaacata    1980
gtgatcccca ccagtgagat tacgcaaccc atcacgagca tcaaactgga gatcgtgacg    2040
tcaaaatccg gcggtcaggc aggtgaccag atgtcttggt ccgcaagcgg aagtttggcc    2100
gtgacaattc acgggggaa ttaccccggc gcactcaggc ccgtgaccct cgtcgcctac    2160
gaaagagttg caacgggaag tgtagtgaca gtcgctggag tgagtaactt cgaactcatc    2220
cctaatcccg agctcgccaa aaatctcgtc acggagtatg ggaggtttga tcccggcgcc    2280
atgaactaca caaaactgat attgtccgaa agggataggt tgggcattaa aaccgtgtgg    2340
cctactaggg aatacaccga tttccgcgaa tattttatgg aggtcgcgga tctgaactct    2400
cccctgaaga tagcaggcgc ttttgggttc aaggatatta tccgggcgtt gcggcggtag    2460
tgtgccttct agttccagc catctgttgt ttgcccctcc ccgtgccctt ccttgaccct    2520
ggaaggtgcc actcccactg tccttttccta ataaaatgag gaaattgcat cgcattgtct    2580
gagtaggtgt cattctattc tggggggtgg ggtggggcag gacagcaagg gggaggattg    2640
ggaagacaat agcaggcatg ctgggatgc ggtgggctct atggtgtaca taattcttat    2700
ttatctttaa tccatgagga gcattttat tttaaaaatg tcagccgcca gccctataac    2760
cctagatcgc aactgatccc tagtctgcgt tatttgtctt gcaatctttt cgcacgcctt    2820
tgtgagtgca tacaatgccc cctgctcgc ttttctgaaa tcgcgtcggg tcattaatgt    2880
gtcggctatc acaatgcgag atgtactcga catgtccgtg tctgtactat gggattgta    2940 aatagtcgac cgcgaatcat cagagtcgga atctgtaaag gatacagatt ccgactctga    3000
gcgcttatga atgggatcca ctcggacgtt gttgaacttc cgttcggatt ctgcttcagt    3060
caacaccggc ccccgatagc tactaaggtt gggggtttg tgggttgttt gtgaaactgc    3120
tttgcggtgt gcattaccac gggggtgtg gggaagtatc tgtttccacg atgcgataac    3180
gttcggtggc ggaggggcg attcattctc tagtgtacgc gtttcaactt caggaacgtg    3240
attatttctt tcaggacact ctttccaatt tccttcttcc ttcacttcgg gtacaggtat    3300
```

```
attcttaatg tttacataca tgtcgtctgc tcgtctcaac tgcggggtta tgatgggtgg    3360
tggtgacagt ctctccgaat gatcg                                          3385

<210> SEQ ID NO 23
<211> LENGTH: 3538
<212> TYPE: DNA
<213> ORGANISM: Artificial Sequence
<220> FEATURE:
<223> OTHER INFORMATION: DNA sequence Transfer plasmid for HVT-IBD #9

<400> SEQUENCE: 23
atggcagcga gcatgggata ttcatcctcg tcatcgttaa catctctacg ggttcagaat      60
gtttggcatg tcgtcgatcc tttgcccatc gttgcaaatt acaagtccga tcgccatgac    120
cgcgataagc ctgtaccatg tggcattagg gtgacatctc gatcatacat tataagacca    180
acgtgcgagt cttccaaaga cctgcacgcc ttcttcttcg gattgtcaac gggttcttca    240
gaatctatgc ccatatctgg cgttgagacc attgtgcgtt taatgaacaa taaagcggca    300
tgccatggaa aggagggctg cagatctcca ttttctcacg ccactatcct ggacgctgta    360
gacgataatt ataccatgaa atagagggg gtatgtttcc actgccactg tgatgataag    420
ttttctccag attgttggat atctgcattt tctgctgccg aacaaacttc atcgctatgc    480
aaagagatgc gtgtgtacac gcgccgttga gtatacggga aactaaatgt tcatagaggt    540 cttgggcta tatgttatta ataaaaataa ttgaccagtg ttgacattga ttattgacta    600
gttattaata gtaatcaatt acggggtcat tagttcatag cccatatatg gagttccgcg    660
ttacataact tacggtaaat ggcccgcctg gctgaccgcc caacgacccc cgcccattga    720
cgtcaataat gacgtatgtt cccatagtaa cgccaatagg gactttccat tgacgtcaat    780
gggtggagta tttacggtaa actgcccact tggcagtaca tcaagtgtat catatgccaa    840
gtacgccccc tattgacgtc aatgacggta aatggcccgc ctggcattat gcccagtaca    900
tgaccttatg ggactttcct acttggcagt acatctacgt attagtcatc gctattacca    960
tggtgatgcg gttttggcag tacatcaatg ggcgtggata gcggtttgac tcacggggat   1020
ttccaagtct ccaccccatt gacgtcaatg ggagtttgtt ttggcaccaa aatcaacggg   1080
actttccaaa atgtcgtaac aactccgccc cattgacgca aatgggcggt aggcgtgtac   1140
ggtgggaggt ctatataagc agagctctct ggctaactag agaacccact gcttactggc   1200
ttatcgaaat taatacgact cactataggg agacccaagc tggctagcgt ttaaacttaa   1260
gcttaccgcc accatgacca atctccagga ccagacccag cagattgtgc cttttattag   1320
gagtctcttg atgcctacaa ccggccccgc cagcatcccg gacgacacac tggaaaaaca   1380
tacactgaga agcgagacat ctacatacaa tttgaccgtg ggcgataccg gctccgggct   1440
tatcgtgttc ttcccaggtt ttcccggatc tatcgtagga gcgcactaca ccctccaaag   1500
taacggcaat tacaaattcg accagatgct cctgacagcc cagaaccttc ctgcttctta   1560
caattactgt agacttgtgt ccaggtccct gactgtgcgg agtagcacgc ttccaggagg   1620
cgtatacgcc ctgaacggaa ctataaacgc cgtcaccttc cagggctcct tgtccgaact   1680
taccgacgtg tcctacaatg gcctcatgag cgcaacggcc aacataaacg ataagatcgg   1740
caatgttctt gtgggcgagg gggttacagt cctttctctg ccaaccagtt atgatctggg   1800
atacgtgcgg cttggcgatc ccattcccgc tatcggtctc gaccctaaaa tggtggctac   1860
ttgcgactca tctgaccgcc caagggtcta taacatactgc agccgatg actatcagtt   1920 ttccagccaa taccagccag ggggtgtgac aatcacactt ttcagcgcca atattgacgc   1980
```

```
tatcacatcc ctctcaatcg gaggtgagct tgtgttccag acttctgttc agggcttggt    2040
attgggcgcc actatttact tgatcgggtt cgacgggacc gcagtgatca ctcgggcagt    2100
ggctgcggat aacggactca ctgccggaac tgacaacctt atgccttta atctggtcat     2160 ccccactaac gagatcaccc agcctattac ctccataaag ctcgaaattg tgaccagcaa    2220
gagcggaggg caggcaggcg accaaatgag ttggtctgca agcgggtccc tcgccgtgac    2280
catccacggt ggcaactatc ctggggcgct cagacccgtc accctggtag cctacgaaag    2340
ggttgccaca ggctcagttg tcacggtggc tggagtaagc aatttcgagc tcatcccgaa    2400
tcctgagctc gctaaaaatc ttgtgaccga gtatggaagg ttcgaccctg cgcaatgaa     2460 ttacacaaag ctgattctgt ccgaacggga taggctgggt atcaagacag tttggcccac    2520
gcgcgaatac acagatttca gggagtactt tatggaggtc gcagatttga atagcccact    2580
taagatcgct ggagcatttg ctttaaggga tattatccgc gcaatcagaa ggtagtgtgc    2640
cttctagttg ccagccatct gttgtttgcc cctcccccgt gccttccttg accctggaag    2700
gtgccactcc cactgtcctt tcctaataaa atgaggaaat tgcatcgcat tgtctgagta    2760
ggtgtcattc tattctgggg ggtggggtgg ggcaggacag caaggggag gattgggaag     2820 acaatagcag gcatgctggg gatgcggtgg gctctatggt gtttaatgtt agtttattca    2880
atgcattggt tgcaaatatt cattacttct ccaatcccag gtcattcttt agcgagatga    2940
tgttatgaca ttgctgtgaa aattactaca ggatatattt ttaagatgca ggagtaacaa    3000
tgtgcatagt aggcgtagtt atcgcagacg tgcaacgctt cgcatttgag ttaccgaagt    3060
gcccaacagt gctgcggtta tggtttatgc gcacagaatc catgcatgtc ctaattgaac    3120
catccgattt ttctttaat cgcgatcgtt gtttgggcaa ctgcgttatt tcagatctaa     3180
aaaatttacc ctttatgacc atcacatctc tctggctcat accccgcttg gataagatat    3240
catgtagatt ccgcccctaag aaatgcaaac taacattatt gtcggttcca tatacacttc    3300
catcttgtcc ttcgaaaata acaaactcgc gcaatagacc gtccgtacat gcatggccga    3360
tgtgtgtcaa catcattggt ctgctagatc ccgatgggac gaatcgtaca gtcgtcgctc    3420
cagcattggc aaaaatcccc agatacctc catgcggcaa atctaaattg cgaccccgaa     3480
gagactgcac caaagtctta tcgacgcacg ctgatttttt tgaacagcgg gagcccat      3538
```

<210> SEQ ID NO 24
<211> LENGTH: 3511
<212> TYPE: DNA
<213> ORGANISM: Artificial Sequence
<220> FEATURE:
<223> OTHER INFORMATION: DNA sequence Transfer plasmid for HVT-IBD #30

<400> SEQUENCE: 24

```
gccactgtat gggccattta tgtttatcga gtctaaaagt cgtggaagcg cctggccatc     60
gccagtctcg acctgccact gctgagttcg gcttcaattc cagcatccca gaaatgtcgc    120
agtcaccatc acgccgtgca tcgcttccta cgaggccttt tgacgcttct gatttgggca    180
catacaccct ggacatactc caccgctatt cgctcgtaga tttagtacaa ctactgaatg    240
acttgccgcg taacattacc tccacgcccg cttctaatgt agaaaccatg gcaaaaatta    300
atgttttaag ggccatttgc gtaggatttg ccgaggtccg tcgccacaac gacgcgcgaa    360
ctttacagcg aacggcaatg tttgccgccg acgacgtcgc atcacggatc agaccatcca    420
ttggattaaa gcgcacctac ccaccgggta tattttccac agctattacc gtatctaatt    480
```

```
ccgaggatga agagcgaaat tcgtgatcgt aaaaataaaa aatacaagat attgacattg    540
attattgact agttattaat agtaatcaat tacggggtca ttagttcata gcccatatat    600
ggagttccgc gttacataac ttacggtaaa tggcccgcct ggctgaccgc ccaacgaccc    660
ccgcccattg acgtcaataa tgacgtatgt tcccatagta acgccaatag gactttccat    720
ttgacgtcaa tgggtggagt atttacggta aactgcccac ttggcagtac atcaagtgta    780
tcatatgcca agtacgcccc ctattgacgt caatgacggt aaatggcccg cctggcatta    840
tgcccagtac atgaccttat gggactttcc tacttggcag tacatctacg tattagtcat    900
cgctattacc atggtgatgc ggttttggca gtacatcaat gggcgtggat agcggtttga    960
ctcacgggga tttccaagtc tccaccccat tgacgtcaat gggagtttgt tttggcacca   1020
aaatcaacgg gactttccaa aatgtcgtaa caactccgcc ccattgacgc aaatgggcgg   1080
taggcgtgta cggtgggagg tctatataag cagagctctc tggctaacta gagaacccac   1140
tgcttactgg cttatcgaaa ttaatacgac tcactatagg gagacccaag ctggctagcg   1200
tttaaactta agcttaccgc caccatgacc aatctccagg accagaccca gcagattgtg   1260
cctttttatta ggagtctctt gatgcctaca accggccccg ccagcatccc ggacgacaca   1320
ctggaaaaac atacactgag aagcgagaca tctacataca atttgaccgt gggcgatacc   1380
ggctccgggc ttatcgtgtt cttcccaggt tttcccggat ctatcgtagg agcgcactac   1440
accctccaaa gtaacggcaa ttacaaattc gaccagatgc tcctgacagc ccagaacctt   1500
cctgcttctt acaattactg tagacttgtg tccaggtccc tgactgtgcg gagtagcacg   1560
cttccaggag gcgtatacgc cctgaacgga actataaacg ccgtcacctt ccagggctcc   1620
ttgtccgaac ttaccgacgt gtcctacaat ggcctcatga gcgcaacggc aacataaac    1680
gataagatcg gcaatgttct tgtgggcgag ggggttacag tcctttctct gccaaccagt   1740
tatgatctgg atacgtgcg gcttggcgat cccattcccg ctatcggtct cgaccctaaa    1800
atggtggcta cttgcgactc atctgaccgc ccaagggtct atacaattac tgcagccgat   1860
gactatcagt tttccagcca ataccagcca ggggtgtga caatcacact tttcagcgcc    1920
aatattgacg ctatcacatc cctctcaatc ggaggtgagc ttgtgttcca gacttctgtt   1980
cagggcttgg tattgggcgc cactatttac ttgatcgggt tcgacgggac cgcagtgatc   2040
actcgggcag tggctgcgga taacggactc actgccggaa ctgacaacct tatgcctttt   2100
aatctggtca tccccactaa cgagatcacc cagcctatta cctccataaa gctcgaaatt   2160
gtgaccagca agagcggagg gcaggcaggc gaccaaatga gttggtctgc aagcgggtcc   2220
ctcgccgtga ccatccacgg tggcaactat cctggggcgc tcagacccgt cacccctggta   2280
gcctacgaaa gggttgccac aggctcagtt gtcacggtgg ctggagtaag caatttcgag   2340
ctcatcccga atcctgagct cgctaaaaat cttgtgaccg agtatggaag gttcgacccct   2400
ggcgcaatga attacacaaa gctgattctg tccgaacggg ataggctggg tatcaagaca   2460
gtttggccca cgcgcgaata cacagatttc agggagtact tatgaggt cgcagatttg     2520
aatagcccac ttaagatcgc tggagcattt ggctttaagg atattatccg cgcaatcaga   2580
aggtagtgtg ccttctagtt gccagccatc tgttgtttgc ccctcccccg tgccttcctt   2640
gaccctggaa ggtgccactc ccactgtcct ttcctaataa aatgaggaaa ttgcatcgca   2700
ttgtctgagt aggtgtcatt ctattctggg gggtggggtg gggcaggaca gcaagggga    2760
ggattgggaa gacaatagca ggcatgctgg ggatgcggtg gctctatgg tgtacataat    2820
tctttattat ctttaatcca tgaggagcat ttttattta aaaatgtcag ccgccagccc    2880
```

```
tataacccta gatcgcaact gatccctagt ctgcgttatt tgtcttgcaa tcttttcgca    2940
cgcctttgtg agtgcataca atgccccct gctcgctttt ctgaaatcgc gtcgggtcat    3000
taatgtgtcg gctatcacaa tgcgagatgt actcgacatg tccgtgtctg tactattggg    3060
attgtaaata gtcgaccgcg aatcatcaga gtcggaatct gtaaaggata cagattccga    3120
ctctgagcgc ttatgaatgg gatccactcg gacgttgttg aacttccgtt cggattctgc    3180
ttcagtcaac accggccccc gatagctact aaggttgggg ggtttgtggg ttgtttgtga    3240
aactgctttg cggtgtgcat taccacgggg ggtgtgggga agtatctgtt tccacgatgc    3300
gataacgttc ggtggcggag ggggcgattc attctctagt gtacgcgttt caacttcagg    3360
aacgtgatta tttcttcag gacactcttt ccaatttcct tcttccttca cttcgggtac    3420
aggtatattc ttaatgttta catacatgtc gtctgctcgt ctcaactgcg gggttatgat    3480
gggtggtggt gacagtctct ccgaatgatc g                                  3511

<210> SEQ ID NO 25
<211> LENGTH: 4102
<212> TYPE: DNA
<213> ORGANISM: Artificial Sequence
<220> FEATURE:
<223> OTHER INFORMATION: DNA sequence Transfer plasmid for HVT-IBD #31

<400> SEQUENCE: 25
gccactgtat gggccattta tgtttatcga gtctaaaagt cgtggaagcg cctggccatc      60
gccagtctcg acctgccact gctgagttcg gcttcaattc cagcatccca gaaatgtcgc     120
agtcaccatc acgccgtgca tcgcttccta cgaggccttt tgacgcttct gatttgggca     180 catcaccct ggacatactc caccgctatt cgctcgtaga tttagtacaa ctactgaatg      240
acttgccgcg taacattacc tccacgcccg cttctaatgt agaaaccatg gcaaaaatta     300
atgttttaag ggccatttgc gtaggatttg ccgaggtccg tcgccacaac gacgcgcgaa     360
ctttacagcg aacggcaatg tttgccgccg acgacgtcgc atcacggatc agaccatcca     420
ttggattaaa gcgcacctac ccaccgggta tattttccac agctattacc gtatctaatt     480
ccgaggatga agagcgaaat tcgtgatcgt aaaaataaaa aatacaagat atcgaggtga     540
gccccacgtt ctgcttcact ctccccatct cccccccctc cccaccccca attttgtatt     600 tattttt taattatt tgtgcagcga tggggcggg gggggggggg gcgcgcgcca           660
ggcggggcgg ggcggggcga ggggcggggc ggggcgaggc ggagaggtgc ggcggcagcc     720
aatcagagcg cgcgctccg aaagtttcct tttatggcga ggcggcggcg gcggcggccc     780
tataaaaagc gaagcgcgcg gcgggcggga gtcgctgcgt tgccttcgcc ccgtgccccg     840
ctccgcgccg cctcgcgccg cccgcccggg ctctgactga ccgcgttact cccacaggtg     900
agcgggcggg acggcccttc tcctccgggc tgtaattagc gcttggttta atgacggctc     960
gtttcttttc tgtggctgcg tgaaagcctt aaagggctcc gggagggccc tttgtgcggg    1020 gggagcggc tcggggggtg cgtgcgtgtg tgtgtgcgtg gggagcgccg cgtgcggccc     1080
gcgctgcccg gcggctgtga gcgctgcggg cgcggcgcgg ggctttgtgc gctccgcgtg    1140
tgcgcgaggg gagcgcggcc ggggggcggtg ccccgcggtg cgggggggct gcgagggaaa    1200
caaaggctgc gtgcggggtg tgtgcgtggg ggggtgagca ggggggtgtgg gcgcggcgt     1260 cgggctgtaa cccccctg cacccccctc ccgagttgc tgagcacggc ccggcttcgg       1320
gtgcggggct ccgtgcgggg cgtggcgcgg ggctcgcgt gccgggcggg gggtggcggc     1380
```

```
aggtggggggt gccgggcggg gcggggccgc ctcgggccgg ggagggctcg ggggaggggc    1440
gcggcggccc cggagcgccg gcggctgtcg aggcgcggcg agccgcagcc attgcctttt    1500
atggtaatcg tgcgagaggg cgcagggact tcctttgtcc caaatctggc ggagccgaaa    1560
tctgggaggc gccgccgcac ccctctagc gggcgcgggc gaagcggtgc ggcgccggca    1620
ggaaggaaat gggcgggag ggccttcgtg cgtcgccgcg ccgccgtccc cttctccatc    1680
tccagcctcg gggctgccgc aggggacgg ctgccttcgg ggggacggg gcagggcggg    1740 gttcggcttc tggcgtgtga ccggcgggt ttatatcttc ccttctctgt tcctccgcag    1800
ccagccatgg ccaccatgac caatctccag gaccagaccc agcagattgt gccttttatt    1860
aggagtctct tgatgcctac aaccggcccc gccagcatcc cggacgacac actggaaaaa    1920
catacactga gaagcgagac atctacatac aatttgaccg tgggcgatac cggctccggg    1980
cttatcgtgt tcttcccagg ttttcccgga tctatcgtag gagcgcacta caccctccaa    2040
agtaacggca attacaaatt cgaccagatg ctcctgacag cccagaacct tcctgcttct    2100
tacaattact gtagacttgt gtccaggtcc ctgactgtgc ggagtagcac gcttccagga    2160
ggcgtatacg ccctgaacgg aactataaac gccgtcacct tccagggctc cttgtccgaa    2220
cttaccgacg tgtcctacaa tggcctcatg agcgcaacgg ccaacataaa cgataagatc    2280
ggcaatgttc ttgtgggcga gggggttaca gtcctttctc tgccaaccag ttatgatctg    2340
ggatacgtgc ggcttggcga tcccattccc gctatcggtc tcgaccctaa aatggtggct    2400
acttgcgact catctgaccg cccaagggtc tatacaatta ctgcagccga tgactatcag    2460
ttttccagcc aataccagcc aggggtgtg acaatcacac ttttcagcgc caatattgac    2520
gctatcacat ccctctcaat cggaggtgag cttgtgttcc agacttctgt tcagggcttg    2580
gtattgggcg ccactattta cttgatcggg ttcgacggga ccgcagtgat cactcgggca    2640
gtggctgcgg ataacggact cactgccgga actgacaacc ttatgccttt taatctggtc    2700
atccccacta cgagatcac ccagcctatt acctccataa agctcgaaat tgtgaccagc    2760
aagagcggag ggcaggcagg cgaccaaatg agttggtctg caagcgggtc cctcgccgtg    2820
accatccacg gtggcaacta tcctgggcg ctcagacccg tcaccctggt agcctacgaa    2880
agggttgcca caggctcagt tgtcacggtg gctggagtaa gcaatttcga gctcatcccg    2940
aatcctgagc tcgctaaaaa tcttgtgacc gagtatggaa ggttcgaccc tggcgcaatg    3000
aattacacaa agctgattct gtccgaacgg dataggctgg gtatcaagac agtttggccc    3060
acgcgcgaat acacagattt cagggagtac tttatggagg tcgcagattt gaatagccca    3120
cttaagatcg ctggagcatt tggcttttaag gatattatcc gcgcaatcag aaggtagtgt    3180
gccttctagt tgccagccat ctgttgtttg cccctccccc gtgccttcct tgaccctgga    3240
aggtgccact cccactgtcc tttcctaata aaatgaggaa attgcatcgc attgtctgag    3300
taggtgtcat tctattctgg ggggtgggggt ggggcaggac agcaagggg aggattggga    3360 agacaatagc aggcatgctg gggatgcggt gggctctatg gtgtacataa ttcttatta    3420 tctttaatcc atgaggagca tttttatttt aaaatgtcat gccgccagcc ctataaccct    3480
agatcgcaac tgatcctag tctgcgttat ttgtcttgca atcttttcgc acgcctttgt    3540
gagtgcatac aatgcccccc tgctcgcttt tctgaaatcg cgtcgggtca ttaatgtgtc    3600
ggctatcaca atgcgagatg tactcgacat gtccgtgtct gtactattgg gattgtaaat    3660
agtcgaccgc gaatcatcag agtcggaatc tgtaaaggat acagattccg actctgagcg    3720
cttatgaatg ggatccactc ggacgttgtt gaacttccgt tcggattctg cttcagtcaa    3780
```

```
caccggcccc cgatagctac taaggttggg gggtttgtgg gttgtttgtg aaactgcttt    3840
gcggtgtgca ttaccacggg gggtgtgggg aagtatctgt ttccacgatg cgataacgtt    3900
cggtggcgga gggggcgatt cattctctag tgtacgcgtt tcaacttcag gaacgtgatt    3960
atttctttca ggacactctt tccaatttcc ttcttccttc acttcgggta caggtatatt    4020
cttaatgttt acatacatgt cgtctgctcg tctcaactgc ggggttatga tgggtggtgg    4080
tgacagtctc tccgaatgat cg                                             4102

<210> SEQ ID NO 26
<211> LENGTH: 3394
<212> TYPE: DNA
<213> ORGANISM: Artificial Sequence
<220> FEATURE:
<223> OTHER INFORMATION: DNA sequence Transfer plasmid for HVT-IBD #32

<400> SEQUENCE: 26
gccactgtat gggccattta tgtttatcga gtctaaaagt cgtggaagcg cctggccatc      60
gccagtctcg acctgccact gctgagttcg gcttcaattc cagcatccca gaaatgtcgc     120
agtcaccatc acgccgtgca tcgcttccta cgaggccttt tgacgcttct gatttgggca     180
catacaccct ggacatactc caccgctatt cgctcgtaga tttagtacaa ctactgaatg     240
acttgccgcg taacattacc tccacgcccg cttctaatgt agaaaccatg gcaaaaatta     300 atgtttttaag ggccatttgc gtaggatttg ccgaggtccg tcgccacaac gacgcgcgaa    360
ctttacagcg aacggcaatg tttgccgccg acgacgtcgc atcacggatc agaccatcca     420
ttggattaaa gcgcacctac ccaccgggta tattttccac agctattacc gtatctaatt     480
ccgaggatga gagcgaaat tcgtgatcgt aaaaataaaa aatacaagat aactctcagt      540
acaatctgct ctgatgccgc atagttaagc cagtatctgc tccctgcttg tgtgttggag     600
gtcgctgagt agtgcgcgag caaaatttaa gctacaacaa gcaaggcttg accgacaat     660 tgcatgaaga atctgcttag ggttaggcgt tttgcgctgc ttcgcgatgt acgggccaga     720
tatacgcgta tctgagggga ctagggtgtg tttaggcgaa aagcggggct tcggttgtac     780
gcggttagga gtccctcag gatatagtag tttcgctttt gcatagggag ggggaaatgt     840
agtcttatgc aatactcttg tagtcttgca acatggtaac gatgagttag caacatgcct     900
tacaaggaga gaaaaagcac cgtgcatgcc gattggtgga agtaaggtgg tacgatcgtg     960
ccttattagg aaggcaacag acgggtctga catggattgg acgaaccact gaattccgca    1020
ttgcagagat attgtattta agtgcctagc tcgatacaat aaacgccatt tgaccattca    1080
ccacattggt gtgcacctcc agccaccatg accaatctcc aggaccagac ccagcagatt    1140 gtgccttttta ttaggagtct cttgatgcct acaaccggcc ccgccagcat cccggacgac    1200
acactggaaa acatacact gagaagcgag acatctacat acaatttgac cgtgggcgat    1260
accggctccg gcttatcgt gttcttccca ggttttcccg gatctatcgt aggagcgcac    1320
tacaccctcc aaagtaacgg caattacaaa ttcgaccaga tgctcctgac agcccagaac    1380
cttcctgctt cttacaatta ctgtagactt gtgtccaggt ccctgactgt gcggagtagc    1440
acgcttccag gaggcgtata cgccctgaac ggaactataa acgccgtcac cttccagggc    1500
tccttgtccg aacttaccga cgtgtcctac aatggcctca tgagcgcaac ggccaacata    1560
aacgataaga tcggcaatgt tcttgtgggc gaggggggtta cagtcctttc tctgccaacc    1620
agttatgatc tgggatacgt gcggcttggc gatcccattc ccgctatcgg tctcgaccct    1680
```

-continued

```
aaaatggtgg ctacttgcga ctcatctgac cgcccaaggg tctatacaat tactgcagcc    1740
gatgactatc agtttccag ccaataccag ccagggggtg tgacaatcac acttttcagc    1800
gccaatattg acgctatcac atccctctca atcggaggtg agcttgtgtt ccagacttct    1860
gttcagggct tggtattggg cgccactatt tacttgatcg ggttcgacgg gaccgcagtg    1920
atcactcggg cagtggctgc ggataacgga ctcactgccg gaactgacaa ccttatgcct    1980
tttaatctgg tcatccccac taacgagatc acccagccta ttacctccat aaagctcgaa    2040
attgtgacca gcaagagcgg agggcaggca ggcgaccaaa tgagttggtc tgcaagcggg    2100
tccctcgccg tgaccatcca cggtggcaac tatcctgggg cgctcagacc cgtcaccctg    2160
gtagcctacg aaagggttgc cacaggctca gttgtcacgg tggctggagt aagcaatttc    2220
gagctcatcc cgaatcctga gctcgctaaa atcttgtga ccgagtatgg aaggttcgac    2280
cctggcgcaa tgaattacac aaagctgatt ctgtccgaac gggataggct gggtatcaag    2340
acagtttggc ccacgcgcga atacacagat ttcagggagt actttatgga ggtcgcagat    2400
ttgaatagcc cacttaagat cgctggagca tttggcttta aggatattat ccgcgcaatc    2460
agaaggtagt gtgccttcta gttgccagcc atctgttgtt tgcccctccc ccgtgccttc    2520
cttgaccctg gaaggtgcca ctcccactgt cctttcctaa taaaatgagg aaattgcatc    2580
gcattgtctg agtaggtgtc attctattct gggggtggg gtgggcagg acagcaaggg    2640 ggaggattgg gaagacaata gcaggcatgc tgggatgcg gtgggctcta tggtgtacat    2700
aattcttatt tatctttaat ccatgaggag cattttatt ttaaaaatgt cagccgccag    2760
ccctataacc ctagatcgca actgatccct agtctgcgtt atttgtcttg caatcttttc    2820
gcacgccttt gtgagtgcat acaatgcccc cctgctcgct tttctgaaat cgcgtcgggt    2880
cattaatgtg tcggctatca caatgcgaga tgtactcgac atgtccgtgt ctgtactatt    2940
gggattgtaa atagtcgacc gcgaatcatc agagtcggaa tctgtaaagg atacagattc    3000
cgactctgag cgcttatgaa tgggatccac tcggacgttg ttgaacttcc gttcggattc    3060
tgcttcagtc aacaccggcc cccgatagct actaaggttg gggggtttgt gggttgtttg    3120
tgaaactgct ttgcggtgtg cattaccacg ggggtgtgg ggaagtatct gtttccacga    3180
tgcgataacg ttcggtggcg gaggggggcga ttcattctct agtgtacgcg tttcaacttc    3240
aggaacgtga ttatttctttt caggacactc tttccaattt ccttcttcct tcacttcggg    3300
tacaggtata ttcttaatgt ttacatacat gtcgtctgct cgtctcaact gcggggttat    3360
gatgggtggt ggtgacagtc tctccgaatg atcg                                 3394
```

<210> SEQ ID NO 27
<211> LENGTH: 3243
<212> TYPE: DNA
<213> ORGANISM: Artificial Sequence
<220> FEATURE:
<223> OTHER INFORMATION: DNA sequence Transfer plasmid for HVT-IBD #33

<400> SEQUENCE: 27

```
gccactgtat gggccattta tgtttatcga gtctaaaagt cgtggaagcg cctggccatc      60
gccagtctcg acctgccact gctgagttcg gcttcaattc cagcatccca gaaatgtcgc    120
agtcaccatc acgccgtgca tcgcttccta cgaggccttt tgacgcttct gatttgggca    180
catacaccct ggacatactc caccgctatt cgctcgtaga tttagtacaa ctactgaatg    240
acttgccgct taacattacc tccacgcccg cttctaatgt agaaaccatg gcaaaaatta    300
atgttttaag ggccatttgc gtaggatttg ccgaggtccg tcgccacaac gacgcgcgaa    360
```

```
ctttacagcg aacggcaatg tttgccgccg acgacgtcgc atcacggatc agaccatcca    420
ttggattaaa gcgcacctac ccaccgggta tattttccac agctattacc gtatctaatt    480
ccgaggatga agagcgaaat tcgtgatcgt aaaaataaaa aatacaagat agcgcagcac    540
catggcctga ataacctct gaaagaggaa cttggttagc taccttctga ggcggaaaga    600
accagctgtg aatgtgtgt cagttagggt gtggaaagtc cccaggctcc ccagcaggca    660
gaagtatgca aagcatgcat ctcaattagt cagcaaccag gtgtggaaag tcccaggct    720
ccccagcagg cagaagtatg caaagcatgc atctcaatta gtcagcaacc atagtcccgc    780
ccctaactcc gccatcccg ccctaactc cgcccagttc cgcccattct ccgccccatg    840
gctgactaat ttttttatt tatgcagagg ccgaggccgc ctctgcctct gagctattcc    900
agaagtagtg aggaggcttt tttggaggcc taggcttttg caaaaagctc gccaccatga    960
ccaatctcca ggaccagacc cagcagattg tgcctttat taggagtctc ttgatgccta   1020
caaccggccc cgccagcatc ccggacgaca cactggaaaa acatacactg agaagcgaga   1080
catctacata caatttgacc gtgggcgata ccggctccgg gcttatcgtg ttcttcccag   1140
gttttcccgg atctatcgta ggagcgcact acaccctcca aagtaacggc aattacaaat   1200
tcgaccagat gctcctgaca gcccagaacc ttcctgcttc ttacaattac tgtagacttg   1260
tgtccaggtc cctgactgtg cggagtagca cgcttccagg aggcgtatac gccctgaacg   1320
gaactataaa cgccgtcacc ttccagggct ccttgtccga acttaccgac gtgtcctaca   1380
atggcctcat gagcgcaacg gccaacataa acgataagat cggcaatgtt cttgtgggcg   1440
aggggttac agtcctttct ctgccaacca gttatgatct gggatacgtg cggcttggcg   1500
atcccattcc cgctatcggt ctcgacccta aatggtggc tacttgcgac tcatctgacc   1560
gcccaagggt ctatacaatt actgcagccg atgactatca gttttccagc caataccagc   1620
caggggtgt gacaatcaca cttttcagcg ccaatattga cgctatcaca tccctctcaa   1680
tcggaggtga gcttgtgttc cagacttctg ttcagggctt ggtattgggc gccactattt   1740
acttgatcgg gttcgacggg accgcagtga tcactcgggc agtggctgcg gataacggac   1800
tcactgccgg aactgacaac cttatgcctt ttaatctggt catccccact aacgagatca   1860
cccagcctat tacctccata aagctcgaaa ttgtgaccag caagagcgga gggcaggcag   1920
gcgaccaaat gagttggtct gcaagcgggt ccctcgccgt gaccatccac ggtggcaact   1980
atcctggggc gctcagaccc gtcaccctgg tagcctacga aagggttgcc acaggctcag   2040
ttgtcacggt ggctggagta agcaatttcg agctcatccc gaatcctgag ctcgctaaaa   2100
atcttgtgac cgagtatgga aggttcgacc ctggcgcaat gaattacaca aagctgattc   2160
tgtccgaacg ggataggctg ggtatcaaga cagtttggcc cacgcgcgaa tacacagatt   2220
tcagggagta ctttatggag gtcgcagatt tgaatagccc acttaagatc gctggagcat   2280
ttggctttaa ggatattatc cgcgcaatca gaaggtagtg tgccttctag ttgccagcca   2340
tctgttgttt gccccctccc cgtgccttcc ttgaccctgg aaggtgccac tcccactgtc   2400
ctttcctaat aaaatgagga aattgcatcg cattgtctga gtaggtgtca ttctattctg   2460
gggggtgggg tggggcagga cagcaagggg gaggattggg aagacaatag caggcatgct   2520
ggggatgcgg tgggctctat ggtgtacata attcttattt atctttaatc catgaggagc   2580
attttttattt taaaaatgtc agccgccagc cctataaccc tagatcgcaa ctgatcccta   2640
gtctgcgtta tttgtcttgc aatctttccg cacgcctttg tgagtgcata caatgccccc   2700
```

```
ctgctcgctt ttctgaaatc gcgtcgggtc attaatgtgt cggctatcac aatgcgagat    2760
gtactcgaca tgtccgtgtc tgtactattg ggattgtaaa tagtcgaccg cgaatcatca    2820
gagtcggaat ctgtaaagga tacagattcc gactctgagc gcttatgaat gggatccact    2880
cggacgttgt tgaacttccg ttcggattct gcttcagtca acaccggccc ccgatagcta    2940
ctaaggttgg ggggtttgtg ggttgtttgt gaaactgctt tgcggtgtgc attaccacgg    3000
ggggtgtggg gaagtatctg tttccacgat gcgataacgt tcggtggcgg aggggggcgat   3060 tcattctcta gtgtacgcgt ttcaacttca ggaacgtgat tatttctttc aggacactct    3120
ttccaatttc cttcttcctt cacttcgggt acaggtatat tcttaatgtt tacatacatg    3180
tcgtctgctc gtctcaactg cggggttatg atgggtggtg gtgacagtct ctccgaatga    3240
tcg                                                                 3243
```

<210> SEQ ID NO 28
<211> LENGTH: 4124
<212> TYPE: DNA
<213> ORGANISM: Artificial Sequence
<220> FEATURE:
<223> OTHER INFORMATION: DNA sequence Transfer plasmid for HVT-IBD #34

<400> SEQUENCE: 28

```
atgggctccc gctgttcaaa aaaatcagcg tgcgtcgata agactttggt gcagtctctt      60
cggggtcgca atttagattt gccgcatgga gggtatctgg ggattttgc caatgctgga     120 gcgacgactg tacgattcgt cccatcggga tctagcagac caatgatgtt gacacacatc    180
ggccatgcat gtacgacgg tctattgcgc gagtttgtta ttttcgaagg acaagatgga     240
agtgtatatg gaaccgacaa taatgttagt ttgcatttct tagggcggaa tctacatgat    300
atcttatcca gcgggtat gagccagaga gatgtgatgg tcataaaggg taaattttt      360 agatctgaaa taacgcagtt gcccaaacaa cgatcgcgat taaagaaaa atcggatggt    420 tcaattagga catgcatgga ttctgtgcgc ataaaccata accgcagcac tgttgggcac    480
ttcggtaact caaatgcgaa gcgttgcacg tctgcgataa ctacgcctac tatgcacatt    540
gttactcctg catcttaaaa atatatcctg tagtaatttt cacagcaatg tcataacatc    600
atctcgctaa agaatgacct gggattggag aagtaatgaa tatttgcaac caatgcattg    660
aataaactaa cattaaactc gaggtgagcc ccacgttctg cttcactctc ccatctcccc    720
ccccctcccc accccaatt ttgtatttat ttattttta attatttttgt gcagcgatgg     780 gggcgggggg ggggggggcg cgcgccaggc ggggcgggc ggggcgaggg gcggggcggg    840
gcgaggcgga gaggtgcggc ggcagccaat cagagcggcg cgctccgaaa gtttccttt    900 atggcgaggc ggcggcggcg gcggccctat aaaaagcgaa gcgcgcggcg ggcgggagtc    960
gctgcgttgc cttcgccccg tgccccgctc cgcgccgcct cgcgccgccc gccccggctc   1020
tgactgaccg cgttactccc acaggtgagc gggcgggacg gccccttctcc tccgggctgt   1080 aattagcgct tggtttaatg acggctcgtt tcttttctgt ggctgcgtga aagccttaaa    1140
gggctccggg agggcccttt gtgcgggggg gagcggctcg gggggtgcgt gcgtgtgtgt    1200
gtgcgtgggg agcgccgcgt gcggcccgcg ctgcccggcg gctgtgagcg ctgcgggcgc    1260 ggcgcgggc tttgtgcgct ccgcgtgtgc gcgaggggag cgcggccggg ggcggtgccc    1320
cgcggtgcgc gggggctgcg agggaacaaa aggctgcgtg cggggtgtgt gcgtgggggg   1380
gtgagcaggg ggtgtgggcg cggcggtcgg gctgtaaccc cccctgcac ccccctcccc     1440 gagttgctga gcacggcccg gcttcgggtg cggggctccg tgcggggcgt ggcgcgggc    1500
```

```
tcgccgtgcc gggcgggggg tggcggcagg tgggggtgcc gggcgggggcg gggccgcctc    1560
gggccgggga gggctcgggg gaggggcgcg gcggccccgg agcgccggcg gctgtcgagg    1620
cgcggcgagc cgcagccatt gccttttatg gtaatcgtgc gagagggcgc agggacttcc    1680
tttgtcccaa atctggcgga gccgaaatct gggaggcgcc gccgcacccc ctctagcggg    1740
cgcgggcgaa gcggtgcggc gccggcagga aggaaatggg cggggagggc cttcgtgcgt    1800
cgccgcgccg ccgtccccctt ctccatctcc agcctcgggg ctgccgcagg gggacggctg    1860
ccttcggggg ggacggggca gggcggggtt cggcttctgg cgtgtgaccg gcggggttta    1920
tatcttccct tctctgttcc tccgcagcca gccatggcca ccatgacaaa cctgcaagat    1980
caaacccaac agattgttcc gttcatacgg agccttctga tgccaacaac cggaccggcg    2040
tccattccgg acgacaccct ggagaagcac actctcaggt cagagacctc gacctacaat    2100
ttgactgtgg gggacacagg gtcagggcta attgtctttt tccctggatt ccctggctca    2160
attgtgggtg ctcactacac actgcagagc aatgggaact acaagttcga tcagatgctc    2220
ctgactgccc agaacctacc ggccagctac aactactgca gactagtgag tcggagtctc    2280
acagtgaggt caagcacact ccctggtggc gtttatgcac taaacggcac cataaacgcc    2340
gtgaccttcc aaggaagcct gagtgaactg acagatgtta gctacaatgg gttgatgtct    2400
gcaacagcca acatcaacga caaaattggg aatgtcctgg tagggaagg ggtcactgtc    2460
ctcagcctac ccacatcata tgatcttggg tatgtgaggc ttggtgaccc cattcccgct    2520
atagggcttg acccaaaaat ggtagctaca tgcgacagca gtgacaggcc cagagtctac    2580
accataactg cagccgatga ttaccaattc tcatcacagt accaaccagg tggggtaaca    2640
atcacactgt tctcagccaa cattgatgct atcacaagcc tcagcattgg gggagagctc    2700
gtgtttcaaa caagcgtcca aggccttgta ctgggcgcca ccatctacct tataggcttt    2760
gatgggactg cggtaatcac cagagctgta gccgcagata tgggctgac ggccggcacc    2820
gacaatctta tgccattcaa tcttgtcatt ccaaccaatg agataaccca gccaatcaca    2880
tccatcaaac tggagatagt gacctccaaa agtggtggtc aggcagggga tcagatgtca    2940
tggtcggcaa gtgggagcct agcagtgacg atccatggtg gcaactatcc aggggccctc    3000
cgtcccgtca cactagtagc ctacgaaaga gtggcaacag gatccgtcgt tacggtcgct    3060
ggggtgagta acttcgagct gattccaaat cctgaactag caaagaacct ggttacagaa    3120
tacggccgat ttgacccagg agccatgaac tacacaaaat tgatactgag tgagagggac    3180
cgtcttggca tcaagaccgt ctggccaaca agggagtaca ctgattttcg tgagtacttc    3240
atggaggtgg ccgacctcaa ctctccctg aagattgcag gagcatttgg cttcaaagac    3300
ataatccggg ctataaggag gtaagctgtg ccttctagtt gccagccatc tgttgtttgc    3360
ccctccccg tgccttcctt gaccctggaa ggtgccactc ccactgtcct ttcctaataa    3420
aatgaggaaa ttgcatcgca ttgtctgagt aggtgtcatt ctattctggg gggtggggtg    3480
gggcaggaca gcaagggga ggattggaa acaatagca ggcatgctgg ggatgcggtg    3540
ggctctatgg tcaattattt tatttaataa catatagccc aaagacctct atgaacattt    3600
agtttcccgt atactcaacg gcgcgtgtac acacgcatct ctttgcatag cgatgaagtt    3660
tgttcggcag cagaaaatgc agatatccaa caatctggag aaaacttatc atcacagtgg    3720
cagtggaaac atacccccctc tatattcatg gtataattat cgtctacagc gtccaggata    3780
gtggcgtgag aaaatggaga tctgcagccc tcctttccat ggcatgccgc tttattgttc    3840
```

| | |
|---|---|
| attaaacgca caatggtctc aacgccagat atgggcatag attctgaaga acccgttgac | 3900 |
| aatccgaaga agaaggcgtg caggtctttg gaagactcgc acgttggtct tataatgtat | 3960 |
| gatcgagatg tcaccctaat gccacatggt acaggcttat cgcggtcatg gcgatcggac | 4020 |
| ttgtaatttg caacgatggg caaaggatcg acgacatgcc aaacattctg aacccgtaga | 4080 |
| gatgttaacg atgacgagga tgaatatccc atgctcgctg ccat | 4124 |

<210> SEQ ID NO 29
<211> LENGTH: 4572
<212> TYPE: DNA
<213> ORGANISM: Artificial Sequence
<220> FEATURE:
<223> OTHER INFORMATION: DNA sequence of Transfer plasmid for HVT-ND #38

<400> SEQUENCE: 29

| | |
|---|---|
| gccactgtat gggccattta tgtttatcga gtctaaaagt cgtggaagcg cctggccatc | 60 |
| gccagtctcg acctgccact gctgagttcg gcttcaattc cagcatccca gaaatgtcgc | 120 |
| agtcaccatc acgccgtgca tcgcttccta cgaggccttt tgacgcttct gatttgggca | 180 |
| catacaccct ggacatactc caccgctatt cgctcgtaga tttagtacaa ctactgaatg | 240 |
| acttgccgcg taacattacc tccacgcccg cttctaatgt agaaaccatg gcaaaaatta | 300 |
| atgttttaag ggccatttgc gtaggatttg ccgaggtccg tcgccacaac gacgcgcgaa | 360 |
| ctttacagcg aacggcaatg tttgccgccg acgacgtcgc atcacggatc agaccatcca | 420 |
| ttggattaaa gcgcacctac ccaccgggta tattttccac agctattacc gtatctaatt | 480 |
| ccgaggatga agagcgaaat tcgtgatcgt aaaaataaaa aatacaagat agaattcact | 540 |
| agtggatccc ccaactccgc ccgttttatg actagaacca atagttttta atgccaaatg | 600 |
| cactgaaatc ccctaatttg caaagccaaa cgcccctat gtgagtaata cggggacttt | 660 |
| ttacccaatt tcccaagcgg aaagccccct aatacactca tatggcatat gaatcagcac | 720 |
| ggtcatgcac tctaatggcg gcccataggg actttccaca tagggggcgt tcaccatttc | 780 |
| ccagcatagg ggtggtgact caatggcctt tacccaagta cattgggtca atgggaggta | 840 |
| agccaatggg ttttttccat tactggcaag cacactgagt caaatgggac tttccactgg | 900 |
| gttttgccca gtacattgg gtcaatggga ggtgagccaa tgggaaaaac ccattgctgc | 960 |
| caagtacact gactcaatag ggactttcca atgggttttt ccattgttgg caagcatata | 1020 |
| aggtcaatgt gggtgagtca atagggactt tccattgtat tctgcccagt acataaggtc | 1080 |
| aataggggt gaatcaacag gaaagtccca ttggagccaa gtacactgcg tcaataggga | 1140 |
| ctttccattg ggttttgccc agtacataag gtcaataggg gatgagtcaa tgggaaaaac | 1200 |
| ccattggagc caagtacact gactcaatag ggactttcca ttgggttttg cccagtacat | 1260 |
| aaggtcaata gggggtgagt caacaggaaa gtcccattgg agccaagtac attgagtcaa | 1320 |
| tagggacttt ccaatgggtt tgcccagta cataaggtca atgggaggta agccaatggg | 1380 |
| ttttttccat tactggcacg tatactgagt cattagggac tttccaatgg ttttgcccca | 1440 |
| gtacataagg tcaatagggg tgaatcaaca ggaaagtccc attggagcca agtacactga | 1500 |
| gtcaataggg actttccatt gggttttgcc cagtacaaaa ggtcaatagg gggtgagtca | 1560 |
| atgggttttt cccattattg gcacgtacat aaggtcaata ggggtgagtc attgggtttt | 1620 |
| tccagccaat ttaattaaaa cgccatgtac tttcccacca ttgacgtcaa tgggctattg | 1680 |
| aaactaatgc aacgtgacct ttaaacggta ctttcccata gctgattaat gggaaagtac | 1740 |
| cgttctcgag ccaatacacg tcaatgggaa gtgaaagggc agccaaaacg taacaccgcc | 1800 |

```
ccggttttcc cctggaaatt ccatattggc acgcattcta ttggctgagc tgcgttctac    1860
gtgggtataa gaggcgcgac cagcgtcggt accgtcgcag tcttcggtct gaccaccgta    1920
gaacgcagag ctcctcgctg caggcggccg ctctagaact cgtcgatcgc agcgatgggc    1980
tccagatctt ctaccaggat cccagtacct ctgatgctga ccgtccgaat catgttggca    2040
ctgagttgcg tctgtccgac cagctcccct tgatggcagg ctcttgcagc tgcagggatt    2100
gtggtaacag gagacaaagc agtcaacata tacacctcat ctcagacagg gtcaatcata    2160
atcaagttac tcccaaatat gcccaaggat aaagaggcgt gtgcaaaagc cccattggaa    2220
gcatacaaca ggacattgac tactttgctc acccccttg gtgattctat ccgtaggata     2280
caagagtctg tgaccacatc cggaggaggg aaacagggac gtcttatagg cgccattatc    2340
ggtggtgtag ctctcggggt tgcaaccgct gcacagataa cagcagcctc ggctctgata    2400
caagccaatc aaaatgctgc caacatcctc cggctcaaag agagcattgc tgcaaccaat    2460
gaggctgtgc acgaggtcac tgacggatta tcacaactag cagtggcagt tgggaagatg    2520
cagcaatttg ttaatgacca gtttaataaa acagctcagg aattggactg tataaaaatt    2580
acacagcagg ttggtgtaga actcaacctg tacctaactg aattgactac agtattcggg    2640
ccacaaatca cttcccctgc cttaactcag ctgactatcc aggcgcttta caatctagct    2700
ggtgggaata tggattactt gttgactaag ttaggtgtag gaaacaacca actcagctca    2760
ttaattggta gtggcctgat taccggcaac cctatcctgt acgactcaca gactcaactc    2820
ttgggtatac aggtcaccct accctcagtc gggaatctaa ataatatgcg tgccacctac    2880
ctggaaacct tgtctgtaag tacaaccaaa ggatttgcct cagcacttgt cccaaaagta    2940
gtgacacagg ttggttccgt gatagaagag cttgacacct cgtactgtat cgagaccgat    3000
ttggacctat attgtacaag aatagtgaca ttccctatgt ctcctggtat ttattcctgt    3060
ttgagtggca atacatctgc ttgcatgtat tcaaagactg aaggcgcact cactacgccg    3120
tatatgaccc tcaaaggctc agttattgcc aactgtaaga tgacaacatg tagatgtgca    3180
gaccccccgg gtatcatatc gcagaattat ggagaagctg tgtctctaat agataggcaa    3240
tcatgcaata tcttatcctt agacgggata actttgaggc tcagtgggga atttgatgca    3300
acttatcaaa agaatatctc aatacaagat tctcaagtaa tagttacagg caatcttgac    3360
atctcgactg agcttgggaa tgtcaacaac tcgataagta atgctttgga taagttagag    3420
gaaagcaaca gcaaactaga caaggtcaat gttaaactga ccagcacatc cgctcttatt    3480
acctatatcg ttttaactgt catatctctt gtatgtggta tacttagcct ggttctagca    3540
tgctacctga tgtacaagca aaaggcgcaa cagaagacct tgttgtggct tgggaataat    3600
accctagacc agatgagggc cactacaaaa atgtagcttg atctagagcg gccgcgggga    3660
tccagacatg ataagataca ttgatgagtt tggacaaacc acaactagaa tgcagtgaaa    3720
aaaatgcttt atttgtgaaa tttgtgatgc tattgcttta tttgtaacca ttataagctg    3780
caataaacaa gttaacaaca acaattgcat tcatttatg tttcaggttc agggggaggt     3840
gtgggaggtt ttttcggatc ctctagagtc gagtacataa ttcttattta tctttaatcc    3900
atgaggagca ttttttatttt aaaaatgtca gccgccagcc ctataaccct agatcgcaac    3960
tgatccctag tctgcgttat ttgtcttgca atcttttcgc acgcctttgt gagtgcatac    4020
aatgcccccc tgctcgcttt tctgaaatcg cgtcgggtca ttaatgtgtc ggctatcaca    4080
atgcgagatg tactcgacat gtccgtgtct gtactattgg gattgtaaat agtcgaccgc    4140
```

```
gaatcatcag agtcggaatc tgtaaaggat acagattccg actctgagcg cttatgaatg    4200
ggatccactc ggacgttgtt gaacttccgt tcggattctg cttcagtcaa caccggcccc    4260
cgatagctac taaggttggg gggtttgtgg gttgtttgtg aaactgcttt gcggtgtgca    4320
ttaccacggg gggtgtgggg aagtatctgt ttccacgatg cgataacgtt cggtggcgga    4380
gggggcgatt cattctctag tgtacgcgtt tcaacttcag gaacgtgatt atttctttca    4440
ggacactctt tccaatttcc ttcttccttc acttcgggta caggtatatt cttaatgttt    4500
acatacatgt cgtctgctcg tctcaactgc ggggttatga tgggtggtgg tgacagtctc    4560
tccgaatgat cg                                                         4572

<210> SEQ ID NO 30
<211> LENGTH: 4402
<212> TYPE: DNA
<213> ORGANISM: Artificial Sequence
<220> FEATURE:
<223> OTHER INFORMATION: DNA sequence Transfer plasmid for HVT-ND #39

<400> SEQUENCE: 30
gccactgtat gggccattta tgtttatcga gtctaaaagt cgtggaagcg cctggccatc      60
gccagtctcg acctgccact gctgagttcg gcttcaattc cagcatccca gaaatgtcgc     120
agtcaccatc acgccgtgca tcgcttccta cgaggccttt tgacgcttct gatttgggca     180
catacaccct ggacatactc caccgctatt cgctcgtaga tttagtacaa ctactgaatg     240
acttgccgcg taacattacc tccacgcccg cttctaatgt agaaaccatg gcaaaaatta     300 atgtttttaag ggccatttgc gtaggatttg ccgaggtccg tcgccacaac gacgcgcgaa    360
ctttacagcg aacggcaatg tttgccgccg acgacgtcgc atcacggatc agaccatcca     420
ttggattaaa gcgcacctac ccaccgggta tattttccac agctattacc gtatctaatt     480
ccgaggatga agagcgaaat tcgtgatcgt aaaaataaaa aatacaagat atcgaggtga     540
gccccacgtt ctgcttcact ctccccatct ccccccctc cccaccccca atttttgtatt     600 tattatttt ttaattattt tgtgcagcga tgggggcggg ggggggggg gcgcgcgcca       660 ggcggggcgg ggcggggcga ggggcggggc ggggcgaggc ggagaggtgc ggcggcagcc     720
aatcagagcg gcgcgctccg aaagtttcct tttatggcga ggcggcggcg gcggcggccc     780
tataaaaagc gaagcgcgcg gcgggcggga gtcgctgcgt tgccttcgcc ccgtgccccg     840
ctccgcgccg cctcgcgccg cccgcccgg ctctgactga ccgcgttact cccacaggtg      900
agcgggcggg acgccccttc tcctccgggc tgtaattagc gcttggttta atgacggctc     960
gtttcttttc tgtggctgcg tgaaagcctt aaagggctcc gggagggccc tttgtgcggg    1020
ggggagcggc tcgggggtg cgtgcgtgtg tgtgtgcgtg gggagcgccg cgtgcggccc     1080
gcgctgcccg gcggctgtga gcgctgcggg cgcggcgcgg ggctttgtgc gctccgcgtg    1140
tgcgcgaggg gagcgcggcc ggggcggtg cccgcggtg cggggggct gcgaggggaa       1200 caaaggctgc gtgcggggtg tgtgcgtggg ggggtgagca ggggtgtgg gcgcggcggt     1260 cgggctgtaa ccccccctg caccccctc cccgagttgc tgagcacggc ccggcttcgg      1320
gtgcggggct ccgtgcgggg cgtggcgcgg ggctcgccgt gccggcggg gggtggcggc     1380 aggtgggggt gccgggcggg gcggggccgc ctcgggccgg ggagggctcg ggggaggggc    1440
gcggcggccc cggagcgccg gcggctgtcg aggcgcggcg agccgcagcc attgccttt     1500 atggtaatcg tgcgagaggg cgcagggact tcctttgtcc caaatctggc ggagccgaaa    1560
tctgggaggc gccgccgcac cccctctagc gggcgcgggc gaagcggtgc ggcgccggca    1620
```

```
ggaaggaaat gggcggggag ggccttcgtg cgtcgccgcg ccgccgtccc cttctccatc    1680
tccagcctcg gggctgccgc aggggacgg ctgccttcgg gggggacggg gcagggcggg    1740
gttcggcttc tggcgtgtga ccggcggggt ttatatcttc ccttctctgt tcctccgcag    1800
ccagccatgg ccaccatggg ctccagatct tctaccagga tcccagtacc tctgatgctg    1860
accgtccgaa tcatgttggc actgagttgc gtctgtccga ccagctccct tgatggcagg    1920
cctcttgcag ctgcagggat tgtggtaaca ggagacaaag cagtcaacat atacacctca    1980
tctcagacag ggtcaatcat aatcaagtta ctcccaaata tgcccaagga taaagaggcg    2040
tgtgcaaaag ccccattgga agcatacaac aggacattga ctactttgct cacccccctt    2100
ggtgattcta tccgtaggat acaagagtct gtgaccacat ccggaggagg gaaacaggga    2160
cgtcttatag gcgccattat cggtggtgta gctctcgggg ttgcaaccgc tgcacagata    2220
acagcagcct cggctctgat acaagccaat caaaatgctg ccaacatcct ccggctcaaa    2280
gagagcattg ctgcaaccaa tgaggctgtg cacgaggtca ctgacggatt atcacaacta    2340
gcagtggcag ttgggaagat gcagcaattt gttaatgacc agtttaataa aacagctcag    2400
gaattggact gtataaaaat tacacagcag gttggtgtag aactcaacct gtacctaact    2460
gaattgacta cagtattcgg gccacaaatc acttcccctg ccttaactca gctgactatc    2520
caggcgcttt acaatctagc tggtgggaat atggattact tgttgactaa gttaggtgta    2580
ggaaacaacc aactcagctc attaattggt agtggcctga ttaccggcaa ccctatcctg    2640
tacgactcac agactcaact cttgggtata caggtcaccc taccctcagt cgggaatcta    2700
aataatatgc gtgccaccta cctggaaacc ttgtctgtaa gtacaaccaa aggatttgcc    2760
tcagcacttg tcccaaaagt agtgacacag gttggttccg tgatagaaga gcttgacacc    2820
tcgtactgta tcgagaccga tttggaccta tattgtacaa gaatagtgac attccctatg    2880
tctcctggta tttattcctg tttgagtggc aatacatctg cttgcatgta ttcaaagact    2940
gaaggcgcac tcactacgcc gtatatgacc ctcaaaggct cagttattgc caactgtaag    3000
atgacaacat gtagatgtgc agacccccccg ggtatcatat cgcagaatta tggagaagct    3060
gtgtctctaa tagataggca atcatgcaat atcttatcct tagacgggat aactttgagg    3120
ctcagtgggg aatttgatgc aacttatcaa aagaatatct caatacaaga ttctcaagta    3180
atagttacag gcaatcttga catctcgact gagcttggga atgtcaacaa ctcgataagt    3240
aatgctttgg ataagttaga ggaaagcaac agcaaactag acaaggtcaa tgttaaactg    3300
accagcacat ccgctcttat tacctatatc gttttaactg tcatatctct tgtatgtggt    3360
atacttagcc tggttctagc atgctacctg atgtacaagc aaaaggcgca acagaagacc    3420
ttgttgtggc ttgggaataa taccctagac cagatgaggg ccactacaaa aatgtagtgt    3480
gccttctagt tgccagccat ctgttgtttg cccctccccc gtgccttcct tgaccctgga    3540
aggtgccact cccactgtcc tttcctaata aaatgaggaa attgcatcgc attgtctgag    3600
taggtgtcat tctattctgg ggggtgggt ggggcaggac agcaagggg aggattggga    3660 agacaatagc aggcatgctg gggatgcggt gggctctatg gtgtacataa ttcttattta    3720
tctttaatcc atgaggagca ttttattttt aaaaatgtca gccgccagcc ctataaccct    3780
agatcgcaac tgatccctag tctgcgttat ttgtcttgca atctttttcgc acgcctttgt    3840 gagtgcatac aatgcccccc tgctcgcttt tctgaaatcg cgtcgggtca ttaatgtgtc    3900
ggctatcaca atgcgagatg tactcgacat gtccgtgtct gtactattgg gattgtaaat    3960
```

```
agtcgaccgc gaatcatcag agtcggaatc tgtaaaggat acagattccg actctgagcg      4020
cttatgaatg ggatccactc ggacgttgtt gaacttccgt tcggattctg cttcagtcaa      4080
caccggcccc cgatagctac taaggttggg gggtttgtgg gttgtttgtg aaactgcttt      4140
gcggtgtgca ttaccacggg gggtgtgggg aagtatctgt ttccacgatg cgataacgtt      4200
cggtggcgga gggggcgatt cattctctag tgtacgcgtt tcaacttcag gaacgtgatt      4260
atttctttca ggacactctt tccaatttcc ttcttccttc acttcgggta caggtatatt      4320
cttaatgttt acatacatgt cgtctgctcg tctcaactgc ggggttatga tgggtggtgg      4380
tgacagtctc tccgaatgat cg                                              4402

<210> SEQ ID NO 31
<211> LENGTH: 4413
<212> TYPE: DNA
<213> ORGANISM: Artificial Sequence
<220> FEATURE:
<223> OTHER INFORMATION: DNA sequence Transfer plasmid for HVT-ND #40

<400> SEQUENCE: 31
gccactgtat gggccattta tgtttatcga gtctaaaagt cgtggaagcg cctggccatc        60
gccagtctcg acctgccact gctgagttcg gcttcaattc cagcatccca gaaatgtcgc       120
agtcaccatc acgccgtgca tcgcttccta cgaggccttt tgacgcttct gatttgggca       180
catacaccct ggacatactc caccgctatt cgctcgtaga tttagtacaa ctactgaatg       240
acttgccgcg taacattacc tccacgcccg cttctaatgt agaaaccatg caaaaatta        300 atgttttaag ggccatttgc gtaggatttg ccgaggtccg tcgccacaac gacgcgcgaa       360
ctttacagcg aacggcaatg tttgccgccg acgacgtcgc atcacggatc agaccatcca       420
ttggattaaa gcgcacctac ccaccgggta tattttccac agctattacc gtatctaatt       480
ccgaggatga agagcgaaat tcgtgatcgt aaaaataaaa aatacaagat atcgaggtga       540
gccccacgtt ctgcttcact ctccccatct cccccccctc cccacccca atttttgtatt      600 tatttatttt ttaattattt tgtgcagcga tggggggcggg ggggggggggg gcgcgcgcca       660 ggcggggcgg ggcggggcga ggggcggggc ggggcgaggc ggagaggtgc ggcggcagcc       720
aatcagagcg gcgcgctccg aaagtttcct tttatggcga ggcggcggcg cggcggcccc       780
tataaaaagc gaagcgcgcg gcgggcggga gtcgctgcgt tgccttcgcc ccgtgccccg       840
ctccgcgccg cctcgcgccg cccgcccggg ctctgactga ccgcgttact cccacaggtg       900
agcgggcggg acgcccttc tcctccgggc tgtaattagc gcttggttta atgacggctc       960
gtttctttcc tgtggctgcg tgaaagcctt aaagggctcc gggagggccc tttgtgcggg      1020 gggagcggc tcgggggggtg cgtgcgtgtg tgtgtgcgtg gggagcgccg cgtgcggccc      1080
gcgctgcccg gcggctgtga gcgctgcggg cgcggcgcgg ggctttgtgc gctccgcgtg      1140
tgcgcgaggg gagcgcggcc ggggggcggtc cccgcggtg cggggggggct gcgaggggaa       1200 caaaggctgc gtgcggggtg tgtgcgtggg ggggtgagca ggggtgtgg gcgcggcggt       1260 cgggctgtaa ccccccctg cacccccctc cccgagttgc tgagcacggc ccggcttcgg       1320
gtgcggggct ccgtgcgggg cgtggcgcgg ggctcgccgt gccggggcggg gggtggcggc       1380 aggtgggggt gccgggcggg gcggggccgc ctcgggccgg ggagggctcg ggggaggggc       1440
gcggcggccc cggagcgccg gcggctgtcg aggcgcggcg agccgcagcc attgcctttt       1500
atggtaatcg tgcgagaggg cgcagggact tcctttgtcc caaatctggc ggagccgaaa       1560
tctgggaggc gccgccgcac cccctctagc gggcgcgggc gaagcggtgc ggcgccggca       1620
```

```
ggaaggaaat gggcggggag ggccttcgtg cgtcgccgcg ccgccgtccc cttctccatc    1680
tccagcctcg gggctgccgc aggggacggg ctgccttcgg gggggacggg gcagggcggg    1740
gttcggcttc tggcgtgtga ccggcggggt ttatatcttc ccttctctgt tcctccgcag    1800
ccagccatgg ccaccatggg ctccagatct tctaccagga tcccagtacc tctgatgctg    1860
accgtccgaa tcatgttggc actgagttgc gtctgtccga ccagctccct tgatggcagg    1920
cctcttgcag ctgcagggat tgtggtaaca ggagacaaag cagtcaacat atacacctca    1980
tctcagacag ggtcaatcat aatcaagtta ctcccaaata tgcccaagga taaagaggcg    2040
tgtgcaaaag ccccattgga agcatacaac aggacattga ctactttgct caccccctt     2100 ggtgattcta tccgtaggat acaagagtct gtgaccacat ccggaggagg gaaacaggga    2160
cgtcttatag gcgccattat cggtggtgta gctctcgggg ttgcaaccgc tgcacagata    2220
acagcagcct cggctctgat acaagccaat caaaatgctg ccaacatcct ccggctcaaa    2280
gagagcattg ctgcaaccaa tgaggctgtg cacgaggtca ctgacggatt atcacaacta    2340
gcagtggcag ttgggaagat gcagcaattt gttaatgacc agtttaataa acagctcag    2400 gaattggact gtataaaaat tacacagcag gttggtgtag aactcaacct gtacctaact    2460
gaattgacta cagtattcgg gccacaaatc acttcccctg ccttaactca gctgactatc    2520
caggcgcttt acaatctagc tggtgggaat atggattact tgttgactaa gttaggtgta    2580
ggaaacaacc aactcagctc attaattggt agtggcctga ttaccggcaa ccctatcctg    2640
tacgactcac agactcaact cttgggtata caggtcaccc taccctcagt cgggaatcta    2700
aataatatgc gtgccaccta cctggaaacc ttgtctgtaa gtacaaccaa aggatttgcc    2760
tcagcacttg tcccaaaagt agtgacacag gttggttccg tgatagaaga gcttgacacc    2820
tcgtactgta tcgagaccga tttggaccta tattgtacaa gaatagtgac attccctatg    2880
tctcctggta tttattcctg tttgagtggc aatacatctg cttgcatgta ttcaaagact    2940
gaaggcgcac tcactacgcc gtatatgacc ctcaaaggct cagttattgc caactgtaag    3000
atgacaacat gtagatgtgc agaccccccg ggtatcatat cgcagaatta tggagaagct    3060
gtgtctctaa tagataggca atcatgcaat atcttatcct tagacgggat aactttgagg    3120
ctcagtgggg aatttgatgc aacttatcaa aagaatatct caatacaaga ttctcaagta    3180
atagttacag gcaatcttga catctcgact gagcttggga atgtcaacaa ctcgataagt    3240
aatgctttgg ataagttaga ggaaagcaac agcaaactag acaaggtcaa tgttaaactg    3300
accagcacat ccgctcttat tacctatatc gttttaactg tcatatctct tgtatgtggt    3360
atacttagcc tggttctagc atgctacctg atgtacaagc aaaaggcgca acagaagacc    3420
ttgttgtggc ttgggaataa taccctagac cagatgaggg ccactacaaa aatgtagctt    3480
gatctagagc ggccgcgggg atccagacat gataagatac attgatgagt ttggacaaac    3540
cacaactaga atgcagtgaa aaaaatgctt tatttgtgaa atttgtgatg ctattgcttt    3600
atttgtaacc attataagct gcaataaaca agttaacaac aacaattgca ttcattttat    3660
gtttcaggtt cagggggagg tgtgggaggt ttttcggat cctctagagt cgagtacata    3720
attcttattt atctttaatc catgaggagc atttttattt taaaaatgtc agccgccagc    3780
cctataaccc tagatcgcaa ctgatcccta gtctgcgtta tttgtcttgc aatcttttcg    3840
cacgcctttg tgagtgcata caatgccccc ctgctcgctt ttctgaaatc gcgtcgggtc    3900
attaatgtgt cggctatcac aatgcgagat gtactcgaca tgtccgtgtc tgtactattg    3960
```

-continued

```
ggattgtaaa tagtcgaccg cgaatcatca gagtcggaat ctgtaaagga tacagattcc    4020
gactctgagc gcttatgaat gggatccact cggacgttgt tgaacttccg ttcggattct    4080
gcttcagtca acaccggccc ccgatagcta ctaaggttgg ggggtttgtg ggttgtttgt    4140
gaaactgctt tgcggtgtgc attaccacgg gggtgtggg gaagtatctg ttttccacgat    4200 gcgataacgt tcggtggcgg aggggggcgat tcattctcta gtgtacgcgt ttcaacttca    4260
ggaacgtgat tatttctttc aggacactct ttccaatttc cttcttcctt cacttcgggt    4320
acaggtatat tcttaatgtt tacatacatg tcgtctgctc gtctcaactg cggggttatg    4380
atgggtggtg gtgacagtct ctccgaatga tcg                                 4413
```

<210> SEQ ID NO 32
<211> LENGTH: 3849
<212> TYPE: DNA
<213> ORGANISM: Artificial Sequence
<220> FEATURE:
<223> OTHER INFORMATION: DNA sequence Transfer plasmid for HVT-ND #41a

<400> SEQUENCE: 32

```
atggcagcga gcatgggata ttcatcctcg tcatcgttaa catctctacg ggttcagaat      60
gtttggcatg tcgtcgatcc tttgcccatc gttgcaaatt acaagtccga tcgccatgac    120
cgcgataagc ctgtaccatg tggcattagg gtgacatctc gatcatacat tataagacca    180
acgtgcgagt cttccaaaga cctgcacgcc ttcttcttcg gattgtcaac gggttcttca    240
gaatctatgc ccatatctgg cgttgagacc attgtgcgtt taatgaacaa taaagcggca    300
tgccatggaa aggagggctg cagatctcca ttttctcacg ccactatcct ggacgctgta    360
gacgataatt ataccatgaa tatagagggg gtatgtttcc actgccactg tgatgataag    420
ttttctccag attgttggat atctgcattt tctgctgccg aacaaacttc atcgctatgc    480
aaagagatgc gtgtgtacac gcgccgttga gtatacggga actaaatgt tcatagaggt    540 ctttgggcta tatgttatta ataaaaataa ttgaccagtg ttgacattga ttattgacta    600
gttattaata gtaatcaatt acggggtcat tagttcatag cccatatatg gagttccgcg    660
ttacataact tacggtaaat ggcccgcctg gctgaccgcc caacgacccc cgcccattga    720
cgtcaataat gacgtatgtt cccatagtaa cgccaatagg gactttccat tgacgtcaat    780
gggtggagta tttacggtaa actgcccact tggcagtaca tcaagtgtat catatgccaa    840 gtacgcccc tattgacgtc aatgacggta aatggcccgc ctggcattat gcccagtaca    900
tgaccttatg ggactttcct acttggcagt acatctacgt attagtcatc gctattacca    960
tggtgatgcg gttttggcag tacatcaatg ggcgtggata gcggtttgac tcacggggat   1020
ttccaagtct ccaccccatt gacgtcaatg ggagtttgtt ttggcaccaa atcaacggg    1080 actttccaaa atgtcgtaac aactccgccc cattgacgca aatgggcggt aggcgtgtac   1140
ggtgggaggt ctatataagc agagctctct ggctaactag agaacccact gcttactggc   1200
ttatcgaaat taatacgact cactataggg agacccaagc tggctagcgt ttaaacttaa   1260
gcttaccgcc accatgggct ccagatcttc taccaggatc ccagtacctc tgatgctgac   1320
cgtccgaatc atgttggcac tgagttgcgt ctgtccgacc agctcccttg atggcaggcc   1380
tcttgcagct gcagggattg tggtaacagg agacaaagca gtcaacatat acacctcatc   1440
tcagacaggg tcaatcataa tcaagttact cccaaatatg cccaaggata agaggcgtg   1500 tgcaaaagcc ccattggaag catacaacag gacattgact actttgctca cccccttgg    1560 tgattctatc cgtaggatac aagagtctgt gaccacatcc ggaggaggga acagggacg    1620
```

```
tcttataggc gccattatcg gtggtgtagc tctcggggtt gcaaccgctg cacagataac    1680
agcagcctcg gctctgatac aagccaatca aaatgctgcc aacatcctcc ggctcaaaga    1740
gagcattgct gcaaccaatg aggctgtgca cgaggtcact gacggattat cacaactagc    1800
agtggcagtt gggaagatgc agcaatttgt taatgaccag tttaataaaa cagctcagga    1860
attggactgt ataaaaatta cacagcaggt tggtgtagaa ctcaacctgt acctaactga    1920
attgactaca gtattcgggc cacaaatcac ttcccctgcc ttaactcagc tgactatcca    1980
ggcgctttac aatctagctg gtgggaatat ggattacttg ttgactaagt taggtgtagg    2040
aaacaaccaa ctcagctcat taattggtag tggcctgatt accggcaacc ctatcctgta    2100
cgactcacag actcaactct tgggtataca ggtcacccta ccctcagtcg ggaatctaaa    2160
taatatgcgt gccacctacc tggaaacctt gtctgtaagt acaaccaaag gatttgcctc    2220
agcacttgtc ccaaaagtag tgacacaggt tggttccgtg atagaagagc ttgacacctc    2280
gtactgtatc gagaccgatt tggacctata ttgtacaaga atagtgacat tccctatgtc    2340
tcctggtatt tattcctgtt tgagtggcaa tacatctgct tgcatgtatt caaagactga    2400
aggcgcactc actacgccgt atatgaccct caaaggctca gttattgcca actgtaagat    2460
gacaacatgt agatgtgcag accccccggg tatcatatcg cagaattatg agaagctgt    2520 gtctctaata gataggcaat catgcaatat cttatcctta gacgggataa ctttgaggct    2580
cagtggggaa tttgatgcaa cttatcaaaa gaatatctca atacaagatt ctcaagtaat    2640
agttacaggc aatcttgaca tctcgactga gcttgggaat gtcaacaact cgataagtaa    2700
tgctttggat aagttagagg aaagcaacag caaactagac aaggtcaatg ttaaactgac    2760
cagcacatcc gctcttatta cctatatcgt tttaactgtc atatctcttg tatgtggtat    2820
acttagcctg gttctagcat gctacctgat gtacaagcaa aaggcgcaac agaagacctt    2880
gttgtggctt gggaataata ccctagacca gatgagggcc actacaaaaa tgtagcttga    2940
tctagagcgg ccgcggggat ccagacatga taagatacat tgatgagttt ggacaaacca    3000
caactagaat gcagtgaaaa aaatgcttta tttgtgaaat ttgtgatgct attgctttat    3060
ttgtaaccat tataagctgc aataaacaag ttaacaacaa caattgcatt cattttatgt    3120
ttcaggttca gggggaggtg tgggaggttt tttcggatcc tctagagtcg agtttaatgt    3180
tagtttattc aatgcattgg ttgcaaatat tcattacttc tccaatccca ggtcattctt    3240
tagcgagatg atgttatgac attgctgtga aaattactac aggatatatt tttaagatgc    3300
aggagtaaca atgtgcatag taggcgtagt tatcgcagac gtgcaacgct tcgcatttga    3360
gttaccgaag tgcccaacag tgctgcggtt atggtttatg cgcacagaat ccatgcatgt    3420
cctaattgaa ccatccgatt tttctttaa tcgcgatcgt tgtttgggca actgcgttat    3480
ttcagatcta aaaatttac cctttatgac catcacatct ctctggctca taccccgctt    3540
ggataagata tcatgtagat tccgccctaa gaaatgcaaa ctaacattat tgtcggttcc    3600
atatacactt ccatcttgtc cttcgaaaat aacaaactcg cgcaatagac cgtccgtaca    3660
tgcatggccg atgtgtgtca acatcattgg tctgctagat cccgatggga cgaatcgtac    3720
agtcgtcgct ccagcattgg caaaaatccc cagatacccct ccatgcggca aatctaaatt    3780
gcgaccccga agagactgca ccaaagtctt atcgacgcac gctgattttt ttgaacagcg    3840
ggagcccat                                                           3849
```

<210> SEQ ID NO 33

```
<211> LENGTH: 4599
<212> TYPE: DNA
<213> ORGANISM: Artificial Sequence
<220> FEATURE:
<223> OTHER INFORMATION: DNA sequence Original Transfer plasmid for
      HVT-ND #42

<400> SEQUENCE: 33
atggcagcga gcatgggata ttcatcctcg tcatcgttaa catctctacg ggttcagaat       60
gtttggcatg tcgtcgatcc tttgcccatc gttgcaaatt acaagtccga tcgccatgac      120
cgcgataagc ctgtaccatg tggcattagg gtgacatctc gatcatacat tataagacca     180
acgtgcgagt cttccaaaga cctgcacgcc ttcttcttcg gattgtcaac gggttcttca      240
gaatctatgc ccatatctgg cgttgagacc attgtgcgtt taatgaacaa taaagcggca      300
tgccatggaa aggagggctg cagatctcca ttttctcacg ccactatcct ggacgctgta      360
gacgataatt ataccatgaa tatagagggg gtatgtttcc actgccactg tgatgataag      420
ttttctccag attgttggat atctgcattt tctgctgccg aacaaacttc atcgctatgc      480
aaagagatgc gtgtgtacac gcgccgttga gtatacggga aactaaatgt tcatagaggt      540
ctttgggcta tatgttatta aataaaataa ttgaccagtg gaattcacta gtggatcccc      600
caactccgcc cgttttatga ctagaaccaa tagttttaa tgccaaatgc actgaaatcc       660
cctaatttgc aaagccaaac gcccctatg tgagtaatac ggggactttt acccaattt       720 cccaagcgga aagccccta atacactcat atggcatatg aatcagcacg gtcatgcact       780
ctaatggcgg cccatagga ctttccacat aggggcgtt caccatttcc cagcataggg       840
gtggtgactc aatggccttt acccaagtac attgggtcaa tgggaggtaa gccaatgggt      900
ttttcccatt actggcaagc acactgagtc aaatgggact ttccactggg ttttgcccaa      960
gtacattggg tcaatgggag gtgagccaat gggaaaaacc cattgctgcc aagtacactg     1020
actcaatagg gactttccaa tgggttttc cattgttggc aagcatataa ggtcaatgtg      1080
ggtgagtcaa tagggacttt ccattgtatt ctgcccagta cataaggtca ataggggtg      1140 aatcaacagg aaagtcccat ggagccaag tacactgcgt caatagggac tttccattgg     1200
gttttgccca gtacataagg tcaatagggg atgagtcaat gggaaaaacc cattggagcc     1260
aagtacactg actcaatagg gactttccat tgggttttgc ccagtacata aggtcaatag     1320
ggggtgagtc aacaggaaag tcccattgga gccaagtaca ttgagtcaat agggactttc     1380
caatgggttt tgcccagtac ataaggtcaa tgggaggtaa gccaatgggt ttttcccatt     1440
actggcacgt atactgagtc attagggact ttccaatggg ttttgcccag tacataaggt     1500 caatagggt gaatcaacag gaaagtccca ttggagccaa gtacactgag tcaataggga     1560 cttccattg gttttgccc agtacaaaag gtcaataggg ggtgagtcaa tgggttttc      1620 ccattattgg cacgtacata aggtcaatag gggtgagtca ttgggttttt ccagccaatt     1680
taattaaaac gccatgtact ttcccaccat tgacgtcaat gggctattga actaatgca     1740 acgtgacctt taaacggtac tttcccatag ctgattaatg ggaaagtacc gttctcgagc     1800
caatacacgt caatgggaag tgaaagggca gccaaaacgt aacaccgccc cggttttccc     1860
ctggaaattc catattggca cgcattctat tggctgagct gcgttctacg tgggtataag     1920
aggcgcgacc agcgtcggta ccgtcgcagt cttcggtctg accaccgtag aacgcagagc     1980
tcctcgctgc aggcggccgc tctagaactc gtcgatcgca gcgatgggct ccagatcttc     2040
taccaggatc ccagtacctc tgatgctgac cgtccgaatc atgttggcac tgagttgcgt     2100
```

```
ctgtccgacc agctcccttg atggcaggcc tcttgcagct gcagggattg tggtaacagg    2160
agacaaagca gtcaacatat acacctcatc tcagacaggg tcaatcataa tcaagttact    2220
cccaaatatg cccaaggata aagaggcgtg tgcaaaagcc ccattggaag catacaacag    2280
gacattgact actttgctca cccccttgg tgattctatc cgtaggatac aagagtctgt     2340
gaccacatcc ggaggaggga acagggacg tcttataggc gccattatcg gtggtgtagc     2400
tctcggggtt gcaaccgctg cacagataac agcagcctcg gctctgatac aagccaatca    2460
aaatgctgcc aacatcctcc ggctcaaaga gagcattgct gcaaccaatg aggctgtgca    2520
cgaggtcact gacggattat cacaactagc agtggcagtt gggaagatgc agcaatttgt    2580
taatgaccag tttaataaaa cagctcagga attggactgt ataaaaatta cacagcaggt    2640
tggtgtagaa ctcaacctgt acctaactga attgactaca gtattcgggc cacaaatcac    2700
ttcccctgcc ttaactcagc tgactatcca ggcgctttac aatctagctg gtgggaatat    2760
ggattacttg ttgactaagt taggtgtagg aaacaaccaa ctcagctcat taattggtag    2820
tggcctgatt accggcaacc ctatcctgta cgactcacag actcaactct gggtataca    2880
ggtcacccta ccctcagtcg ggaatctaaa taatatgcgt gccacctacc tggaaacctt    2940
gtctgtaagt acaaccaaag gatttgcctc agcacttgtc ccaaaagtag tgacacaggt    3000
tggttccgtg atagaagagc ttgacacctc gtactgtatc gagaccgatt tggacctata    3060
ttgtacaaga atagtgacat tccctatgtc tcctggtatt tattcctgtt tgagtggcaa    3120
tacatctgct tgcatgtatt caaagactga aggcgcactc actacgccgt atatgaccct    3180
caaaggctca gttattgcca actgtaagat gacaacatgt agatgtgcag acccccggg    3240
tatcatatcg cagaattatg gagaagctgt gtctctaata gataggcaat catgcaatat    3300
cttatcctta gacgggataa ctttgaggct cagtggggaa tttgatgcaa cttatcaaaa    3360
gaatatctca atacaagatt ctcaagtaat agttacaggc aatcttgaca tctcgactga    3420
gcttgggaat gtcaacaact cgataagtaa tgctttggat aagttagagg aaagcaacag    3480
caaactagac aaggtcaatg ttaaactgac cagcacatcc gctcttatta cctatatcgt    3540
tttaactgtc atatctcttg tatgtggtat acttagcctg gttctagcat gctacctgat    3600
gtacaagcaa aaggcgcaac agaagacctt gttgtggctt gggaataata ccctagacca    3660
gatgagggcc actacaaaaa tgtagcttga tctagagcgg ccgcgggat ccagacatga    3720
taagatacat tgatgagttt ggacaaacca caactagaat gcagtgaaaa aaatgcttta    3780
tttgtgaaat ttgtgatgct attgctttat ttgtaaccat tataagctgc aataaacaag    3840
ttaacaacaa caattgcatt catttttatgt ttcaggttca gggggaggtg tgggaggttt   3900
tttcggatcc tctagagtcg agtttaatgt tagtttattc aatgcattgg ttgcaaatat    3960
tcattacttc tccaatccca ggtcattctt tagcgagatg atgttatgac attgctgtga    4020
aaattactac aggatatatt tttaagatgc aggagtaaca atgtgcatag taggcgtagt    4080
tatcgcagac gtgcaacgct tcgcatttga gttaccgaag tgcccaacag tgctgcggtt    4140
atggtttatg cgcacagaat ccatgcatgt cctaattgaa ccatccgatt tttctttaa    4200
tcgcgatcgt tgtttgggca actgcgttat ttcagatcta aaaaatttac cctttatgac    4260
catcacatct ctctggctca taccccgctt ggataagata tcatgtagat tccgccctaa    4320
gaaatgcaaa ctaacattat tgtcggttcc atatacactt ccatcttgtc cttcgaaaat    4380
aacaaactcg cgcaatagac cgtccgtaca tgcatgccg atgtgtgtca acatcattgg    4440
tctgctagat cccgatggga cgaatcgtac agtcgtcgct ccagcattgg caaaaatccc    4500
```
cagataccct ccatgcggca aatctaaatt gcgaccccga agagactgca ccaaagtctt    4560
atcgacgcac gctgattttt ttgaacagcg ggagcccat                          4599

<210> SEQ ID NO 34
<211> LENGTH: 3974
<212> TYPE: DNA
<213> ORGANISM: Artificial Sequence
<220> FEATURE:
<223> OTHER INFORMATION: DNA sequence of Cloning plasmid for pSiteB

<400> SEQUENCE: 34
tctgcttaga aaaactcatc gagcatcaaa tgaaactgca atttattcat atcaggatta      60
tcaataccat attttgaaa aagccgtttc tgtaatgaag gagaaaactc accgaggcag     120
ttccatagga tggcaagatc ctggtatcgg tctgcgattc cgactcgtcc aacatcaata     180
caacctatta atttcccctc gtcaaaaata aggttatcaa gtgagaaatc accatgagtg     240
acgactgaat ccggtgagaa tggcaaaagt ttatgcattt ctttccagac ttgttcaaca     300
ggccagccat tacgctcgtc atcaaaatca ctcgcatcaa ccaaaccgtt attcattcgt     360
gattgcgcct gagcgaggcg aaatacgcga tcgctgttaa aaggacaatt acaaacagga     420
atcgagtgca accggcgcag gaacactgcc agcgcatcaa caatattttc acctgaatca     480
ggatattctt ctaatacctg gaacgctgtt tttccgggga tcgcagtggt gagtaaccat     540
gcatcatcag gagtacggat aaaatgcttg atggtcggaa gtggcataaa ttccgtcagc     600
cagtttagtc tgaccatctc atctgtaaca tcattggcaa cgctaccttt gccatgtttc     660
agaaacaact ctggcgcatc gggcttccca tacaagcgat agattgtcgc acctgattgc     720
ccgacattat cgcgagccca tttatacccca tataaatcag catccatgtt ggaatttaat     780
cgcggcctcg acgtttcccg ttgaatatgg ctcatattct ccttttttca atattattga     840
agcatttatc agggttattg tctcatgagc ggatacatat ttgaatgtat ttagaaaaat     900
aaacaaatag gggtcagtgt tacaaccaat taaccaattc tgaacattat cgcgagccca     960
tttatacctg aatatggctc ataacacccc ttgcagtgcg actaacggca tgaagctcgt    1020
cggggctgga tcgcttcgta ttgcgagctg tgcggctgag ttgacgtatc tgtgctggat    1080
gattactcat aacggcaccg ctatcaaacg tgccacgttc atgtccgtgt cgcccttcgc    1140
tgaaactagt ctctacactt cttgttaaat ggaaagtgca tttgcttgtt cttacaatcg    1200
gcccgagtct cgttcacagc gcctcgttca cacttaaacc acaaatagtc tacaggctat    1260
atgggagcca gactgaaact cacatatgac taatattcgg gggtgttagt cacgtgtagc    1320
ccattgtgtg catataacga tgttggacgc gtccttattc gcggtgtact tgatactatg    1380
gcagcgagca tgggatattc atcctcgtca tcgttaacat ctctacgggt tcagaatgtt    1440
tggcatgtcg tcgatccttt gcccatcgtt gcaaattaca agtccgatcg ccatgaccgc    1500
gataagcctg taccatgtgg cattagggtg acatctcgat catacattat aagaccaacg    1560
tgcgagtctt ccaaagacct gcacgccttc ttcttcggat tgtcaacggg ttcttcagaa    1620
tctatgccca tatctggcgt tgagaccatt gtgcgtttaa tgaacaataa agcggcatgc    1680
catggaaagg agggctgcag atctccattt tctcacgcca ctatcctgga cgctgtagac    1740
gataattata ccatgaatat agaggggggta tgtttccact gccactgtga tgataagttt    1800
tctccagatt gttggatatc tgcatttttct gctgccgaac aaacttcatc gctatgcaaa    1860
gagatgcgtg tgtacacgcg ccgttgagta tacgggaaac taaatgttca tagaggtctt    1920

```
tgggctatat gttattaaat aaaataattg ggcgcgccac cggtacgagt cactggatcc    1980
tctagtcagc ctcgagtgac tagcgtgcta gcagtggccg gccgtttaat gttagtttat    2040
tcaatgcatt ggttgcaaat attcattact tctccaatcc caggtcattc tttagcgaga    2100
tgatgttatg acattgctgt gaaaattact acaggatata ttttaagat gcaggagtaa     2160
caatgtgcat agtaggcgta gttatcgcag acgtgcaacg cttcgcattt gagttaccga    2220
agtgcccaac agtgctgcgg ttatggttta tgcgcacaga atccatgcat gtcctaattg    2280
aaccatccga ttttcttt aatcgcgatc gttgtttggg caactgcgtt atttcagatc      2340
taaaaatt accctttatg accatcacat ctctctggct catacccgc ttggataaga      2400
tatcatgtag attccgccct aagaaatgca aactaacatt attgtcggtt ccatatacac    2460
ttccatcttg tccttcgaaa ataacaaact cgcgcaatag accgtccgta catgcatggc    2520
cgatgtgtgt caacatcatt ggtctgctag atccgatgg gacgaatcgt acagtcgtcg     2580
ctccagcatt ggcaaaaatc cccagatacc ctccatgcgg caaatctaaa ttgcgacccc    2640
gaagagactc accaaagtc ttatcgacgc acgctgattt tttgaacag cgggagccca    2700
ttatcttcag tggagcgtag acgggcgagg ctaattatgt gacatagcaa cactgcatgt    2760
atgttttat aaatcaataa gagtacataa tttattacgt atcatttccg tttgtaatat     2820
actcctgcag gcgtcaaaag ggcgacacac tgtcattagc aactccttgt ccttcgatct    2880
cgtcaacaac agcttgcagt tcaaatacaa gacccagaag gcgactattc tggaagcgag    2940
cttgaagcca gacgctgagt acgaaaaggg gcccgagctt aagactggcc gtcgttttac    3000
aacacagaaa gagtttgtag aaacgcaaaa aggccatccg tcaggggcct tctgcttagt    3060
ttgatgcctg gcagttccct actctcgcct tccgcttcct cgctcactga ctcgctgcgc    3120
tcggtcgttc ggctgcggcg agcggtatca gctcactcaa aggcggtaat acggttatcc    3180
acagaatcag gggataacgc aggaaagaac atgtgagcaa aaggccagca aaaggccagg    3240
aaccgtaaaa aggccgcgtt gctggcgttt ttccataggc tccgcccccc tgacgagcat    3300
cacaaaaatc gacgctcaag tcagaggtgg cgaaacccga caggactata aagataccag    3360
gcgtttcccc ctggaagctc cctcgtgcgc tctcctgttc cgaccctgcc gcttaccgga    3420
tacctgtccg cctttctccc ttcgggaagc gtggcgcttt ctcatagctc acgctgtagg    3480
tatctcagtt cggtgtaggt cgttcgctcc aagctgggct gtgtgcacga accccccgtt    3540
cagcccgacc gctgcgcctt atccggtaac tatcgtcttg agtccaaccc ggtaagacac    3600
gacttatcgc cactggcagc agccactggt aacaggatta gcagagcgag gtatgtaggc    3660
ggtgctacag agttcttgaa gtggtgggct aactacggct acactagaag aacagtattt    3720
ggtatctgcg ctctgctgaa gccagttacc ttcggaaaaa gagttggtag ctcttgatcc    3780
ggcaaacaaa ccaccgctgg tagcggtggt ttttttgttt gcaagcagca gattacgcgc    3840
agaaaaaag gatctcaaga agatcctttg atcttttcta cggggtctga cgctcagtgg    3900
aacgacgcgc gcgtaactca cgttaaggga ttttggtcat gagcttgcgc cgtcccgtca    3960
agtcagcgta atgc                                                      3974
```

<210> SEQ ID NO 35
<211> LENGTH: 7246
<212> TYPE: DNA
<213> ORGANISM: Artificial Sequence
<220> FEATURE:
<223> OTHER INFORMATION: DNA sequence Final Transfer plasmid for pSiteB-#42

<400> SEQUENCE: 35

```
tctgcttaga aaaactcatc gagcatcaaa tgaaactgca atttattcat atcaggatta      60
tcaataccat atttttgaaa aagccgtttc tgtaatgaag gagaaaactc accgaggcag     120
ttccatagga tggcaagatc ctggtatcgg tctgcgattc cgactcgtcc aacatcaata     180
caacctatta atttccctc gtcaaaaata aggttatcaa gtgagaaatc accatgagtg     240
acgactgaat ccggtgagaa tggcaaaagt ttatgcattt ctttccagac ttgttcaaca     300
ggccagccat tacgctcgtc atcaaaatca ctcgcatcaa ccaaaccgtt attcattcgt     360
gattgcgcct gagcgaggcg aaatacgcga tcgctgttaa aaggacaatt acaaacagga     420
atcgagtgca accggcgcag gaacactgcc agcgcatcaa caatattttc acctgaatca     480
ggatattctt ctaatacctg gaacgctgtt tttccgggga tcgcagtggt gagtaaccat     540
gcatcatcag gagtacggat aaaatgcttg atggtcggaa gtggcataaa ttccgtcagc     600
cagtttagtc tgaccatctc atctgtaaca tcattggcaa cgctacccttt gccatgtttc     660
agaaacaact ctggcgcatc gggcttccca tacaagcgat agattgtcgc acctgattgc     720
ccgacattat cgcgagccca tttatacccca tataaatcag catccatgtt ggaatttaat     780
cgcggcctcg acgtttcccg ttgaatatgg ctcatattct ccttttttca atattattga     840
agcatttatc agggttattg tctcatgagc ggatacatat ttgaatgtat ttagaaaaat     900
aaacaaatag gggtcagtgt tacaaccaat taaccaattc tgaacattat cgcgagccca     960
tttatacctg aatatggctc ataacacccc ttgcagtgcg actaacggca tgaagctcgt    1020
cggggctgga tcgcttcgta ttgcgagctg tgcggctgag ttgacgtatc tgtgctggat    1080
gattactcat aacggcaccg ctatcaaacg tgccacgttc atgtccgtgt cgcccttcgc    1140
tgaaactagt ctctacactt cttgttaaat ggaaagtgca tttgcttgtt cttacaatcg    1200
gcccgagtct cgttcacagc gcctcgttca cacttaaacc acaaatagtc tacaggctat    1260
atgggagcca gactgaaact cacatatgac taatattcgg gggtgttagt cacgtgtagc    1320
ccattgtgtg catataacga tgttggacgc gtccttattc gcggtgtact tgatactatg    1380
gcagcgagca tgggatattc atcctcgtca tcgttaacat ctctacgggt tcagaatgtt    1440
tggcatgtcg tcgatccttt gcccatcgtt gcaaattaca agtccgatcg ccatgaccgc    1500
gataagcctg taccatgtgg cattagggtg acatctcgat catacattat aagaccaacg    1560
tgcgagtctt ccaaagacct gcacgccttc ttcttcggat tgtcaacggg ttcttcagaa    1620
tctatgccca tatctggcgt tgagaccatt gtgcgtttaa tgacaataa agcggcatgc    1680
catggaaagg agggctgcag atctccattt tctcacgcca ctatcctgga cgctgtagac    1740
gataattata ccatgaatat agaggggta tgtttccact gccactgtga tgataagttt    1800
tctccagatt gttggatatc tgcattttct gctgccgaac aaacttcatc gctatgcaaa    1860
gagatgcgtg tgtacacgcg ccgttgagta tacgggaaac taaatgttca tagaggtctt    1920
tgggctatat gttattaaat aaaataattg ggcgcgccaa ctccgcccgt tttatgacta    1980
gaaccaatag tttttaatgc caaatgcact gaaatcccct aatttgcaaa gccaaacgcc    2040
ccctatgtga gtaatacggg gacttttttac ccaatttccc aagcggaaag cccctaata    2100
cactcatatg gcatatgaat cagcacggtc atgcactcta atggcggccc atagggactt    2160
tccacatagg gggcgttcac catttcccag catagggtg gtgactcaat ggcctttacc    2220
caagtacatt gggtcaatgg gaggtaagcc aatgggtttt tcccattact ggcaagcaca    2280
ctgagtcaaa tgggactttc cactgggttt tgcccaagta cattgggtca atgggaggtg    2340
```

```
agccaatggg aaaaacccat tgctgccaag tacactgact caatagggac tttccaatgg   2400 gttttttccat tgttggcaag catataaggt caatgtgggt gagtcaatag ggactttcca   2460
ttgtattctg cccagtacat aaggtcaata gggggtgaat caacaggaaa gtcccattgg   2520
agccaagtac actgcgtcaa tagggacttt ccattgggtt ttgcccagta cataaggtca   2580 atagggatg agtcaatggg aaaaacccat tggagccaag tacactgact caatagggac   2640
tttccattgg gttttgccca gtacataagg tcaataggg gtgagtcaac aggaaagtcc   2700
cattggagcc aagtacattg agtcaatagg actttccaa tgggttttgc ccagtacata   2760
aggtcaatgg gaggtaagcc aatgggtttt tcccattact ggcacgtata ctgagtcatt   2820
agggactttc caatgggttt tgcccagtac ataaggtcaa taggggtgaa tcaacaggaa   2880
agtcccattg gagccaagta cactgagtca atagggactt ccattgggt tttgcccagt   2940 acaaaaggtc aatagggggt gagtcaatgg gttttttccca ttattggcac gtacataagg   3000
tcaatagggg tgagtcattg ggttttttcca gccaatttaa ttaaaacgcc atgtactttc   3060
ccaccattga cgtcaatggg ctattgaaac taatgcaacg tgacctttaa acggtacttt   3120
cccatagctg attaatggga aagtaccgtt ctcgagccaa tacacgtcaa tgggaagtga   3180
aagggcagcc aaaacgtaac accgccccgg ttttcccctg gaaattccat attggcacgc   3240
attctattgg ctgagctgcg ttctacgtgg gtataagagg cgcgaccagc gtcggtaccg   3300
tcgcagtctt cggtctgacc accgtagaac gcagagctcc tcgctgcagg cggccgctct   3360
agaactcgtc gatcgcagcg atgggctcca gatcttctac caggatccca gtacctctga   3420
tgctgaccgt ccgaatcatg ttggcactga gttgcgtctg tccgaccagc tcccttgatg   3480
gcaggcctct tgcagctgca gggattgtgg taacaggaga caaagcagtc aacatataca   3540
cctcatctca gacagggtca atcataatca agttactccc aaatatgccc aaggataaag   3600
aggcgtgtgc aaaagcccca ttggaagcat acaacaggac attgactact ttgctcaccc   3660
cccttggtga ttctatccgt aggatacaag agtctgtgac cacatccgga ggagggaaac   3720
agggacgtct tataggcgcc attatcggtg gtgtagctct cggggttgca accgctgcac   3780
agataacagc agcctcggct ctgatacaag ccaatcaaaa tgctgccaac atcctccggc   3840
tcaaagagag cattgctgca accaatgagc ctgtgcacga ggtcactgac ggattatcac   3900
aactagcagt ggcagttggg aagatgcagc aatttgttaa tgaccagttt aataaaacag   3960
ctcaggaatt ggactgtata aaaattacac agcaggttgg tgtagaactc aacctgtacc   4020
taactgaatt gactacagta ttcgggccac aaatcacttc ccctgcctta actcagctga   4080
ctatccaggc gctttacaat ctagctggtg gaatatgga ttacttgttg actaagttag   4140
gtgtaggaaa caaccaactc agctcattaa ttggtagtgg cctgattacc ggcaacccta   4200
tcctgtacga ctcacagact caactcttgg gtatacaggt caccctaccc tcagtcggga   4260
atctaaataa tatgcgtgcc acctacctgg aaaccttgtc tgtaagtaca accaaaggat   4320
ttgcctcagc acttgtccca aaagtagtga cacaggttgg ttccgtgata aagagcttg   4380 acacctcgta ctgtatcgag accgatttgg acctatattg tacaagaata gtgacattcc   4440
ctatgtctcc tggtatttat tcctgtttga gtggcaatac atctgcttgc atgtattcaa   4500
agactgaagg cgcactcact acgccgtata tgaccctcaa aggctcagtt attgccaact   4560
gtaagatgac aacatgtaga tgtgcagacc ccccgggtat catatcgcag aattatggag   4620
aagctgtgtc tctaatagat aggcaatcat gcaatatctt atccttagac gggataactt   4680
```

-continued

```
tgaggctcag tggggaattt gatgcaactt atcaaaagaa tatctcaata caagattctc    4740
aagtaatagt tacaggcaat cttgacatct cgactgagct tgggaatgtc aacaactcga    4800
taagtaatgc tttggataag ttagaggaaa gcaacagcaa actagacaag gtcaatgtta    4860
aactgaccag cacatccgct cttattacct atatcgtttt aactgtcata tctcttgtat    4920
gtggtatact tagcctggtt ctagcatgct acctgatgta caagcaaaag gcgcaacaga    4980
agaccttgtt gtggcttggg aataataccc tagaccagat gagggccact acaaaaatgt    5040
agcttgatct agagcggccg cggggatcca gacatgataa gatacattga tgagtttgga    5100
caaaccacaa ctagaatgca gtgaaaaaaa tgctttattt gtgaaatttg tgatgctatt    5160
gctttatttg taaccattat aagctgcaat aaacaagtta acaacaacaa ttgcattcat    5220
tttatgtttc aggttcaggg ggaggtgtgg gaggtttttt cggatcctct agagtcgagc    5280
tagcagtggc cggccgttta atgttagttt attcaatgca ttggttgcaa atattcatta    5340
cttctccaat cccaggtcat tctttagcga gatgatgtta tgacattgct gtgaaaatta    5400
ctacaggata tattttttaag atgcaggagt aacaatgtgc atagtaggcg tagttatcgc    5460
agacgtgcaa cgcttcgcat ttgagttacc gaagtgccca acagtgctgc ggttatggtt    5520
tatgcgcaca gaatccatgc atgtcctaat tgaaccatcc gattttctct ttaatcgcga    5580
tcgttgtttg ggcaactgcg ttatttcaga tctaaaaaat ttacccttta tgaccatcac    5640
atctctctgg ctcataccccc gcttggataa gatatcatgt agattccgcc ctaagaaatg    5700
caaactaaca ttattgtcgg ttccatatac acttccatct tgtccttcga aaataacaaa    5760
ctcgcgcaat agaccgtccg tacatgcatg gccgatgtgt gtcaacatca ttggtctgct    5820
agatcccgat gggacgaatc gtacagtcgt cgctccagca ttggcaaaaa tccccagata    5880
ccctccatgc ggcaaatcta aattgcgacc ccgaagagac tgcaccaaag tcttatcgac    5940
gcacgctgat ttttttgaac agcgggagcc cattatcttc agtggagcgt agacgggcga    6000
ggctaattat gtgacatagc aacactgcat gtatgttttt ataaatcaat aagagtacat    6060
aatttattac gtatcattc cgtttgtaat atactcctgc aggcgtcaaa agggcgacac    6120
actgtcatta gcaactcctt gtccttcgat ctcgtcaaca acagcttgca gttcaaatac    6180
aagacccaga aggcgactat tctggaagcg agcttgaagc cagacgctga gtacgaaaag    6240
gggcccgagc ttaagactgg ccgtcgtttt acaacacaga aagagtttgt agaaacgcaa    6300
aaaggccatc cgtcaggggc cttctgctta gtttgatgcc tggcagttcc ctactctcgc    6360
cttccgcttc ctcgctcact gactcgctgc gctcggtcgt tcggctgcgg cgagcggtat    6420
cagctcactc aaaggcggta atacggttat ccacagaatc aggggataac gcaggaaaga    6480
acatgtgagc aaaaggccag caaaaggcca ggaaccgtaa aaaggccgcg ttgctggcgt    6540
ttttccatag gctccgcccc cctgacgagc atcacaaaaa tcgacgctca agtcagaggt    6600
ggcgaaaccc gacaggacta taaagatacc aggcgtttcc ccctggaagc tccctcgtgc    6660
gctctcctgt tccgaccctg ccgcttaccg gatacctgtc cgcctttctc ccttcgggaa    6720
gcgtggcgct ttctcatagc tcacgctgta ggtatctcag ttcggtgtag tcgttcgct    6780 ccaagctggg ctgtgtgcac gaaccccccg ttcagcccga ccgctgcgcc ttatccggta    6840
actatcgtct tgagtccaac ccggtaagac acgacttatc gccactggca gcagccactg    6900
gtaacaggat tagcagagcg aggtatgtag gcggtgctac agagttcttg aagtggtggg    6960
ctaactacgg ctacactaga agaacagtat ttggtatctg cgctctgctg aagccagtta    7020
ccttcggaaa aagagttggt agctcttgat ccggcaaaca aaccaccgct ggtagcggtg    7080
```

-continued

```
gttttttttgt tgcaagcag cagattacgc gcagaaaaaa aggatctcaa gaagatcctt    7140
tgatcttttc tacggggtct gacgctcagt ggaacgacgc gcgcgtaact cacgttaagg    7200
gattttggtc atgagcttgc gccgtcccgt caagtcagcg taatgc                   7246
```

<210> SEQ ID NO 36
<211> LENGTH: 4440
<212> TYPE: DNA
<213> ORGANISM: Artificial Sequence
<220> FEATURE:
<223> OTHER INFORMATION: DNA sequence Transfer plasmid for HVT-ND #44

<400> SEQUENCE: 36

```
atggcagcga gcatgggata ttcatcctcg tcatcgttaa catctctacg ggttcagaat      60
gtttggcatg tcgtcgatcc tttgcccatc gttgcaaatt acaagtccga tcgccatgac     120
cgcgataagc ctgtaccatg tggcattagg gtgacatctc gatcatacat tataagacca    180
acgtgcgagt cttccaaaga cctgcacgcc ttcttcttcg gattgtcaac gggttcttca    240
gaatctatgc ccatatctgg cgttgagacc attgtgcgtt aatgaacaa taaagcggca     300 tgccatggaa aggagggctg cagatctcca tttctcacg ccactatcct ggacgctgta     360
gacgataatt ataccatgaa tatagagggg gtatgtttcc actgccactg tgatgataag    420
ttttctccag attgttggat atctgcattt tctgctgccg aacaaacttc atcgctatgc    480
aaagagatgc gtgtgtacac gcgccgttga gtatacggga aactaaatgt tcatagaggt    540
ctttgggcta tatgttatta aataaaataa ttgaccagtg tcgaggtgag ccccacgttc    600
tgcttcactc tccccatctc ccccccctcc ccaccccaa ttttgtattt atttattttt     660
taattatttt gtgcagcgat gggggcgggg ggggggggg cgcgcgccag gcggggcggg     720
gcggggcgag gggcggggcg gggcgaggcg gagaggtgcg gcggcagcca atcagagcgg    780
cgcgctccga aagtttcctt ttatggcgag gcggcggcgg cggcggccct ataaaaagcg    840
aagcgcgcgg cgggcgggag tcgctgcgtt gccttcgccc cgtgccccgc tccgcgccgc    900
ctcgcgccgc ccgccccggc tctgactgac cgcgttactc ccacaggtga gcgggcggga   960
cggcccttct cctccgggct gtaattagcg cttggtttaa tgacggctcg tttcttttct   1020
gtggctgcgt gaaagcctta aagggctccg ggagggccct tgtgcggg gggagcggct     1080 cggggggtgc gtgcgtgtgt gtgtgcgtgg ggagcgccgc gtgcggcccg cgctgccgg    1140 cggctgtgag cgctgcgggc gcggcgcggg gctttgtgcg ctccgcgtgt gcgcgagggg    1200
agcgcggccg gggcggtgc cccgcggtgc ggggggctg cgaggggaac aaaggctgcg     1260
tgcggggtgt gtgcgtgggg gggtgagcag gggtgtggg cgcggcggtc gggctgtaac    1320 cccccctgc accccctcc ccgagttgct gagcacggcc cggcttcggg tgcgggctc      1380 cgtgcgggc gtggcgcggg gctcgccgtg ccgggcgggg ggtggcggca ggtggggtg     1440 ccgggcgggg cggggccgcc tcgggccggg gagggctcgg gggaggggcg cggcggcccc   1500
ggagcgccgg cggctgtcga ggcgcggcga gccgcagcca ttgccttta tggtaatcgt    1560 gcgagagggc gcagggactt cctttgtccc aaatctggcg gagccgaaat ctggaggcg    1620 ccgccgcacc ccctctagcg ggcgcgggcg aagcggtgcg gcgccggcag gaaggaaatg   1680
ggcggggagg gccttcgtgc gtcgccgcgc cgccgtcccc ttctccatct ccagcctcgg   1740
ggctgccgca gggggacggc tgccttcggg ggggacgggg cagggcgggg ttcggcttct   1800
ggcgtgtgac cggcggggtt tatatcttcc cttctctgtt cctccgcagc cagccatggc   1860
```

```
caccatgggc tccagatctt ctaccaggat cccagtacct ctgatgctga ccgtccgaat    1920
catgttggca ctgagttgcg tctgtccgac cagctcccct tgatggcagg cctcttgcag    1980
tgcagggatt gtggtaacag gagacaaagc agtcaacata tacacctcat ctcagacagg    2040
gtcaatcata atcaagttac tcccaaatat gcccaaggat aaagaggcgt gtgcaaaagc    2100
cccattggaa gcatacaaca ggacattgac tactttgctc acccccccttg gtgattctat   2160 ccgtaggata caagagtctg tgaccacatc cggaggaggg aaacagggac gtcttatagg    2220
cgccattatc ggtggtgtag ctctcggggt tgcaaccgct gcacagataa cagcagcctc    2280
ggctctgata caagccaatc aaaatgctgc aacatcctc cggctcaaag agagcattgc     2340
tgcaaccaat gaggctgtgc acgaggtcac tgacggatta tcacaactag cagtggcagt    2400
tgggaagatg cagcaatttg ttaatgacca gtttaataaa acagctcagg aattggactg    2460
tataaaaatt acacagcagg ttggtgtaga actcaacctg tacctaactg aattgactac    2520
agtattcggg ccacaaatca cttcccctgc cttaactcag ctgactatcc aggcgcttta    2580
caatctagct ggtgggaata tggattactt gttgactaag ttaggtgtag aaacaaacca    2640
actcagctca ttaattggta gtggcctgat taccggcaac cctatcctgt acgactcaca    2700
gactcaactc ttgggtatac aggtcaccct accctcagtc gggaatctaa ataatatgcg    2760
tgccacctac ctggaaacct tgtctgtaag tacaaccaaa ggatttgcct cagcacttgt    2820
cccaaaagta gtgacacagg ttggttccgt gatagaagag cttgacacct cgtactgtat    2880
cgagaccgat ttggacctat attgtacaag aatagtgaca ttccctatgt ctcctggtat    2940
ttattcctgt ttgagtggca atacatctgc ttgcatgtat tcaaagactg aaggcgcact    3000
cactacgccg tatatgaccc tcaaaggctc agttattgcc aactgtaaga tgacaacatg    3060
tagatgtgca gacccccccgg gtatcatatc gcagaattat ggagaagctg tgtctctaat    3120
agataggcaa tcatgcaata tcttatcctt agacgggata actttgaggc tcagtgggga    3180
atttgatgca acttatcaaa agaatatctc aatacaagat tctcaagtaa tagttacagg    3240 caatctgac atctcgactg agcttgggaa tgtcaacaac tcgataagta atgctttgga     3300
taagttagag gaaagcaaca gcaaactaga caaggtcaat gttaaactga ccagcacatc    3360
cgctcttatt acctatatcg ttttaactgt catatctctt gtatgtggta tacttagcct    3420
ggttctagca tgctacctga tgtacaagca aaaggcgcaa cagaagacct tgttgtggct    3480
tgggaataat accctagacc agatgagggc cactacaaaa atgtagcttg atctagagcg    3540
gccgcgggga tccagacatg ataagataca ttgatgagtt tggacaaacc acaactagaa    3600
tgcagtgaaa aaaatgcttt atttgtgaaa tttgtgatgc tattgcttta tttgtaacca    3660
ttataagctg caataaacaa gttaacaaca acaattgcat tcattttatg tttcaggttc    3720
agggggaggt gtgggaggtt ttttcggatc ctctagagtc gagtttaatg ttagtttatt    3780
caatgcattg gttgcaaata ttcattactt ctccaatccc aggtcattct ttagcgagat    3840
gatgttatga cattgctgtg aaaattacta caggatatat ttttaagatg caggagtaac    3900
aatgtgcata gtaggcgtag ttatcgcaga cgtgcaacgc ttcgcatttg agttaccgaa    3960
gtgcccaaca gtgctgcggt tatggtttat gcgcacagaa tccatgcatg tcctaattga    4020
accatccgat ttttctttta atcgcgatcg ttgtttgggc aactgcgtta tttcagatct    4080
aaaaaattta ccctttatga ccatcacatc tctctggctc ataccccgct tggataagat    4140
atcatgtaga ttccgcccta agaaatgcaa actaacatta ttgtcggttc catatacact    4200
tccatcttgt ccttcgaaaa taacaaactc gcgcaataga ccgtccgtac atgcatggcc    4260
```

-continued

| | |
|---|---|
| gatgtgtgtc aacatcattg gtctgctaga tcccgatggg acgaatcgta cagtcgtcgc | 4320 |
| tccagcattg gcaaaaatcc ccagatrccc tccatgcggc aaatctaaat tgcgaccccg | 4380 |
| aagagactgc accaaagtct tatcgacgca cgctgatttt tttgaacagc gggagcccat | 4440 |

<210> SEQ ID NO 37
<211> LENGTH: 3832
<212> TYPE: DNA
<213> ORGANISM: Artificial Sequence
<220> FEATURE:
<223> OTHER INFORMATION: DNA sequence Transfer plasmid for HVT-ND #45

<400> SEQUENCE: 37

| | |
|---|---|
| atgggctccc gctgttcaaa aaatcagcg tgcgtcgata agactttggt gcagtctctt | 60 |
| cggggtcgca atttagattt gccgcatgga gggtatctgg ggattttgc caatgctgga | 120 |
| gcgacgactg tacgattcgt cccatcggga tctagcagac caatgatgtt gacacacatc | 180 |
| ggccatgcat gtacggacgg tctattgcgc gagtttgtta ttttcgaagg acaagatgga | 240 |
| agtgtatatg gaaccgacaa taatgttagt ttgcattct tagggcggaa tctacatgat | 300 |
| atcttatcca gcggggtat gagccagaga gatgtgatgg tcataaaggg taaattttt | 360 |
| agatctgaaa taacgcagtt gcccaaacaa cgatcgcgat taaaagaaaa atcggatggt | 420 |
| tcaattagga catgcatgga ttctgtgcgc ataaaccata accgcagcac tgttgggcac | 480 |
| ttcggtaact caaatgcgaa gcgttgcacg tctgcgataa ctacgcctac tatgcacatt | 540 |
| gttactcctg catcttaaaa atatatcctg tagtaatttt cacagcaatg tcataacatc | 600 |
| atctcgctaa agaatgacct gggattggag aagtaatgaa tatttgcaac caatgcattg | 660 |
| aataaactaa cattaaactt gacattgatt attgactagt tattaatagt aatcaattac | 720 |
| ggggtcatta gttcatagcc catatatgga gttccgcgtt acataactta cggtaaatgg | 780 |
| cccgcctggc tgaccgccca acgacccccg cccattgacg tcaataatga cgtatgttcc | 840 |
| catagtaacg ccaatagga cttttccattg acgtcaatgg gtggagtatt tacggtaaac | 900 |
| tgcccacttg gcagtacatc aagtgtatca tatgccaagt acgccccta ttgacgtcaa | 960 |
| tgacggtaaa tggcccgcct ggcattatgc ccagtacatg accttatggg actttcctac | 1020 |
| ttggcagtac atctacgtat tagtcatcgc tattaccatg gtgatgcggt tttggcagta | 1080 |
| catcaatggg cgtggatagc ggtttgactc acggggattt ccaagtctcc accccattga | 1140 |
| cgtcaatggg agtttgtttt ggcaccaaaa tcaacgggac tttccaaaat gtcgtaacaa | 1200 |
| ctccgcccca ttgacgcaaa tgggcggtag gcgtgtacgg tgggaggtct atataagcag | 1260 |
| agctctctgg ctaactagag aacccactgc ttactggctt atcgaaatta atacgactca | 1320 |
| ctatagggag acccaagctg gctagcgttt aaacttaagc ttaccgccac catgggctcc | 1380 |
| agatcttcta ccaggatccc agtacctctg atgctgaccg tccgaatcat gttggcactg | 1440 |
| agttgcgtct gtccgaccag ctcccttgat ggcaggcctc ttgcagctgc agggattgtg | 1500 |
| gtaacaggag acaaagcagt caacatatac acctcatctc agacagggtc aatcataatc | 1560 |
| aagttactcc caaatatgcc caaggataaa gaggcgtgtg caaaagcccc attggaagca | 1620 |
| tacaacagga cattgactac tttgctcacc cccttggtg attctatccg taggatacaa | 1680 |
| gagtctgtga ccacatccgg aggagggaaa cagggacgtc ttataggcgc cattatcggt | 1740 |
| ggtgtagctc tcggggttgc aaccgctgca cagataacag cagcctcggc tctgatacaa | 1800 |
| gccaatcaaa atgctgccaa catcctccgg ctcaaagaga gcattgctgc aaccaatgag | 1860 |

-continued

```
gctgtgcacg aggtcactga cggattatca caactagcag tggcagttgg gaagatgcag      1920
caatttgtta atgaccagtt taataaaaca gctcaggaat tggactgtat aaaaattaca     1980
cagcaggttg gtgtagaact caacctgtac ctaactgaat tgactacagt attcgggcca     2040
caaatcactt cccctgcctt aactcagctg actatccagg cgctttacaa tctagctggt    2100
gggaatatgg attacttgtt gactaagtta ggtgtaggaa caaccaact cagctcatta     2160 attggtagtg gcctgattac cggcaaccct atcctgtacg actcacagac tcaactcttg    2220
ggtatacagg tcaccctacc ctcagtcggg aatctaaata atatgcgtgc cacctacctg    2280
gaaaccttgt ctgtaagtac aaccaaagga tttgcctcag cacttgtccc aaaagtagtg    2340
acacaggttg gttccgtgat agaagagctt gacacctcgt actgtatcga gaccgatttg    2400
gacctatatt gtacaagaat agtgacattc cctatgtctc ctggtattta ttcctgtttg    2460
agtggcaata catctgcttg catgtattca aagactgaag gcgcactcac tacgccgtat    2520 atgacccctca aaggctcagt tattgccaac tgtaagatga caacatgtag atgtgcagac   2580 ccccccgggta tcatatcgca gaattatgga gaagctgtgt ctctaataga taggcaatca   2640
tgcaatatct tatccttaga cgggataact ttgaggctca gtggggaatt tgatgcaact    2700
tatcaaaaga atatctcaat acaagattct caagtaatag ttacaggcaa tcttgacatc   2760
tcgactgagc ttgggaatgt caacaactcg ataagtaatg ctttggataa gttagaggaa    2820
agcaacagca aactagacaa ggtcaatgtt aaactgacca gcacatccgc tcttattacc    2880
tatatcgttt taactgtcat atctcttgta tgtggtatac ttagcctggt tctagcatgc    2940
tacctgatgt acaagcaaaa ggcgcaacag aagaccttgt tgtggcttgg gaataatacc    3000
ctagaccaga tgagggccac tacaaaaatg tagctgtgcc ttctagttgc cagccatctg    3060
ttgtttgccc ctccccgtg ccttccttga ccctggaagg tgccactccc actgtccttt     3120
cctaataaaa tgaggaaatt gcatcgcatt gtctgagtag gtgtcattct attctggggg    3180
gtggggtggg gcaggacagc aagggggagg attgggaaga caatagcagg catgctgggg   3240
atgcggtggg ctctatggtc aattattta tttaataaca tatagcccaa agacctctat    3300
gaacatttag tttcccgtat actcaacggc gcgtgtacac acgcatctct ttgcatagcg    3360
atgaagtttg ttcggcagca gaaaatgcag atatccaaca atctggagaa aacttatcat    3420
cacagtggca gtgaaacat acccccctcta tattcatggt ataattatcg tctacagcgt    3480
ccaggatagt ggcgtgagaa atggagatc tgcagccctc ctttccatgg catgccgctt    3540
tattgttcat taaacgcaca atggtctcaa cgccagatat gggcatagat tctgaagaac   3600
ccgttgacaa tccgaagaag aaggcgtgca ggtctttgga agactcgcac gttggtctta   3660
taatgtatga tcgagatgtc accctaatgc cacatggtac aggcttatcg cggtcatggc   3720
gatcggactt gtaatttgca acgatgggca aaggatcgac gacatgccaa acattctgaa   3780
cccgtagaga tgttaacgat gacgaggatg aatatcccat gctcgctgcc at            3832
```

<210> SEQ ID NO 38
<211> LENGTH: 4592
<212> TYPE: DNA
<213> ORGANISM: Artificial Sequence
<220> FEATURE:
<223> OTHER INFORMATION: DNA sequence Transfer plasmid for HVT-ND #46

<400> SEQUENCE: 38

```
atgggctccc gctgttcaaa aaaatcagcg tgcgtcgata agactttggt gcagtctctt      60
cggggtcgca atttagattt gccgcatgga gggtatctgg ggattttgc caatgctgga    120
```

```
gcgacgactg tacgattcgt cccatcggga tctagcagac caatgatgtt gacacacatc    180
ggccatgcat gtacggacgg tctattgcgc gagtttgtta ttttcgaagg acaagatgga    240
agtgtatatg gaaccgacaa taatgttagt ttgcatttct tagggcggaa tctacatgat    300
atcttatcca agcggggtat gagccagaga gatgtgatgg tcataaaggg taaatttttt    360
agatctgaaa taacgcagtt gcccaaacaa cgatcgcgat taaagaaaaa atcggatggt    420
tcaattagga catgcatgga ttctgtgcgc ataaaccata accgcagcac tgttgggcac    480
ttcggtaact caaatgcgaa gcgttgcacg tctgcgataa ctacgcctac tatgcacatt    540
gttactcctg catcttaaaa atatatcctg tagtaatttt cacagcaatg tcataacatc    600
atctcgctaa agaatgacct gggattggag aagtaatgaa tatttgcaac caatgcattg    660
aataaactaa cattaaacga attcactagt ggatccccca actccgcccg ttttatgact    720
agaaccaata gtttttaatg ccaaatgcac tgaaatcccc taatttgcaa agccaaacgc    780
cccctatgtg agtaatacgg ggactttta cccaatttcc caagcggaaa gcccctaat    840
acactcatat ggcatatgaa tcagcacggt catgcactct aatggcggcc catagggact    900
ttccacatag ggggcgttca ccatttccca gcataggggt ggtgactcaa tggcctttac    960
ccaagtacat tgggtcaatg ggaggtaagc caatgggttt ttcccattac tggcaagcac   1020
actgagtcaa atgggacttt ccactgggtt tgcccaagt acattgggtc aatgggaggt   1080
gagccaatgg gaaaaaccca ttgctgccaa gtacactgac tcaataggga ctttccaatg   1140
ggttttttcca ttgttggcaa gcatataagg tcaatgtggg tgagtcaata gggacttttcc   1200
attgtattct gcccagtaca taaggtcaat aggggggtgaa tcaacaggaa agtcccattg   1260
gagccaagta cactgcgtca atagggactt tccattgggt tttgcccagt acataaggtc   1320
aatagggat gagtcaatgg gaaaaaccca ttggagccaa gtacactgac tcaataggga   1380
ctttccattg ggtttttgccc agtacataag gtcaataggg ggtgagtcaa caggaaagtc   1440
ccattggagc caagtacatt gagtcaatag ggactttcca atgggttttg cccagtacat   1500
aaggtcaatg ggaggtaagc caatgggttt ttcccattac tggcacgtat actgagtcat   1560
tagggacttt ccaatgggtt tgcccagta cataaggtca atagggggtga atcaacagga   1620
aagtcccatt ggagccaagt acactgagtc aatagggact ttccattggg ttttgcccag   1680
tacaaaaggt caatagggg tgagtcaatg ggttttttccc attattggca cgtacataag   1740
gtcaataggg gtgagtcatt gggttttttcc agccaattta attaaaacgc catgtacttt   1800
cccaccattg acgtcaatgg gctattgaaa ctaatgcaac gtgacccttta acggtactt   1860
tcccatagct gattaatggg aaagtaccgt tctcgagcca atacacgtca atgggaagtg   1920
aaagggcagc caaaacgtaa caccgccccg ttttcccct ggaaattcca tattggcacg   1980
cattctattg gctgagctgc gttctacgtg ggtataagag gcgcgaccag cgtcggtacc   2040
gtcgcagtct tcggtctgac caccgtagaa cgcagagctc ctcgctgcag gcggccgctc   2100
tagaactcgt cgatcgcagc gatgggctcc agatcttcta ccaggatccc agtacctctg   2160
atgctgaccg tccgaatcat gttggcactg agttgcgtct gtccgaccag ctcccttgat   2220
ggcaggcctc ttgcagctgc agggattgtg gtaacaggag acaaagcagt caacatatac   2280
acctcatctc agacagggtc aatcataatc aagttactcc caaatatgcc caaggataaa   2340
gaggcgtgtg caaaagcccc attggaagca tacaacagga cattgactac tttgctcacc   2400
cccccttggtg attctatccg taggatacaa gagtctgtga ccacatccgg aggagggaaa   2460
```

```
cagggacgtc ttataggcgc cattatcggt ggtgtagctc tcggggttgc aaccgctgca      2520
cagataacag cagcctcggc tctgatacaa gccaatcaaa atgctgccaa catcctccgg      2580
ctcaaagaga gcattgctgc aaccaatgag gctgtgcacg aggtcactga cggattatca      2640
caactagcag tggcagttgg gaagatgcag caatttgtta atgaccagtt taataaaaca      2700
gctcaggaat tggactgtat aaaaattaca cagcaggttg gtgtagaact caacctgtac      2760
ctaactgaat tgactacagt attcgggcca caaatcactt ccctgccctt aactcagctg      2820
actatccagg cgctttacaa tctagctggt gggaatatgg attacttgtt gactaagtta      2880
ggtgtaggaa caaccaact cagctcatta attggtagtg gcctgattac cggcaaccct      2940
atcctgtacg actcacagac tcaactcttg ggtatacagg tcaccctacc ctcagtcggg      3000
aatctaaata atatgcgtgc cacctacctg gaaaccttgt ctgtaagtac aaccaaagga      3060
tttgcctcag cacttgtccc aaaagtagtg acacaggttg gttccgtgat agaagagctt      3120
gacacctcgt actgtatcga gaccgatttg gacctatatt gtacaagaat agtgacattc      3180
cctatgtctc ctggtatttta ttcctgtttg agtggcaata catctgcttg catgtattca      3240
aagactgaag gcgcactcac tacgccgtat atgaccctca aaggctcagt tattgccaac      3300
tgtaagatga caacatgtag atgtgcagac cccccgggta tcatatcgca gaattatgga      3360
gaagctgtgt ctctaataga taggcaatca tgcaatatct tatccttaga cgggataact      3420
ttgaggctca gtggggaatt tgatgcaact tatcaaaaga atatctcaat acaagattct      3480
caagtaatag ttacaggcaa tcttgacatc tcgactgagc ttgggaatgt caacaactcg      3540
ataagtaatg ctttggataa gttagaggaa agcaacagca actagacaa ggtcaatgtt      3600 aaactgacca gcacatccgc tcttattacc tatatcgttt taactgtcat atctcttgta      3660
tgtggtatac ttagcctggt tctagcatgc tacctgatga caagcaaaa ggcgcaacag      3720 aagaccttgt tgtggcttgg gaataatacc ctagaccaga tgagggccac tacaaaaatg      3780
tagcttgatc tagagcggcc gcggggatcc agacatgata agatacattg atgagtttgg      3840
acaaaccaca actagaatgc agtgaaaaaa atgctttatt tgtgaaattt gtgatgctat      3900 tgctttatttt gtaaccatta taagctgcaa taaacaagtt aacaacaaca attgcattca      3960
ttttatgttt caggttcagg gggaggtgtg ggaggttttt tcggatcctc tagagtcgac      4020
aattatttta tttaataaca tatagcccaa agacctctat gaacatttag tttcccgtat      4080
actcaacggc gcgtgtacac acgcatctct ttgcatagcg atgaagtttg ttcggcagca      4140
gaaaatgcag atatccaaca atctggagaa aacttatcat cacagtggca gtggaaacat      4200
accccctcta tattcatggt ataattatcg tctacagcgt ccaggatagt ggcgtgagaa      4260
aatggagatc tgcagccctc ctttccatgg catgccgctt tattgttcat taaacgcaca      4320
atggtctcaa cgccagatat gggcatagat tctgaagaac ccgttgacaa tccgaagaag      4380
aaggcgtgca ggtctttgga agactcgcac gttggtctta taatgtatga tcgagatgtc      4440
accctaatgc cacatggtac aggcttatcg cggtcatggc gatcggactt gtaatttgca      4500
acgatgggca aaggatcgac gacatgccaa acattctgaa cccgtagaga tgttaacgat      4560
gacgaggatg aatatcccat gctcgctgcc at                                   4592
```

<210> SEQ ID NO 39
<211> LENGTH: 4433
<212> TYPE: DNA
<213> ORGANISM: Artificial Sequence
<220> FEATURE:
<223> OTHER INFORMATION: DNA sequence Transfer plasmid for HVT-ND #48

<400> SEQUENCE: 39

```
atgggctccc gctgttcaaa aaaatcagcg tgcgtcgata agactttggt gcagtctctt      60
cggggtcgca atttagattt gccgcatgga gggtatctgg ggattttgc caatgctgga      120
gcgacgactg tacgattcgt cccatcggga tctagcagac caatgatgtt gacacacatc     180
ggccatgcat gtacggacgg tctattgcgc gagtttgtta ttttcgaagg acaagatgga    240
agtgtatatg gaaccgacaa taatgttagt ttgcatttct tagggcggaa tctacatgat     300
atcttatcca agcggggtat gagccagaga gatgtgatgg tcataaaggg taaattttt     360
agatctgaaa taacgcagtt gcccaaacaa cgatcgcgat taaagaaaa tcggatggt      420
tcaattagga catgcatgga ttctgtgcgc ataaaccata accgcagcac tgttgggcac    480
ttcggtaact caaatgcgaa gcgttgcacg tctgcgataa ctacgcctac tatgcacatt   540
gttactcctg catcttaaaa atatatcctg tagtaatttt cacagcaatg tcataacatc    600
atctcgctaa agaatgacct gggattggag aagtaatgaa tatttgcaac caatgcattg     660
aataaactaa cattaaactc gaggtgagcc ccacgttctg cttcactctc cccatctccc    720
cccctcccc accccaatt ttgtatttat ttattttta attattttgt gcagcgatgg       780
gggcggggg gggggggcg cgcgccaggc ggggcggggc gggcgaggg gcggggcggg      840
gcgaggcgga gaggtgcggc ggcagccaat cagagcggcg cgctccgaaa gtttccttt    900
atggcgaggc ggcggcggcg gcggccctat aaaaagcgaa gcgcgcggcg ggcgggagtc    960
gctgcgttgc cttcgcccg tgccccgctc cgcgccgcct cgcgccgccc gccccggctc    1020
tgactgaccg cgttactccc acaggtgagc gggcgggacg gcccttctcc tccgggctgt   1080
aattagcgct tggtttaatg acggctcgtt tcttttctgt ggctgcgtga aagccttaaa    1140
gggctccggg agggcccttt gtgcgggggg gagcggctcg ggggtgcgt gcgtgtgtgt   1200
gtgcgtgggg agcgccgcgt gcggcccgcg ctgcccggcg gctgtgagcg ctgcgggcgc  1260
ggcgcgggc tttgtgcgct ccgcgtgtgc gcgaggggag cgcggccggg ggcggtgccc     1320
cgcggtgcgg gggggctgcg aggggaacaa aggctgcgtg cggggtgtgt gcgtgggggg   1380
gtgagcaggg ggtgtgggcg cggcggtcgg gctgtaaccc ccccctgcac ccccctcccc  1440
gagttgctga gcacggcccg gcttcgggtg cggggctccg tgcgggggcgt ggcgcgggc  1500
tcgccgtgcc gggcggggg tggcggcagg tgggggtgcc gggcggggcg gggccgcctc    1560
gggccgggga gggctcgggg gaggggcgcg gcggccccgg agcgccggcg gctgtcgagg   1620
cgcggcgagc cgcagccatt gccttttatg gtaatcgtgc gagagggcgc agggacttcc    1680
tttgtcccaa atctggcgga gccgaaatct gggaggcgcc gccgcacccc ctctagcggg   1740
cgcgggcgaa gcgtgcggc gccggcagga aggaaatggg cggggagggc cttcgtgcgt    1800
cgccgcgccg ccgtcccctt ctccatctcc agcctcgggg ctgccgcagg gggacggctg    1860
ccttcggggg ggacggggca gggcgggtt cggcttctgg cgtgtgaccg gcggggttta   1920
tatcttccct tctctgttcc tccgcagcca gccatggcca ccatgggctc cagatcttct    1980
accaggatcc cagtacctct gatgctgacc gtccgaatca tgttggcact gagttgcgtc   2040
tgtccgacca gctcccttga tggcaggcct cttgcagctg cagggattgt ggtaacagga   2100
gacaaagcag tcaacatata cacctcatct cagacagggt caatcataat caagttactc   2160
ccaaatatgc ccaaggataa agaggcgtgt gcaaaagccc cattggaagc atacaacagg   2220
acattgacta ctttgctcac ccccttggt gattctatcc gtaggataca agagtctgtg    2280
```

-continued

```
accacatccg gaggagggaa acagggacgt cttataggcg ccattatcgg tggtgtagct   2340
ctcggggttg caaccgctgc acagataaca gcagcctcgg ctctgataca agccaatcaa   2400
aatgctgcca acatcctccg gctcaaagag agcattgctg caaccaatga ggctgtgcac   2460
gaggtcactg acggattatc acaactagca gtggcagttg ggaagatgca gcaatttgtt   2520
aatgaccagt ttaataaaac agctcaggaa ttggactgta taaaaattac acagcaggtt   2580
ggtgtagaac tcaacctgta cctaactgaa ttgactacag tattcgggcc acaaatcact   2640 tccctgcct taactcagct gactatccag gcgctttaca atctagctgg tgggaatatg   2700
gattacttgt tgactaagtt aggtgtagga acaaccaac tcagctcatt aattggtagt   2760
ggcctgatta ccggcaaccc tatcctgtac gactcacaga ctcaactctt gggtatacag   2820
gtcaccctac cctcagtcgg gaatctaaat aatatgcgtg ccacctacct ggaaaccttg   2880
tctgtaagta caaccaaagg atttgcctca gcacttgtcc caaaagtagt gacacaggtt   2940
ggttccgtga tagaagagct tgacacctcg tactgtatcg agaccgattt ggacctatat   3000
tgtacaagaa tagtgacatt ccctatgtct cctggtattt attcctgttt gagtggcaat   3060
acatctgctt gcatgtattc aaagactgaa ggcgcactca ctacgccgta tatgacctc    3120 aaaggctcag ttattgccaa ctgtaagatg acaacatgta gatgtgcaga ccccccgggt   3180
atcatatcgc agaattatgg agaagctgtg tctctaatag ataggcaatc atgcaatatc   3240
ttatccttag acgggataac tttgaggctc agtggggaat tgatgcaac ttatcaaaag    3300 aatatctcaa tacaagattc tcaagtaata gttacaggca atcttgacat ctcgactgag   3360
cttgggaatg tcaacaactc gataagtaat gctttggata gttagagga aagcaacagc    3420 aaactagaca aggtcaatgt taaactgacc agcacatccg ctcttattac ctatatcgtt   3480
ttaactgtca tatctcttgt atgtggtata cttagcctgg ttctagcatg ctacctgatg   3540
tacaagcaaa aggcgcaaca gaagaccttg ttgtggcttg gaataatac cctagaccag     3600 atgagggcca ctacaaaaat gtagcttgat ctagagcggc cgcggggatc cagacatgat   3660
aagatacatt gatgagtttg gacaaaccac aactagaatg cagtgaaaaa aatgctttat   3720
ttgtgaaatt tgtgatgcta ttgctttatt tgtaaccatt ataagctgca ataaacaagt   3780
taacaacaac aattgcattc attttatgtt tcaggttcag ggggaggtgt gggaggtttt   3840
ttcggatcct ctagagtcga caattatttt atttaataac atatagccca aagacctcta   3900
tgaacattta gtttcccgta tactcaacgg cgcgtgtaca cacgcatctc tttgcatagc   3960
gatgaagttt gttcggcagc agaaaatgca gatatccaac aatctggaga aaacttatca   4020
tcacagtggc agtggaaaca taccccctct atattcatgg tataattatc gtctacagcg   4080
tccaggatag tggcgtgaga aaatggagat ctgcagccct cctttccatg gcatgccgct   4140
ttattgttca ttaaacgcac aatggtctca acgccagata tgggcataga ttctgaagaa   4200
cccgttgaca atccgaagaa gaaggcgtgc aggtctttgg aagactcgca cgttggtctt   4260
ataatgtatg atcgagatgt caccctaatg ccacatggta caggcttatc gcggtcatgg   4320
cgatcggact tgtaatttgc aacgatgggc aaaggatcga cgacatgcca acattctga    4380 acccgtagag atgttaacga tgacgaggat gaatatccca tgctcgctgc cat          4433
```

<210> SEQ ID NO 40
<211> LENGTH: 59
<212> TYPE: DNA
<213> ORGANISM: Artificial Sequence
<220> FEATURE:
<223> OTHER INFORMATION: DNA sequence of 5'Upstream Sbfi gfp gene

```
                                        mutagenesis primer 1

<400> SEQUENCE: 40
ggctagcgtt taaacttaag cttacctgca ggccaccatg gtgagcaagg gcgccgagc      59

<210> SEQ ID NO 41
<211> LENGTH: 59
<212> TYPE: DNA
<213> ORGANISM: Artificial Sequence
<220> FEATURE:
<223> OTHER INFORMATION: DNA sequence of 5'Upstream Sbfi gfp gene
      mutagenesis primer 2

<400> SEQUENCE: 41
gctcggcgcc cttgctcacc atggtggcct gcaggtaagc ttaagtttaa acgctagcc      59

<210> SEQ ID NO 42
<211> LENGTH: 61
<212> TYPE: DNA
<213> ORGANISM: Artificial Sequence
<220> FEATURE:
<223> OTHER INFORMATION: DNA sequence of 3' downstream Sbfi gfp gene
      mutagenesis primer 1

<400> SEQUENCE: 42
cacggcatgg atgagctgta caagtgacct gcaggtgtgc cttctagttg ccagccatct     60
g                                                                    61

<210> SEQ ID NO 43
<211> LENGTH: 61
<212> TYPE: DNA
<213> ORGANISM: Artificial Sequence
<220> FEATURE:
<223> OTHER INFORMATION: DNA sequence of 3' downstream Sbfi gfp gene
      mutagenesis primer 2

<400> SEQUENCE: 43
cagatggctg gcaactagaa ggcacacctg caggtcactt gtacagctca tccatgccgt     60
g                                                                    61

<210> SEQ ID NO 44
<211> LENGTH: 23
<212> TYPE: DNA
<213> ORGANISM: Artificial Sequence
<220> FEATURE:
<223> OTHER INFORMATION: DNA sequence of upper UL55-gene 3 primer

<400> SEQUENCE: 44
ccaccgggta tattttccac agc                                            23

<210> SEQ ID NO 45
<211> LENGTH: 19
<212> TYPE: DNA
<213> ORGANISM: Artificial Sequence
<220> FEATURE:
<223> OTHER INFORMATION: DNA sequence of lower UL55-gene 3 primer

<400> SEQUENCE: 45
gacccgacgc gatttcaga                                                 19

<210> SEQ ID NO 46
<211> LENGTH: 20
<212> TYPE: DNA
<213> ORGANISM: Artificial Sequence
<220> FEATURE:
```

<223> OTHER INFORMATION: DNA sequence upper UL55-gene3 PCR primer

<400> SEQUENCE: 46
actgccactg tgatgataag                                                    20

<210> SEQ ID NO 47
<211> LENGTH: 19
<212> TYPE: DNA
<213> ORGANISM: Artificial Sequence
<220> FEATURE:
<223> OTHER INFORMATION: DNA sequence lower UL55-gene3 PCR primer

<400> SEQUENCE: 47
ctcgctaaag aatgacctg                                                     19

<210> SEQ ID NO 48
<211> LENGTH: 24
<212> TYPE: DNA
<213> ORGANISM: Artificial Sequence
<220> FEATURE:
<223> OTHER INFORMATION: DNA sequence for upper primer localized within
      IBD VP2 coding region

<400> SEQUENCE: 48
ggccgacctc aactctccac tcaa                                               24

<210> SEQ ID NO 49
<211> LENGTH: 24
<212> TYPE: DNA
<213> ORGANISM: Artificial Sequence
<220> FEATURE:
<223> OTHER INFORMATION: DNA sequence for lower primer downstream within
      HVT IBD #1

<400> SEQUENCE: 49
ttcacagcgc ctcgttcaca ctta                                               24

<210> SEQ ID NO 50
<211> LENGTH: 20
<212> TYPE: DNA
<213> ORGANISM: Artificial Sequence
<220> FEATURE:
<223> OTHER INFORMATION: DNA sequence for upper primer of the upstream
      junction of the insertion site of transfer plasmid HVT IBD#1

<400> SEQUENCE: 50
aatattcggg ggtgttagtc                                                    20

<210> SEQ ID NO 51
<211> LENGTH: 18
<212> TYPE: DNA
<213> ORGANISM: Artificial Sequence
<220> FEATURE:
<223> OTHER INFORMATION: DNA sequence for lower primer within the IBDV
      VP2 coding region of HVT IBD #1

<400> SEQUENCE: 51
tgtggttggc atcagaag                                                      18

<210> SEQ ID NO 52
<211> LENGTH: 24
<212> TYPE: DNA
<213> ORGANISM: Artificial Sequence
<220> FEATURE:
<223> OTHER INFORMATION: DNA sequence for upper primer within the IBDV
      VP2 coding region

```
<400> SEQUENCE: 52
cggcgccatg aactacacaa aact                                          24

<210> SEQ ID NO 53
<211> LENGTH: 24
<212> TYPE: DNA
<213> ORGANISM: Artificial Sequence
<220> FEATURE:
<223> OTHER INFORMATION: DNA sequence for lower primer downstream of the
      UL35/36 integration site of HVT-IBD #5

<400> SEQUENCE: 53
ggggcggaaa caaataaact ctcg                                          24

<210> SEQ ID NO 54
<211> LENGTH: 21
<212> TYPE: DNA
<213> ORGANISM: Artificial Sequence
<220> FEATURE:
<223> OTHER INFORMATION: DNA sequence for upper primer of the UL35/36
      insertion site of HVT IBD #5

<400> SEQUENCE: 54
actcggcggt agggcatttt g                                             21

<210> SEQ ID NO 55
<211> LENGTH: 19
<212> TYPE: DNA
<213> ORGANISM: Artificial Sequence
<220> FEATURE:
<223> OTHER INFORMATION: DNA sequence for lower primer within the hCMV
      promoter of HVT IBD #5

<400> SEQUENCE: 55
gggtcgttgg gcggtcagc                                                19

<210> SEQ ID NO 56
<211> LENGTH: 24
<212> TYPE: DNA
<213> ORGANISM: Artificial Sequence
<220> FEATURE:
<223> OTHER INFORMATION: DNA sequence for upper primer upstream of the
      integration site of HVT IBD #6a

<400> SEQUENCE: 56
tagactcggc ggtaggggca tttg                                          24

<210> SEQ ID NO 57
<211> LENGTH: 21
<212> TYPE: DNA
<213> ORGANISM: Artificial Sequence
<220> FEATURE:
<223> OTHER INFORMATION: DNA sequence for lower primer localized within
      the pec promoter of HVT IBD#6a

<400> SEQUENCE: 57
gggggtcgtt gggcggtcag c                                             21

<210> SEQ ID NO 58
<211> LENGTH: 24
<212> TYPE: DNA
<213> ORGANISM: Artificial Sequence
<220> FEATURE:
<223> OTHER INFORMATION: DNA sequence for upper primer localized within
      the IBD VP2 coding region of HVT IBD #6a

<400> SEQUENCE: 58
```
cggcgccatg aactacacaa aact                                               24

<210> SEQ ID NO 59
<211> LENGTH: 24
<212> TYPE: DNA
<213> ORGANISM: Artificial Sequence
<220> FEATURE:
<223> OTHER INFORMATION: DNA sequence for lower primer localized
      downstream of the UL35/36 insertion site

<400> SEQUENCE: 59
ggggcggaaa caaataaact ctcg                                               24

<210> SEQ ID NO 60
<211> LENGTH: 20
<212> TYPE: DNA
<213> ORGANISM: Artificial Sequence
<220> FEATURE:
<223> OTHER INFORMATION: DNA sequence for upper primer upstream of the
      integration site of UL55/Gene3 for HVT IBD #9

<400> SEQUENCE: 60
actgccactg tgatgataag                                                    20

<210> SEQ ID NO 61
<211> LENGTH: 18
<212> TYPE: DNA
<213> ORGANISM: Artificial Sequence
<220> FEATURE:
<223> OTHER INFORMATION: DNA sequence for lower primer downstream of the
      integration site of UL55/Gene3 for HVT IBD #9

<400> SEQUENCE: 61
ctcgctaaag aatgacct                                                      18

<210> SEQ ID NO 62
<211> LENGTH: 20
<212> TYPE: DNA
<213> ORGANISM: Artificial Sequence
<220> FEATURE:
<223> OTHER INFORMATION: DNA sequence for insert orientation upper
      primer surrounding upstream junction of the HVT IBD #9 VP2 gene
      insertion

<400> SEQUENCE: 62
aatattcggg ggtgttagtc                                                    20

<210> SEQ ID NO 63
<211> LENGTH: 24
<212> TYPE: DNA
<213> ORGANISM: Artificial Sequence
<220> FEATURE:
<223> OTHER INFORMATION: DNA sequence for insert orientation lower
      primer localized within IBDV VP2 coding region for HVT IBD #9

<400> SEQUENCE: 63
ctcgcttctc agtgtatgtt tttc                                               24

<210> SEQ ID NO 64
<211> LENGTH: 24
<212> TYPE: DNA
<213> ORGANISM: Artificial Sequence
<220> FEATURE:
<223> OTHER INFORMATION: DNA sequence for upper primer downstream site
      determining correct integration of the IBDV VP2 coding region for
      HVT IBDV #9

<400> SEQUENCE: 64
atcctgagct cgctaaaaat cttg                                            24

<210> SEQ ID NO 65
<211> LENGTH: 22
<212> TYPE: DNA
<213> ORGANISM: Artificial Sequence
<220> FEATURE:
<223> OTHER INFORMATION: DNA sequence for lower primer downstream site
      determining correct integration of the IBDV VP2 coding region for
      HVT IBDV #9

<400> SEQUENCE: 65
cctcgcccgt ctacgctcca ct                                              22

<210> SEQ ID NO 66
<211> LENGTH: 17
<212> TYPE: DNA
<213> ORGANISM: Artificial Sequence
<220> FEATURE:
<223> OTHER INFORMATION: DNA sequence for upper primer for upstream
      region of integration site of UL55-Gene3 for HVT IBD #30

<400> SEQUENCE: 66
tagcgacccg agtagga                                                    17

<210> SEQ ID NO 67
<211> LENGTH: 24
<212> TYPE: DNA
<213> ORGANISM: Artificial Sequence
<220> FEATURE:
<223> OTHER INFORMATION: DNA sequence for lower primer for upstream
      region of integration site of UL55-Gene3 for HVT IBD #30

<400> SEQUENCE: 67
cgcccacggt caaattgtat gtag                                            24

<210> SEQ ID NO 68
<211> LENGTH: 20
<212> TYPE: DNA
<213> ORGANISM: Artificial Sequence
<220> FEATURE:
<223> OTHER INFORMATION: DNA sequence for upper primer to confirm
      correct orientation of VP2 insert surrounding the 3' junction of
      the insertion site of HVT IBD #30

<400> SEQUENCE: 68
ttatccgcgc aatcagaagg                                                 20

<210> SEQ ID NO 69
<211> LENGTH: 22
<212> TYPE: DNA
<213> ORGANISM: Artificial Sequence
<220> FEATURE:
<223> OTHER INFORMATION: DNA sequence for lower primer to confirm
      correct orientation of VP2 insert surrounding the 3' junction of
      the insertion site of HVT IBD #30

<400> SEQUENCE: 69
atggggcgga aacaaataaa ct                                              22

<210> SEQ ID NO 70
<211> LENGTH: 23
<212> TYPE: DNA
<213> ORGANISM: Artificial Sequence
<220> FEATURE:
<223> OTHER INFORMATION: DNA  upper primer to confirm VP2 insert outside of the expression cassette of HVT IBD #30

<400> SEQUENCE: 70
ccaccgggta tattttccac agc                                         23

<210> SEQ ID NO 71
<211> LENGTH: 19
<212> TYPE: DNA
<213> ORGANISM: Artificial Sequence
<220> FEATURE:
<223> OTHER INFORMATION: DNA sequence for lower primer to confirm  VP2
      insert integration outside of the expression cassette of HVT
      IBD #30

<400> SEQUENCE: 71
gacccgacgc gatttcaga                                              19

<210> SEQ ID NO 72
<211> LENGTH: 24
<212> TYPE: DNA
<213> ORGANISM: Artificial Sequence
<220> FEATURE:
<223> OTHER INFORMATION: DNA sequence for upper primer to confirm
      correct orientation of VP2 insert upstream of the UL35/36
      integration site of HVT IBD #31

<400> SEQUENCE: 72
ctcggcggta ggggcatttg ataa                                        24

<210> SEQ ID NO 73
<211> LENGTH: 24
<212> TYPE: DNA
<213> ORGANISM: Artificial Sequence
<220> FEATURE:
<223> OTHER INFORMATION: DNA sequence for lower primer to confirm
      correct orientation of VP2 insert localized within the chicken
      beta actin promoter of HVT IBD #31

<400> SEQUENCE: 73
agatggggag agtgaagcag aacg                                        24

<210> SEQ ID NO 74
<211> LENGTH: 20
<212> TYPE: DNA
<213> ORGANISM: Artificial Sequence
<220> FEATURE:
<223> OTHER INFORMATION: DNA sequence for upper primer to confirm
      confirmation of VP2 insert localized within the IBDV VP2 coding
      region

<400> SEQUENCE: 74
ttatccgcgc aatcagaagg                                             20

<210> SEQ ID NO 75
<211> LENGTH: 22
<212> TYPE: DNA
<213> ORGANISM: Artificial Sequence
<220> FEATURE:
<223> OTHER INFORMATION: DNA sequence for lower primer to confirm
      correct orientation of VP2 insert located downstream of UL35/36
      integration site of HVT IBD #31

<400> SEQUENCE: 75
atggggcgga aacaaataaa ct                                          22

<210> SEQ ID NO 76
<211> LENGTH: 20

```
<212> TYPE: DNA
<213> ORGANISM: Artificial Sequence
<220> FEATURE:
<223> OTHER INFORMATION: DNA sequence for upper primer targeting the
      downstream integration site of the VP2 insert of HVT IBD #31
      located within the VP2 insert

<400> SEQUENCE: 76
ttatccgcgc aatcagaagg                                                 20

<210> SEQ ID NO 77
<211> LENGTH: 22
<212> TYPE: DNA
<213> ORGANISM: Artificial Sequence
<220> FEATURE:
<223> OTHER INFORMATION: DNA sequence for lower primer localized
      downstream of the UL35/36 site of HVT IBD #31

<400> SEQUENCE: 77
atggggcgga aacaaataaa ct                                              22

<210> SEQ ID NO 78
<211> LENGTH: 24
<212> TYPE: DNA
<213> ORGANISM: Artificial Sequence
<220> FEATURE:
<223> OTHER INFORMATION: DNA sequence for upper primer for upstream
      region of integration site of Gene3-UL55 for HVT-IBD #34

<400> SEQUENCE: 78
cctcgcccgt ctacgctcca ctga                                            24

<210> SEQ ID NO 79
<211> LENGTH: 24
<212> TYPE: DNA
<213> ORGANISM: Artificial Sequence
<220> FEATURE:
<223> OTHER INFORMATION: DNA sequence for lower primer localized within
      chicken beta-actin promoter for HVT-IBD #34

<400> SEQUENCE: 79
ccgcccccat cgctgcacaa aata                                            24

<210> SEQ ID NO 80
<211> LENGTH: 18
<212> TYPE: DNA
<213> ORGANISM: Artificial Sequence
<220> FEATURE:
<223> OTHER INFORMATION: DNA sequence for upper primer localized within
      IBDV VP2 coding region for HVT-IBD #34

<400> SEQUENCE: 80
ggccctccgt cccgtcac                                                   18

<210> SEQ ID NO 81
<211> LENGTH: 24
<212> TYPE: DNA
<213> ORGANISM: Artificial Sequence
<220> FEATURE:
<223> OTHER INFORMATION: DNA sequence for lower primer localized
      downstream of Gene3-UL55 insertion site for HVT IBD #34

<400> SEQUENCE: 81
ttcacagcgc ctcgttcaca ctta                                            24

<210> SEQ ID NO 82
<211> LENGTH: 19
```

```
<212> TYPE: DNA
<213> ORGANISM: Artificial Sequence
<220> FEATURE:
<223> OTHER INFORMATION: DNA sequence for upper primer localized outside
      of the VP2 expression cassette of HVT IBD #34

<400> SEQUENCE: 82
ctcgctaaag aatgacctg                                             19

<210

```
<212> TYPE: DNA
<213> ORGANISM: Artificial Sequence
<220> FEATURE:
<223> OTHER INFORMATION: DNA sequence for upper primer outside of the
      expression cassette of HVT ND #38

<400> SEQUENCE: 88
gaggtccgtc gccacaa                                                    17

<210> SEQ ID NO 89
<211> LENGTH: 22
<212> TYPE: DNA
<213> ORGANISM: Artificial Sequence
<220> FEATURE:
<223> OTHER INFORMATION: DNA sequence for lower primer outside of the
      expression cassette of HVT ND #38

<400> SEQUENCE: 89
gcaagacaaa taacgcagac ta                                              22

<210> SEQ ID NO 90
<211> LENGTH: 24
<212> TYPE: DNA
<213> ORGANISM: Artificial Sequence
<220> FEATURE:
<223> OTHER INFORMATION: DNA sequence for upper primer upstream region
      of integration site of UL35-UL36 for HVT-ND #39

<400> SEQUENCE: 90
ctcggcggta ggggcatttg ataa                                            24

<210> SEQ ID NO 91
<211> LENGTH: 24
<212> TYPE: DNA
<213> ORGANISM: Artificial Sequence
<220> FEATURE:
<223> OTHER INFORMATION: DNA sequence for lower primer localized within
      chicken beta-actin promoter HVT-ND #39

<400> SEQUENCE: 91
agatggggag agtgaagcag aacg                                            24

<210> SEQ ID NO 92
<211> LENGTH: 20
<212> TYPE: DNA
<213> ORGANISM: Artificial Sequence
<220> FEATURE:
<223> OTHER INFORMATION: DNA sequence for upper primer surrounding the
      downstream junction of the insertion localized within poly A
      region of HVT-ND #39

<400> SEQUENCE: 92 tgggatgcg gtgggctcta                                                  20

<210> SEQ ID NO 93
<211> LENGTH: 24
<212> TYPE: DNA
<213> ORGANISM: Artificial Sequence
<220> FEATURE:
<223> OTHER INFORMATION: DNA sequence for lower primer localized
      downstream of UL35-UL36 insertion of HVT-ND #39

<400> SEQUENCE: 93
ggggcggaaa caaataaact ctcg                                            24

<210> SEQ ID NO 94
<211> LENGTH: 23
```

```
<212> TYPE: DNA
<213> ORGANISM: Artificial Sequence
<220> FEATURE:
<223> OTHER INFORMATION: DNA sequence for upper primer outside of the
      expression cassette of HVT-ND #39

<400> SEQUENCE: 94
ccaccgggta tattttccac agc                                           23

<210> SEQ ID NO 95
<211> LENGTH: 19
<212> TYPE: DNA
<213> ORGANISM: Artificial Sequence
<220> FEATURE:
<223> OTHER INFORMATION: DNA sequence for lower primer outside of the
      expression cassette HVT-ND #39

<400> SEQUENCE: 95
gacccgacgc gatttcaga                                                19

<210> SEQ ID NO 96
<211> LENGTH: 24
<212> TYPE: DNA
<213> ORGANISM: Artificial Sequence
<220> FEATURE:
<223> OTHER INFORMATION: DNA sequence for upper primer upstream of the
      UL35/36 integration site for HVT ND #40

<400> SEQUENCE: 96
ctcggcggta ggggcatttg ataa                                          24

<210> SEQ ID NO 97
<211> LENGTH: 24
<212> TYPE: DNA
<213> ORGANISM: Artificial Sequence
<220> FEATURE:
<223> OTHER INFORMATION: DNA sequence for lower primer localized within
      chicken beta actin promoter for HVT ND #40

<400> SEQUENCE: 97
agatggggag agtgaagcag aacg                                          24

<210> SEQ ID NO 98
<211> LENGTH: 24
<212> TYPE: DNA
<213> ORGANISM: Artificial Sequence
<220> FEATURE:
<223> OTHER INFORMATION: DNA sequence for upper primer localized within
      NDVF coding region for HVT ND #40

<400> SEQUENCE: 98
accagatgag ggccactaca aaaa                                          24

<210> SEQ ID NO 99
<211> LENGTH: 24
<212> TYPE: DNA
<213> ORGANISM: Artificial Sequence
<220> FEATURE:
<223> OTHER INFORMATION: DNA sequence for lower primer located at the
      downstream junction of the insertion site for HVT ND #40

<400> SEQUENCE: 99
atggggcgga aacaaataaa ctct                                          24

<210> SEQ ID NO 100
<211> LENGTH: 23
<212> TYPE: DNA
```

```
<213> ORGANISM: Artificial Sequence
<220> FEATURE:
<223> OTHER INFORMATION: DNA sequence for upper primer located outside
      of the expression cassette for HVT ND #40

<400> SEQUENCE: 100
ccaccgggta tattttccac agc                                            23

<210> SEQ ID NO 101
<211> LENGTH: 19
<212> TYPE: DNA
<213> ORGANISM: Artificial Sequence
<220> FEATURE:
<223> OTHER INFORMATION: DNA sequence for lower primer located outside
      of the expression cassette for HVT #40

<400> SEQUENCE: 101
gacccgacgc gatttcaga                                                 19

<210> SEQ ID NO 102
<211> LENGTH: 48
<212> TYPE: DNA
<213> ORGANISM: Artificial Sequence
<220> FEATURE:
<223> OTHER INFORMATION: DNA sequence for upper primer for PCR
      amplification of cassette for HVT ND #42

<400> SEQUENCE: 102
tacttagtca taggcgcgcc aactccgccc gttttatgac tagaacca                 48

<210> SEQ ID NO 103
<211> LENGTH: 49
<212> TYPE: DNA
<213> ORGANISM: Artificial Sequence
<220> FEATURE:
<223> OTHER INFORMATION: DNA sequence for lower primer for PCR
      amplification of cassette for HVT ND #42

<400> SEQUENCE: 103
tgacagtatc tagctagctc gactctagag gatccgaaaa aacctccca                49

<210> SEQ ID NO 104
<211> LENGTH: 20
<212> TYPE: DNA
<213> ORGANISM: Artificial Sequence
<220> FEATURE:
<223> OTHER INFORMATION: DNA sequence for upper primer located outside
      of cassette for HVT ND #42

<400> SEQUENCE: 104
actgccactg tgatgataag                                                20

<210> SEQ ID NO 105
<211> LENGTH: 19
<212> TYPE: DNA
<213> ORGANISM: Artificial Sequence
<220> FEATURE:
<223> OTHER INFORMATION: DNA sequence for lower primer located outside
      of cassette for HVT ND #42

<400> SEQUENCE: 105
ctcgctaaag aatgacctg                                                 19

<210> SEQ ID NO 106
<211> LENGTH: 24
<212> TYPE: DNA
<213> ORGANISM: Artificial Sequence
```

-continued

<220> FEATURE:
<223> OTHER INFORMATION: DNA sequence for upper primer located upstream
      and outside of the expression cassette for HVT ND #42

<400> SEQUENCE: 106
ttcacagcgc ctcgttcaca ctta 24

<210> SEQ ID NO 107
<211> LENGTH: 24
<212> TYPE: DNA
<213> ORGANISM: Artificial Sequence
<220> FEATURE:
<223> OTHER INFORMATION: DNA sequence for lower primer located within ND
      F coding region for HVT ND #42

<400> SEQUENCE: 107
ttcggacggt cagcatcaga ggta 24

<210> SEQ ID NO 108
<211> LENGTH: 20
<212> TYPE: DNA
<213> ORGANISM: Artificial Sequence
<220> FEATURE:
<223> OTHER INFORMATION: DNA sequence for upper primer located upstream
      and outside of the expression cassette for HVT ND #42

<400> SEQUENCE: 108
gcctcggcgt ggtagttctc 20

<210> SEQ ID NO 109
<211> LENGTH: 19
<212> TYPE: DNA
<213> ORGANISM: Artificial Sequence
<220> FEATURE:
<223> OTHER INFORMATION: DNA sequence for lower primer located within ND
      F coding region for HVT ND #42

<400> SEQUENCE: 109
attcggacgg tcagcatca 19

<210> SEQ ID NO 110
<211> LENGTH: 24
<212> TYPE: DNA
<213> ORGANISM: Artificial Sequence
<220> FEATURE:
<223> OTHER INFORMATION: DNA sequence for upper primer located upstream
      and outside of the expression cassette for HVT ND #42

<400> SEQUENCE: 110
ttcacagcgc ctcgttcaca ctta 24

<210> SEQ ID NO 111
<211> LENGTH: 24
<212> TYPE: DNA
<213> ORGANISM: Artificial Sequence
<220> FEATURE:
<223> OTHER INFORMATION: DNA sequence for lower primer located within
      NDV F coding region for HVT ND #42

<400> SEQUENCE: 111
gcttttgcac acgcctcttt atcc 24

<210> SEQ ID NO 112
<211> LENGTH: 24
<212> TYPE: DNA
<213> ORGANISM: Artificial Sequence
<220> FEATURE:

<223> OTHER INFORMATION: DNA sequence for upper primer located upstream
      and outside of the expression

<400> SEQUENCE: 112
ttcacagcgc ctcgttcaca ctta                                              24

<210> SEQ ID NO 113
<211> LENGTH: 24
<212> TYPE: DNA
<213> ORGANISM: Artificial Sequence
<220> FEATURE:
<223> OTHER INFORMATION: DNA sequence for lower primer located within ND
      F coding region for HVT ND #42

<400> SEQUENCE: 113
ttcggacggt cagcatcaga ggta                                              24

<210> SEQ ID NO 114
<211> LENGTH: 24
<212> TYPE: DNA
<213> ORGANISM: Artificial Sequence
<220> FEATURE:
<223> OTHER INFORMATION: DNA sequence for upper primer located upstream
      and outside of the expression cassette for HVT ND #42

<400> SEQUENCE: 114
accagatgag ggccactaca aaaa                                              24

<210> SEQ ID NO 115
<211> LENGTH: 21
<212> TYPE: DNA
<213> ORGANISM: Artificial Sequence
<220> FEATURE:
<223> OTHER INFORMATION: DNA sequence for lower primer located within ND
      F coding region for HVT ND #42

<400> SEQUENCE: 115
cgcccgtcta cgctccactg a                                                 21

<210> SEQ ID NO 116
<211> LENGTH: 18
<212> TYPE: DNA
<213> ORGANISM: Artificial Sequence
<220> FEATURE:
<223> OTHER INFORMATION: DNA sequence for upper primer localized
      upstream of UL55 for HVT ND #44

<400> SEQUENCE: 116
aatattcggg ggtgttag                                                     18

<210> SEQ ID NO 117
<211> LENGTH: 20
<212> TYPE: DNA
<213> ORGANISM: Artificial Sequence
<220> FEATURE:
<223> OTHER INFORMATION: DNA sequence for lower primer localized within
      chicken beta actin promoter for HVT ND #44

<400> SEQUENCE: 117
gggggagatg gggagagtga                                                   20

<210> SEQ ID NO 118
<211> LENGTH: 20
<212> TYPE: DNA
<213> ORGANISM: Artificial Sequence
<220> FEATURE:
<223> OTHER INFORMATION: DNA sequence for upper primer localized upstream of UL55 for HVT ND #44

<400> SEQUENCE: 118
gcctcggcgt ggtagttctc                                                   20

<210> SEQ ID NO 119
<211> LENGTH: 24
<212> TYPE: DNA
<213> ORGANISM: Artificial Sequence
<220> FEATURE:
<223> OTHER INFORMATION: DNA sequence for lower primer localized within
      chicken beta actin promoter for HVT ND #44

<400> SEQUENCE: 119
ccgcccccat cgctgcacaa aata                                              24

<210> SEQ ID NO 120
<211> LENGTH: 24
<212> TYPE: DNA
<213> ORGANISM: Artificial Sequence
<220> FEATURE:
<223> OTHER INFORMATION: DNA sequence for upper primer localized within
      NDV F gene coding sequence for HVT ND #44

<400> SEQUENCE: 120
accagatgag ggccactaca aaaa                                              24

<210> SEQ ID NO 121
<211> LENGTH: 24
<212> TYPE: DNA
<213> ORGANISM: Artificial Sequence
<220> FEATURE:
<223> OTHER INFORMATION: DNA sequence for lower primer localized
      downstream of UL55-Gene3 insertion site for HVT ND #44

<400> SEQUENCE: 121
ctcgcccgtc tacgctccac tgaa 24

<210> SEQ ID NO 122
<211> LENGTH: 20
<212> TYPE: DNA
<213> ORGANISM: Artificial Sequence
<220> FEATURE:
<223> OTHER INFORMATION: DNA sequence for upper primer localized outside of the expression cassette for HVT ND #44

<400> SEQUENCE: 122
actgccactg tgatgataag 20

<210> SEQ ID NO 123
<211> LENGTH: 19
<212> TYPE: DNA
<213> ORGANISM: Artificial Sequence
<220> FEATURE:
<223> OTHER INFORMATION: DNA sequence for lower primer localized outside of the expression cassette for HVT #44

<400> SEQUENCE: 123
ctcgctaaag aatgacctg 19

<210> SEQ ID NO 124
<211> LENGTH: 20
<212> TYPE: DNA
<213> ORGANISM: Artificial Sequence
<220> FEATURE:
<223> OTHER INFORMATION: DNA sequence for upper primer localized outside of the expression cassette for HVT #45

```
<400> SEQUENCE: 124
actgccactg tgatgataag                                               20

<210> SEQ ID NO 125
<211> LENGTH: 19
<212> TYPE: DNA
<213> ORGANISM: Artificial Sequence
<220> FEATURE:
<223> OTHER INFORMATION: DNA sequence for lower primer localized outside
      of the expression cassette for HVT #45

<400> SEQUENCE: 125
ctcgctaaag aatgacctg                                                19

<210> SEQ ID NO 126
<211> LENGTH: 24
<212> TYPE: DNA
<213> ORGANISM: Artificial Sequence
<220> FEATURE:
<223> OTHER INFORMATION: DNA sequence for upper primer located upstream
      and outside of the expression cassette for HVT ND #45

<400> SEQUENCE: 126
ctcgcccgtc tacgctccac tgaa                                          24

<210> SEQ ID NO 127
<211> LENGTH: 24
<212> TYPE: DNA
<213> ORGANISM: Artificial Sequence
<220> FEATURE:
<223> OTHER INFORMATION: DNA sequence for lower primer located within ND
      F coding region for HVT ND #45

<400> SEQUENCE: 127
gcttttgcac acgcctcttt atcc                                          24

<210> SEQ ID NO 128
<211> LENGTH: 18
<212> TYPE: DNA
<213> ORGANISM: Artificial Sequence
<220> FEATURE:
<223> OTHER INFORMATION: DNA sequence for upper primer located upstream
      and outside of the expression cassette for HVT ND #45

<400> SEQUENCE: 128
cacgctgcta ttgtaacg                                                 18

<210> SEQ ID NO 129
<211> LENGTH: 19
<212> TYPE: DNA
<213> ORGANISM: Artificial Sequence
<220> FEATURE:
<223> OTHER INFORMATION: DNA sequence for lower primer located within
      the ND F coding region for HVT ND #45

<400> SEQUENCE: 129
actgggatcc tggtagaag                                                19

<210> SEQ ID NO 130
<211> LENGTH: 24
<212> TYPE: DNA
<213> ORGANISM: Artificial Sequence
<220> FEATURE:
<223> OTHER INFORMATION: DNA sequence for upper primer surrounding the
      downstream junction of the insertion for HVT ND #45
```

```
<400> SEQUENCE: 130
accagatgag ggccactaca aaaa                                            24

<210> SEQ ID NO 131
<211> LENGTH: 24
<212> TYPE: DNA
<213> ORGANISM: Artificial Sequence
<220> FEATURE:
<223> OTHER INFORMATION: DNA sequence for lower primer localized
      downstream of Gene3-UL55 insertion site

<400> SEQUENCE: 131
ttcacagcgc ctcgttcaca ctta                                            24

<210> SEQ ID NO 132
<211> LENGTH: 23
<212> TYPE: DNA
<213> ORGANISM: Artificial Sequence
<220> FEATURE:
<223> OTHER INFORMATION: DNA sequence for upper primer surrounding the
      downstream junction of the insertion for HVT ND #45

<400> SEQUENCE: 132
gcacatccgc tcttattacc tat                                             23

<210> SEQ ID NO 133
<211> LENGTH: 24
<212> TYPE: DNA
<213> ORGANISM: Artificial Sequence
<220> FEATURE:
<223> OTHER INFORMATION: DNA sequence for lower primer localized that
      localized downstream of Gene3-UL55 insertion site

<400> SEQUENCE: 133
ttcacagcgc ctcgttcaca ctta                                            24

<210> SEQ ID NO 134
<211> LENGTH: 23
<212> TYPE: DNA
<213> ORGANISM: Artificial Sequence
<220> FEATURE:
<223> OTHER INFORMATION: DNA sequence for upper primer localized outside
      of the expression cassette for HVT ND #46

<400> SEQUENCE: 134
tagagggggt atgtttccac tgc                                             23

<210> SEQ ID NO 135
<211> LENGTH: 23
<212> TYPE: DNA
<213> ORGANISM: Artificial Sequence
<220> FEATURE:
<223> OTHER INFORMATION: DNA sequence for lower primer localized outside
      of the expression cassette for HVT ND #46

<400> SEQUENCE: 135
gtcataacat catctcgcta aag                                             23

<210> SEQ ID NO 136
<211> LENGTH: 18
<212> TYPE: DNA
<213> ORGANISM: Artificial Sequence
<220> FEATURE:
<223> OTHER INFORMATION: DNA sequence for upper primer located upstream
      and outside of the integration site for HVT ND #46

<400> SEQUENCE: 136
```

```
cacgctgcta ttgtaacg                                                    18

<210> SEQ ID NO 137
<211> LENGTH: 21
<212> TYPE: DNA
<213> ORGANISM: Artificial Sequence
<220> FEATURE:
<223> OTHER INFORMATION: DNA sequence for lower primer located within
      the mCMV promoter for HVT ND #46

<400> SEQUENCE: 137
ggtgaacgcc ccctatgtgg a                                                21

<210> SEQ ID NO 138
<211> LENGTH: 24
<212> TYPE: DNA
<213> ORGANISM: Artificial Sequence
<220> FEATURE:
<223> OTHER INFORMATION: DNA sequence for upper primer localized within
      NDV F gene coding sequence for HVT ND #46

<400> SEQUENCE: 138
accagatgag ggccactaca aaaa                                             24

<210> SEQ ID NO 139
<211> LENGTH: 24
<212> TYPE: DNA
<213> ORGANISM: Artificial Sequence
<220> FEATURE:
<223> OTHER INFORMATION: DNA sequence for lower primer localized
      downstream and outside of expression cassette for HVT ND #46

<400> SEQUENCE:

```
atgtggtata cttagcctgg ttc                                             23

<210> SEQ ID NO 143
<211> LENGTH: 18
<212> TYPE: DNA
<213> ORGANISM: Artificial Sequence
<220> FEATURE:
<223> OTHER INFORMATION: DNA sequence for lower primer localized
      downstream and outside of expression cassette for HVT ND #46

<400> SEQUENCE: 143
aatattcggg ggtgttag                                                   18

<210> SEQ ID NO 144
<211> LENGTH: 23
<212> TYPE: DNA
<213> ORGANISM: Artificial Sequence
<220> FEATURE:
<223> OTHER INFORMATION: DNA sequence for upper primer localized within
      NDV F gene coding sequence for HVT ND #46

<400> SEQUENCE: 144
ggaataatac cctagaccag atg                                             23

<210> SEQ ID NO 145
<211> LENGTH: 23
<212> TYPE: DNA
<213> ORGANISM: Artificial Sequence
<220> FEATURE:
<223> OTHER INFORMATION: DNA sequence for lower primer localized
      downstream and outside of expression cassette for HVT ND #46

<400> SEQUENCE: 145
gtcataacat catctcgcta aag                                             23

<210> SEQ ID NO 146
<211> LENGTH: 24
<212> TYPE: DNA
<213> ORGANISM: Artificial Sequence
<220> FEATURE:
<223> OTHER INFORMATION: DNA sequence for upper primer localized
      upstream region of integration site of Gene 3-UL55 for HVT ND #48

<400> SEQUENCE: 146
cctcgcccgt ctacgctcca ctga                                            24

<210> SEQ ID NO 147
<211> LENGTH: 24
<212> TYPE: DNA
<213> ORGANISM: Artificial Sequence
<220> FEATURE:
<223> OTHER INFORMATION: DNA sequence for lower primer localized within
      chicken beta-actin promoter for HVT ND #48

<400> SEQUENCE: 147
ccgcccccat cgctgcacaa aata                                            24

<210> SEQ ID NO 148
<211> LENGTH: 24
<212> TYPE: DNA
<213> ORGANISM: Artificial Sequence
<220> FEATURE:
<223> OTHER INFORMATION: DNA sequence for upper primer surrounding the
      downstream junction of the insertion for HVT ND #48

<400> SEQUENCE: 148
accagatgag ggccactaca aaaa                                            24
```

<210> SEQ ID NO 149
<211> LENGTH: 24
<212> TYPE: DNA
<213> ORGANISM: Artificial Sequence
<220> FEATURE:
<223> OTHER INFORMATION: DNA sequence for lower primer localized downstream of Gene 3-UL55 insertion site for HVT ND #48

<400> SEQUENCE: 149
ttcacagcgc ctcgttcaca ctta                                          24

<210> SEQ ID NO 150
<211> LENGTH: 23
<212> TYPE: DNA
<213> ORGANISM: Artificial Sequence
<220> FEATURE:
<223> OTHER INFORMATION: DNA sequence for upper primer surrounding the
      downstream junction of the insertion for HVT ND #48

<400> SEQUENCE: 150
gcacatccgc tcttattacc tat 23

<210> SEQ ID NO 151
<211> LENGTH: 24
<212> TYPE: DNA
<213> ORGANISM: Artificial Sequence
<220> FEATURE:
<223> OTHER INFORMATION: DNA sequence for lower primer localized
      downstream of Gene 3-UL55 insertion site for HVT ND #48

<400> SEQUENCE: 151
ttcacagcgc ctcgttcaca ctta 24

<210> SEQ ID NO 152
<211> LENGTH: 20
<212> TYPE: DNA
<213> ORGANISM: Artificial Sequence
<220> FEATURE:
<223> OTHER INFORMATION: DNA sequence for upper primer located outside
      of the expression cassette for HVT ND #48

<400> SEQUENCE: 152
actgccactg tgatgataag 20

<210> SEQ ID NO 153
<211> LENGTH: 19
<212> TYPE: DNA
<213> ORGANISM: Artificial Sequence
<220> FEATURE:
<223> OTHER INFORMATION: DNA sequence for lower primer located outside
      of the expression cassette for HVT ND #48

<400> SEQUENCE: 153
ctcgctaaag aatgacctg 19

<210> SEQ ID NO 154
<211> LENGTH: 48
<212> TYPE: DNA
<213> ORGANISM: Artificial Sequence
<220> FEATURE:
<223> OTHER INFORMATION: DNA sequence for upper primer for amplification
      of the NDV F expression cassette of HVT ND #42 for HVT-IBD-ND
      #42-#30

<400> SEQUENCE: 154
tacttagtca taggcgcgcc aactccgccc gttttatgac tagaacca 48

<210> SEQ ID NO 155
<211> LENGTH: 49
<212> TYPE: DNA
<213> ORGANISM: Artificial Sequence
<220> FEATURE:
<223> OTHER INFORMATION: DNA sequence for lower primer for amplification of the NDV F expression cassette of HVT ND #42 for HVT-IBD-ND #42-#30

<400> SEQUENCE: 155
tgacagtatc tagctagctc gactctagag gatccgaaaa aacctccca        49

<210> SEQ ID NO 156
<211> LENGTH: 52
<212> TYPE: DNA
<213> ORGANISM: Artificial Sequence
<220> FEATURE:
<223> OTHER INFORMATION: DNA sequence for upper primer for amplification of the IBD gene expression cassette of plasmid #30 for HVT-IBD-ND #42-#30

<400> SEQUENCE: 156
ctgtcagacg agtaccggtt tgacattgat tattgactag ttattaatag ta 52

<210> SEQ ID NO 157
<211> LENGTH: 42
<212> TYPE: DNA
<213> ORGANISM: Artificial Sequence
<220> FEATURE:
<223> OTHER INFORMATION: DNA sequence for lower primer for amplification of the IBD gene expression cassette of plasmid #30 for HVT-IBD-ND #42-#30

<400> SEQUENCE: 157
tctagtactg atggtaccac catagagccc accgcatccc ca 42

<210> SEQ ID NO 158
<211> LENGTH: 570
<212> TYPE: DNA
<213> ORGANISM: Artificial Sequence
<220> FEATURE:
<223> OTHER INFORMATION: DNA sequence for RSV LTR promoter

<400> SEQUENCE: 158
actctcagta caatctgctc tgatgccgca tagttaagcc agtatctgct ccctgcttgt 60
gtgttggagg tcgctgagta gtgcgcgagc aaaatttaag ctacaacaag gcaaggcttg 120
accgacaatt gcatgaagaa tctgcttagg gttaggcgtt ttgcgctgct tcgcgatgta 180
cgggccagat atacgcgtat ctgaggggac tagggtgtgt ttaggcgaaa agcggggctt 240
cggttgtacg cggttaggag tcccctcagg atatagtagt ttcgcttttg catagggagg 300
gggaaatgta gtcttatgca atactcttgt agtcttgcaa catggtaacg atgagttagc 360
aacatgcctt acaaggagag aaaaagcacc gtgcatgccg attggtggaa gtaaggtggt 420
acgatcgtgc cttattagga aggcaacaga cgggtctgac atggattgga cgaaccactg 480
aattccgcat tgcagagata ttgtatttaa gtgcctagct cgatacaata aacgccattt 540
gaccattcac cacattggtg tgcacctcca 570

RECOMBINANT HERPESVIRUS OF TURKEY VECTORS EXPRESSING ANTIGENS OF AVIAN PATHOGENS AND USES THEREOF

CROSS REFERENCE TO RELATED APPLICATIONS

This application claims the benefit under 35 USC 119(e) to U.S. Provisional Application No. 62/898,651 filed on Sep. 11, 2019, which is hereby incorporated by reference in its entirety.

FIELD OF THE INVENTION

The invention relates to recombinant viral vectors for the insertion and expression of foreign genes for use in safe immunizations to protect against a variety of pathogens. It also relates to multivalent compositions or vaccine comprising one or more recombinant viral vectors for protection against a variety of pathogens. The present invention relates to methods of making an using said recombinant viral vectors.

BACKGROUND

Marek's disease, a highly contagious lymphoproliferative disease, is one of the most prevalent avian infections that predominantly affect young chickens. Marek's disease is caused by Marek's Disease virus. Marek's Disease Virus (MDV), a herpesvirus, is a member of the genus Mardivirus, that has three serotypes (species): MDV-1 (Gallid herpesvirus 2), MDV-2 (Gallid herpesvirus 3) and MDV-3 (Meleagrid herpesvirus 1, Turkey Herpesvirus (HVT)). MDV-1 is the most virulent of the three serotypes causing widespread disease in unvaccinated poultry. Birds infected with MDV-1 show neurologic, visceral and cutaneous clinical symptoms such as paralysis of legs, wings and neck; eye lesions and vision impairment, weight loss, cancerous tumors in many organs, such as the thymus, heart, lungs, gonads, muscles and feather follicles. Morbidity of affected birds is 10-50% and mortality can be up to 100%. Even though Marek's disease can affect birds at any age, acute Marek's disease causes death in large number of unvaccinated birds at an early age of four to eight weeks. Marek disease is spread by direct or indirect exposure to chicken dander of infected chicken and the virus is taken in by inhalation. MDV-2 and MDV-3 represent avirulent viral strains and have been used in preparation of vaccination against the related and virulent MDV-1.

In addition to Marek's Disease there are several pathogens that affect poultry and pose a threat to poultry farming. Producers must rely on immunity provided by vaccines to protect flocks from viral, bacterial and other pathogens. Live, killed and recombinant vaccines have been used in vaccinating birds. Live vaccines have the advantage of strong and long-lasting immunity, but they must be handled carefully as they might cause mild to severe reaction. On the other hand, killed vaccines are more stable and safer than live vaccines but generate a weaker immune response thus requiring multiple administrations. Both live and killed vaccines have proven safe and effective however a need remains to develop and continually improve upon multivalent vaccines to provide protection against more than one pathogen in one vaccination.

Recombinant vectored vaccines have been developed to provide immunity to multiple pathogens simultaneously. These vaccines are made by removing some non-essential gene sections within the host genome of a non-pathogenic organism and replacing these with one or more genes coding for antigens that are responsible for producing an immune response against a pathogenic organism. The newly produced vector is then used to infect the host, where it will replicate and express the antigens of the virulent organism(s) to elicit immune response. Recombinant vectored vaccines combine the advantages of live and killed vaccines. Recombinant vectors, similar to live vaccine, provides longer lasting immunity and at the same time causing milder reaction after vaccination as killed vaccines. Additionally, both the vector and the inserted gene (s) can provide immunity protecting the birds from two or more diseases.

Marek Disease Viruses are one of the most efficacious vectors for multivalent vaccines to immunize against poultry diseases since these viruses induce lifetime protection with just one vaccination. Additionally, these viruses are limited to avian hosts, therefore there is no danger of infecting other animals and the people working in poultry farms. Among Marek Disease Viruses, Herpes Virus of Turkeys (HVT) has been used more extensively both as live vaccine and as recombinant vaccine vector against the more virulent MDV-1. HVT was first isolated from turkeys in 1969-1970 and it was soon found to be protective against MDV and licensed as vaccine in 1971. Herpes virus of Turkeys (HVT) has similar antigenic features as Marek's disease virus (MDV-1), but it is not pathogenic to chickens. In addition, HVT is not sensitive to maternally derived antibodies against MDV or HVT therefore live HVT vaccine have been used to effectively vaccinate against MDV-1 in ovo or at an early age before hatching. In addition, the HVT genome has been used as vaccine vector to harbor foreign DNA sequences of other avian pathogens.

SUMMARY OF THE INVENTION

The invention provides recombinant viral vectors for the insertion and expression of foreign genes for use in safe immunizations to protect avians against a variety of pathogens. The invention also provides multivalent compositions or vaccines comprising one or more recombinant HVT viral vectors for protection against a variety of pathogens. Additionally, the invention provides methods of making and using the recombinant viral vectors alone or in combination with other vaccines or pharmaceutical compositions.

In one aspect the present invention provides a recombinant Herpesvirus of turkey (HVT) genome comprising one or more nucleotide sequence(s) coding for one or more heterologous antigen(s) inserted into the intergenic loci UL 35/UL 36 in the unique long (UL) region of the HVT genome.

In one aspect the present invention provides a recombinant Herpesvirus of Turkey (HVT) genome comprising one or more nucleotide sequences coding for one or more heterologous antigens or antigens inserted into the intergenic loci UL 35/UL 36 in the unique long region of the HVT genome and one or more nucleotide sequences or sequences coding for one or more heterologous antigens inserted at the UL55/Gene 3 site in the unique long region (UL) of the HVT genome.

In one or more embodiments the present invention provides a recombinant HVT wherein the one or more heterologous antigens or antigens are protective against avian pathogens or pathogens selected from the group consisting of: Infectious Bursal Disease Virus (IBDV); Newcastle disease virus (NDV); Infectious Bronchitis Virus (IBV);

Infectious Laryngotracheitis Virus (ILTV); Chicken Anemia Virus (CAV); and Avian Influenza Virus (AIV).

In one or more embodiments the present invention provides a recombinant HVT wherein the one or one or more heterologous antigens are selected from the group consisting of: the VP2, VP3 or VP4 proteins of the Infectious Bursal Disease Virus (IBDV); the VP1 or VP2 proteins of the Chicken Anemia Virus (CAV); the F/HN chimera protein or the F, NP, P, M, HN, or L proteins of the Newcastle Disease Virus (NDV); the S1, S2 or M proteins of Infectious Bronchitis Virus (IBV); the gB, gC, gD, gE, gH, gI or gL proteins of the Infectious Laryngotracheitis Virus (ILTV); and any of the HA, NA, NP or M proteins of the Avian Influenza Virus (AIV).

In one or more embodiments the recombinant HVT of the present invention provides that the one or more heterologous antigen is protective against IBDV. In one embodiment the recombinant HVT of the present invention provides the one or more heterologous antigen is the VP2 protein of IBDV. In one embodiment the recombinant HVT of the present invention provides the VP2 protein is encoded by the nucleotide sequence comprising at least 80% sequence identity to the nucleotide sequence comprising SEQ ID NO. 5 or SEQ ID NO. 10. In one embodiment the recombinant HVT of the present invention provides the VP2 protein encoded by the nucleotide sequence comprising either SEQ ID NO. 5 or SEQ ID NO.10.

In one or more embodiments the recombinant HVT of the present invention provides the one or more heterologous antigen or antigen is protective against Newcastle Disease Virus (NDV). In one embodiment the recombinant HVT of the present invention provides the one or more heterologous antigen is the F protein of NDV. In one embodiment the recombinant HVT of the present invention provides that the F protein of NDV is encoded by a nucleotide sequence comprising at least 80% sequence identity to the nucleotide sequence comprising SEQ ID NO. 3. In one embodiment the recombinant HVT of the present invention the F protein of NDV is encoded by the nucleotide sequences comprising SEQ ID NO. 3.

In one or more embodiments the recombinant HVT of the present invention provides the one or more heterologous antigens are protective against NDV and IBDV. In one or more embodiments the recombinant HVT of the present invention provides that the at least one heterologous antigens are the F protein of NDV and the VP2 protein of IBDV.

In one or more embodiments the recombinant HVT of the present invention provides the F protein of NDV encoded by a nucleotide sequence comprising at least 80% sequence identity to the nucleotide sequence comprising SEQ ID NO. 3 and the VP2 protein of IBDV encoded by the nucleotide sequence comprising at least 80% sequence identity to the nucleotide sequence comprising SEQ ID NO. 5 or SEQ ID NO.10.

In one or more embodiments the recombinant HVT of the present invention provides the F protein of NDV encoded by the nucleotide sequence comprising SEQ ID NO. 3 and the VP2 protein of IBDV is encoded by the nucleotide sequence comprising SEQ ID NO. 5 or SEQ ID NO.10.

In one or more embodiments the recombinant HVT of the present invention comprises a genome comprising one or more expression cassette or cassettes comprising one or more nucleotide sequence or sequences that encode one or more heterologous antigen or antigens. In one embodiment the recombinant HVT comprises a recombinant HVT genome an expression cassette that comprises a nucleotide sequence encoding promoters that are operatively linked to one or more nucleotides that encode antigens to be expressed. In one embodiment the antigen to be expressed comprises the F protein of NDV. In one embodiment the antigen to be expressed comprise the VP2 protein of IBDV. In one embodiment the antigens to be expressed comprise both the F protein of NDV and the VP2 protein of IBDV.

In one embodiment the recombinant HVT of the present invention provides the one or more promoters are selected from the group consisting of: immediate early cytomegalovirus human (hCMV) promoter: guinea pig immediate early CMV promoter; murine immediate early CMV promoter; Pec promoter; β-chicken actin promoter; SV40 promoter; Pseudorabies Virus promoters of glycoprotein X promoter; Herpes Simplex Virus-1 alpha 4 promoter; Marek's Disease Virus promoters of glycoproteins gA, gC, gB, gE, or gI promoter; Infectious Laryngotracheitis Virus promoters of glycoprotein gB, gE, gl, gD promoter; and Bovine Herpesvirus 1/1 VP8 promoter. In one embodiment the recombinant HVT comprises the human CMV promoter. In one embodiment the recombinant HVT comprises the murine CMV promoter. In one embodiment the recombinant HVT comprises the hCMV and mCMV promoter.

In one or more embodiments the recombinant HVT comprises a nucleotide sequence encoding a poly adenylation (polyA) signal. In one or more embodiments the recombinant HVT comprises a nucleotide sequence encoding a poly A signal and is selected from BGH poly A (SEQ ID NO.6) or SV40 poly A sequence (SEQ ID NO.12). In one embodiment the poly A signal is a BGH poly A signal. In one embodiment the poly A signal is an SV40 poly A signal.

In one aspect the recombinant HVT of the present invention comprises a CMV promoter operatively linked to a nucleotide sequence encoding a VP2 protein from an IBDV further comprising a nucleotide sequence coding for a polyadenylation signal, all part of a VP2 expression cassette inserted in a non-coding region of the HVT genome. In one embodiment the CMV promoter comprises an hCMV promoter (SEQ ID NO.1). In one embodiment the nucleotide sequence encoding the VP2 protein of IBDV is selected from SEQ ID NO.5 or SEQ ID NO.10. In one embodiment the nucleotide sequence encoding the VP2 protein comprises SEQ ID NO.5. In one embodiment the nucleotide sequence encoding the VP2 protein comprises SEQ ID NO.10. In one embodiment the polyadenylation signal comprises SEQ ID NO. 6. In one embodiment the polyadenylation signal comprises SEQ IDNO.12. In one embodiment the promoter, the nucleotide sequence encoding the VP2 protein and the poly A signal comprise an expression cassette. In one embodiment the expression cassette is inserted into the HVT genome at the UL55/gene 3 site. In one embodiment the expression cassette is inserted into the HVT genome at the UL35/36 site within the genome. In one embodiment the expression cassette comprises, in order, SEQ ID NO.1, SEQ ID NO.5 or SEQ ID NO.10 and SEQ ID NO.6 inserted into the HVT genome at the UL55/gene 3 site.

In one aspect the recombinant HVT of the present invention comprises a CMV promoter operatively linked to a nucleotide sequence encoding an F protein of an NDV further comprising a nucleotide sequence coding for a polyadenylation signal all part of an NDV F cassette inserted into a non-coding location within the HVT genome. In one embodiment the CMV promoter comprises an mCMV (SEQ ID NO.2) promoter. In one embodiment the nucleotide sequence encoding the F protein of an NDV which comprises SEQ ID NO.3. In one embodiment the polyadenylation signal is coded for by nucleotide sequence comprising SEQ ID NO.12. In one embodiment the promoter, the nucleotide sequence encoding the F protein and the poly A signal comprise an expression cassette. In one embodiment the expression cassette is inserted into the HVT genome at the UL55/gene 3 site. In one embodiment the expression cassette is inserted into the HVT genome at the UL35/36 site within the genome. In one embodiment the expression cassette comprises, in order, SEQ ID NO.2, SEQ ID NO.3 and SEQ ID NO.12 inserted into the HVT genome at the UL55/gene 3 site.

In one aspect the recombinant HVT of the present invention comprises a CMV promoter operatively linked to a nucleotide sequence encoding a VP2 protein of an IBDV further comprising a nucleotide sequence coding for a polyadenylation signal, all comprising a VP2 expression cassette inserted into a non-coding location within the HVT genome. In one embodiment the recombinant HVT of the present invention further comprises a CMV promoter operatively linked to a nucleotide sequence encoding the F protein of an NDV further comprising a nucleotide sequence coding for a polyadenylation signal as part of an NDV F expression cassette inserted into the same insertion site as the VP2 cassette. In one embodiment the recombinant HVT of the present further comprises a CMV promoter operatively linked to a nucleotide sequence encoding an F protein of NDV further comprising a nucleotide sequence coding for a polyadenylation signal as part of an NDV F expression cassette inserted into a different site as the VP2 cassette.

In one embodiment the recombinant HVT of the present invention provides a VP2 expression cassette comprising, in order, a nucleotide sequence encoding hCMV promoter (SEQ ID NO. 1), nucleotide sequence encoding IBDV VP2 (selected from SEQ ID NO.5 or SEQ ID NO.10) and nucleotide sequence encoding BGH polyadenylation signal (SEQ ID NO.6) inserted into the HVT genome in the UL35/36 non-coding region and, in order, nucleotide sequence encoding mCMV promoter (SEQ ID NO.2), a nucleotide sequence encoding the F protein from NDV (SEQ ID NO.3) and a nucleotide sequence encoding an SV40 polyadenylation signal (SEQ ID NO.12) inserted into the HVT genome in the UL55/gene 3 non-coding region. In one aspect the recombinant HVT of the present invention comprises a promoter operatively linked to a nucleotide sequence encoding an Infectious Laryngotracheitis Virus antigen further comprising a nucleotide sequence coding for a polyadenylation signal. In one embodiment the ILT antigen comprises one or more antigens selected from the group consisting of: the gB, gC, gD, gE, gH, gI, gL or chimeric proteins of one or more of the ILT antigens of the Infectious Laryngotracheitis Virus (ILTV). In one embodiment the recombinant HVT of the present invention further comprises a nucleotide sequence that encodes one or more antigens selected from the group consisting of Infectious Bursal Disease Virus, Chicken Anemia Virus, Newcastle Disease Virus, Infectious Bronchitis Virus and Avian Influenza Virus. In one embodiment the recombinant HVT of the present invention further provides a promoter operatively linked to a nucleotide sequence encoding antigens selected from the group consisting of: a VP1, VP2, VP3 or VP4 antigen of the Infectious Bursal Disease Virus (IBDV); the VP1 or VP2 proteins of the Chicken Anemia Virus (CAV); the F/HN chimera protein or the F, NP, P, M, HN, or L proteins of the Newcastle Disease Virus (NDV); the 51, S2 or M proteins of Infectious Bronchitis Virus (IBV); and any of the HA, NA, NP or M proteins of the Avian Influenza Virus (AIV).

In one embodiment the recombinant HVT of the present invention comprises one or more ILT antigens as part of an expression cassette comprising a promoter that is operatively linked to the nucleotide encoding the ILT antigen and further comprising a nucleotide sequence encoding a polyadenylation signal. In one embodiment the recombinant HVT of the present invention comprises a second and a third expression cassette each comprising nucleotide sequences encoding a promoter operatively linked to a nucleotide sequence encoding avian antigens selected from the group consisting of a VP1, VP2, VP3 or VP4 antigen of the Infectious Bursal Disease Virus (IBDV); the VP1 or VP2 proteins of the Chicken Anemia Virus (CAV); the F/HN chimera protein or the F, NP, P, M, HN, or L proteins of the Newcastle Disease Virus (NDV); the S1, S2 or M proteins of Infectious Bronchitis Virus (IBV); and any of the HA, NA, NP or M proteins of the Avian Influenza Virus (AIV) and further comprising a nucleotide sequence encoding a polyadenylation signal.

In one or more aspects the present invention provides a recombinant DNA encoding the recombinant HVT genome of the present invention.

In one or more aspects the present invention provides an immunogenic composition comprising the recombinant HVT of the present invention and further comprising a pharmaceutically acceptable carrier, excipient or adjuvant.

In one or more aspects the present invention provides a vaccine composition comprising the recombinant HVT of the invention and further comprising a pharmaceutically acceptable carrier, excipient or adjuvant.

In one embodiment the vaccine of the present invention further comprises an additional Marek's disease Virus (MDV) selected from the group consisting of: naturally attenuated MDV-1 strain Rispens (CVI-988); or a Gallid Herpesvirus 3 strain SB-1 virus. In one embodiment the vaccine of the present invention provides that the additional MDV comprises a recombinant genome. In one embodiment the vaccine of the present invention provides that the additional recombinant MDV genome comprises one or more nucleotide sequence(s) encoding one or more heterologous antigen(s) that are protective against one or more avian pathogen(s).

In one embodiment the vaccine of the present invention provides for use in vaccinating an avian against one or more diseases caused by one or more avian pathogen(s). In one or more embodiments the vaccine of the present invention provides for use in protecting an avian against clinical symptoms caused by one or more avian pathogen(s). In one or more embodiments the vaccine of the present invention provides for use in protecting an avian against clinical symptoms caused by Marek's Disease Virus and clinical symptoms caused by one or more avian pathogen(s). In one or more embodiments the vaccine of the present invention provides the one or more avian pathogen(s) selected from a group consisting of: Infectious Bursal Disease Virus (IBDV); Newcastle disease virus (NDV); Infectious Bronchitis Virus (IBV); Infectious Laryngotracheitis Virus (ILTV); Chicken Anemia Virus (CAV); and Avian Influenza Virus (AIV). In one embodiment the vaccine of the present invention provides that the one or more avian pathogen comprises the Newcastle Disease Virus. In one embodiment the vaccine of the present invention provides that the one or more avian pathogen comprises the Infectious Bursal Disease Virus (IBDV). In one embodiment the vaccine of the present invention provides that the one or more avian pathogen comprises the Newcastle Disease Virus and the Infectious Bursal Disease Virus.

In one or more embodiments the vaccine of the present invention provides for use in vaccinating an avian wherein the vaccine is administered by at least one administration of the vaccine by spray administration, in ovo administration, subcutaneous administration, intramuscular administration, oral administration, nasal administration or combination thereof. In one embodiment the vaccine of the present invention provides that the vaccine is administered by in ovo administration. In one embodiment the vaccine of the present invention provides that the in ovo administration occurs in an embryonated egg between about 16-22 days of development. In one or more embodiments the vaccine of the present invention provides that the in ovo administration occurs in an embryonated egg at about 18 days of development. In one embodiment the vaccine of the present invention provides that the administration of the vaccine comprises in ovo administration followed by spray administration. In one embodiment the vaccine of the present invention provides that the administration of the vaccine comprises spray administration.

In one aspect the present invention provides a method of vaccinating an avian to treat or prevent Marek's disease and one or more avian diseases caused by one or more avian pathogens comprises the step of administering an effective amount of the vaccine composition the present invention. In one embodiment the method of the present invention provides that the one or more avian pathogens are selected from a group consisting of Infectious Bursal Disease Virus (IBDV); Newcastle disease virus (NDV); Infectious Bronchitis Virus (IBV); Infectious Laryngotracheitis Virus (ILTV); Chicken Anemia Virus (CAV); and Avian Influenza Virus (AIV). In one embodiment the method of the present invention provides that the one or more avian pathogen comprises the Infectious Bursal Disease Virus (IBDV). In one embodiment the method of the present invention provides that the one or more avian pathogen comprises the Newcastle Disease Virus (NDV). In one embodiment the method of the present invention provides that the one or more avian pathogens comprises the Infectious Bursal Disease Virus (IBDV) and the Newcastle Disease Virus (NDV).

An aspect of the invention provides a method of inducing an immune response in an avian animal to Marek's Disease Virus and one or more avian pathogen(s), comprising the step of administering to an avian an effective amount of an immunogenic or vaccine composition of the invention. In one embodiment the method of the present invention provides that the one or more avian pathogen(s) are selected from a group consisting of Infectious Bursal Disease Virus (IBDV); Newcastle disease virus (NDV); Infectious Bronchitis Virus (IBV); Infectious Laryngotracheitis Virus (ILTV); Chicken Anemia Virus (CAV); and Avian Influenza Virus (AIV). In one embodiment the method of the present invention provides that the one or more avian pathogen(s) comprises the Infectious Bursal Disease Virus (IBDV). In one embodiment the method of the present invention provides that the one or more avian pathogen(s) comprises the Newcastle Disease Virus (NDV). In one embodiment the method of the present invention provides that the one or more avian pathogens comprise the Infectious Bursal Disease Virus (IBDV) and the Newcastle Disease Virus (NDV). In one or more embodiments the method of the present invention provides that the administration is performed by spray administration, in ovo administration, subcutaneous administration, intramuscular administration, oral administration or nasal administration. In one embodiment the method comprises in ovo administration. In one embodiment the method provides that the in ovo administration occurs in an embryonated egg between about 16-22 days of development. In one or more embodiments the method provides that the in ovo administration occurs in an embryonated egg at about 18 days of development. In one or more embodiments the method provides that the administration route comprises in ovo administration followed by spray administration. In one embodiment the method provides that the administration route comprises spray administration. In one or more embodiments the method provides that the avian is selected from the group consisting of chicken, turkey, goose, duck, pheasant, ostrich, pigeon and quail. In one embodiment the method provides that the avian comprises a chicken.

An aspect of the present invention provides a vaccine composition comprising the recombinant HVT of the invention which comprises a nucleotide sequence encoding the F protein from the Newcastle Disease Virus further comprising a composition comprising an attenuated Infectious Bursal Virus and an antibody that specifically binds to the Infectious Bursal Virus. In one or more embodiments the composition comprising the IBDV is the attenuated IBD strain 2512 and comprises the Bursaplex™ vaccine. In one or more embodiments the composition comprising the IBDV is the attenuated IBD strain V877 comprises the Magniplex™ vaccine.

BRIEF DESCRIPTION OF THE FIGURES

FIG. 6 is a representation of a Western blot analysis of infected cell lysate using a monoclonal antibody against IBDVR63 showing a protein band of about 50 KD for HVT IBD 6a.

FIGS. 7A and 7B is a representation of a PCR reactions demonstrating correct VP2 gene integration at the UL35/36 site in the HVT genome for HVT IBD 6a.

FIGS. 12A, 12 B and 12C are representations of PCR reactions demonstration correct VP2 gene integration at the UL55/gene 3 integration site in the HVT genome for HVT IBD 34.

FIGS. 20A, 20B, 20C is a representation of PCR reactions demonstrating the correct orientation of the NDVF insert for HVT NDV 46.

FIG. 21 is a linear representation of the HVT genome denoting insertion site A, UL35 (HVT043)-UL36 (HVT044).

FIG. 22 is a linear representation of the HVT genome denoting insertion site B, UL55 (HVT065)-Gene 3 (HVT066).

FIG. 23 is a representation of the IBDV VP2 Faragher strain F52/70.

FIG. 24 is a representation of the synthesis of plasmid pHVT-IBD #30.

FIG. 25 is a representation of the synthesis of plasmid pHVT-ND #42.

FIG. 26 is a representation of the circular map of Transfer Plasmid pSiteA #30.

FIG. 27 is a representation of the circular map of Transfer Plasmid pSite B #42.

FIG. 28 is a representation of the production of the intermediate recombinant HVT-ND #42.

FIG. 29 is a representation of the production of HVT-IBD #30-ND #42.

FIG. 30 is a representation of the construct characterization of HVT-IBD #30-ND #42 based on PCR and restriction endonuclease digestion of site A.

FIG. 31 is a representation of the construct characterization of HVT-IBD #30-ND #42 based on PCR and restriction endonuclease digestion of site B.

FIG. 32 is a representation of a western blot analysis of HVT-IBD #30-ND #42 target protein expression of IBD VP2.

FIG. 33 is a representation of western blot analysis of HVT-IBD #30-ND #42 target protein expression of NDV F.

| BRIEF DESCRIPTION OF THE SEQUENCES | |
|---|---|
| SEQ ID NO. 1 | DNA sequence of human CMV (hCMV) promoter |
| SEQ ID NO. 2 | DNA sequence of mouse CMV (mCMV) promoter |
| SEQ ID NO. 3 | DNA sequence of strain D26-76 NDV F protein |
| SEQ ID NO. 4 | Amino acid sequence of strain D26-76 NDV F protein |
| SEQ ID NO. 5 | DNA Sequence of vIBDV (F52/70) VP2 |
| SEQ ID NO. 6 | DNA sequence of Bovine Growth Hormone Poly A |
| SEQ ID NO. 7 | DNA Sequence of HVT UL55 Flanking |
| SEQ ID NO. 8 | DNA Sequence of HVT Gene 3 Flanking |
| SEQ ID NO. 9 | DNA Sequence of Pec Promoter |
| SEQ ID NO. 10 | DNA Sequence of vvIBDV VP2 |
| SEQ ID NO. 11 | DNA Sequence SV40 promoter |
| SEQ ID NO. 12 | DNA Sequence SV40 polyA sequence |
| SEQ ID NO. 13 | DNA Sequence of HVT UL35 Flanking |
| SEQ ID NO. 14 | DNA Sequence of HVT UL36 Flanking |
| SEQ ID NO. 15 | DNA Sequence of Chicken Beta-actin Promoter |
| SEQ ID NO. 16 | DNA Sequence of Modified transfer plasmid for HVT-gfp-A #14* |
| SEQ ID NO. 17 | DNA sequence Original transfer plasmid for HVT-gfp-A #14 |
| SEQ ID NO. 18 | DNA Sequence Transfer plasmid for HVT-gfp-B #13 |
| SEQ ID NO. 19 | DNA sequence Transfer plasmid for HVT-gfp-B #13a |
| SEQ ID NO. 20 | DNA sequence Transfer plasmid for HVT-IBD #1 |
| SEQ ID NO. 21 | DNA sequence Transfer plasmid for HVT-IBD #5 |
| SEQ ID NO. 22 | DNA Sequence Transfer plasmid for HVT-IBD #6a |
| SEQ ID NO. 23 | DNA sequence Transfer plasmid for HVT-IBD #9 |
| SEQ ID NO. 24 | DNA sequence Transfer plasmid for HVT-IBD #30 |
| SEQ ID NO. 25 | DNA sequence Transfer plasmid for HVT-IBD #31 |
| SEQ ID NO. 26 | DNA sequence Transfer plasmid for HVT-IBD #32 |
| SEQ ID NO. 27 | DNA sequence Transfer plasmid for HVT-IBD #33 |
| SEQ ID NO. 28 | DNA sequence Transfer plasmid for HVT-IBD #34 |
| SEQ ID NO. 29 | DNA sequence of Transfer plasmid for HVT-ND #38 |
| SEQ ID NO. 30 | DNA sequence Transfer plasmid for HVT-ND #39 |
| SEQ ID NO. 31 | DNA sequence Transfer plasmid for HVT-ND #40 |
| SEQ ID NO. 32 | DNA sequence Transfer plasmid for HVT-ND #41a |
| SEQ ID NO. 33 | DNA sequence Original Transfer plasmid for HVT-ND #42 |
| SEQ ID NO. 34 | DNA sequence of Cloning plasmid for pSiteB |
| SEQ ID NO. 35 | DNA sequence Final Transfer plasmid for pSiteB-#42 |
| SEQ ID NO. 36 | DNA sequence Transfer plasmid for HVT-ND #44 |
| SEQ ID NO. 37 | DNA sequence Transfer plasmid for HVT-ND #45 |
| SEQ ID NO. 38 | DNA sequence Transfer plasmid for HVT-ND #46 |
| SEQ ID NO. 39 | DNA sequence Transfer plasmid for HVT-ND #48 |
| SEQ ID NO. 40 | DNA sequence of 5'Upstream Sbfi gfp gene mutagenesis primer 1 |
| SEQ ID NO. 41 | DNA sequence of 5'Upstream Sbfi gfp gene mutagenesis primer 2 |
| SEQ ID NO. 42 | DNA sequence of 3' downstream Sbfi gfp gene mutagenesis primer 1 |
| SEQ ID NO. 43 | DNA sequence of 3' downstream Sbfi gfp gene mutagenesis primer 2 |
| SEQ ID NO. 44 | DNA sequence of upper UL55-gene 3 primer |
| SEQ ID NO. 45 | DNA sequence of lower UL55-gene 3 primer |
| SEQ ID NO. 46 | DNA sequence upper UL55-gene3 PCR primer |
| SEQ ID NO. 47 | DNA sequence lower UL55-gene3 PCR primer |

Figure 1:
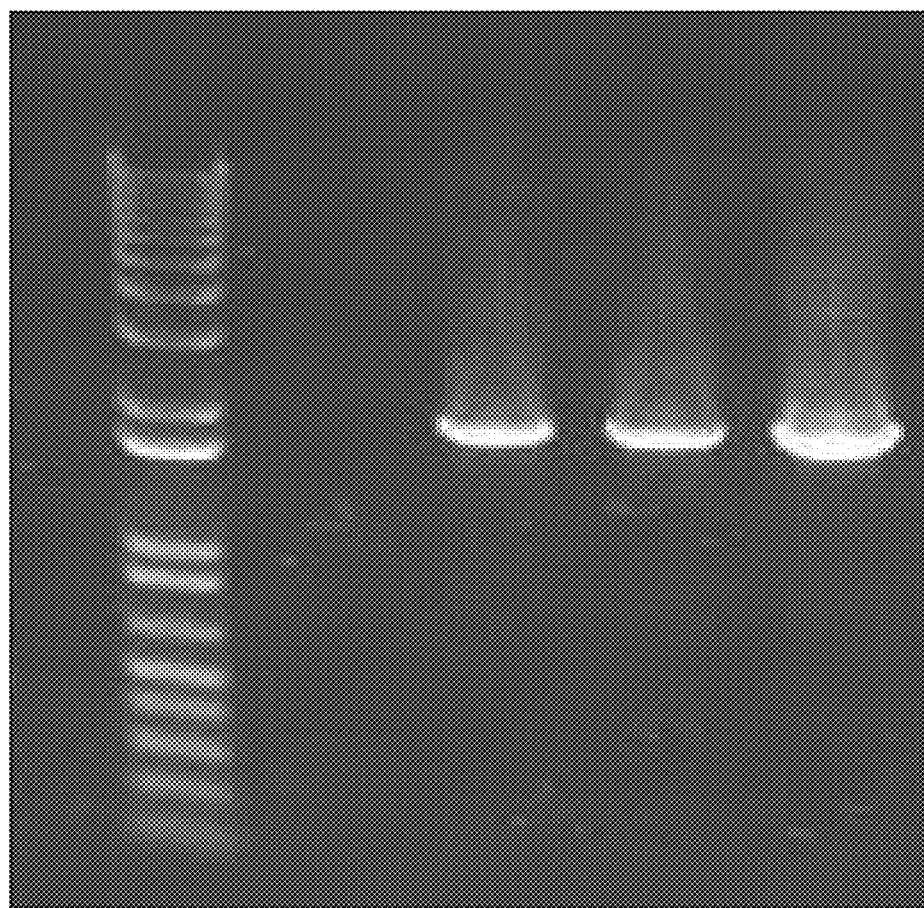
FIG. 1 is a representation of a PCR reaction demonstrating the correct insertion of a gfp gene at the UL55/Gene 3 site of the HVT genome.

| BRIEF DESCRIPTION OF THE SEQUENCES | |
|---|---|
| SEQ ID NO. 48 | DNA sequence for upper primer localized within IBD VP2 coding region |
| SEQ ID NO. 49 | DNA sequence for lower primer downstream within HVT IBD#1 |
| SEQ ID NO. 50 | DNA sequence for upper primer of the upstream junction of the insertion site of transfer plasmid HVT IBD#1 |
| SEQ ID NO. 51 | DNA sequence for lower primer within the IBDV VP2 coding region of HVT IBD #1 |
| SEQ ID NO. 52 | DNA sequence for upper primer within the IBDV VP2 coding region |
| SEQ ID NO. 53 | DNA sequence for lower primer downstream of the UL35/36 integration site of HVT-IBD #5 |
| SEQ ID NO. 54 | DNA sequence for upper primer of the UL35/36 insertion site of HVT IBD #5 |
| SEQ ID NO. 55 | DNA sequence for lower primer within the hCMV promoter of HVT IBD #5 |
| SEQ ID NO. 56 | DNA sequence for upper primer upstream of the integration site of HVT IBD #6a |
| SEQ ID NO. 57 | DNA sequence for lower primer localized within the pec promoter of HVT IBD#6a |
| SEQ ID NO. 58 | DNA sequence for upper primer localized within the IBD VP2 coding region of HVT IBD #6a |
| SEQ ID NO. 59 | DNA sequence for lower primer localized downstream of the UL35/36 insertion site |
| SEQ ID NO. 60 | DNA sequence for upper primer upstream of the integration site of UL55/Gene3 for HVT IBD#9 |
| SEQ ID NO. 61 | DNA sequence for lower primer downstream of the integration site of UL55/Gene3 for HVT IBD#9 |
| SEQ ID NO. 62 | DNA sequence for insert orientation upper primer surrounding upstream junction of the HVT IBD#9 VP2 gene insertion |
| SEQ ID NO. 63 | DNA sequence for insert orientation lower primer localized within IBDV VP2 coding region for HVT IBD#9 |
| SEQ ID NO. 64 | DNA sequence for upper primer downstream site determining correct integration of the IBDV VP2 coding region for HVT IBDV #9 |
| SEQ ID NO. 65 | DNA sequence for lower primer downstream site determining correct integration of the IBDV VP2 coding region for HVT IBDV #9 |
| SEQ ID NO. 66 | DNA sequence for upper primer for upstream region of integration site of UL55-Gene3 for HVT IBD#30 |
| SEQ ID NO. 67 | DNA sequence for lower primer for upstream region of integration site of UL55-Gene3 for HVT IBD#30 |
| SEQ ID NO. 68 | DNA sequence for upper primer to confirm correct orientation of VP2 insert surrounding the 3' junction of the insertion site of HVT IBD#30 |
| SEQ ID NO. 69 | DNA sequence for lower primer to confirm correct orientation of VP2 insert surrounding the 3' junction of the insertion site of HVT IBD#30 |
| SEQ ID NO. 70 | DNA sequence for upper primer to confirm correct orientation of VP2 insert integration outside of the expression cassette of HVT IBD#30 |
| SEQ ID NO. 71 | DNA sequence for lower primer to confirm correct orientation of VP2 insert integration outside of the expression cassette of HVT IBD#30 |
| SEQ ID NO. 72 | DNA sequence for upper primer to confirm correct orientation of VP2 insert upstream of the UL35/36 integration site of HVT IBD #31 |
| SEQ ID NO. 73 | DNA sequence for lower primer to confirm correct orientation of VP2 insert localized within the chicken beta actin promoter of HVT IBD#31 |
| SEQ ID NO. 74 | DNA sequence for upper primer to confirm confirmation of VP2 insert localized within the IBDV VP2 coding region |
| SEQ ID NO. 75 | DNA sequence for lower primer to confirm correct orientation of VP2 insert located downstream of UL35/36 integration site of HVT IBD#31 |
| SEQ ID NO. 76 | DNA sequence for upper primer targeting the downstream integration site of the VP2 insert of HVT IBD#31 located within the VP2 insert |
| SEQ ID NO. 77 | DNA sequence for lower primer localized downstream of the UL35/36 site of HVT IBD#31 |
| SEQ ID NO. 78 | DNA sequence for upper primer for upstream region of integration site of Gene3-UL55 for HVT-IBD #34 |
| SEQ ID NO. 79 | DNA sequence for lower primer localized within chicken beta-actin promoter for HVT-IBD #34 |
| SEQ ID NO. 80 | DNA sequence for upper primer localized within IBDV VP2 coding region for HVT-IBD #34 |
| SEQ ID NO. 81 | DNA sequence for lower primer localized downstream of Gene3-UL55 insertion site for HVT IBD#34 |
| SEQ ID NO. 82 | DNA sequence for upper primer localized outside of the VP2 expression cassette of HVT IBD #34 |
| SEQ ID NO. 83 | DNA sequence for lower primer localized outside of the VP2 expression cassette of HVT IBD #34 |
| SEQ ID NO. 84 | DNA sequence for upper primer for upstream region of integration site of UL35-UL36 of HVT ND#38 |

-continued

| BRIEF DESCRIPTION OF THE SEQUENCES | |
|---|---|
| SEQ ID NO. 85 | DNA sequence for lower primer that localized within NDV F coding region of HVT ND#38 |
| SEQ ID NO. 86 | DNA sequence for upper primer surrounding the 3' junction of the insertion localized within NDV F coding region of HVT ND#38 |
| SEQ ID NO. 87 | DNA sequence for lower primer localized downstream of UL35-UL36 insertion site of HVT ND#38 |
| SEQ ID NO. 88 | DNA sequence for upper primer outside of the expression cassette of HVT ND#38 |
| SEQ ID NO. 89 | DNA sequence for lower primer outside of the expression cassette of HVT ND#38 |
| SEQ ID NO. 90 | DNA sequence for upper primer upstream region of integration site of UL35-UL36 for HVT-ND #39 |
| SEQ ID NO. 91 | DNA sequence for lower primer localized within chicken beta-actin promoter HVT-ND #39 |
| SEQ ID NO. 92 | DNA sequence for upper primer surrounding the downstream junction of the insertion localized within poly A region of HVT-ND #39 |
| SEQ ID NO. 93 | DNA sequence for lower primer localized downstream of UL35-UL36 insertion of HVT-ND #39 |
| SEQ ID NO. 94 | DNA sequence for upper primer outside of the expression cassette of HVT-ND #39 |
| SEQ ID NO. 95 | DNA sequence for lower primer outside of the expression cassette HVT-ND #39 |
| SEQ ID NO. 96 | DNA sequence for upper primer upstream of the UL35/36 integration site for HVT ND#40 |
| SEQ ID NO. 97 | DNA sequence for lower primer localized within chicken beta actin promoter for HVT ND#40 |
| SEQ ID NO. 98 | DNA sequence for upper primer localized within NDVF coding region for HVT ND#40 |
| SEQ ID NO. 99 | DNA sequence for lower primer located at the downstream junction of the insertion site for HVT ND#40 |
| SEQ ID NO. 100 | DNA sequence for upper primer located outside of the expression cassette for HVT ND#40 |
| SEQ ID NO. 101 | DNA sequence for lower primer located outside of the expression cassette for HVT#40 |
| SEQ ID NO. 102 | DNA sequence for upper primer for PCR amplification of cassette for HVT ND#42 |
| SEQ ID NO. 103 | DNA sequence for lower primer for PCR amplification of cassette for HVT ND#42 |
| SEQ ID NO. 104 | DNA sequence for upper primer located outside of cassette for HVT ND#42 |
| SEQ ID NO. 105 | DNA sequence for lower primer located outside of cassette for HVT ND #42 |
| SEQ ID NO. 106 | DNA sequence for upper primer located upstream and outside of the expression cassette for HVT ND #42 |
| SEQ ID NO. 107 | DNA sequence for lower primer located within ND F coding region for HVT ND #42 |
| SEQ ID NO. 108 | DNA sequence for upper primer located upstream and outside of the expression cassette for HVT ND #42 |
| SEQ ID NO. 109 | DNA sequence for lower primer located within ND F coding region for HVT ND #42 |
| SEQ ID NO. 110 | DNA sequence for upper primer located upstream and outside of the expression cassette for HVT ND #42 |
| SEQ ID NO. 111 | DNA sequence for lower primer located within NDV F coding region for HVT ND #42 |
| SEQ ID NO. 112 | DNA sequence for upper primer located upstream and outside of the expression |
| SEQ ID NO. 113 | DNA sequence for lower primer located within ND F coding region for HVT ND #42 |
| SEQ ID NO. 114 | DNA sequence for upper primer located upstream and outside of the expression cassette for HVT ND #42 |
| SEQ ID NO. 115 | DNA sequence for lower primer located within ND F coding region for HVT ND #42 |
| SEQ ID NO. 116 | DNA sequence for upper primer localized upstream of UL55 for HVT ND #44 |
| SEQ ID NO. 117 | DNA sequence for lower primer localized within chicken beta actin promoter for HVT ND #44 |
| SEQ ID NO. 118 | DNA sequence for upper primer localized upstream of UL55 for HVT ND #44 |
| SEQ ID NO. 119 | DNA sequence for lower primer localized within chicken beta actin promoter for HVT ND #44 |
| SEQ ID NO. 120 | DNA sequence for upper primer localized within NDV F gene coding sequence for HVT ND#44 |
| SEQ ID NO. 121 | DNA sequence for lower primer localized downstream of UL55-Gene3 insertion site for HVT ND#44 |
| SEQ ID NO. 122 | DNA sequence for upper primer localized outside of the expression cassette for HVT ND#44 |

-continued

| | BRIEF DESCRIPTION OF THE SEQUENCES |
|---|---|
| SEQ ID NO. 123 | DNA sequence for lower primer localized outside of the expression cassette for HVT#44 |
| SEQ ID NO. 124 | DNA sequence for upper primer localized outside of the expression cassette for HVT#45 |
| SEQ ID NO. 125 | DNA sequence for lower primer localized outside of the expression cassette for HVT#45 |
| SEQ ID NO. 126 | DNA sequence for upper primer located upstream and outside of the expression cassette for HVT ND#45 |
| SEQ ID NO. 127 | DNA sequence for lower primer located within ND F coding region for HVT ND#45 |
| SEQ ID NO. 128 | DNA sequence for upper primer located upstream and outside of the expression cassette for HVT ND#45 |
| SEQ ID NO. 129 | DNA sequence for lower primer located within the ND F coding region for HVT ND#45 |
| SEQ ID NO. 130 | DNA sequence for upper primer surrounding the downstream junction of the insertion for HVT ND#45 |
| SEQ ID NO. 131 | DNA sequence for lower primer localized downstream of Gene3-UL55 insertion site |
| SEQ ID NO. 132 | DNA sequence for upper primer surrounding the downstream junction of the insertion for HVT ND#45 |
| SEQ ID NO. 133 | DNA sequence for lower primer localized that localized downstream of Gene3-UL55 insertion site |
| SEQ ID NO. 134 | DNA sequence for upper primer localized outside of the expression cassette for HVT ND#46 |
| SEQ ID NO. 135 | DNA sequence for lower primer localized outside of the expression cassette for HVT ND#46 |
| SEQ ID NO. 136 | DNA sequence for upper primer located upstream and outside of the integration site for HVT ND#46 |
| SEQ ID NO. 137 | DNA sequence for lower primer located within the mCMV promoter for HVT ND#46 |
| SEQ ID NO. 138 | DNA sequence for upper primer localized within NDV F gene coding sequence for HVT ND#46 |
| SEQ ID NO. 139 | DNA sequence for lower primer localized downstream and outside of expression cassette for HVT ND#46 |
| SEQ ID NO. 140 | DNA sequence for upper primer localized within NDV F gene coding sequence for HVT ND#46 |
| SEQ ID NO. 141 | DNA sequence for lower primer localized downstream and outside of expression cassette for HVT ND#46 |
| SEQ ID NO. 142 | DNA sequence for upper primer localized within NDV F gene coding sequence for HVT ND#46 |
| SEQ ID NO. 143 | DNA sequence for lower primer localized downstream and outside of expression cassette for HVT ND#46 |
| SEQ ID NO. 144 | DNA sequence for upper primer localized within NDV F gene coding sequence for HVT ND#46 |
| SEQ ID NO. 145 | DNA sequence for lower primer localized downstream and outside of expression cassette for HVT ND#46 |
| SEQ ID NO. 146 | DNA sequence for upper primer localized upstream region of integration site of Gene 3-UL55 for HVT ND#48 |
| SEQ ID NO. 147 | DNA sequence for lower primer localized within chicken beta-actin promoter for HVT ND#48 |
| SEQ ID NO. 148 | DNA sequence for upper primer surrounding the downstream junction of the insertion for HVT ND#48 |
| SEQ ID NO. 149 | DNA sequence for lower primer localized downstream of Gene 3-UL55 insertion site for HVT ND#48 |
| SEQ ID NO. 150 | DNA sequence for upper primer surrounding the downstream junction of the insertion for HVT ND#48 |
| SEQ ID NO. 151 | DNA sequence for lower primer localized downstream of Gene 3-UL55 insertion site for HVT ND#48 |
| SEQ ID NO. 152 | DNA sequence for upper primer located outside of the expression cassette for HVT ND#48 |
| SEQ ID NO. 153 | DNA sequence for lower primer located outside of the expression cassette for HVT ND#48 |
| SEQ ID NO. 154 | DNA sequence for upper primer for amplification of the NDV F expression cassette of HVT ND#42 for HVT-IBD-ND #42-#30 |
| SEQ ID NO. 155

DETAILED DESCRIPTION OF THE INVENTION

The following is a detailed description provided to aid those skilled in the art. Those of ordinary skill in the art may make modifications and variations in the embodiments described herein without departing from the spirit or scope of the present invention.

The present invention relates to vaccines for avian use based on live recombinant avian herpesviruses, namely, in particular, Marek's disease virus (MDV) and more especially on HVT virus (herpesvirus of turkeys), into which has been inserted one or more nucleotide sequence(s) coding for and expressing an antigenic polypeptide of a pathogenic agent, under conditions affording an immunization leading to an effective protection of the vaccinated animal against the said pathogenic agent or agents. Marek's Disease (MD) is a common lymphoproliferative disease of chickens, caused by Marek's Disease virus (MDV), which can result in significant losses in the poultry industry. Currently, MD is controlled in poultry using vaccines using serotype 3 of MDV, which is the related Herpesvirus of Turkeys (HVT). By introducing genes from poultry viruses other than MDV into the HVT genome at particular genetic positions, the inventors have been able to develop novel recombinant viral vaccines that enable simultaneous protection in poultry against MD and one or more additional diseases through administration of a single viral vaccine.

The invention provides recombinant viral vectors for the insertion and expression of foreign genes for use in safe immunizations to protect avians against a variety of pathogens. The invention also provides multivalent compositions or vaccines comprising one or more recombinant HVT viral vectors for protection against a variety of pathogens. Additionally, the invention provides methods of making and using the recombinant viral vectors alone or in combination with other vaccines or pharmaceutical compositions.

In one aspect the present invention provides a recombinant Herpesvirus of turkey (HVT) genome comprising one or more nucleotide sequence(s) coding for one or more heterologous antigen(s) inserted into the intergenic loci UL 35/UL 36 in the unique long (UL) region of the HVT genome.

In one aspect the present invention provides a recombinant Herpesvirus of Turkey (HVT) genome comprising one or more nucleotide sequences coding for one or more heterologous antigens or antigens inserted into the intergenic loci UL 35/UL 36 in the unique long region of the HVT genome and one or more nucleotide sequences or sequences coding for one or more heterologous antigens inserted at the UL55/Gene 3 site in the unique long region (UL) of the HVT genome.

In one or more embodiments the present invention provides a recombinant HVT wherein the one or more heterologous antigens or antigens are protective against avian pathogens or pathogens selected from the group consisting of: Infectious Bursal Disease Virus (IBDV); Newcastle disease virus (NDV); Infectious Bronchitis Virus (IBV); Infectious Laryngotracheitis Virus (ILTV); Chicken Anemia Virus (CAV); and Avian Influenza Virus (AIV).

In one or more embodiments the present invention provides a recombinant HVT wherein the one or one or more heterologous antigens are selected from the group consisting of: the VP2, VP3 or VP4 proteins of the Infectious Bursal Disease Virus (IBDV); the VP1 or VP2 proteins of the Chicken Anemia Virus (CAV); the F/HN chimera protein or the F, NP, P, M, HN, or L proteins of the Newcastle Disease Virus (NDV); the S1, S2 or M proteins of Infectious Bronchitis Virus (IBV); the gB, gC, gD, gE, gH, gI or gL proteins of the Infectious Laryngotracheitis Virus (ILTV); and any of the HA, NA, NP or M proteins of the Avian Influenza Virus (AIV).

In one or more embodiments the recombinant HVT of the present invention provides that the one or more heterologous antigen is protective against IBDV. In one embodiment the recombinant HVT of the present invention provides the one or more heterologous antigen is the VP2 protein of IBDV. In one embodiment the recombinant HVT of the present invention provides the VP2 protein is encoded by the nucleotide sequence comprising at least 80% sequence identity to the nucleotide sequence comprising SEQ ID NO. 5 or SEQ ID NO. 10. In one embodiment the recombinant HVT of the present invention provides the VP2 protein encoded by the nucleotide sequence comprising either SEQ ID NO. 5 or SEQ ID NO.10.

In one or more embodiments the recombinant HVT of the present invention provides the one or more heterologous antigen or antigen is protective against Newcastle Disease Virus (NDV). In one embodiment the recombinant HVT of the present invention provides the one or more heterologous antigen is the F protein of NDV. In one embodiment the recombinant HVT of the present invention provides that the F protein of NDV is encoded by a nucleotide sequence comprising at least 80% sequence identity to the nucleotide sequence comprising SEQ ID NO. 3. In one embodiment the recombinant HVT of the present invention the F protein of NDV is encoded by the nucleotide sequences comprising SEQ ID NO. 3.

In one or more embodiments the recombinant HVT of the present invention provides the one or more heterologous antigens are protective against NDV and IBDV. In one or more embodiments the recombinant HVT of the present invention provides the at least one heterologous antigens are the F protein of NDV and the VP2 protein of IBDV.

In one or more embodiments the recombinant HVT of the present invention provides the F protein of NDV encoded by a nucleotide sequence comprising at least 80% sequence identity to the nucleotide sequence comprising SEQ ID NO. 3 and the VP2 protein of IBDV encoded by the nucleotide sequence comprising at least 80% sequence identity to the nucleotide sequence comprising SEQ ID NO. 5 or SEQ ID NO.10.

In one or more embodiments the recombinant HVT of the present invention provides the F protein of NDV encoded by the nucleotide sequence comprising SEQ ID NO. 3 and the VP2 protein of IBDV is encoded by the nucleotide sequence comprising SEQ ID NO. 5 or SEQ ID NO.10.

In one or more embodiments the recombinant HVT of the present invention comprises a genome comprising one or more expression cassette or cassettes comprising one or more nucleotide sequence or sequences that encode one or more heterologous antigen or antigens. In one embodiment the recombinant HVT comprises a recombinant HVT genome an expression cassette that comprises a nucleotide sequence encoding promoters that are operatively linked to one or more nucleotides that encode antigens to be expressed. In one embodiment the antigen to be expressed comprises the F protein of NDV. In one embodiment the antigen to be expressed comprise the VP2 protein of IBDV. In one embodiment the antigens to be expressed comprise both the F protein of NDV and the VP2 protein of IBDV.

In one embodiment the recombinant HVT of the present invention provides the one or more promoters are selected from the group consisting of: immediate early cytomegalovirus human (hCMV) promoter: guinea pig immediate early CMV promoter; murine immediate early CMV promoter; Pec promoter; β-chicken actin promoter; SV40 promoter; Pseudorabies Virus promoters of glycoprotein X promoter; Herpes Simplex Virus-1 alpha 4 promoter; Marek's Disease Virus promoters of glycoproteins gA, gC, gB, gE, or gI promoter; Infectious Laryngotracheitis Virus promoters of glycoprotein gB, gE, gI, gD promoter; and Bovine Herspesvirus 1/1 VP8 promoter. In one embodiment the recombinant HVT comprises the human CMV promoter. In one embodiment the recombinant HVT comprises the murine CMV promoter. In one embodiment the recombinant HVT comprises the hCMV and mCMV promoter.

In one or more embodiments the recombinant HVT comprises a nucleotide sequence encoding a poly adenylation (polyA) signal. In one or more embodiments the recombinant HVT comprises a nucleotide sequence encoding a poly A signal and is selected from BGH poly A (SEQ ID NO.6) or SV40 poly A sequence (SEQ ID NO.12). In one embodiment the poly A signal is a BGH poly A signal. In one embodiment the poly A signal is an SV40 poly A signal.

In one aspect the recombinant HVT of the present invention comprises a CMV promoter operatively linked to a nucleotide sequence encoding a VP2 protein from a IBDV further comprising a nucleotide sequence coding for a polyadenylation signal, all part of a VP2 expression cassette inserted in a non-coding region of the HVT genome. In one embodiment the CMV promoter comprises an hCMV promoter (SEQ ID NO.1). In one embodiment the nucleotide sequence encoding the VP2 protein of IBDV is selected from SEQ ID NO.5 or SEQ ID NO.10. In one embodiment the nucleotide sequence encoding the VP2 protein comprises SEQ ID NO.5. In one embodiment the nucleotide sequence encoding the VP2 protein comprises SEQ ID NO.10. In one embodiment the polyadenylation signal comprises SEQ ID NO. 6. In one embodiment the polyadenylation signal comprises SEQ ID NO.12. In one embodiment the promoter, the nucleotide sequence encoding the VP2 protein and the poly A signal comprise an expression cassette. In one embodiment the expression cassette is inserted into the HVT genome at the UL55/gene 3 site. In one embodiment the expression cassette is inserted into the HVT genome at the UL35/36 site within the genome. In one embodiment the expression cassette comprises, in order, SEQ ID NO.1, SEQ ID NO.5 or SEQ ID NO.10 and SEQ ID NO.6 inserted into the HVT genome at the UL55/gene 3 site.

In one aspect the recombinant HVT of the present invention comprises a CMV promoter operatively linked to a nucleotide sequence encoding an F protein of an NDV further comprising a nucleotide sequence coding for a polyadenylation signal all part of an NDV F cassette inserted into a non-coding location within the HVT genome. In one embodiment the CMV promoter comprises an mCMV (SEQ ID NO.2) promoter. In one embodiment the nucleotide sequence encoding the F protein of an NDV which comprises SEQ ID NO.3. In one embodiment the polyadenylation signal is coded for by nucleotide sequence comprising SEQ ID NO.12. In one embodiment the promoter, the nucleotide sequence encoding the F protein and the poly A signal comprise an expression cassette. In one embodiment the expression cassette is inserted into the HVT genome at the UL55/gene 3 site. In one embodiment the expression cassette is inserted into the HVT genome at the UL35/36 site within the genome. In one embodiment the expression cassette comprises, in order, SEQ ID NO.2, SEQ ID NO.3 and SEQ ID NO.12 inserted into the HVT genome at the UL55/gene 3 site.

In one aspect the recombinant HVT of the present invention comprises a CMV promoter operatively linked to a nucleotide sequence encoding a VP2 protein of an IBDV further comprising a nucleotide sequence coding for a polyadenylation signal, all comprising a VP2 expression cassette inserted into a non-coding location within the HVT genome. In one embodiment the recombinant HVT of the present invention further comprises a CMV promoter operatively linked to a nucleotide sequence encoding the F protein of an NDV further comprising a nucleotide sequence coding for a polyadenylation signal as part of an NDV F expression cassette inserted into the same insertion site as the VP2 cassette. In one embodiment the recombinant HVT of the present further comprises a CMV promoter operatively linked to a nucleotide sequence encoding an F protein of NDV further comprising a nucleotide sequence coding for a polyadenylation signal as part of an NDV F expression cassette inserted into a different site as the VP2 cassette.

In one embodiment the recombinant HVT of the present invention provides a VP2 expression cassette comprising, in order, a nucleotide sequence encoding hCMV promoter (SEQ ID NO. 1), nucleotide sequence encoding IBDV VP2 (selected from SEQ ID NO.5 or SEQ ID NO.10) and nucleotide sequence encoding BGH polyadenylation signal (SEQ ID NO.6) inserted into the HVT genome in the UL35/36 non-coding region and, in order, nucleotide sequence encoding mCMV promoter (SEQ ID NO.2), a nucleotide sequence encoding the F protein from NDV (SEQ ID NO.3) and a nucleotide sequence encoding an SV40 polyadenylation signal (SEQ ID NO.12) inserted into the HVT genome in the UL55/gene 3 non-coding region. In one embodiment the recombinant HVT of the present invention further comprises a nucleotide sequence that encodes one or more antigens selected from the group consisting of Infectious Bursal Disease Virus, Chicken Anemia Virus, Newcastle Disease Virus, Infectious Bronchitis Virus, Infectious Laryngotracheitis Virus and Avian Influenza Virus. In one embodiment the recombinant HVT of the present invention further provides a promoter operatively linked to a nucleotide sequence encoding antigens selected from the group consisting of: a VP1, VP2, VP3 or VP4 antigen of the Infectious Bursal Disease Virus (IBDV); the VP1 or VP2 proteins of the Chicken Anemia Virus (CAV); the F/HN chimera protein or the F, NP, P, M, HN, or L proteins of the Newcastle Disease Virus (NDV); the S1, S2 or M proteins of Infectious Bronchitis Virus (IBV); and any of the HA, NA, NP or M proteins of the Avian Influenza Virus (AIV).

In one embodiment the recombinant HVT of the present invention comprises one or more ILT antigens as part of an expression cassette comprising a promoter that is operatively linked to the nucleotide encoding the ILT antigen and further comprising a nucleotide sequence encoding a polyadenylation signal. In one embodiment the recombinant HVT of the present invention comprises a second and a third expression cassette each comprising nucleotide sequences encoding a promoter operatively linked to a nucleotide sequence encoding avian antigens selected from the group consisting of a VP1, VP2, VP3 or VP4 antigen of the Infectious Bursal Disease Virus (IBDV); the VP1 or VP2 proteins of the Chicken Anemia Virus (CAV); the F/HN chimera protein or the F, NP, P, M, HN, or L proteins of the Newcastle Disease Virus (NDV); the S1, S2 or M proteins of Infectious Bronchitis Virus (IBV); and any of the HA, NA, NP or M proteins of the Avian Influenza Virus (AIV) and further comprising a nucleotide sequence encoding a polyadenylation signal.

In one or more aspects the present invention provides a recombinant DNA encoding the recombinant HVT genome of the present invention.

In one or more aspects the present invention provides an immunogenic composition comprising the recombinant HVT of the present invention and further comprising a pharmaceutically acceptable carrier, excipient or adjuvant.

In one or more aspects the present invention provides a vaccine composition comprising the recombinant HVT of the invention and further comprising a pharmaceutically acceptable carrier, excipient or adjuvant.

In one embodiment the vaccine of the present invention further comprises an additional Marek's disease Virus (MDV) selected from the group consisting of: naturally attenuated MDV-1 strain Rispens (CVI-988); or a Gallid Herpesvirus 3 strain SB-1 virus. In one embodiment the vaccine of the present invention provides that the additional MDV comprises a recombinant genome. In one embodiment the vaccine of the present invention provides that the additional recombinant MDV genome comprises one or more nucleotide sequence(s) encoding one or more heterologous antigen(s) that are protective against one or more avian pathogen(s).

In one embodiment the vaccine of the present invention provides for use in vaccinating an avian against one or more diseases caused by one or more avian pathogen(s). In one or more embodiments the vaccine of the present invention provides for use in protecting an avian against clinical symptoms caused by one or more avian pathogen(s). In one or more embodiments the vaccine of the present invention provides for use in protecting an avian against clinical symptoms caused by Marek's Disease Virus and clinical symptoms caused by one or more avian pathogen(s). In one or more embodiments the vaccine of the present invention provides the one or more avian pathogen(s) selected from a group consisting of: Infectious Bursal Disease Virus (IBDV); Newcastle disease virus (NDV); Infectious Bronchitis Virus (IBV); Infectious Laryngotracheitis Virus (ILTV); Chicken Anemia Virus (CAV); and Avian Influenza Virus (AIV). In one embodiment the vaccine of the present invention provides that the one or more avian pathogen comprises the Newcastle Disease Virus. In one embodiment the vaccine of the present invention provides that the one or more avian pathogen comprises the Infectious Bursal Disease Virus (IBDV). In one embodiment the vaccine of the present invention provides that the one or more avian pathogen comprise the Newcastle Disease Virus and the Infectious Bursal Disease Virus.

In one or more embodiments the vaccine of the present invention provides for use in vaccinating an avian wherein the vaccine is administered by at least one administration of the vaccine by spray administration, in ovo administration, subcutaneous administration, intramuscular administration, oral administration, nasal administration or combination thereof. In one embodiment the vaccine of the present invention provides that the vaccine is administered by in ovo administration. In one embodiment the vaccine of the present invention provides that the in ovo administration occurs in an embryonated egg between about 16-22 days of development. In one or more embodiments the vaccine of the present invention provides that the in ovo administration occurs in an embryonated egg at about 18 days of development. In one embodiment the vaccine of the present invention provides that the administration of the vaccine comprises in ovo administration followed by spray administration. In one embodiment the vaccine of the present invention provides that the administration of the vaccine comprises spray administration.

In one aspect the present invention provides a method of vaccinating an avian to treat or prevent Marek's disease and one or more avian diseases caused by one or more avian pathogens comprises the step of administering an effective amount of the vaccine composition the present invention. In one embodiment the method of the present invention provides that the one or more avian pathogens are selected from a group consisting of Infectious Bursal Disease Virus (IBDV); Newcastle disease virus (NDV); Infectious Bronchitis Virus (IBV); Infectious Laryngotracheitis Virus (ILTV); Chicken Anemia Virus (CAV); and Avian Influenza Virus (AIV). In one embodiment the method of the present invention provides that the one or more avian pathogen comprises the Infectious Bursal Disease Virus (IBDV). In one embodiment the method of the present invention provides that the one or more avian pathogen comprises the Newcastle Disease Virus (NDV). In one embodiment the method of the present invention provides that the one or more avian pathogens comprises the Infectious Bursal Disease Virus (IBDV) and the Newcastle Disease Virus (NDV).

An aspect of the invention provides a method of inducing an immune response in an avian animal to Marek's Disease Virus and one or more avian pathogen(s), comprising the step of administering to an avian an effective amount of an immunogenic or vaccine composition of the invention. In one embodiment the method of the present invention provides that the one or more avian pathogen(s) are selected from a group consisting of Infectious Bursal Disease Virus (IBDV); Newcastle disease virus (NDV); Infectious Bronchitis Virus (IBV); Infectious Laryngotracheitis Virus (ILTV); Chicken Anemia Virus (CAV); and Avian Influenza Virus (AIV). In one embodiment the method of the present invention provides that the one or more avian pathogen(s) comprises the Infectious Bursal Disease Virus (IBDV). In one embodiment the method of the present invention provides that the one or more avian pathogen(s) comprises the Newcastle Disease Virus (NDV). In one embodiment the method of the present invention provides that the one or more avian pathogens comprise the Infectious Bursal Disease Virus (IBDV) and the Newcastle Disease Virus (NDV). In one or more embodiments the method of the present invention provides that the administration is performed by spray administration, in ovo administration, subcutaneous administration, intramuscular administration, oral administration or nasal administration. In one embodiment the method comprises in ovo administration. In one embodiment the method provides that the in ovo administration occurs in an embryonated egg between about 16-22 days of development. In one or more embodiments the method provides that the in ovo administration occurs in an embryonated egg at about 18 days of development. In one or more embodiments the method provides that the administration route comprises in ovo administration followed by spray administration. In one embodiment the method provides that the administration route comprises spray administration. In one or more embodiments the method provides that the avian is selected from the group consisting of chicken, turkey, goose, duck, pheasant, ostrich, pigeon and quail. In one embodiment the method provides that the avian comprises a chicken.

General Methodologies:

It should be understood that this invention is not limited to the particular methodology, protocols, and reagents, etc. described herein and as such may vary. The terminology used herein is for the purpose of describing particular embodiments only and is not intended to limit the scope of the present invention.

Unless otherwise defined, scientific and technical terms used in connection with the invention described herein shall have the meanings that are commonly understood by those of ordinary skill in the art. Further, unless otherwise required by context, singular terms shall include pluralities and plural terms shall include the singular. Generally, nomenclatures utilized in connection with, and techniques of, cell and tissue culture, molecular biology, and protein and oligo- or polynucleotide chemistry and hybridization described herein are those well-known and commonly used in the art.

Standard techniques are used for recombinant DNA, oligonucleotide synthesis, and tissue culture and transfection that are well known to those of skill in the art. Enzymatic reactions and purification techniques are performed according to manufacturer's specifications or as commonly accomplished in the art or as described herein. The foregoing techniques and procedures are generally performed according to conventional methods well known in the art and as described, but not limited to the various general and more specific references that are cited and discussed throughout the present specification, See ex. Sambrook et al. MOLECULAR CLONING: LAB. MANUAL (3$^{rd}$ ed., Cold Spring Harbor Lab. Press, Cold Spring Harbor, N.Y., 2001) and Ausubel et al. Current Protocols in Molecular Biology (New York: Greene Publishing Association J Wiley Interscience), Oligonucleotide Synthesis (M. J. Gait, ed., 1984); *Methods in Molecular Biology*, Humana Press; *Cell Biology: A Laboratory Notebook* (J. E. Cellis, ed., 1998) Academic Press; *Animal Cell Culture* (R. I. Freshney, ed. 1987); *Introduction to Cell and Tissue Culture* (I. P. Mather and P. E. Roberts, 1998) Plenum Press; *Cell and Tissue Culture: Laboratory Procedures* (A. Doyle, J. B. Griffiths, and D. G. Newell, eds., 1993-1998) J. Wiley and Sons; *Methods in Enzymology* (Academic Press, Inc.); *Handbook of Experimental Immunology* (D. M. Weir and C. C. Blackwell, eds.); Gene Transfer Vectors for Mammalian Cells (J. M. Miller and M. P. Calos, eds., 1987); *Current Protocols in Molecular Biology* (F. M. Ausubel et al., eds., 1987); *PCR: The Polymerase Chain Reaction*, (Mullis et al., eds., 1994); *Current Protocols in Immunology* (E. Coligan et al., eds., 1991); *Short Protocols in Molecular Biology* (Wiley and Sons, 1999); *Immunobiology* (C. A. Janeway and P. Travers, 1997); *Antibodies* (P. Finch, 1997); *Antibodies: a practical approach* (D. Catty., ed., IRL Press, 1988-1989); *Monoclonal antibodies: a practical approach* (P. Shepherd and C. Dean, eds., Oxford University Press, 2000); *Using antibodies: a laboratory manual* (E. Harlow and D. Lane (Cold Spring Harbor Laboratory Press, 1999); *The Antibodies* (M. Zanetti and J. D. Capra, eds., Harwood Academic Publishers, 1995); and *Cancer: Principles and Practice of Oncology* (Y. T. DeVita et al., eds., J.B. Lippincott Company, 1993).

Other than in the operating examples, or where otherwise indicated, all numbers expressing quantities of ingredients or reaction conditions used herein should be understood as modified in all instances by the term "about".

All patents and other publications identified are expressly incorporated herein by reference for the purpose of describing and disclosing, for example, the methodologies described in such publications that might be used in connection with the present invention. These publications are provided solely for their disclosure prior to the filing date of the present application.

Definitions

Before describing the present invention in detail, several terms used in the context of the present invention will be defined. In addition to these terms, others are defined elsewhere in the specification as necessary. Unless otherwise expressly defined herein, terms of art used in this specification will have their art-recognized meanings.

It is noted that in this disclosure, terms such as "comprises", "comprised", "comprising", "contains", "containing", "consisting", "consisted", "consisting essentially of", "includes", "included" and the like are defined according to standard United States and international patent law practice.

The term "about" is used herein to indicate that a value includes the standard deviation of error for the device or method being employed to determine the value. The use of the term "or" in the claims is used to mean "and/or" unless explicitly indicated to refer to alternatives only or the alternatives are mutually exclusive, although the disclosure supports a definition that refers to only alternatives and to "and/or." When not used in conjunction closed wording in the claims or specifically noted otherwise, the words "a" and "an" denote "one or more." The term "conferred by a transgene," for example, thus encompasses one or more transgene(s).

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, ex. hydroxyproline, γ-carboxyglutamate, and O-phosphoserine. Amino acid analogs refer to compounds that have the same basic chemical structure as a naturally occurring amino acid, i.e., an α carbon that is bound to a hydrogen, a carboxyl group, an amino group, and an R group, ex. homoserine, norleucine, methionine sulfoxide, methionine methyl sulfonium. Such analogs have modified R groups (ex. norleucine) or modified peptide backbones but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes. Macromolecular structures such as polypeptide structures may be described in terms of various levels of organization. "Primary structure" refers to the amino acid sequence of a particular peptide. "Secondary structure" refers to locally ordered, three dimensional structures within a polypeptide. These structures are commonly known as domains, for example enzymatic domains, extracellular domains, transmembrane domains, pore domains, or cytoplasmic tail domains. Domains are portions of a polypeptide that form a compact unit of the polypeptide. Exemplary domains include domains with enzymatic activity. A domain may be made up of sections of lesser organization such as stretches of β-sheet and α-helices. "Tertiary structure" refers to the complete three-dimensional structure of a polypeptide monomer. "Quaternary structure" refers to the three-dimensional structure formed by the noncovalent association of independent tertiary units. Anisotropic terms are also known as energy terms.

As used herein, an "antibody" refers to a polypeptide comprising a framework region from an immunoglobulin gene or fragments thereof that specifically binds and recognizes an antigen. The recognized immunoglobulin genes may include the kappa, lambda, alpha, gamma, delta, epsilon, and mu constant region genes, as well as the myriad immunoglobulin variable region genes. Light chains may be classified as either kappa or lambda. Heavy chains may be classified as gamma, mu, alpha, delta, or epsilon, which in turn define the immunoglobulin classes, IgY, IgG, IgM, IgA, IgD, and IgE, respectively.

An exemplary immunoglobulin (antibody) structural unit may comprise a tetramer, with each tetramer composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain and variable heavy chain refer to these light and heavy chains. Antibodies exist, ex. as intact immunoglobulins or as several well-characterized fragments produced by digestion with various peptidases. While various antibody fragments are defined in terms of the digestion of an intact antibody, one of skill will appreciate that such fragments may be synthesized de novo either chemically or by using recombinant DNA methodology. Thus, the term "antibody," as used herein, also includes antibody fragments either produced by the modification of whole antibodies, or those synthesized de novo using recombinant DNA methodologies or those identified using other methods known in the art.

For preparation of antibodies, ex. recombinant, monoclonal, or polyclonal antibodies, many techniques known in the art may be used. The genes encoding the heavy and light chains of an antibody of interest can be cloned from a cell and used to produce a recombinant monoclonal antibody. Gene libraries encoding heavy and light chains of monoclonal antibodies may also be used. Random combinations of the heavy and light chain gene products generate a large pool of antibodies with different antigenic specificity. Techniques to produce single chain antibodies or recombinant antibodies are found in the art and may be adapted to produce antibodies to polypeptides according to the invention. Phage display technology may also be used to identify antibodies and heteromeric fragments that specifically bind to selected antigens. Antibodies may also be made bispecific, i.e., able to recognize two different antigens, or heteroconjugates, ex. two covalently joined antibodies, or immunotoxins.

As used herein, an "antigen" refers to a viral protein or polypeptide, such as a viral polypeptide, as well as viral particles. In some embodiments, an antigen in accordance with the invention may also be a viral nucleic acid. An antigen is a molecule that is recognized by the immune system and is capable of inducing an immune response in a host organism. The antigen may comprise a whole, attenuated, killed or live organism or a subunit or portion of an organism. It can also be a piece or fragment of DNA, a polypeptide, an epitope, a hapten or any combination of these that can induce immune response.

The term "avian" as used herein, includes poultry such as members of the order Galliformes. More particularly a class of birds more with economical and/or agronomical interest, such as chicken, turkeys, goose, duck, pheasant, ostrich, pigeon and quail and the like.

As used herein, a "biological sample" or "sample" may include blood and blood parts including, but not limited to serum, plasma, platelets, or red blood cells; sputum, cloacal swabs, mucosa, tissue, cultured cells, including primary cultures, explants, and transformed cells; biological fluids, stool, and urine. A biological sample may also include sections of tissues such as biopsy and autopsy samples, and frozen sections taken for histologic purposes. A biological sample may be obtained from a eukaryotic organism, such as a bird, including, but not limited to, a bird from the order Galliformes, such as chickens, quails and turkeys. Any tissue appropriate for use in accordance with the invention may be used, for instance, skin, brain, spinal cord, adrenals, pectoral muscle, lung, heart, liver, crop, proventriculus, ventriculus, duodenum, small intestine, large intestine, cloaca, kidney, bursa of fabricus, spleen, pancreas, adrenal gland, bone marrow, lumbosacral spinal cord, or blood.

The term "conservative amino acid substitution" indicates any amino acid substitution for a given amino acid residue, where the substitute residue is so chemically similar to that of the given residue that no substantial decrease in polypeptide function (e.g., enzymatic activity) results. Conservative amino acid substitutions are commonly known in the art and examples thereof are described, e.g., in U.S. Pat. Nos. 6,790,639, 6,774,107, 6,194,167, or 5,350,576. In a preferred embodiment, a conservative amino acid substitution will be anyone that occurs within one of the following six groups:

1. Small aliphatic, substantially non-polar residues: Ala, Gly, Pro, Ser, and Thr;

2. Large aliphatic, non-polar residues: lie, Leu, and Val; Met;

3. Polar, negatively charged residues and their amides: Asp and Glu;

4. Amides of polar, negatively charged residues: Asn and Gin; His;

5. Polar, positively charged residues: Arg and Lys; His; and

6. Large aromatic residues: Trp and Tyr; Phe.

In a preferred embodiment, a conservative amino acid substitution will be any one of the following, which are listed as Native Residue (Conservative Substitutions) pairs: Ala (Ser); Arg (Lys); Asn (Gin; His); Asp (Glu); Gin (Asn); Glu (Asp); Gly (Pro); His (Asn; Gln); lie (Leu; Val); Leu (lie; Val); Lys (Arg; Gin; Glu); Met (Leu; lie); Phe (Met; Leu; Tyr); Ser (Thr); Thr (Ser); Trp (Tyr); Tyr (Trp; Phe); and Val (lie; Leu).

The phrase "functional effects" in the context of assays for testing compounds that modulate activity of a virus as described herein includes the determination of a parameter that is indirectly or directly under the influence of such a virus, ex. a phenotypic or chemical effect. "Functional effects" may include in vitro, in vivo, and ex vivo activities and may be measured by any means known to those skilled in the art, such as changes in spectroscopic characteristics, shape, chromatographic, or solubility properties for a protein, measuring inducible markers or transcriptional activation of a protein; measuring binding activity or binding assays, e.g. binding to antibodies; measuring changes in ligand or substrate binding activity, measuring viral replication, measuring cell surface marker expression, measurement of changes in protein levels, measurement of RNA stability, identification of downstream or reporter gene expression via, for example, chemiluminescence, fluorescence, colorimetric reactions, antibody binding, and/or inducible markers.

The term "gene" refers to components that comprise viral DNA or RNA, cDNA, viral intron and exon DNA, artificial viral DNA polynucleotide, or other DNA that encodes a viral peptide, viral polypeptide, viral protein, or viral RNA transcript molecule, and the genetic elements that may flank the coding sequence that are involved in the regulation of expression, such as, promoter regions, 5' leader regions, 3' untranslated region that may exist as native genes or transgenes in a viral genome. The gene or a fragment thereof can be subjected to polynucleotide sequencing methods that determines the order of the nucleotides that comprise the gene.

The term "Herpesvirus of Turkey (HVT)" is defined as a nonpathogenic virus of domestic turkeys and it is classified as the third serotype within the Marek's disease virus group of antigenically and genetically related lymphotropic avian herpes viruses.

The term "heterologous" when used with reference to portions of a nucleic acid indicates that the nucleic acid comprises two or more sequences that are not found in the same relationship to each other in nature. For instance, the nucleic acid is typically recombinantly produced, having two or more sequences from unrelated genes arranged to make a new functional nucleic acid, ex. a promoter from one source and a coding region from another source. Similarly, a heterologous protein indicates that the protein comprises two or more subsequences that are not found in the same relationship to each other in nature (ex. a fusion protein). Heterologous may also refer to a viral sequence, such as a gene or transgene, or a portion thereof, being inserted into a viral genome in which it is not typically found, or a gene introduced into an organism in which it is not typically found.

The term "host cell" means any cell of any organism that is selected, modified, transformed, grown, or used or manipulated in any way, to produce a substance by the cell, for example the expression by the cell of a gene, a DNA or RNA sequence, a protein or an enzyme. A host cell is intended to include any individual cell or cell culture which can be or has been a recipient for vectors or for the incorporation of exogenous nucleic acid molecules, polynucleotides, and/or proteins. It also is intended to include progeny of a single cell. The progeny may not necessarily be completely identical (in morphology or in genomic or total DNA complement) to the original parent cell due to natural, accidental, or deliberate mutation. The cells may be prokaryotic or eukaryotic.

As used herein, the term "host," "subject," "patient," or "organism" may include animals, particularly birds, especially poultry. For veterinary applications, birds may be from the order Galliformes, which includes chickens, quails and turkeys, and the like. The term "living host" refers to a host as noted above or another organism that is alive. The term may also refer to the entire host or organism and not just a part excised (ex. a brain or other organ) from the living host. These terms also include an individual in all stages of development, including embryonic and fetal stages.

The terms "identical" or "percent identity," in the context of two or more nucleic acids or polypeptide sequences, refer to two or more sequences or subsequences that are the same or have a specified percentage of amino acid residues or nucleotides that are the same (i.e., about 60% identity, preferably 65%, 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using a BLAST or BLAST 2.0 sequence comparison algorithms with default parameters described below, or by manual alignment and visual inspection (see, ex. the NCBI web site found at ncbi.nlm.nih.gov/BLAST/ or the like). Such sequences are then referred to as "substantially identical." This definition also refers to, or applies to, the compliment of a particular sequence. The definition may also include sequences that have deletions, additions, and/or substitutions.

For sequence comparison, one sequence typically serves as a reference sequence, to which other sequences are compared. When using a sequence comparison algorithm, reference and comparison sequences may be entered into a computer, and sequence algorithm program parameters are selected as desired. Percent sequence identities are then generated for the comparison sequences relative to the reference sequence, based on the parameters selected. An example of an algorithm that may be suitable for determining percent sequence identity and sequence similarity are the BLAST and BLAST 2.0 algorithms, which are described in Altschul et al., (*Nuc Acids Res* 25:3389-3402, 1977) and Altschul et al., (*J Mol Biol* 215:403-410, 1990), respectively. BLAST and BLAST 2.0 are well known in the art and may be used to determine percent sequence identity for any nucleic acids or proteins, such as those described herein.

As used herein, an "immunogenic composition" or "pharmaceutical composition" or "vaccine" is meant to encompass a composition comprising an antigen suitable for administration to a subject, such as an avian subject. Said composition is generally meant to elicit an immune response in a subject. The immune response can include a T cell response, a B cell response, or both a T cell and B cell response. The composition may serve to sensitize the subject patient by the presentation of antigen in association with MHC molecules at the cell surface. In addition, antigen-specific T-lymphocytes or antibodies can be generated to allow for the future protection of an immunized host. An "immunogenic composition" may contain a live, attenuated, or killed/inactivated vaccine comprising a whole microorganism or an immunogenic portion derived therefrom that induces either a cell-mediated (T cell) immune response or an antibody-mediated (B cell) immune response, or both, and may protect the animal from one or more symptoms associated with infection by the microorganism, or may protect the animal from death due to the infection with the microorganism. In general, an "immunogenic composition" is sterile, and preferably free of contaminants that can elicit an undesirable response within the subject (ex. the compound(s) in the immunogenic composition is pharmaceutical grade) Immunogenic compositions may be designed for administration to subjects in need thereof via a number of different routes of administration including in ovo, oral, intravenous, buccal, rectal, parenteral, intraperitoneal, intradermal, intracheal, intramuscular, subcutaneous, inhalational, and the like.

The term "immunogenic" protein or peptide as used herein includes polypeptides that are immunologically active in the sense that once administered to the host, it is able to evoke an immune response of the humoral and/or cellular type directed against the protein. Preferably the protein fragment is such that it has substantially the same immunological activity as the full-length protein. Thus, a protein fragment according to the invention comprises or consists essentially of or consists of at least one epitope or antigenic determinant. An "immunogenic" protein or polypeptide, as used herein, includes the full-length sequence of the protein, analogs thereof, or immunogenic fragments thereof. By "immunogenic fragment" is meant a fragment of a protein which includes one or more epitopes and thus elicits the immunological response described above.

The term "immunogenic protein or peptide" further contemplates deletions, additions and substitutions to the sequence, as long as the polypeptide functions to produce an immunological response as defined herein. The term "conservative variation" denotes the replacement of an amino acid residue by another biologically similar residue, or the replacement of a nucleotide in a nucleic acid sequence such that the encoded amino acid residue does not change or is another biologically similar residue. In this regard, particularly preferred substitutions will generally be conservative in nature, i.e., those substitutions that take place within a family of amino acids. For example, amino acids are generally divided into four families: (1) acidic-aspartate and glutamate; (2) basic-lysine, arginine, histidine; (3) non-polar-alanine, valine, leucine, isoleucine, proline, phenylalanine, methionine, tryptophan; and (4) uncharged polar-glycine, asparagine, glutamine, cysteine, serine, threonine, tyrosine. Phenylalanine, tryptophan, and tyrosine are sometimes classified as aromatic amino acids. Examples of conservative variations include the substitution of one hydrophobic residue such as isoleucine, valine, leucine or methionine for another hydrophobic residue, or the substitution of one polar residue for another polar residue, such as the substitution of arginine for lysine, glutamic acid for aspartic acid, or glutamine for asparagine, and the like; or a similar conservative replacement of an amino acid with a structurally related amino acid that will not have a major effect on the biological activity. Proteins having substantially the same amino acid sequence as the reference molecule but possessing minor amino acid substitutions that do not substantially affect the immunogenicity of the protein are, therefore, within the definition of the reference polypeptide. All of the polypeptides produced by these modifications are included herein. The term "conservative variation" also includes the use of a substituted amino acid in place of an unsubstituted parent amino acid provided that antibodies raised to the substituted polypeptide also immunoreact with the unsubstituted polypeptide.

An "immunologically effective amount" as used herein refers to the amount of antigen or vaccine sufficient to elicit an immune response, either a cellular (T cell) or humoral (B cell or antibody) response, as measured by standard assays known to one skilled in the art. For example, with respect to the present invention, an "immunologically effective amount" is a minimal protection dose (titer). The effectiveness of an antigen as an immunogen, can be measured either by proliferation assays, by cytolytic assays, such as chromium release assays to measure the ability of a T cell to lyse its specific target cell, or by measuring the levels of B cell activity by measuring the levels of circulating antibodies specific for the antigen in serum or other assays which are known and used by those of skill in the art. Furthermore, the level of protection of the immune response may be measured by challenging the immunized host with the antigen that has been injected. For example, if the antigen to which an immune response is desired is a virus or a tumor cell, the level of protection induced by the "immunologically effective amount" of the antigen is measured by detecting the percent survival or the percent mortality after virus or tumor cell challenge of the animals.

Determination of what is an immunologically effective amount of the vaccine according to the invention is well within reach of the skilled person, for instance by monitoring the immunological response following vaccination, or after a challenge infection, e.g. by re-isolation of the pathogen, or by monitoring the targets' clinical signs of disease, or serological parameters, and comparing these to responses seen in mock-vaccinated animals. The dosing scheme for applying the vaccine according to the invention to a target organism can be in single or multiple doses, which may be given at the same time or sequentially, in a manner compatible with the formulation of the vaccine, and in such an amount as will be immunologically effective.

The terms "inhibitors," activators," and "modulators" of viral nucleic acid and polypeptide sequences are used to refer to activating, inhibitory, or modulating molecules identified using in vitro and in vivo assays of the viral nucleic acid and polypeptide sequences. Inhibitors are compounds that may bind to, partially or totally block activity, decrease, prevent, delay activation, inactivate, desensitize, or down regulate the activity or expression of a virus. Activators refer to compounds that increase, open, activate, facilitate, enhance activation, sensitize, agonize, or up regulate viral activity. Inhibitors, activators, or modulators also include genetically modified versions of a virus as described herein, ex. versions with altered activity, as well as naturally occurring and synthetic ligands, substrates, antagonists, agonists, antibodies, peptides, cyclic peptides, nucleic acids, antisense molecules, ribozymes, small chemical molecules and the like. Assays for inhibitors and activators include, ex. expressing a virus is the invention in vitro, in cells, or cell membranes, applying putative modulator compounds, and then determining the functional effects on activity, as described herein.

Test samples or assays comprising a virus of the invention that are treated with a potential activator, inhibitor, or modulator may be compared to a control sample lacking the inhibitor, activator, or modulator in order to determine the extent of inhibition. Control samples to which a test sample or assay is compared may be assigned a relative protein activity value of 100%. Inhibition of virus is achieved when the activity value of the test sample relative to the control sample is less than about 80%, including about 75%, about 70%, about 65%, about 60%, about 55%, about 50%, about 45%, about 40%, about 35%, about 30%, about 25%, about 20%, about 15%, about 10%, about 5%, and about 0%.

Intergenic loci, as described herein, is defined as a region of DNA sequence located between genes, including untranslated regions, 5' and 3' flanking regions, introns, etc. Intergenic regions are part of the noncoding DNA that may contain gene control elements such as promoters and enhancers. The term "isolated" means a substance that has been substantially separated from, or enriched relative to, other substances with which it occurs in nature. Isolated substances are usually at least about 80%, at least 90% pure, at least 98% pure, or at least about 99% pure, by weight.

A "label" or a "detectable moiety" is a composition detectable by spectroscopic, photochemical, biochemical, immunochemical, chemical, or other physical means. For example, useful labels include $^{32}P$, fluorescent dyes, electron-dense reagents, enzymes (ex. as commonly used in an ELISA), biotin, digoxigenin, or haptens and proteins which can be made detectable, ex. by incorporating a radiolabel into the peptide or used to detect antibodies specifically reactive with the peptide.

As used herein "Marek's Disease Virus" or "MDV" refers to any alphaherpesvirus of the genus Mardivirus, which includes the Herpesvirus of Turkeys (HVT), as described herein. In a specific embodiment, the invention relates to the Marek's disease virus, its genetic components, genes, and proteins produced thereby. As used herein, such a virus may include the genetic components of the virus, i.e., the genome and transcripts thereof, proteins encoded by the genome (including structural and nonstructural proteins), and functional or nonfunctional viral particles. The polynucleotide and polypeptide sequences encoding such viruses are well known in the art and would be easily found by one of skill in the art.

The terms "mutant" and "mutation" mean any detectable change in genetic material, ex. DNA, or any process, mechanism, or result of such a change. This includes gene mutations, in which the structure (ex. DNA sequence) of a gene is altered, any gene or DNA arising from any mutation process, and any expression product (ex. protein or enzyme) expressed by a modified gene or DNA sequence. The term "variant" may also be used to indicate a modified or altered gene, DNA sequence, enzyme, cell, etc., i.e., any kind of mutant.

As used herein, the term "nucleic acid" refers to a single or double-stranded polymer of deoxyribonucleotide bases or ribonucleotide bases read from the 5' to the 3' end. A "nucleic acid" may also optionally contain non-naturally occurring or altered nucleotide bases that permit correct read through by a polymerase and do not reduce expression of a polypeptide encoded by that nucleic acid. The term "nucleotide sequence" or "nucleic acid sequence" refers to both the sense and antisense strands of a nucleic acid as either individual single strands or in the duplex. The term "ribonucleic acid" (RNA) is inclusive of RNAi (inhibitory RNA), dsRNA (double stranded RNA), siRNA (small interfering RNA), mRNA (messenger RNA), miRNA (micro-RNA), tRNA (transfer RNA, whether charged or discharged with a corresponding acylated amino acid), and cRNA (complementary RNA). The terms "nucleic acid segment," "nucleotide sequence segment," or more generally, "segment," will be understood by those in the art as a functional term that includes genomic sequences, ribosomal RNA sequences, transfer RNA sequences, messenger RNA sequences, operon sequences, and smaller engineered nucleotide sequences that express or may be adapted to express, proteins, polypeptides or peptides. The nomenclature used herein is that required by Title 37 of the United States Code of Federal Regulations § 1.822 and set forth in the tables in WIPO Standard ST.25 (1998), Appendix 2, Tables 1 and 3.

The term "operably linked" is used herein to refer to an arrangement of flanking sequences wherein the flanking sequences so described are configured or assembled to perform their usual function. Thus, a flanking sequence operably linked to a coding sequence may be capable of effecting the replication, transcription and/or translation of the coding sequence. For example, a promoter or enhancer is operably linked to a coding sequence if it affects the transcription of the sequence. A flanking sequence need not be contiguous with the coding sequence, so long as it functions correctly. Thus, for example, intervening untranslated yet transcribed sequences can be present between a promoter sequence and the coding sequence and the promoter sequence can still be considered "operably linked" to the coding sequence.

The term "pharmaceutically acceptable carrier" refers to an ingredient in a pharmaceutical formulation, other than an active ingredient, that is physiologically compatible to administer to a subject. Pharmaceutically acceptable carrier includes, but is not limited to a buffer, excipient, stabilizer, adjuvant, preservative, diluent, aqueous or non-aqueous vehicle and other additives. Additionally, this term refers to an element of an immunogenic composition or vaccine that is generally approved by a regulatory agency of a Federal, a state government, or other regulatory agency, or listed in the U.S. Pharmacopeia or other generally recognized pharmacopeia for use in both human and non-human animals. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. The formulation should suit the mode of administration.

As used herein, "poultry" refers to a domestic or commercial bird kept for the eggs they produce, as well as their meat and feathers. In some embodiments, poultry may include a bird from the order Galliformes, which includes chickens, quails, and turkeys, and may also include geese, ducks, swan, guinea, pigeons, and the like.

Polynucleotides as described herein may be complementary to all or a portion of a viral gene sequence, including a promoter, intron, coding sequence, exon, 5' untranslated region, and 3' untranslated region.

A particular nucleic acid sequence may also encompass "splice variants." Similarly, a particular protein encoded by a nucleic acid implicitly encompasses any protein encoded by a splice variant of that nucleic acid. Splice variants are products of alternative splicing of a gene. After transcription, an initial nucleic acid transcript may be spliced such that different (alternate) nucleic acid splice products encode different polypeptides. Mechanisms to produce splice variants vary but include alternate splicing of exons. Alternate polypeptides derived from the same nucleic acid by readthrough transcription are also encompassed by this definition. Any products of a splicing reaction, including recombinant forms of the splice products, are included in this definition.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

The terms "polyvalent vaccine", "combination or combo vaccine" and "multivalent vaccine" are used interchangeably to refer to a vaccine containing more than one antigen. The polyvalent vaccine may contain two, three, four or more antigens. The polyvalent vaccine may comprise recombinant viral vectors, active or attenuated or killed wild-type viruses, or a mixture of recombinant viral vectors and wild-type viruses in active or attenuated or killed forms.

"Promoters", as used herein, refer to DNA sequences that define where transcription of a gene by RNA polymerase begins. Promoters are typically located upstream of the transcription initiation site. A promoter can also comprise a distal enhancer or repressor elements, which can be located as much as several thousand nucleotides from transcription start site. Promoters define the direction of transcription and indicate which DNA strand will be transcribed. A promoter can be derived from sources including viral, bacterial, fungal, plants, insects, and animals. A promoter can regulate the expression of a gene component constitutively or differentially with respect to cell, the tissue or organ in which expression occurs or, with respect to the developmental stage at which expression occurs, or in response to external stimuli such as physiological stresses, pathogens, metal ions, or inducing agents. Representative examples of promoters include the bacteriophage T7 promoter, bacteriophage T3 promoter, SP6 promoter, lac operator-promoter, tac promoter, RSV-LTR promoter, CMV IE promoter, human CMV promoter; murine CMV promoter; Pec promoter; β-chicken actin promoter; a guinea pig CMV promoter, a Pseudorabies Virus promoter; a glycoprotein X promoter, a Herpes Simplex Virus-1 promoter; a Marek's Disease Virus promoter; and an SV40 promoter.

As used herein, the terms "prophylactically treat" or "prophylactically treating" refers to completely or partially preventing a disease or symptom thereof and/or may be therapeutic in terms of a partial or complete cure for a disease and/or adverse effect attributable to the disease.

The term "recombinant" when used with reference, ex. to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, under expressed or not expressed at all. In some embodiments, recombinant sequences may also include nucleic acids, proteins, or recombinant genomes, such as viral genomes. Recombinant viral vectors as described herein may contain transgenes that are operatively linked to a heterologous promoter in order to effect transcription of the transgene.

The phrase "stringent hybridization conditions" refers to conditions under which a probe will hybridize to its target subsequence, typically in a complex mixture of nucleic acids, but to no other sequences. Stringent conditions may be sequence-dependent and will be different in different circumstances. Longer sequences hybridize specifically at higher temperatures. Stringent conditions may be achieved with the addition of destabilizing agents such as formamide.

Appropriate stringency conditions that promote DNA hybridization are well known to one of skill in the art and may include, for example, 6× sodium chloride/sodium citrate (SSC) at about 45° C., followed by a wash of 2×SSC at 50° C. The salt concentration in the wash step may be selected from a low stringency of approximately 2×SSC at 50° C. to a high stringency of about 0.2×SSC at 50° C. The temperature in the wash step may be increased from low stringency conditions at room temperature, about 22° C., to high stringency conditions at about 65° C. The temperature and/or salt conditions may be varied as appropriate for optimum results. In accordance with the invention, a nucleic acid may exhibit at least from about 80% to about 100% sequence identity with one or more nucleic acid molecules as described herein, for example at least from about 80%, about 85%, about 90%, about 95%, about 98%, about 99%, or about 100% sequence identity.

Nucleic acids that do not hybridize to each other under stringent conditions are still substantially identical if the polypeptides which they encode are substantially identical. This occurs, for example, when a copy of a nucleic acid is created using the maximum codon degeneracy permitted by the genetic code. In such cases, the nucleic acids typically hybridize under moderately stringent hybridization conditions.

The term "therapeutically effective amount," "effective amount," or "therapeutically effective dose" as used herein refers to a dose that produces an effect for which it is administered. Such a dose or amount may also refer to the amount of an embodiment of the agent being administered that will relieve to some extent one or more of the symptoms of the disease, i.e., infection, being treated, and/or that amount that will prevent, to some extent, one or more of the symptoms of the disease, i.e., infection, that the host being treated has or is at risk of developing. The exact dose will depend on the purpose of the treatment, and one of skill in the art will be able to determine such a dose using techniques known in the art.

As used herein, a "transgene" refers to a segment of DNA containing a heterologous coding sequence or other genetic material for introduction from one organism into another. For instance, in certain embodiments, a transgene according to the present invention may comprise an antigenic coding sequence, such as a viral gene, or a sequence encoding a viral protein.

As used herein, the terms "treatment," "treating," and "treat" are defined as acting upon a disease, disorder, or condition with an agent to reduce or ameliorate the pharmacologic and/or physiologic effects of the disease, disorder, or condition and/or its symptoms. "Treatment," as used herein, covers any treatment of a disease in a subject or host (ex. an animal of veterinary interest), and includes: (a) reducing the risk of occurrence of the disease in a subject determined to be predisposed to the disease but not yet diagnosed as infected with the disease, (b) impeding the development of the disease, and (c) relieving the disease, i.e., causing regression of the disease and/or relieving one or more disease symptoms. "Treatment" is also meant to encompass delivery of an inhibiting agent to provide a pharmacologic effect, even in the absence of a disease or condition. For example, "treatment" encompasses delivery of a disease or pathogen inhibiting agent that provides for enhanced or desirable effects in the subject (ex. reduction of pathogen load, reduction of disease symptoms, etc.).

The term "unit dosage form," as used herein, refers to physically discrete units suitable as unitary dosages for animal subjects, each unit containing a predetermined quantity of a compound (ex. an antiviral compound, as described herein) calculated in an amount sufficient to produce the desired effect in association with a pharmaceutically acceptable diluent, carrier, or vehicle. The specifications for unit dosage forms depend on the particular compound employed, the route and frequency of administration, the effect to be achieved, and the pharmacodynamics associated with each compound in the host.

The terms "vaccine" or "vaccine composition", which are herein used interchangeably, refer to pharmaceutical compositions comprising at least one immunogenic composition of the invention that induces an immune response in subject. A vaccine or vaccine composition may protect the subject from disease or possible death and may or may not include one or more additional components that enhance the immunological activity of the active component. The composition of the invention that induces a protective immune response comprises a recombinant HVT virus having one or more heterologous antigen encoding genes inserted into the HVT genome at intergenic region UL 35/36. In some embodiments the composition of the invention comprises a recombinant HVT virus having one or more heterologous antigen encoding genes inserted into the HVT genome at UL 35/36 and one or more antigen encoding genes inserted into the HVT genome at UL55. In some embodiments the antigen encoding genes are antigens derived from poultry pathogens such as Newcastle Disease Virus, Infectious Bursal Disease Virus, Infectious Bronchitis Virus, Avian Influenza Virus, Infectious Laryngotracheitis Virus and/or Chicken Anemia Virus. In some embodiments the recombinant HVT is combined with another recombinant Marek's Disease Virus vaccine that causes a protective immune response in poultry. The vaccine or vaccine composition of the invention may additionally comprise further components typical to vaccines or vaccine compositions, including, for example, an adjuvant or an immunomodulator. A vaccine may comprise one or simultaneously more than one of the elements described above.

The vaccine of the invention may further comprise a suitable pharmaceutical carrier. The term "pharmaceutically acceptable carrier" is intended to include any and all solvents, dispersion media, coatings, antibacterial and antifungal agents, isotonic and absorption delaying agents, to hosts. The term "carrier" refers to a diluent, adjuvant, excipient, or vehicle with which the pharmaceutical composition is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained release formulations and the like. The composition can be formulated with traditional binders and carriers such as triglycerides depending on the method of administration. Particular formulations can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. The formulation should suit the mode of administration. The appropriate carrier is evident to those skilled in the art and will depend in large part upon the route of administration. Additional components that may be present in this invention are adjuvants, preservatives, surface active agents, chemical stabilizers, suspending or dispersing agents. Typically, stabilizers, adjuvants and preservatives are optimized to determine the best formulation for efficacy in the target subject A "variant" peptide refers herein to a peptide which differs in amino acid sequence from a "parent" vaccine peptide amino acid sequence by virtue of addition, deletion, and/or substitution of one or more amino acid residue(s) in the parent peptide sequence and retains at least one desired activity of the parent vaccine peptide. For example, the variant may comprise at least one, ex. from about one to about ten, and preferably from about two to about five, substitutions in one or more amino acid sequences of the peptide to be used as part of the vaccine of the present invention. Ordinarily, the variant will have an amino acid sequence having at least 50% amino acid sequence identity with the parent amino acid sequences, preferably at least 65%, more preferably at least 70%, more preferably at least 75%, more preferably at least 80%, more preferably at least 85%, more preferably at least 90%, and most preferably at least 95% sequence identity. Identity or homology with respect to this sequence is defined herein as the percentage of amino acid residues in the candidate sequence that are identical with the parent peptide residues, after aligning the sequences and introducing gaps, if necessary, to achieve the maximum percent sequence identity. None of N-terminal, C-terminal, or internal extensions, deletions, or insertions into the peptide sequence shall be construed as affecting sequence identity or homology. The variant retains the ability to elicit an immune response and preferably has desired activities which are superior to those of the parent peptide.

Variant peptides may be fully functional or may lack function in one or more activities. Fully functional variants typically contain only conservative variations or variations in non-critical residues or in non-critical regions. Functional variants can also contain substitution of similar amino acids that result in no change or an insignificant change in function. Alternatively, such substitutions may positively or negatively affect function to some degree. Non-functional variants typically contain one or more non-conservative amino acid substitutions, deletions, insertions, inversions, or truncation or a substitution, insertion, inversion, or deletion in a critical residue or critical region.

Moreover, polypeptides often contain amino acids other than the twenty "naturally occurring" amino acids. Further, many amino acids, including the terminal amino acids, may be modified by natural processes, such as processing and other post-translational modifications, or by chemical modification techniques well known in the art. Known modifications include, but are not limited to, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent crosslinks, formation of cystine, formation of pyroglutamate, formylation, gamma carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination. Such modifications are well known to those of skill in the art and have been described in great detail in the scientific literature. Several particularly common modifications, glycosylation, lipid attachment, sulfation, gamma-carboxylation of glutamic acid residues, hydroxylation and ADP ribosylation, for instance, are described in most basic texts, such as Proteins-Structure and Molecular Properties (2nd ed., T. E. Creighton, W. H. Freeman & Co., NY, 1993). Many detailed reviews are available on this subject, such as by Wold, Posttranslational Covalent Modification of proteins, 1-12 (Johnson, ed., Academic Press, N Y, 1983); Seifter et al. 182 Meth. Enzymol. 626-46 (1990); and Rattan et al. 663 Ann. NY Acad. Sci. 48-62 (1992).

Accordingly, the peptides of the present invention also encompass derivatives or analogs in which a substituted amino acid residue is not one encoded by the genetic code. Similarly, the additions and substitutions in the amino acid sequence as well as variations, and modifications just described may be equally applicable to the amino acid sequence of antigen and/or epitope or peptides thereof and are thus encompassed by the present invention.

A "variant" nucleic acid refers herein to a molecule which differs in sequence from a "parent" nucleic acid. Polynucleotide sequence divergence may result from mutational changes such as deletions, substitutions, or additions of one or more nucleotides. Each of these changes may occur alone or in combination, one or more times in a given sequence.

Just as a polypeptide may contain conservative amino acid substitution(s), a polynucleotide thereof may contain conservative codon substitution(s). A codon substitution is considered conservative if, when expressed, it produces a conservative amino acid substitution, as described above. Degenerate codon substitution, which results in no amino acid substitution, is also useful in polynucleotides according to the present invention. Thus, for example, a polynucleotide encoding a selected polypeptide useful in an embodiment of the present invention may be mutated by degenerate codon substitution in order to approximate the codon usage frequency exhibited by an expression host cell to be transformed therewith, or to otherwise improve the expression thereof.

As used herein, "vector" means a construct, which is capable of delivering, and preferably expressing, one or more gene(s) or sequence(s) of interest in a host cell. Examples of vectors include, but are not limited to, viral vectors, naked DNA or RNA expression vectors, plasmid, cosmid or phage vectors, DNA or RNA expression vectors associated with cationic condensing agents, DNA or RNA expression vectors encapsulated in liposomes, and certain eukaryotic cells, such as producer cells. Vectors, as described herein, have expression control sequences meaning that a nucleic acid sequence that directs transcription of a nucleic acid. An expression control sequence can be a promoter, such as a constitutive or an inducible promoter, or an enhancer. The expression control sequence is 'operably linked' to the nucleic acid sequence to be transcribed. A nucleic acid is "operably linked" when it is placed into a functional relationship with another nucleic acid sequence. For example, DNA for a pre-sequence or secretory leader is operably linked to DNA for a polypeptide if it is expressed as a pre-protein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

As used herein, "viral proteins" or "viral polypeptides" refers to a protein encoded by a virus described herein, including structural and non-structural proteins. Such proteins may include naturally occurring or non-naturally occurring viral proteins from MDV, NDV, and/or IBDV, including VP2, F, and/or HN, NP, P, M, or L proteins. Such proteins may also include naturally occurring or non-naturally occurring viral proteins from ILTV such as gB, gC, gD, gE, gH, gI or gL, the 51, S2 or M proteins from Infectious Bronchitis Virus (IBV) the VP1 or VP2 proteins of the Chicken Anemia Virus (CAV) and/or any of the HA, NA, NP or M proteins of the Avian Influenza Virus (AIV)

In accordance with the invention, recombinant viral vectors as described herein may enable protection of poultry against two or more different viral pathogens by providing recombinant viral vectors that express genes from such viral pathogens. In some embodiments, the recombinant viral vectors of the present invention may be provided to poultry in an immunogenic composition as described herein. Genes from any viral pathogen suitable for use with a recombinant viral vector as described herein may be used. For example, in some embodiments, the recombinant viral vector may express genes from Newcastle disease Virus (NDV), infectious bursal disease virus (IBDV), avian influenza virus (AIV), Chicken Anemia Virus (CAV), Infectious Bronchitis Virus (IBV), and Infectious Laryngotracheitis Virus (ILTV) or the like.

In accordance with the invention, a transgene conferring protection from or resistance to a particular virus or viruses may be inserted into the viral genome at a specific location. For example, in some embodiments, a transgene as described herein may be inserted into the viral genome in an intergenic region flanked by HVT UL 35/UL 36 in the unique long region of the genome. In another embodiment of the present invention the transgene is described herein as comprising one or more heterologous genes inserted into the viral genome in an intergenic region flanked by HVT UL 35/UL 36 of the HVT genome in addition to a second site used wherein one or more heterologous genes are inserted into the UL55 site within the HVT genome. In other embodiments, more than one transgene may be inserted into one or both of these regions.

In some embodiments, the recombinant viral vector may express multiple genes from a single virus species or may express genes from more than one virus species in order to obtain resistance to multiple viruses. For instance, in one embodiment, the invention provides a recombinant viral vector comprising the HVT genome and at least one transgene from a different viral pathogen, thus providing protection in a bird such as poultry against Marek's disease, and at least one other viral disease. For example, in one embodiment, a recombinant viral vector in accordance with the invention may provide protection in poultry against MDV and NDV, or may provide protection against MDV and IBDV, or may provide protection against MDV, NDV, and IBDV.

Viral antigens for expression in poultry by a recombinant viral vector of the present invention may be encoded by a viral gene, such as a viral gene as described herein. One of skill in the art will appreciate in this regard that it may not be required to incorporate the entirety of a particular viral gene in order to obtain a desired viral resistance. Rather, a portion of such a gene may be used. It may be desirable to choose a particular portion of a desired gene that is specific to any given targeted virus or viruses. Optimization of a desired viral protein or sequence encoding such a protein regardless of the length of the protein may be readily carried out using the methodologies known in the art that are appropriate for use with the present invention. One of skill in the art will appreciate that modifications may be made to a viral gene or genes, or the proteins encoded thereby, to increase the activity of the viral protein when introduced into the subject. Modifications made to viral genes or proteins may increase or decrease the response in a host to a specific virus.

In certain embodiments, a recombinant Marek's disease virus or recombinant viral vector of the invention may have a transgene encoding an IBDV viral protein or gene product, such as an IBDV VP2 protein or gene product. In another embodiment, such a recombinant virus or viral vector may have a transgene encoding an NDV viral protein or gene product, such as an NDV F or HN protein or gene product. In another embodiment, such a recombinant virus or viral vector may have a transgene encoding an Avian Influenza Virus (AIV) viral protein or gene product, such as an AIV HA or N protein or gene product. In another embodiment, such a recombinant virus or viral vector may have a transgene encoding an Infectious Bronchitis Virus (IBV) viral protein or gene product, such as IBV S1 or S2 protein or gene product. A transgene of the invention may have more than one gene, including a gene-fusion protein or gene product, such as an NDV F-HN fusion protein, chimera, or gene product. In some embodiments, the complete coding sequence of such a gene may be used such that a full-length or fully functional protein or polypeptide is produced. Alternatively, a portion or fragment of a viral protein or polypeptide may be sufficient to provide protection from or resistance to a particular virus or viruses.

In certain embodiments, a recombinant Marek's disease virus or recombinant viral vector of the invention may have a transgene encoding an immunomodulator such as a cytokine protein or gene product. In accordance with the invention, a cytokine may be an interleukin (IL) including, but not limited to, IL2, IL6, IL7, IL8, IL12, IL18, or the like. Such a transgene encoding a cytokine may be inserted into one or both genomic sites as described herein. In some embodiments, a transgene encoding may be inserted into one site described herein and a transgene encoding a viral protein inserted into the other site. Other immunomodulators may be useful, such as interferons, chemokines, glucans, granulocyte colony stimulating factors, oligodeoxynucleotides may also be used in accordance with the invention.

Isolation of Viral Genes or Proteins

In embodiments of the invention, a viral gene as described herein may be isolated using nucleic acid probes and/or oligonucleotides under stringent hybridization conditions, PCR or microarray, screening DNA libraries, or using any other methods known in the art. One of skill in the art will readily understand how to isolate viral genes or proteins for use according to the invention. Alternatively, expression libraries may be used to clone a virus, polymorphic variants thereof, orthologs, or alleles by detecting homologs immunologically with antisera or purified antibodies directed against a virus from another species or portions thereof.

Methods for making and screening cDNA libraries are well known in the art. For example, to make a cDNA library to clone viral genes expressed by the genome, mRNA may be reverse-transcribed into cDNA using reverse transcriptase. The cDNA may then be ligated into a vector, such as recombinant vector, and introduced into a host cell or organism for propagation, screening, and cloning.

For a genomic library, DNA may be extracted from a desired tissue and may be digested using biological enzymes or may be mechanically sheared. The resulting DNA fragments may then be isolated from undesired DNA fragments and constructed into an appropriate vector, which may then be packaged in vitro. Recombinant vectors may be analyzed by any method known in the art.

Methods such as polymerase chain reaction (PCR and RT-PCR) and ligase chain reaction (LCR) may be used to amplify nucleic acid sequences directly from mRNA, from cDNA, from genomic libraries or cDNA libraries. Degenerate oligonucleotides can be designed to amplify homologs using the sequences provided herein. Restriction endonuclease sites may be incorporated into the primers. Polymerase chain reaction or other in vitro amplification methods may also be useful, for example, to clone nucleic acid sequences that code for proteins to be expressed, to make nucleic acids to use as probes for detecting the presence of the disease to be targeted, such as MDV, NDV, and/or IBDV, encoding mRNA in biological samples, for nucleic acid sequencing, or for other purposes. Genes amplified by PCR may be purified from agarose and cloned into an appropriate vector.

Expression of viral genes may also be analyzed by techniques known in the art, ex. reverse transcription and amplification of mRNA, isolation of total RNA or polyA RNA, northern blotting, dot blotting, in situ hybridization, RNase protection, high density polynucleotide array technology, and the like.

Nucleic acids encoding a viral genome or protein may be used with high density oligonucleotide array technology (ex. GeneChip™) to identify viral genes, orthologs, alleles, variants thereof, and polymorphic variants in this invention. The gene of choice may be cloned into an intermediate vector before transformation into prokaryotic or eukaryotic cells for replication and/or expression. These intermediate vectors may be prokaryote vectors, ex. plasmids, or shuttle vectors.

Modification of Nucleic Acids

Any number of methods well known to those skilled in the art can be used to isolate and manipulate a DNA molecule. For example, polymerase chain reaction (PCR) technology may be used to amplify a particular starting DNA molecule and/or to produce variants of the starting DNA molecule. DNA molecules, or fragments thereof, can also be obtained by any techniques known in the art, including directly synthesizing a fragment by chemical means. Thus, all or a portion of a nucleic acid as described herein may be synthesized.

As used herein, the term "complementary nucleic acids" refers to two nucleic acid molecules that are capable of specifically hybridizing to one another, wherein the two molecules can form an anti-parallel, double-stranded nucleic acid structure. In this regard, a nucleic acid molecule is said to be the complement of another nucleic acid molecule if they exhibit complete complementarity. Two molecules are said to be "minimally complementary" if they can hybridize to one another with sufficient stability to permit them to remain annealed to one another under at least conventional low-stringency conditions. Similarly, the molecules are said to be complementary if they can hybridize to one another with sufficient stability to permit them to remain annealed to one another under conventional high-stringency conditions. Conventional stringency conditions are described by Sambrook, et al. (1989), and by Haymes et al. (1985). Departures from complete complementarity are permissible, as long as the capacity of the molecules to form a double-stranded structure remains. Thus, in order for a nucleic acid molecule or a fragment of the nucleic acid molecule to serve as a primer or probe such a molecule or fragment need only be sufficiently complementary in sequence to be able to form a stable double-stranded structure under the particular solvent and salt concentrations employed.

As used herein, the terms "sequence identity," "sequence similarity," or "homology" are used to describe sequence relationships between two or more nucleotide sequences. The percentage of "sequence identity" between two sequences is determined by comparing two optimally aligned sequences over a specific number of nucleotides, wherein the portion of the sequence in the comparison window may comprise additions or deletions (i.e., gaps) as compared to a reference sequence. Two sequences are said to be identical if nucleotide at every position is the same. A nucleotide sequence when observed in the 5' to 3' direction is said to be a "complement" of, or complementary to, a second nucleotide sequence observed in the 3' to 5' direction if the first nucleotide sequence exhibits complete complementarity with the second or reference sequence. As used herein, nucleic acid sequence molecules are said to exhibit "complete complementarity" when every nucleotide of one of the sequences read 5' to 3' is complementary to every nucleotide of the other sequence when read 3' to 5'. A nucleotide sequence that is complementary to a reference nucleotide sequence will exhibit a sequence identical to the reverse complement sequence of the reference nucleotide sequence.

Recombinant Vectors and Host Cells

A recombinant DNA vector may be, for example, a linear or circular plasmid. The vector system may be a single vector or plasmid or two or more vectors or plasmids that together contain the total DNA to be introduced into the genome of a host cell. A recombinant vector as described herein may be an expression vector, for example to enable production of a desired protein in a host cell such as a bacterial cell. Nucleic acid molecules as described herein, or complements or fragments thereof, may be inserted into a vector under the control of a suitable promoter that functions in one or more microbial hosts to drive expression of a linked coding sequence or other DNA sequence. Many vectors are available and known in the art for this purpose, and selection of the appropriate vector depends on the size of the nucleic acid to be inserted into the vector and the host cell to be transformed with the vector. Each vector may contain various components depending on its function (ex. amplification of DNA or expression of DNA) and the particular host cell with which it is compatible. Vector components for bacterial transformation generally include, but are not limited to, one or more of the following: a signal sequence, an origin of replication, one or more selectable marker genes, and an inducible promoter allowing the expression of exogenous DNA.

As used herein, a "recombinant Marek's Disease Virus" or "recombinant HVT" or "recombinant virus" denotes an infective virus or viral particle that has been genetically modified by the incorporation into the viral genome of one or more heterologous nucleic acid sequences, i.e. DNA coding for a viral gene or fragment or portion thereof not identical to the nucleic acid sequence of a gene naturally present in the virus. On infection of a cell by the recombinant Marek's disease virus, the recombinant virus expresses the heterologous gene in the form of a heterologous polypeptide.

A "recombinant viral vector" or "viral vector" as used herein refers to a recombinant construct that is inserted into a virus for introduction into a host cell. Such a vector according to the invention may be derived from any HVT strain. As appropriate, viral genes or protein-coding sequences may be incorporated into such a recombinant viral vector as described herein for introduction into a chicken or other poultry for protection from one or more viral diseases.

As used herein, an "insertion site" refers to a region in a viral genome into which a transgene or exogenous DNA is inserted. The insertion sites of the present invention may be intergenic regions. An intergenic region in accordance with the invention may be flanked by HVT UL35 and HVT UL36 in the unique long region of the genome. In some embodiments of the present invention one or more heterologous nucleotide encoding antigens may also be inserted into the regions defined by the UL55 locus of the HVT genome. In some embodiments, the insertion sites of the present invention may include all or a portion of a flanking gene on either side of the intergenic region. Insertion of one or more transgenes into one of these regions enables the production of a recombinant viral vector that can then be introduced into a chicken or other poultry for protection against one or more diseases.

As used herein, the term "operably linked" when used in reference to a regulatory sequence and a nucleotide sequence, means that the regulatory sequence causes regulated expression of the linked structural nucleotide sequence. The terms "regulatory sequences," "regulatory elements," or "control elements" refer to nucleotide sequences located upstream (5' sequences), within, or downstream (3' sequences) of a structural nucleotide sequence. Such sequences influence the timing and level or amount of transcription, RNA processing or stability, or translation of an associated structural nucleotide sequence. Regulatory sequences may include but are not limited to promoters, leader sequences, introns, enhancers, stem-loop structures, repressor binding sequences, and polyadenylation recognition sequences, including, but not limited to, a bovine growth hormone polyA signal, a Simian virus 40 (SV40) polyA signal, an *Autographa californica* nuclear polyhedrosis virus (AcNPV) 1629 ORF poly(A) signal, and a herpes simplex virus (HSV) thymidine kinase (TK) polyA signal. One of skill in the art will recognize that different combinations of promoters and/or regulatory elements may be used to increase or decrease expression of a transgene as described herein.

Promoters that function in different species are also well known in the art. Promoters useful for expression of polypeptides include those that are inducible, viral, synthetic, or constitutive, and/or promoters that are tissue-specific, temporally regulated, spatially regulated, and spatial-temporally regulated. For example, a promoters useful in accordance with the invention may include, but is not limited to, an immediate early (IE) cytomegalovirus (CMV) promoter, guinea pig CMV promoter, an SV40 promoter, Pseudorabies Virus promoters such as that of glycoprotein X promoter, Herpes Simplex Virus-1, such as the alpha 4 promoter, Marek's disease viruses promoters, including any isolate or strain of MDV, such as MDV-1, MDV-2, and HVT, for example a promoter controlling expression of glycoproteins such as gC, gB, gE, or gI, Infectious Laryngotracheitis Virus promoters such as those of glycoprotein gB, gE, gI, gD genes, or any other suitable promoters. One of skill in the art would be aware of how to identify a promoter useful in accordance with the invention.

In accordance with the invention, a recombinant Marek's disease virus or recombinant viral vector as described herein may comprise one or more transgenes operatively linked to one or more promoters for expression of one or more viral proteins or peptides or fragments or portions thereof. In some embodiments, a single transgene may be operatively linked to a single promoter, or more than one transgene may be operatively linked to a single promoter. In other embodiments, more than one transgene may be present in a recombinant vector wherein a first transgene is operatively linked to a first promoter, a second transgene is operatively linked to a second promoter.

Construction and Selection of Vectors

Construction of vectors containing one or more components as described herein useful for inserting genes or transgenes, or portions thereof, into a target site is known to one of skill in the art and may employ standard recombinant DNA techniques. A recombinant DNA vector or construct may comprise a selectable marker that confers a selectable phenotype to a cell. Selectable markers may also be used to select for cells that contain the exogenous nucleic acids encoding polypeptides or proteins as described herein. Such a marker may encode for example, biocide resistance, or antibiotic resistance (ex. kanamycin, G418, bleomycin, hygromycin, etc.). Selectable markers are well known to one of skill in the art and may include any markers suitable for use in accordance with the invention.

A recombinant vector or construct may also include a screenable marker, which may be used to monitor expression but which may not result in death of a cell. Suitable screenable markers may include for example, a β-glucuronidase or uidA gene (GUS), one or more of the various fluorescent protein genes, such as green fluorescent protein (GFP), red fluorescent protein (RFP), or any one of a large family of proteins which fluoresce at characteristic wavelengths, a gene that encodes an enzyme for which various chromogenic substrates are known, a luciferase gene, a xylE gene, which encodes a catechol dioxygenase that converts chromogenic catechols, an β-amylase gene, a tyrosinase gene, which encodes an enzyme capable of oxidizing tyrosine to DOPA and dopaquinone, which in turn condense to melanin, or an α-galactosidase, which catalyzes a chromogenic α-galactose substrate.

Expression of Proteins in Host Cells

To obtain high level expression of a cloned viral gene as described herein, a nucleic acid may be subcloned into an expression vector that contains a strong promoter to direct transcription, and a transcription/translation terminator. For encoded proteins, a ribosome binding site for translation initiation may also be included. Suitable promoters for use in expression vectors are well known in the art, such as a bacterial promoter, a viral promoter, or the like. Expression systems for expressing a protein are available in several prokaryotic and eukaryotic species known in the art. Commercial kits for such expression systems are also readily available. Eukaryotic expression systems for mammalian cells, yeast, and insect cells are well known in the art and are also commercially available.

Selection of an appropriate promoter to direct expression of a heterologous nucleic acid will depend on the particular application. Such a promoter may be positioned a distance from the heterologous transcription start site that is similar to the distance in its natural setting, although one of skill in the art will understand that some variation in this distance may be permitted without loss of promoter function.

In addition to a promoter, an expression vector typically contains a transcriptional or expression cassette that contains all elements required for expression of a nucleic acid in a host cell. Any conventional vectors known in the art that may be used for expression in eukaryotic or prokaryotic cells may be used to transport genetic information into a cell. A typical expression cassette thus contains a promoter operably linked to a nucleic acid sequence encoding the nucleic acid of choice and corresponding signals required for efficient processing, ex. ribosome binding sites, polyadenylation, and translation termination. Additional elements may include enhancers and, for the case of genomic DNA as the structural gene, introns with functional splice donor and acceptor sites.

In addition to a promoter sequence, such as a promoter set forth herein, an expression cassette may also contain a transcription termination region downstream of the structural gene in order to provide for efficient termination of transcription. The termination region may be from the same gene as the promoter sequence, or it may be from a different gene. Markers such as fluorescent proteins, green or red fluorescent protein, β-gal, CAT, and the like can be included in the vectors as markers for vector transduction. Epitope tags or sequence tags may also be added to recombinant proteins to provide convenient methods of isolation.

Expression vectors containing regulatory elements from eukaryotic viruses are typically used in eukaryotic expression vectors, ex. SV40 vectors, papilloma virus vectors, retroviral vectors, and vectors derived from Epstein-Barr virus. Other exemplary eukaryotic vectors include pMSG, pAV009/A+, pMTO10/A+, pMAMneo-5, baculovirus pDSVE, and any other vector allowing expression of proteins under the direction of the CMV promoter, S V40 early promoter, SV40 late promoter, metallothionein promoter, murine mammary tumor virus promoter, Rous sarcoma virus promoter, polyhedrin promoter, or other promoters known in the art that may be effective for expression in eukaryotic cells.

Expression of proteins from eukaryotic vectors can be also be regulated using inducible promoters. With inducible promoters, expression levels are tied to the concentration of inducing agents, such as tetracycline or ecdysone, by the incorporation of response elements for these agents into the promoter. High levels of expression may be obtained from inducible promoters in the presence of an inducing agent. Some expression systems have markers such as thymidine kinase and dihydrofolate reductase, which provide gene amplification.

An expression vector may also include a replicon that functions in *E. coli*, an antibiotic resistance gene for selection of bacteria harboring recombinant plasmids, and unique restriction sites in nonessential regions of the plasmid to allow insertion of eukaryotic sequences. Any antibiotic resistance gene suitable for use with the present invention may be employed.

Standard transfection methods known in the art may be used to produce bacterial, mammalian, yeast, or insect cell lines that express large quantities of protein. Such cell lines may then be purified using standard techniques known in the art, and prokaryotic and/or eukaryotic cells may be transformed according to any method known in the art for introducing cloned genomic DNA, cDNA, synthetic DNA or other foreign genetic material into a host cell. Such methods may include, but are not limited to plasmid or viral vectors, calcium phosphate transfection, protoplast fusion, electroporation, biolistics, liposomes, microinjection, or any methods available in the art.

After an expression vector or transgene is introduced into a host cell, the cell may then be cultured under conditions optimum for expression of the desired protein, which may be recovered using standard techniques known in the art. Viral pathogens or viral proteins such as those described herein may then be purified for use in diagnostic assays, for making antibodies and immunogenic compositions, and for identification of antiviral compounds. Naturally occurring proteins may be purified from biological samples, such as a tissue sample from a bird infected with a virus as described herein, while recombinant proteins may be purified using any suitable methods or expression systems known in the art.

A number of procedures for purifying recombinant protein are available in the art. For example, proteins having established molecular adhesion properties can be reversibly fused to another protein. Additionally, a specific protein may be selectively adsorbed to a purification column and then freed from the column in a relatively pure form using appropriate ligands or substrates. The fused protein may then be removed by enzymatic activity. Protein may also be purified using affinity columns. Recombinant protein can be purified from any suitable source.

Purification of Protein from Recombinant Bacteria

Recombinant proteins may be expressed by bacteria in large amounts, for example using an inducible or constitutive promoter. Promoter induction using IPTG is an example of an inducible promoter system. Bacteria may be grown from fresh or frozen culture according to standard procedures known in the art.

Proteins expressed in bacteria may form insoluble aggregates called inclusion bodies. Suitable protocols for purification of protein inclusion bodies are known in the art. Lysing of bacterial for recovery of expressed proteins may be performed using any methods known in the art, which may include introduction of chemical buffers, sonication, mechanical disruption, and the like. Inclusion bodies may also be solubilized, and the lysed cell suspension may be centrifuged to remove unwanted cellular debris. Inclusion body proteins may be renatured by dilution or dialysis with an appropriate buffer.

Recombinant proteins may also be obtained from bacteria periplasm. After lysis of bacterial cells, the periplasmic fraction of the bacteria may be isolated by any methods known in the art. Recombinant proteins present in the supernatant may be separated from host proteins by standard separation techniques well known to those of skill in the art.

Proteins may be separated using any techniques known in the art, for example, solubility fractionation or size differential filtration, which isolates a protein on the basis of molecular weight using filtration through membranes of different pore size. Column chromatography may be used for isolation of a protein from other proteins on the basis of size, net surface charge, hydrophobicity, or affinity for ligands or substrates. In addition, antibodies raised against a protein of interest may be conjugated to a column and the proteins immunopurified. All of these methods are well known in the art. It will be apparent to one of skill that chromatographic techniques may be performed on any scale and using any appropriate commercial equipment.

Antibody Production

Methods of producing polyclonal and monoclonal antibodies that react specifically with viral proteins, virus particles, and/or nucleic acids are known in the art. Such techniques may include antibody preparation by selection of antibodies from recombinant antibody libraries in phage or other vectors, as well as preparation of polyclonal and monoclonal antibodies by immunizing rabbits or mice.

A number of antigens or antigenic regions comprising a viral protein or portions thereof, virus particles, and/or nucleic acids may be used to produce antibodies specifically reactive to a desired viral pathogen. For example, a recombinant viral protein or an antigenic fragment thereof, may be isolated using any methods described herein or known in the art. Recombinant proteins may be expressed in prokaryotic or eukaryotic cells and purified as described herein. Monoclonal and/or polyclonal antibodies may be produced using naturally occurring (in pure or impure form) or recombinant proteins using methods known in the art. Synthetic peptides derived from a viral sequence may also be used to generate antibodies and may be conjugated to a carrier protein and injected into an animal capable of producing antibodies (ex. rabbit).

Methods of production of polyclonal antibodies are known to those of skill in the art. For example, an inbred strain of mice or rabbits may be immunized with a protein using a standard adjuvant, such as an adjuvant described herein, using a standard immunization protocol known in the art. When appropriately high titers of antibody to the protein are obtained, antisera may be prepared, and enrichment performed to obtain antibodies reactive to the protein.

Monoclonal antibodies may also be obtained by various methods known in the art. For example, spleen cells from an animal immunized with a desired antigen may be immortalized, commonly by fusion with a myeloma cell or through transformation with Epstein Barr Virus (EBV), oncogenes, or retroviruses, or other methods well known in the art. The immortalized cells may then be screened for production of antibodies of the desired specificity and affinity for the antigen. Yield of the monoclonal antibodies produced by such cells may be enhanced by various techniques known in the art, for example by injection into the peritoneal cavity of a vertebrate host.

Monoclonal antibodies and polyclonal sera may be collected and titered against the desired antigen or protein in an immunoassay, for example, a solid phase immunoassay with the protein immobilized on a solid support. Antibodies specific only for a particular viral protein may also be made by subtracting out other cross-reacting proteins. In this manner, antibodies that bind only to the protein of choice may be obtained.

Once the specific antibodies against the desired viral antigen, such as protein, virus, and/or nucleic acid are available, the desired antigen may be detected using a variety of immunoassay methods. The antibody may also be used therapeutically.

Protein either associated with or distinct from a viral particle as described herein may be detected and/or quantified using any of a number of well recognized immunological binding assays. Viral particles may be detected based on an epitope defined by the viral proteins as presented in a viral particle and/or an epitope defined by a viral protein that is separate from a viral particle (ex. such as may be present in an infected cell) Immunological assays may use an antibody that specifically binds to a protein or antigen of choice. The antibody may be produced by any of a number of methods well known to those of skill in the art Immunoassays may also use a labeling agent to specifically bind to the complex formed by the antibody and antigen for detection purposes. The labeling agent may itself be one of the moieties comprising the antibody/antigen complex. Thus, the labeling agent may be a labeled viral protein nucleic acid or a labeled antiviral antibody. Alternatively, the labeling agent may be a third moiety, such as a secondary antibody, that specifically binds to the antibody/antigen complex. A secondary antibody may be specific to antibodies of the species from which the first antibody is derived. A labeling agent can be modified with a detectable moiety, such as biotin, to which another molecule can specifically bind, such as streptavidin. A variety of detectable moieties are well known to those skilled in the art.

Immunoassays for detecting viral protein, virus, and/or nucleic acid in samples are well known in the art. Such assays may be either competitive or noncompetitive and may be either quantitative or non-quantitative. Noncompetitive immunoassays are assays in which antigen may be directly detected and, in some instances, the amount of antigen directly measured. In competitive assays, viral antigen present in a sample is detected indirectly by a detectable signal associated with a known, added (exogenous) viral antigen displaced from an antiviral antigen antibody by the viral antigen present in a sample. In this manner, such assays can also be adapted to provide for an indirect measurement of the amount of viral antigen present in the sample. Competitive binding immunoassays may also be used to determine cross-reactivity, in which any cross-reacting antibodies may be removed from pooled antisera. Additional assay types, including but not limited to western blot or liposome immunoassays may also be used in accordance with the present invention.

One of skill in the art will appreciate that it is often desirable to minimize nonspecific binding in immunoassays. Particularly, where the assay involves an antigen or antibody immobilized on a solid substrate it is desirable to minimize the amount of nonspecific binding to the substrate. Means of reducing such non-specific binding are well known to those of skill in the art.

An assay as described herein may include a label or detectable group that does not significantly interfere with the specific binding of the antibody used in the assay. A detectable group may be any material having a detectable physical or chemical property. Such detectable labels are known in the art and generally, any label useful in such methods may be applied to the present invention. Thus, a "label" as used herein may be any composition detectable by spectroscopic, photochemical, biochemical, immunochemical, electrical, optical or chemical means. Useful labels in the present invention may include magnetic beads (ex. DYNABEADS™), fluorescent dyes (ex. fluorescein isothiocyanate, Texas red, rhodamine, and the like), radiolabels (ex. $^3$H, $^{125}$I, $^{35}$S, or $^{32}$P), enzymes (ex. horse radish peroxidase, alkaline phosphatase, and/or any others known in the art and used in ELISA), and colorimetric labels such as colloidal gold or colored glass or plastic beads (ex. polystyrene, polypropylene, latex, etc.).

A label in accordance with the invention may be coupled directly or indirectly to the desired component of the assay according to methods well known in the art. As described above, a wide variety of labels may be used, with the choice of label depending on sensitivity, ease of conjugation with the compound, stability requirements, or available instrumentation, among others.

Non-radioactive labels may be attached by indirect means. Generally, a ligand molecule (ex. biotin) is covalently bound to the molecule. The ligand may then bind to another molecule (ex. streptavidin), which may be either inherently detectable or covalently bound to a signal system, such as a detectable enzyme, a fluorescent compound, or a chemiluminescent compound. The ligands and their corresponding targets may be used in any suitable combination with antibodies that recognize a viral antigen, or secondary antibodies that recognize an antiviral antigen. The molecules may also be conjugated directly to signal generating compounds, ex. by conjugation to an enzyme or fluorophore. Enzymes of interest to be used as labels may be hydrolases, for example phosphatases, esterases and glycosidases, or oxidotases, such as peroxidases. Fluorescent compounds may include fluorescein and its derivatives, rhodamine and its derivatives, dansyl, umbelliferone, and the like. Chemiluminescent compounds may include luciferin, 2,3-dihydrophthalazinediones, ex. luminol, or others known in the art.

Means of detecting labels are well known to those of skill in the art and will depend on the type of label used. For example, autoradiography may be used to detect a radioactive label, or fluorochromes may be used to detect a fluorescent label. Fluorescence may be detected visually, for example by electronic detectors such as charge coupled devices (CCDs) or photomultipliers, and the like. Similarly, enzymatic labels may be detected by providing the appropriate substrates for the enzyme and detecting the resulting reaction product. Colorimetric or chemiluminescent labels may be detected by observing a color associated with a particular label. In some embodiments, an assay formats may not require the use of a labeled component but rather may be detected by simple visual inspection.

Pharmaceutical/Immunogenic Compositions and Administration Thereof

In some aspects recombinant vectors comprising one or more transgenes expressing one or more viral proteins or peptides or fragments thereof as described herein may be used as pharmaceutical compositions or immunogenic compositions for administering to a subject such as a chicken or other poultry in order to provide protection from one or more viruses. For example, an immunogenic composition as described herein comprise a recombinant vector with one or more transgenes as described herein which are inserted into the viral genome, for example in an intergenic region flanked by the intergenic loci UL 35/UL 36 in the unique long (UL) region of the HVT genome. In one aspect the present invention provides a recombinant Herpesvirus of Turkey (HVT) genome comprising one or more nucleotide sequence(s) coding for one or more heterologous antigen(s) inserted into the intergenic loci UL 35/UL 36 in the unique long region of the HVT genome and one or more nucleotide sequence(s) coding for one or more heterologous antigens inserted at the UL55 site in the unique long region (UL) of the HVT genome.

In other aspects, proteins or peptides and immunogenic fragments thereof, and/or polynucleotides, as well as antiviral antibodies and/or T cells, may be incorporated into pharmaceutical compositions or immunogenic compositions (ex. vaccines). In another embodiment, an immunogenic composition according to the invention may comprise at least a third transgene, a fourth transgene, or the like, which may encode additional viral proteins. In such a way, it is possible to provide an immunogenic composition to a subject such as poultry that provides protection from any desired number of viruses. Whole virus vaccine (live and attenuated, or replication incompetent, or killed) or subunit vaccines, such as structural or non-structural viral proteins or immunogenic fragments thereof, can be used to treat or prevent viral infections by eliciting an immune response in a subject. Alternatively, a pharmaceutical composition may comprise an antigen-presenting cell transfected with a viral polynucleotide such that the antigen-presenting cell expresses a viral peptide.

Immunogenic compositions in accordance with the invention may be designed to generate antibody immunity and/or cellular immunity in a subject. Such compositions may comprise one or more such compounds along with a non-naturally occurring pharmaceutically acceptable carrier. In other embodiments, an immunogenic composition in accordance with the invention may include more than one adjuvants or pharmaceutically acceptable carriers such that at least one is non-naturally occurring. A pharmaceutically acceptable carrier or adjuvant may be any substance that enhances an immune response in a subject to an exogenous antigen, including but not limited to, adjuvants, liposomes, biodegradable microspheres. A pharmaceutically acceptable carrier or adjuvant may contain a substance designed to protect the antigen from rapid catabolism, such as aluminum hydroxide or mineral oil, or a stimulator of immune responses, such as proteins derived from Bortadella pertussis or *Mycobacterium tuberculosis*. Commercially available adjuvants may include for example, Freund's Incomplete Adjuvant and Complete Adjuvant, Merck Adjuvant 65, aluminum salts such as aluminum hydroxide gel (alum) or aluminum phosphate; CpG oligonucleotides, salts of calcium, iron or zinc; an insoluble suspension of acylated tyrosine; acylated sugars; cationically or anionic ally derivatized polysaccharides; polyphosphazenes; biodegradable microspheres; and monophosphoryl lipid A. One of skill in the art will be able to identify appropriate pharmaceutically acceptable carriers for use with the present invention.

Pharmaceutical or immunogenic compositions and/or vaccines within the scope of the present invention may also contain other compounds, which may be biologically active or inactive. For example, one or more immunogenic portions of other antigens may be present, either incorporated into a fusion polypeptide or as a separate compound, within a composition or vaccine according to the invention. In some embodiments, polypeptides useful with the present invention may be conjugated to other macromolecules. Pharmaceutical or immunogenic compositions and vaccines may generally be used for prophylactic and/or therapeutic purposes. For example, in accordance with the invention, a composition as described herein may be provided to a subject, such as a bird, prior to infection with or exposure to a virus in order to provide protection against infection with one or more viruses or development of symptoms of infection. In other embodiments, such a composition may be provided to a subject, such as a bird, after infection with or exposure to one or more viruses in order to provide treatment of the viruses in the subject, such as by reducing or eliminating infection in the subject.

Nucleic acid vaccines encoding a genome, structural or non-structural protein, or a fragment thereof of a virus described herein may also be used to elicit an immune response to treat or prevent viral infection. Numerous gene delivery techniques are well known in the art. Appropriate nucleic acid expression systems may contain the necessary DNA sequences for expression in a subject (such as a suitable promoter and termination signal). In some embodiments, a DNA as described herein may be introduced using a viral expression system (ex. Marek's disease virus or HVT), which may involve the use of a non-pathogenic, replication competent virus.

Pharmaceutical or immunogenic compositions may be provided in single-dose or multi-dose containers, such as sealed ampoules or vials. Such containers may be sealed to preserve sterility of the composition until use. In general, compositions as described herein may be stored as suspensions, solutions, or emulsions in oily or aqueous vehicles. Alternatively, such a composition may be stored in a freeze-dried condition requiring only the addition of a sterile liquid carrier immediately prior to use.

As described herein, an immunogenic composition may be combined with a pharmaceutically acceptable carrier. The selection of a suitable carrier may be determined in part by the particular composition being administered (ex. nucleic acid, protein, modulatory compounds, or transduced cell), as well as by the particular method used to administer the composition. Accordingly, a wide variety of suitable formulations of pharmaceutical or immunogenic compositions are available that may of use in the present invention. Administration may be in any convenient manner, ex. by injection, oral administration, inhalation, transdermal application, or rectal administration. Injection of a recombinant vector or an immunogenic composition as described herein may be provided to a subject such as poultry in a single administration or dose, or may be administered more than once, such as repeated doses.

Formulations suitable for parenteral administration, such as, for example, by intraarticular (in the joints), intravenous, intramuscular, intradermal, intraperitoneal, in ovo, and subcutaneous routes, include aqueous and non-aqueous, isotonic sterile injection solutions, which can contain antioxidants, buffers, bacteriostats, and solutes that render the formulation isotonic with the blood of the intended subject, and aqueous and nonaqueous sterile suspensions that can include suspending agents, solubilizers, thickening agents, stabilizers, and preservatives. In the practice of this invention, compositions may be administered, for example, by intravenous infusion, orally, topically, intraperitoneally, intravesically or intrathecally.

Such compositions may also comprise buffers (ex. neutral buffered saline or phosphate buffered saline), carbohydrates (ex. glucose, mannose, sucrose or dextrans), mannitol, proteins, polypeptides or amino acids such as glycine, antioxidants, bacteriostats, chelating agents such as EDTA or glutathione, adjuvants (ex. aluminum hydroxide), solutes that render the formulation isotonic, hypotonic, or weakly hypertonic with the blood of a subject, suspending agents, thickening agents, and/or preservatives. Alternatively, compositions of the present invention may be formulated as a lyophilizate. Compounds may also be encapsulated within liposomes using methods known in the art.

Injection solutions and suspensions may be prepared from sterile powders, granules, and tablets as described herein. Cells transduced by nucleic acids for ex vivo therapy may also be administered intravenously or parenterally as described above. An injection as described herein may involve a suspension of one or more of a killed, inactivated, attenuated, or otherwise non-virulent virus culture, purified or non-purified solution of a viral protein, or a nucleic acid as described herein. An injection solution may also contain a pharmaceutically acceptable carrier as described herein.

Formulations suitable for oral administration may consist of (a) liquid solutions, such as an effective amount of the packaged viral protein or nucleic acid suspended in diluents, such as water, saline or PEG 400; (b) capsules or tablets, each containing a predetermined amount of the active ingredient, as liquids, solids, granules or gelatin; (c) suspensions in an appropriate liquid; or (d) suitable emulsions. Tablet forms may include one or more of lactose, sucrose, mannitol, sorbitol, calcium phosphates, corn starch, potato starch, microcrystalline cellulose, gelatin, colloidal silicon dioxide, talc, magnesium stearate, stearic acid, and other excipients, colorants, fillers, binders, diluents, buffering agents, moistening agents, preservatives, flavoring agents, dyes, disintegrating agents, and pharmaceutically compatible carriers. Lozenge forms may comprise the active ingredient in a flavor, ex. sucrose, as well as pastilles comprising the active ingredient in an inert base, such as gelatin and glycerin or sucrose and acacia emulsions, gels, and the like containing, in addition to the active ingredient, carriers known in the art.

The compound of choice, alone or in combination with other suitable components, may be made into aerosol formulations to be administered via inhalation. Aerosol formulations may be placed into pressurized acceptable propellants, such as dichlorodifluoromethane, propane, nitrogen, and the like.

The dose administered to a subject in the context of the present invention should be sufficient to affect a beneficial therapeutic response in the subject over time. The dose will be determined by the efficacy of the particular vector employed and the condition of the subject, as well as the body weight and/or surface area of the patient to be treated. The size of the dose also may be determined by the existence, nature, and extent of any adverse side-effects that accompany the administration of a particular vector, or transduced cell type in a particular patient. For compositions comprising a vector as described herein, the effective amount of the vector to be administered may be determined in part based on circulating plasma levels of the vector, vector toxicities, health of the subject, and production of anti-vector antibodies.

For administration, compounds and transduced cells of the present invention can be administered at a rate determined by the LD-50 of the inhibitor, vector, or transduced cell type, and the side-effects of the inhibitor, vector or cell type at various concentrations, as applied to the mass and overall health of the subject. Administration may be accomplished via single, multiple, or divided doses.

Immunological Detection of Polypeptides and Nucleic Acids

Immunoassays may be used to detect viral proteins, virus particles, and/or nucleic acids. Such assays may be useful for therapeutic and/or diagnostic applications, such as those described herein. Immunoassays are well known in the art and may be used to qualitatively or quantitatively analyze proteins, virus particles, and/or nucleic acids.

Assays for Viral Proteins and Antibodies to Viral Antigens

In one embodiment of the present invention, the presence of a virus as described herein, a viral nucleic acid, or a viral protein in a sample may be determined by an immunoassay. Enzyme-mediated immunoassays such as immunofluorescence assays (IFA), enzyme linked immunosorbent assays (ELISA), capture assays, micro-agglutination tests, and immunoblotting assays (ex. western blot) can be readily adapted to accomplish detection of a virus or viral proteins. An ELISA method may be effective for detection of a virus or viral protein as described herein. Such an ELISA may, for example, have steps such as: (1) bind an antiviral antibody or antigen to a substrate; (2) contact the bound receptor with a biological sample containing a virus, a viral antigen, a viral protein, or antibodies to the virus; (3) contact the biological sample with an antibody bound to a detectable moiety (ex. horseradish peroxidase enzyme or alkaline phosphatase enzyme); (4) contact the biological sample with the substrate for the enzyme; (5) contact the biological sample with a detecting reagent, such as a color reagent; (6) observe a detectable result. In some embodiments, a biological sample suitable for use in such an ELISA may be blood or other fluids. In another embodiment, an ELISA as described herein may detect a virus or viral protein in a tissue sample. Such methods may be readily modified by those of skill to detect the presence of an antiviral antibody in a sample, or a specific viral protein, as well as the virus. In certain embodiments, an ELISA according to the invention may detect the presence of an antiviral antibody.

ELISA assays as described herein may include a nitrocellulose strip impregnated with a viral protein as described herein. The nitrocellulose strip may produce a visual result when contacted with a test sample containing antiviral nucleoprotein antibodies. Such a test may identify a subject already having antibodies against a viral protein and thus the subject may have immunity to the virus. Administration of an immunogenic composition to prevent viral infection such as described herein may be unnecessary in such a subject and therefore, identification of subjects already having immunogenic antibodies may prevent unnecessary administration of an immunogenic compound to such a subject. In this regard, an embodiment of the present invention may involve identifying a subject lacking antiviral antibodies using an assay as described herein, such as an ELISA assay, and then providing an immunogenic composition as described herein to that subject in order to prevent viral infection. In another embodiment, a nitrocellulose strip for use in an ELISA according to the invention may be impregnated with an antibody, such as antiviral antibody, and may produce a visual result when contacted with a test sample containing a viral protein. Such a test may identify a subject infected with a virus as described herein.

Another immunologic technique that can be useful in the detection of a virus is a competitive inhibition assay. Such an assay utilizes monoclonal antibodies (MABs) reactive with a specific virus. A biological fluid (ex. blood) from a subject may be contacted with a first antibody bound to a substrate, and a labeled monoclonal antibody contacted with the first antibody-virus complex. The amount of inhibition of monoclonal antibody binding is measured relative to a control.

As will be readily understood by one of skill in the art, a biological sample for use in the above assays may be taken directly from a subject or may be in a partially purified form. An antibody specific for a particular virus will react by binding to the virus as a primary reaction. Thereafter, a secondary reaction with an antibody bound to or labeled with a detectable moiety may also be added in order to enhance the detection of the primary reaction. Generally, in the secondary reaction, an antibody or other ligand which is reactive, either specifically or nonspecifically with a different binding site (epitope) of the virus will be selected for its ability to react with multiple sites on the complex of antibody and virus. Thus, for example, several molecules of the antibody in the secondary reaction can react with each complex formed by the primary reaction, making the primary reaction more detectable.

The detectable moiety can allow visual detection of a precipitate or a color change, visual detection by microscopy, or automated detection by spectrometry, radiometric measurement or the like. Examples of detectable moieties include fluorescein and rhodamine (for fluorescence microscopy), horseradish peroxidase (for either light or electron microscopy and biochemical detection), biotin-streptavidin (for light or electron microscopy) and alkaline phosphatase (for biochemical detection by color change). The detection methods and moieties used can be selected, for example, from any disclosed herein or available in the art.

Detecting the Presence of a Viral Nucleic Acid

In some embodiments, a viral infection as described herein may be detected based on the level of a particular RNA or DNA in a biological sample. Primers from a particular virus or viral pathogen may be used for detection, diagnosis, and determination of the presence of a virus. Any suitable primer may be used to detect genomic DNA or any sequence therein, an open reading frame or gene, or a protein of choice, using any appropriate methods known in the art. A suitable nucleic acid sequence may be used as single- or double-stranded probes or primers for detection of viral mRNA or cDNA generated therefrom, as may be present in a biological sample. Viral polynucleotides as described herein may also be used to generate additional copies of the polynucleotides, in order to generate antisense oligonucleotides, or as triple-strand forming oligonucleotides. For example, two oligonucleotide primers may be used in a PCR-based assay to amplify a portion of a viral cDNA derived from a biological sample, wherein at least one of the oligonucleotide primers is specific for (i.e., hybridizes to)

the viral polynucleotide. Such primers may be any length sufficient to hybridize to and enable amplification of a viral nucleic acid as described herein, including at least or about 10 nucleotides, 11 nucleotides, 12 nucleotides, 13 nucleotides, 14 nucleotides, 15 nucleotides, 16 nucleotides, 17 nucleotides, 18 nucleotides, 19 nucleotides, 20 nucleotides, 21 nucleotides, 22 nucleotides, 23 nucleotides, 24 nucleotides, 25 nucleotides, 26 nucleotides, 27 nucleotides, 28 nucleotides, 29 nucleotides, 30 nucleotides, 35 nucleotides, 40 nucleotides, 45 nucleotides, or 50 nucleotides; or from about 12 to about 50 nucleotides in length, 15 to 30 nucleotides in length, 15 to 25 nucleotides in length, or 20 to 30 nucleotides in length. DNA primers suitable for use with the present invention may be any primers described herein, such as those set forth as SEQ ID NOs:40-157

An amplified nucleotide, for example a cDNA, may then be separated and detected using techniques well known in the art, such as gel electrophoresis. Similarly, oligonucleotide probes that specifically hybridize to a viral polynucleotide may be used in a hybridization assay to detect the presence of a viral polynucleotide in a biological sample.

Nucleic acid probes or primers specific to a virus as described herein may be generated using the polynucleotide sequences disclosed herein. The probes are preferably at least about 12, 15, 16, 18, 20, 22, 24, or 25 nucleotide fragments or other polynucleotide sequence encoding a viral nucleic acid or polypeptide. Nucleic acid probes can be less than about 200 bp, 150 bp, 100 bp, 75 bp, 50 bp, 60 bp, 40 bp, 30 bp, 25 bp 2 kb, 1.5 kb, 1 kb, 0.5 kb, 0.25 kb, 0.1 kb, or 0.05 kb in length. The probes can be produced by, for example, chemical synthesis, PCR amplification, generation from longer polynucleotides using restriction enzymes, or other methods well known in the art. The polynucleotides described herein may also be used in methods or assays that involve the use of solid substrates, such as arrays. Such an array may have one or more different polynucleotides, which may be immobilized on the arrays using methods known in the art.

In some embodiments, a polynucleotide of the invention may be detectably labeled. Detectable labels may include, but are not limited to, radiolabels, fluorochromes, including fluorescein isothiocyanate (FITC), rhodamine, Texas Red, phycoerythrin, allophycocyanin, 6-carboxyfluorescein (6-FAM), 2',7'-dimethoxy-4',5'-dichloro-6-carboxyfluorescein, 6-carboxy-X-rhodamine (ROX), 6-carboxy-2',4',7',4, 7-hexachlorofluorescein (HEX), 5-carboxy fluorescein (5-FAM) or N,N,N',N'-tetramethyl-6-carboxyrho-damine (TAMRA); radioactive labels such as $^{32}P$, $^{35}S$, and $^{3}H$), and the like. In some embodiments, a detectable label may involve multiple steps (ex. biotin-avidin, hapten-anti-hapten antibody, and the like). In accordance with the invention, any suitable qualitative or quantitative methods known in the art for detecting specific viral nucleic acids (ex. RNA or DNA) may be used. A viral nucleic acid as described herein may be detected by, for example, in situ hybridization in tissue sections, using methods that detect single base pair differences between hybridizing nucleic acid, by reverse transcriptase-PCR, or in northern blots containing poly A mRNA, or other methods well known in the art. For detection of viral polynucleotides in blood or blood-derived samples, methods that allow for detection of single base pair mismatches may be employed.

A viral nucleic acid sequence may be present in a biological sample obtained from an infected individual at relatively low levels, and thus amplification techniques known in the art (ex. PCR) may be used to amplify the sequence prior to performing a hybridization assays.

Nucleic acid probes may be prepared using a viral genome as described herein. Such a probe may include at least about 8 nucleotides or more and may be prepared synthetically or by excision from recombinant polynucleotides. A probe as described herein may hybridize with a viral nucleic acid, and thus such a probe may be useful for detection of a particular virus in a biological sample. Probes as described herein may also be useful for identification of infected subjects, as well as for further characterization of viral genomes. A probe for detecting viral polynucleotides (natural or derived) may be of a specific length or have a sequence which allows the detection of unique viral sequences by hybridization. While about 6-8 nucleotides may be useful, longer sequences may be preferred, ex. sequences of about 10-12 nucleotides, or about 20 nucleotides or more. One of skill in the art will be aware how to make and use a probe as described herein.

Nucleic acid probes may be prepared using routine methods, including, but not limited to, automated oligonucleotide synthetic methods. A sequence useful for preparing such a probe may include a complement to any unique portion of a viral genome, for example a portion of the viral genome that allows for distinguishing a particular virus from other viruses that may be present in the sample. A probe as described herein may have complete complementarity to the target sequence of interest or may have one or more mismatches. A probe useful in accordance with the invention having one of more mismatches will still hybridize to the target sequence of interest. For use of such probes as diagnostics, the biological sample to be analyzed may be treated prior to analysis, if desired, to extract the nucleic acids contained therein. The resulting nucleic acids from the sample may be subjected to gel electrophoresis or other size separation techniques. A probe may be labeled with a detectable label as described herein. Suitable labels, and methods for labeling probes are known in the art and may include any labels described herein or others useful with the present invention.

A probe may be completely complementary to a viral genome or portion thereof (ex. to all or a portion of a sequence encoding a viral protein as described herein). High stringency conditions may be desirable in order to prevent or at least minimize false positive results. The stringency of hybridization may be determined by several factors during hybridization and washing, including temperature, ionic strength, length of time, and concentration of reagents. A probe or nucleic acid from a sample may be provided in solution for such assays or may be affixed to a support (ex. solid or semi-solid support). Examples of supports that may be used include but are not limited to nitrocellulose (ex. membrane or microtiter well form), polyvinyl chloride (ex. sheets or microtiter wells), polystyrene latex (ex. beads or microtiter plates, polyvinylidine fluoride, diazotized paper, nylon membranes, activated beads, and Protein A beads).

In one embodiment, a probe or sample nucleic acid may be provided on an array for detection. Arrays may be created by, for example, spotting polynucleotide probes onto a substrate (ex. glass, nitrocellulose, and the like) in a two-dimensional matrix or array. The probes may be bound to the substrate by either covalent bonds or by non-specific interactions, such as hydrophobic interactions. Samples of polynucleotides can be detectably labeled (ex. using radioactive or fluorescent labels) and then hybridized to the probes. Double stranded polynucleotides, comprising the labeled sample polynucleotides bound to probe polynucleotides, may be detected once the unbound portion of a sample is removed. Techniques for constructing arrays and methods of using these arrays are known in the art. Arrays may be used for a single sample to be analyzed for the presence of two or more nucleic acid target regions. In such a case, the probes for each of the target regions, as well as controls (both positive and negative) may be provided on a single array. Arrays thus facilitate rapid and convenience analysis.

Diagnostic Tests and Kits

The invention further provides diagnostic reagents and kits comprising one or more such reagents for use in a variety of diagnostic assays, including for example, immunoassays such as ELISA and "sandwich"-type immunoassays, as well as nucleic acid assays, ex. PCR assays. In a related embodiment, an assay may be performed in a flow-through or strip test format, wherein the binding agent is immobilized on a membrane, such as nitrocellulose. Such kits may preferably include at least a first peptide, or a first antibody or antigen binding fragment of the invention, a functional fragment thereof, or a cocktail thereof, or a first oligonucleotide pair, and means for signal generation. In some embodiments, a kit may comprise an immunogenic composition, such as a recombinant virus as described herein. Reagents and other compounds, such as a pharmaceutically acceptable carrier may be included in the kit. An immunogenic composition when provided in such a kit may be in a solution such as in a pre-measured dose or amount, or may be a dry composition, such as in desiccated or lyophilized form suitable for rehydration or resuspension. The kit components may be pre-attached to a solid support or may be applied to the surface of a solid support when the kit is used. The signal generating means may come pre-associated with an antibody or nucleic acid of the invention or may require combination with one or more components, ex. buffers, nucleic acids, antibody-enzyme conjugates, enzyme substrates, or the like, prior to use.

Kits may also include additional reagents, ex. blocking reagents for reducing nonspecific binding to the solid phase surface, washing reagents, enzyme substrates, enzymes, and the like. The solid phase surface may be in the form of microtiter plates, microspheres, or other materials suitable for immobilizing nucleic acids, proteins, peptides, or polypeptides. An enzyme that catalyzes the formation of a chemiluminescent or chromogenic product or the reduction of a chemiluminescent or chromogenic substrate is one such component of the signal generating means. Such enzymes are well known in the art. Where a radiolabel, chromogenic, fluorigenic, or other type of detectable label or detecting means is included within the kit, the labeling agent may be provided either in the same container as the diagnostic or therapeutic composition itself or may alternatively be placed in a second distinct container into which this second composition may be placed and suitably aliquoted. Alternatively, the detection reagent and the label may be prepared in a single container means.

All patents and other publications identified are expressly incorporated herein by reference for the purpose of describing and disclosing, for example, the methodologies described in such publications that might be used in connection with the present invention. These publications are provided solely for their disclosure prior to the filing date of the present application.

The present invention is further illustrated and supported by the following examples. However, these examples should in no way be considered to further limit the scope of the invention. To the contrary, one having ordinary skill in the art would readily understand that there are other embodiments, modifications, and equivalents of the present invention without departing from the spirit of the present invention and/or the scope of the appended claims.

EXAMPLES

Example 1

Construction of HVT-Gfp Plasmids

HVT-Green Fluorescent Protein (Gfp)-B Transfer Plasmid Construction

HVT-gfp-B transfer plasmid (SEQ ID NO.18) was chemically synthesized by GeneArt, ThermoFisher). 2.5 ug of the plasmid was transfected into secondary CEF cells using LTX transfection reagent (Invitrogen) in 6-well plate. About 4-6 hours later, the transfected cells were infected with HVT at 0.006 moi ($1.5 \times 10^4$ pfu/$2.5 \times 10^6$ cells). Three days later, the cells were passaged 1:15 to T75 with fresh CEF ($1 \times 10^7$ cells/T75). The cells were then plated 1:50 onto 24 well-plates three days later. Cells from wells that contain green fluorescent foci were plated onto 96-well plate at 1:200, 1:500 and 1:1000 dilutions with fresh cells ($6 \times 10^4$ cells/well). The wells that contain single green foci were purified 3 rounds by limiting dilution method using 96-well plates. The purified virus was expanded using CEF cells and frozen stock made. It was designated as "HVT-gfp-B".

PCR analysis of three purified clone using primers just outside of integration site of UL55-Gene3 (upper primer: SEQ ID NO. 49; lower primer: 5'-SEQ ID NO. 50) gave a band of 1.893 kb as predicted. HVT gave a band of 0.15 kb as expected. Please refer to FIG. 1.

HVT-Gfp-A Modified Transfer Plasmid Construction

Modified transfer plasmid HVT-gfp-A (SEQ ID NO.16) was created by applying site-specific mutagenesis using two pairs of primers (upper primer pairs to generate SbfI upstream of gfp gene: SEQ ID NO.40 and SEQ ID NO 41; lower primers to generate SbfI downstream of gfp gene:— SEQ ID NO. 42 and SEQ ID NO.43 for original transfer plasmid HVT-gfp-A (SEQ ID NO. 17) that was chemically synthesized by GeneArt, ThermoFisher. 0.01 ug of modified transfer plasmid HVT-gfp-A was co-transfected with 2.5 ug HVT DNA using 7.5 uL PEI (Polyethylenimine) onto secondary CEF cells on 6-well plate. Green fluorescent foci became apparent at passage 1. After three rounds of purification by limiting dilution method, 1 clone of HVT-gfp-A was further expanded and frozen stocks made.

Figure 2:
FIG. 2 is a representation of a PCR reaction demonstration the integration site of a gfp gene at the UL35/36 integration site of the HVT genome.
Figure 4A:
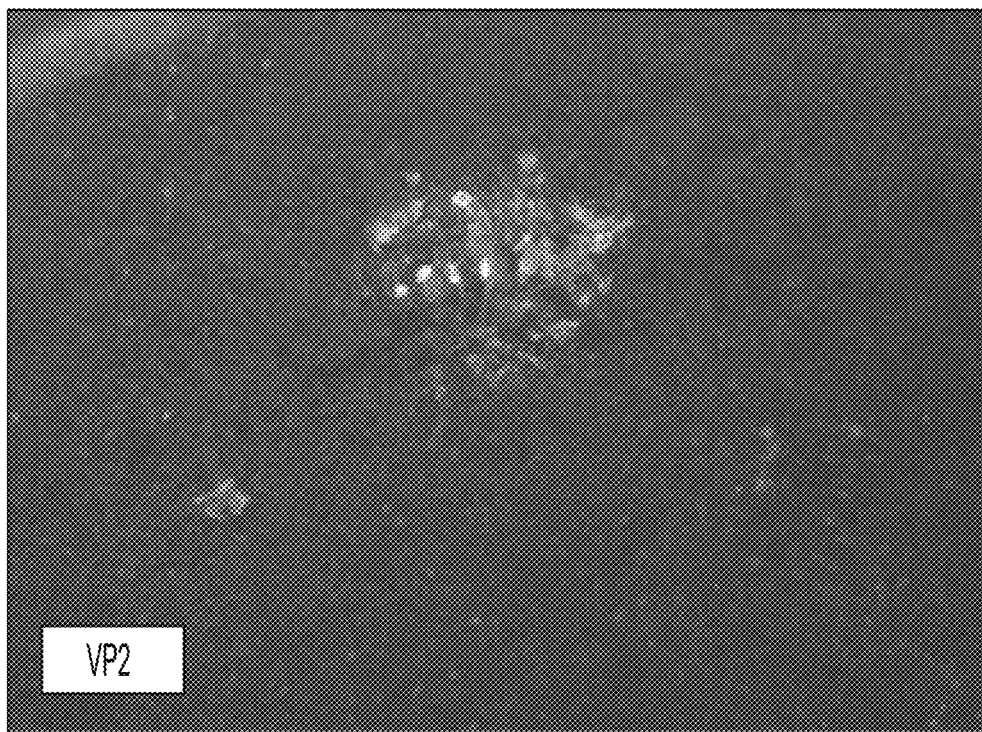
FIGS. 4A and 4B are representations of transfected/infected JBJ-1 cells staining for IBDV VP2 (panel A) and HVT infection (panel B) for HVT IBD 5.
Figure 4B:
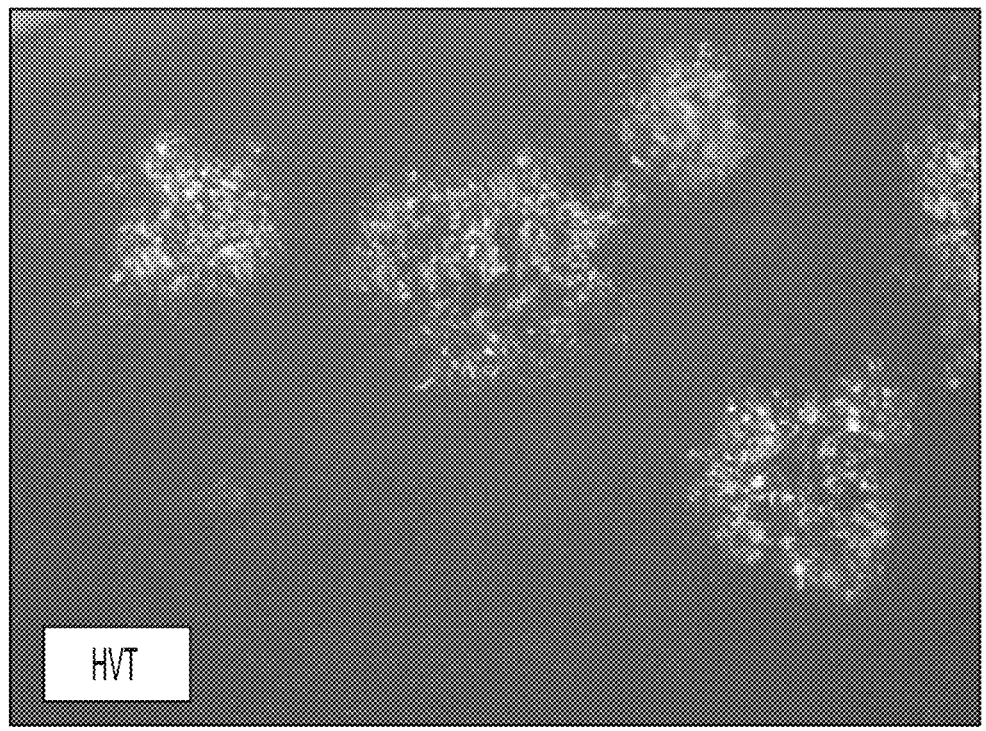

PCR analysis of the purified clone (left lane) using primers just outside of integration site of UL35-UL36 (upper primer: SEQ ID NO. 44; lower primer: SEQ ID NO. 45) gave a 1.922 kb band as predicted (FIG. 4). The DNA of modified transfer plasmid HVT-gfp-A was used as control (right lane). Please refer to FIG. 2.

Example 2

HVT-IBD Construction

Construction of HVT-IBD #1

HVT-IBD #1 transfer plasmid (SEQ ID NO. 20) was chemically synthesized by GeneArt, ThermoFisher). 2.5 ug of the plasmid was transfected into secondary CEF cells using LTX transfection reagent (Invitrogen) in 6-well plate. Approximately 4-6 hours later, the transfected cells were infected with HVT at 0.055 moi. Three days later, the cells were passaged 1:7.5 to T75 with fresh CEF ($1 \times 10^7$ cells/T75). The cells were then plated onto 10 of 96 well-plates and duplicate plates were made three days later. One set of plates were fixed and stained with anti-IBDV chicken serum. Two wells that contained foci that positively stained for IBD were identified. The corresponding wells that contain positive staining foci were purified three rounds by limiting dilution method using 96-well plates. The purified virus was expanded using CEF cells and frozen stock made. It was designated as "HVT-IBD #1".

Figure 3A:
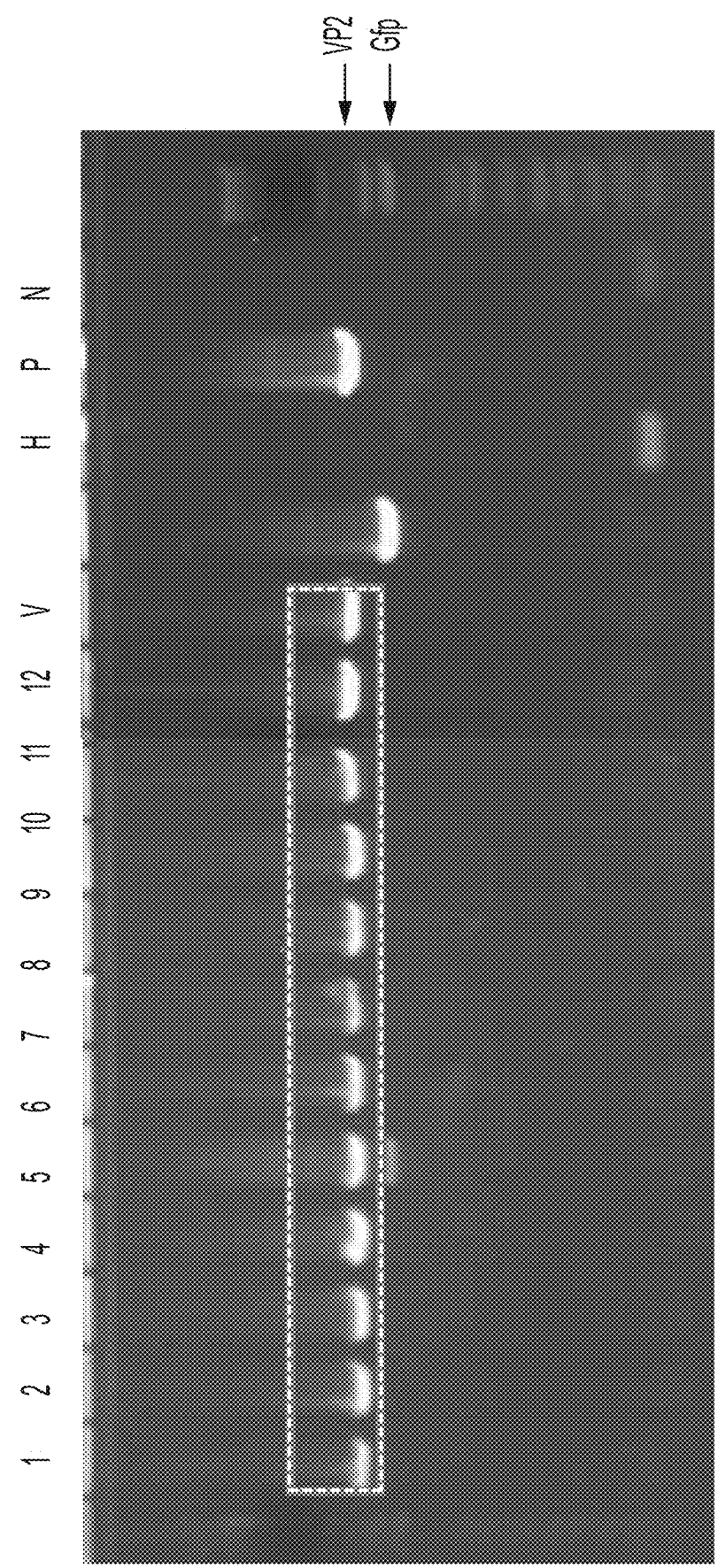
FIGS. 3A, 3B, 3C are representations of PCR reactions demonstrating the correct integration of the VP2 gene into the HVT genome for HVT IBD 1.
Figure 3B:
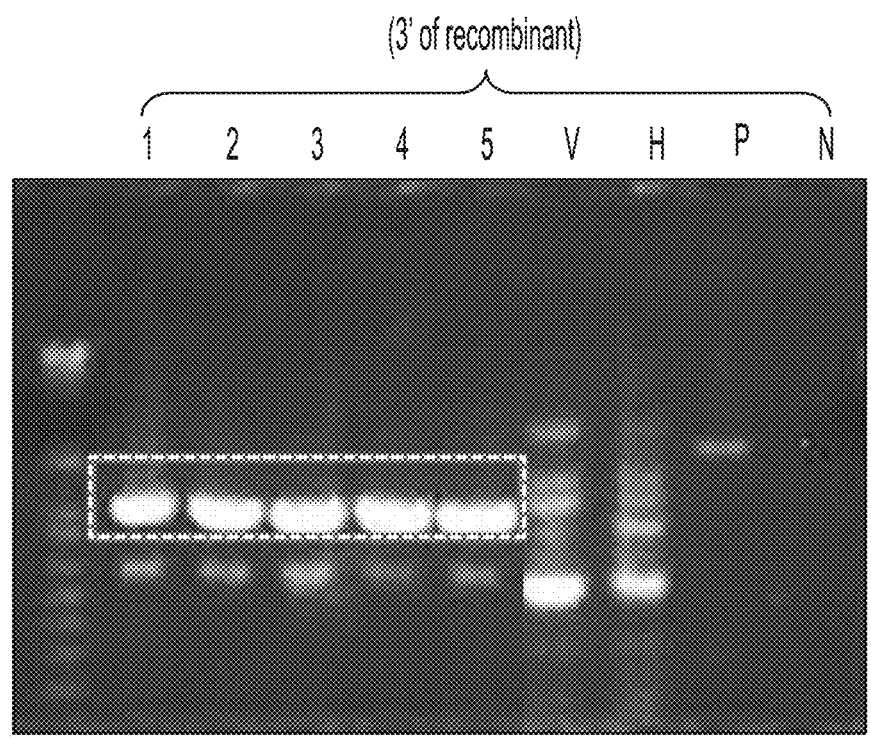
Figure 3C:
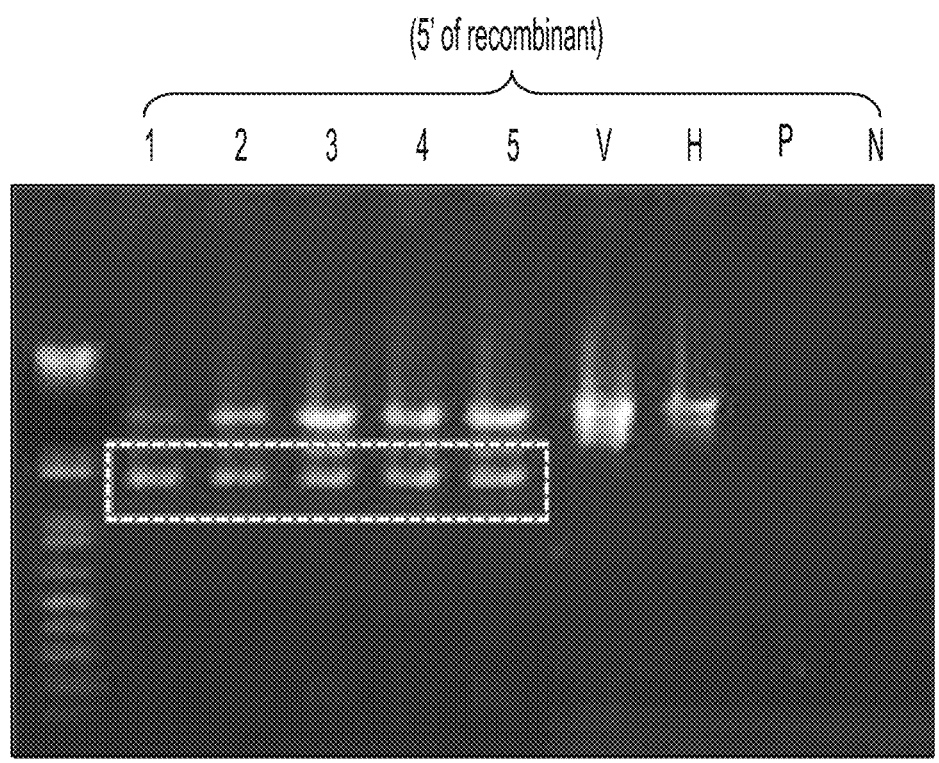

PCR analysis of the different clones using primers just outside of integration site of UL55-Gene3 (upper primer: SEQ ID NO. 46; lower primer: SEQ ID NO. 47, panel A) gave a band of 2.414 kb, while the PCR band of original vector is 1.922 kb. The correct integration was further confirmed by using primers surrounding the downstream junction of the insertion (upper primer SEQ ID NO. 48 that localized within IBDV VP2 coding region; lower primer SEQ ID NO.49 that localized downstream of the transfer plasmid. Panel B). A PCR band of 1.118 kb was obtained as expected. The correct integration for upstream integration site was performed using primers surrounding the upstream junction of the insertion (upper primer SEQ ID NO.50 that localized upstream of the transfer plasmid; lower primer SEQ ID NO.51 that within IBDV VP2 coding region, Panel C). A PCR band of 1.428 kb was obtained as expected. Please refer to FIGS. 3A, B and C.

Construction of HVT-IBD #5

HVT-IBD #5 transfer plasmid (SEQ ID NO. 21) was chemically synthesized by GeneArt, ThermoFisher). JBJ-1 cells (a chicken fibroblast cell line) in a 6 well plate was transfected with 2.5 ug of the plasmid using LTX transfection reagent (Invitrogen). The transfected cells were infected with HVT at an moi of 0.05 approximately 5 hours post transfection. The transfected/infected cells were amplified via serial passage (1:4-1:10) and a portion subsequently seeded in 96 well plates in limiting dilutions. IBDV VP2 antigen expression was assessed by staining live cells the monolayers with antibody without fixation. Please see FIGS. 4A and 4B. Stained foci were harvested via trypsinization of the cells with cloning cylinders placed around the positive foci. This "live staining" followed by cloning cylinder passage was repeated 4 times and yielded pure VP2 positive cultures. The cultures were amplified via serial passage on JBJ-1 cells and before a final amplification on primary CEF cells in roller bottles. The harvested CEF cells were used to make a frozen cell stock and designated as, "HVT-IBD #5".

Figure 5:
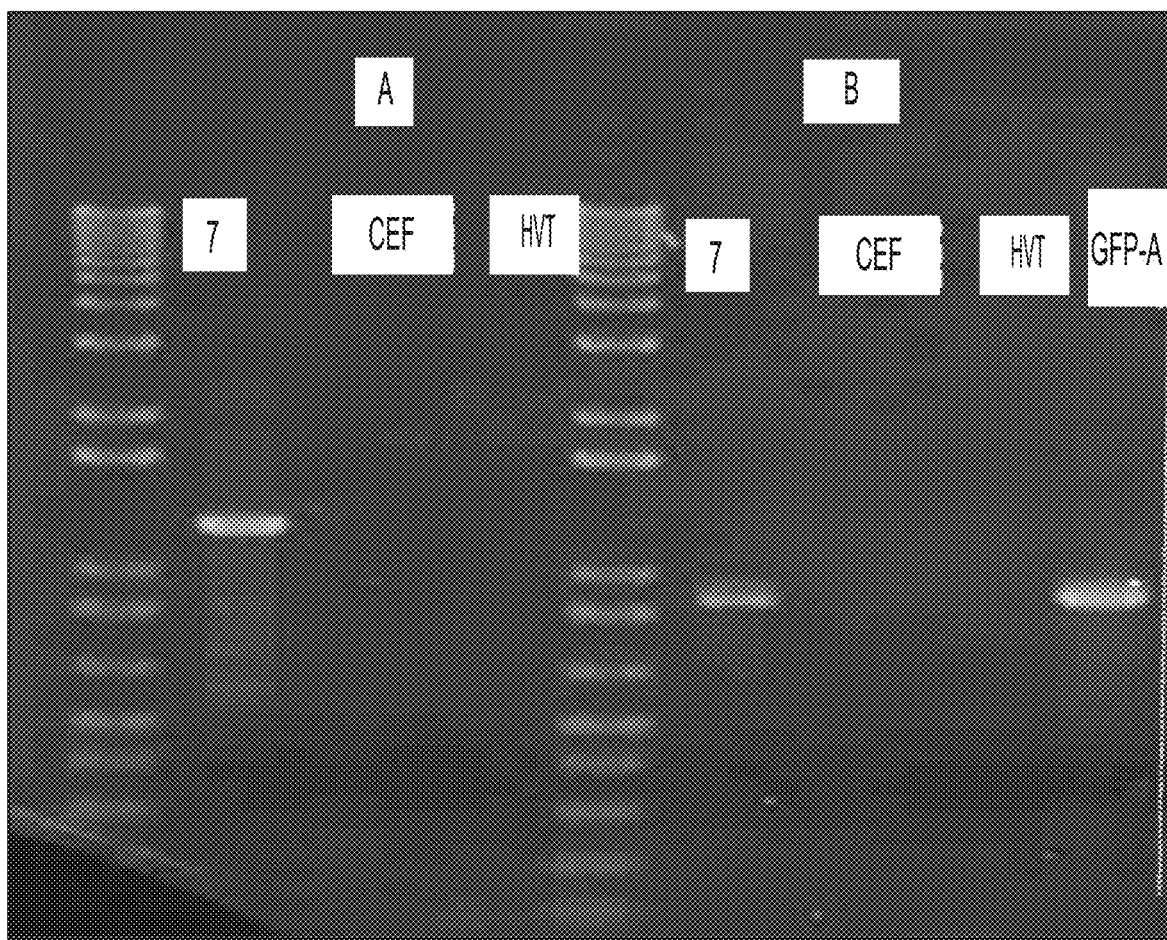
FIG. 5 is a representation of PCR reactions performed to confirm correct orientation of the VP2 insert into the UL35/36 integration site of the HVT genome for HVT IBD 5.

PCR analysis of clone #7 using 2 sets of primers to confirm integration of the insert across both insertion sites. In PCR A, the upper primer (SEQ ID NO.52) binds to the IBDV VP2 coding region, while the lower primer (SEQ ID NO.53) binds downstream of integration site of UL35-UL36. This set of primers yielded a PCR band of 1.244 kb as expected. In PCR B, the upper primer (SEQ ID NO. 54) binds upstream of the UL35-UL36 insertion site, and the lower primer (SEQ ID NO.55) binds within the human CMV promoter of the insert and yielded a PCR band of 0.926 kb as expected. Please refer to FIG. 5.

Construction of HVT-IBD #6a

HVT-IBD #6a transfer plasmid (SEQ ID NO.22) was chemically synthesized by BioBasic Inc. 0.1 ug and 0.01 ug of linearized transfer plasmid (by digestion with EcoR1 and HindIII) was co-transfected with 2.5 ug of the HVT-gfp-A that was digested with SbfI into secondary CEF cells using PEI (Polyethylenimine) transfection reagent in 6-well plate. 4 days post transfection, 4 non-green foci were seen for 0.01 ug transfer plasmid transfection and 3 non-green foci were seen for 0.1 ug transfer plasmid transfection, while no foci were seen with HVT-gfp-A digested with SbfI alone. 2 non-green foci were purified 3 times by limiting dilution method using 96-well plate. The purified virus was expanded using CEF cells and frozen stock made. It was designated as "HVT-IBD #6a".

Figure 6:
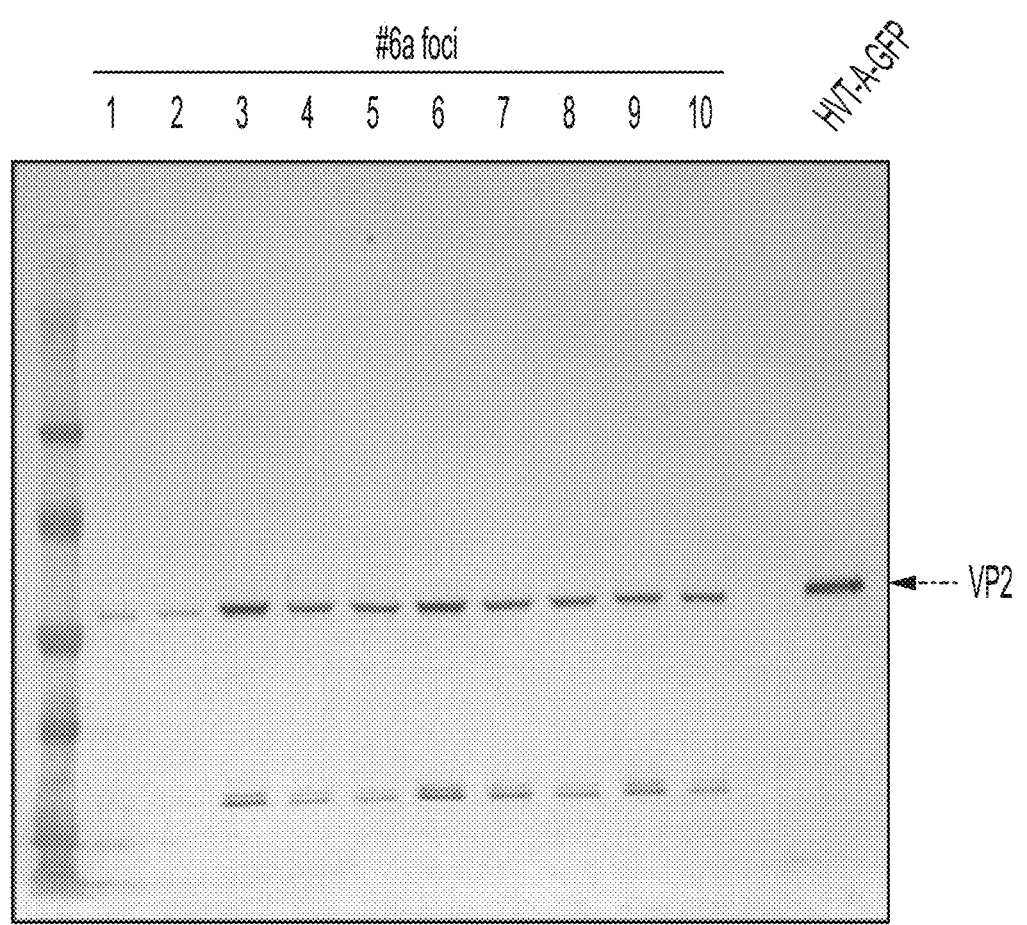

Infected cell lysate was prepared, and Western Blot analysis was performed using monoclonal antibody against IBDV R63. A protein band of about 50 KD was seen in all lanes, except the lane that contain the lysate of HVT-gfp-A vector. Please refer to FIG. 6.

Figure 7A:
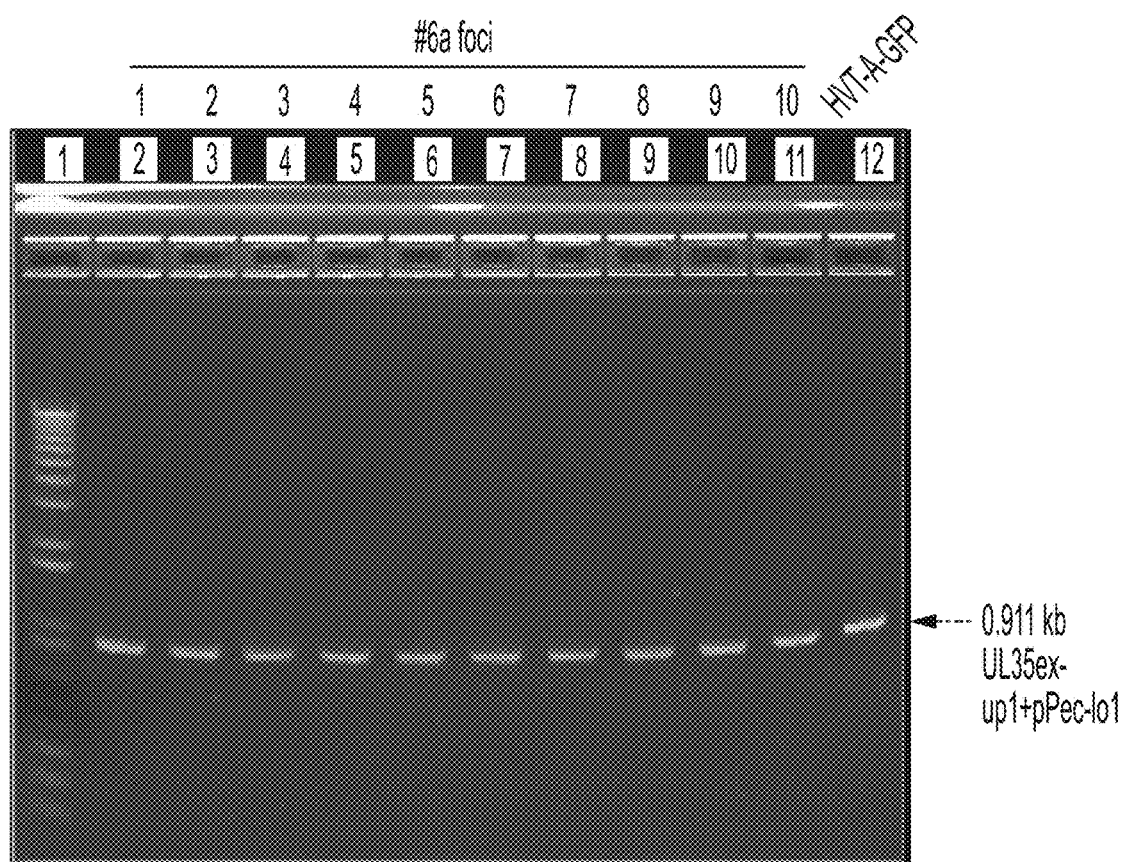
Figure 7B:

PCR analysis of the clones using 2 sets of primers to confirm the correct integration. The first primer set targeting the upstream integration site: upper primer 5'—SEQ ID NO.56 that localized upstream of UL35-UL36 integration site; lower primer SEQ ID NO. 57 that localized within the Pec promoter. This set of primers gave a PCR band of 0.911 kb as expected. The second primer set targeting downstream integration site: upper primer 5'—SEQ ID NO. 58 that localized within the IBDV VP2 coding region; lower primer 5'-SEQ ID NO. 59 that localized downstream of the UL35-UL36 insertion site. A PCR band of 1.244 kb was obtained as expected. Please refer to FIGS. 7A and 7B.

Construction of HVT-IBD #9

HVT-IBD #9 transfer plasmid (SEQ ID NO.23) was chemically synthesized by GeneArt, ThermoFisher). 2.5 ug of the plasmid was transfected into secondary CEF cells using LTX transfection reagent (Invitrogen) in 6-well plate. About 4-6 hours later, the transfected cells were infected with HVT-gfp-B at 0.075 moi. Three days later, the cells were passaged 1:10 to T75 with fresh CEF (1×10^7 cells/T75) 3 times. The cells were then plated onto 10 of 96 well-plates and 90 non-green foci were obtained. Three of those were stained positive with anti-IBDV chicken serum. Two clones were purified 3 rounds by limiting dilution method using 96-well plates. The purified virus was expanded using CEF cells and frozen stock made. It was designated as "HVT-IBD #9".

Figure 8A:
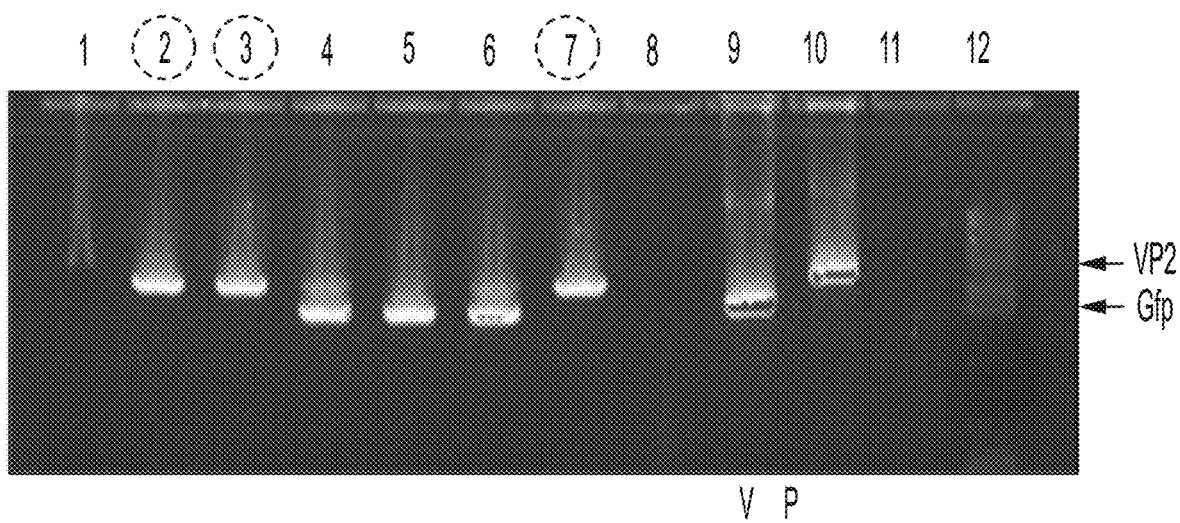
FIGS. 8A and 8B are representations of PCR reactions demonstrating the correct VP2 gene integration at the UL55/gene3 site in the HVT genome for HVT IBD 9.
Figure 8B:
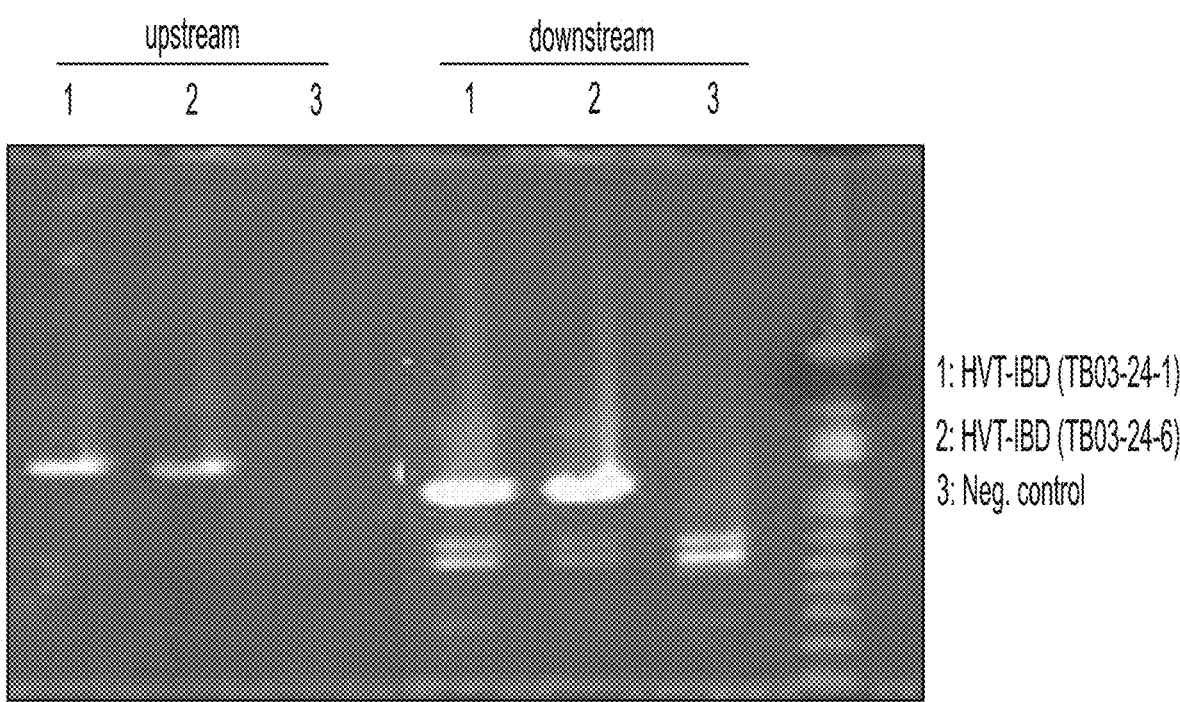

PCR analysis of the different clones using primers just outside of integration site of UL55-Gene3 (upper primer: SEQ ID NO.60; lower primer: SEQ ID NO. 61, panel A) gave a band of 2.536 kb, while the PCR band of original vector HVT-gfp-B is 1.922 kb. The correct integration was further confirmed by using primers surrounding the upstream junction of the insertion (upper primer SEQ ID NO. 62 that localized upstream of UL55-Gene3 insertion site; lower primer SEQ ID NO. 63 localized within IBDV VP2 coding region. A PCR band of 1.482 kb was obtained as expected. The correct integration for downstream site was performed using primers surrounding the downstream junction of the insertion (upper primer SEQ ID NO. 64 that localized within the IBDV VP2 sequence; lower primer SEQ ID NO. 65 that localize downstream of the UL55-Gene3 insertion site. A PCR band of 1.166 kb was obtained as expected. Please refer to FIGS. 8A and B.

Construction of HVT-IBD #30

HVT-IBD #30 transfer plasmid (SEQ ID NO.24) was chemically synthesized by GeneArt, ThermoFisher. Secondary CEF cells were co-transfected with 0.1 ug of the plasmid and 2.5 ug of HVT using PEI (Polyethylenimine) transfection reagent in 6-well plate. Three days later, the cells were passaged 1:12 onto fresh CEF cells. Foci expressing IBD VP2 were visualized by staining unfixed cultures with chicken polyclonal serum against IBDV, and these foci marked with the aid of a fluorescent microscope. A total of 16 positive foci were passaged onto fresh CEF cells via trypsinization using cloning cylinders to segregate the foci from non VP2 expressing foci. Four of these cultures were clone three times following the same procedure before being amplified on primary CEF cells in roller bottles. A frozen stock of cells was put down and designated as "HVT-IBD #30".

Figure 9A:
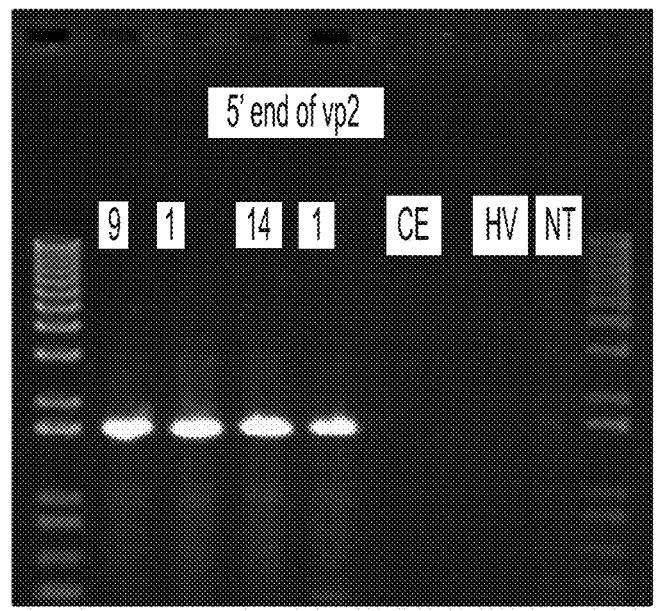
FIGS. 9A, 9B and 9C are representations of PCR reactions demonstrating the correct VP2 gene integration at the UL55/gene 3 site in the HVT genome for HVT IBD 30.
Figure 9B:
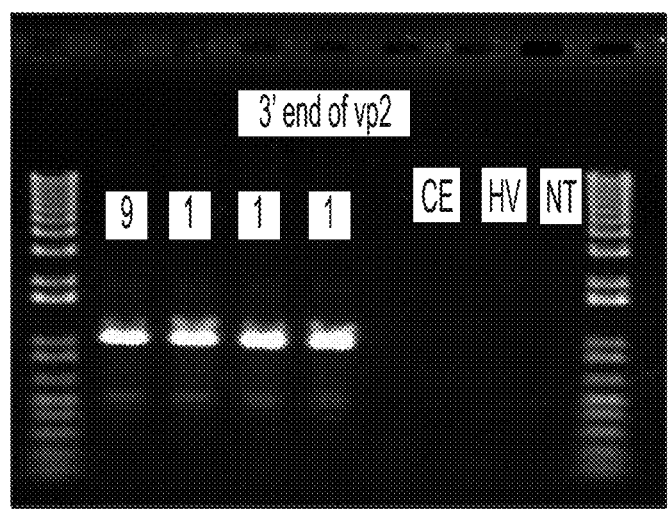
Figure 9C:
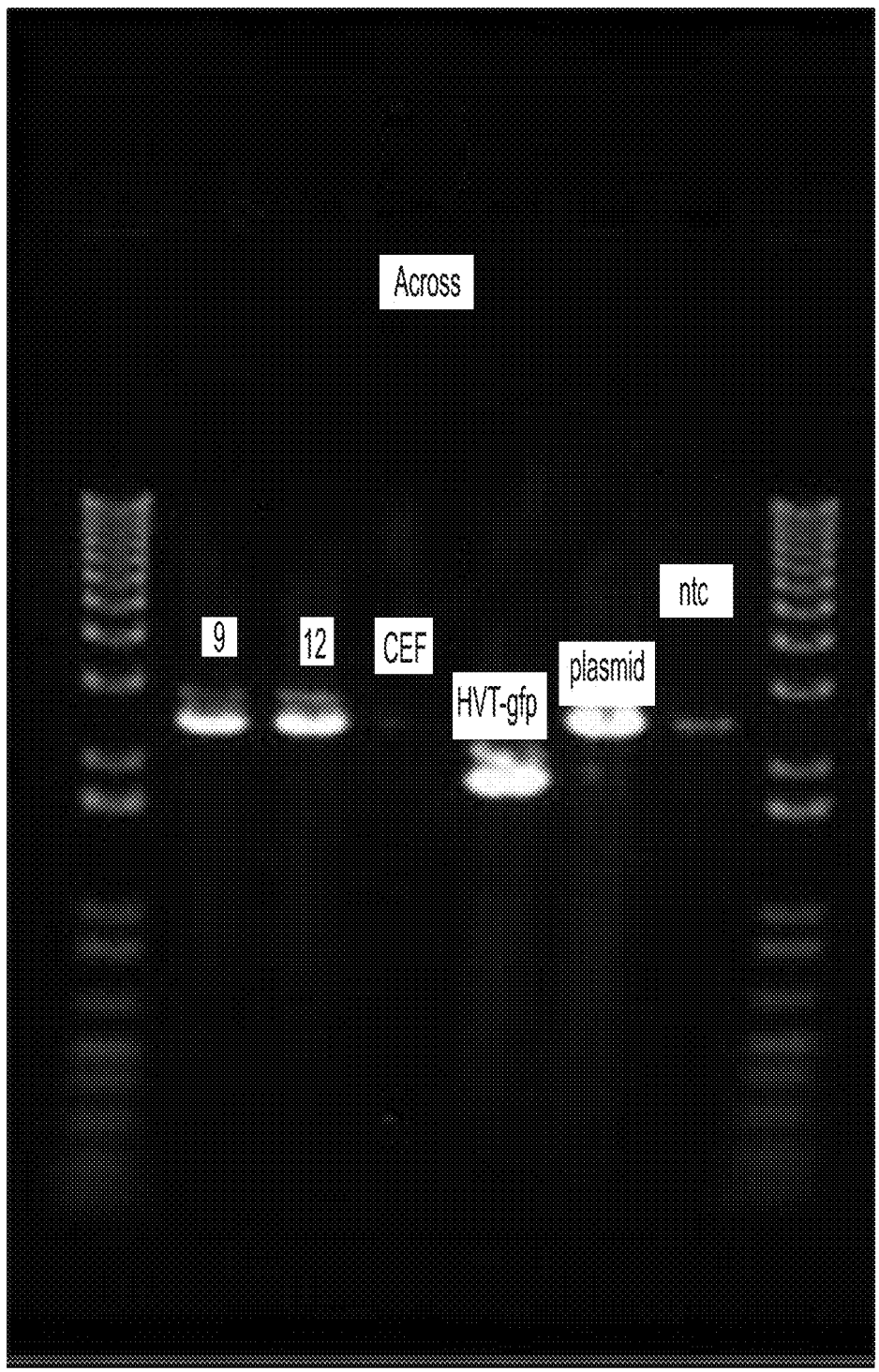

PCR analysis of 4 different clones using primers for upstream region of integration site of UL55-Gene3 (upper primer: SEQ ID NO.66; lower primer: SEQ ID NO.67, panel A) gave a band of 1.673 kb. The correct integration was further confirmed by using primers surrounding the 3' junction of the insertion (upper primer SEQ ID NO. 68 that localized within IBDV VP2 coding region; lower primer SEQ ID NO. 69 that localized downstream of UL55-Gene3 insertion site, panel B). A PCR band of 1.082 kb was obtained as expected. The correct integration for downstream site was further confirmed by using primers outside of the expression cassette (upper primer SEQ ID NO.70; lower primer SEQ ID NO. 71 (panel C). A PCR band of 2.558 kb was obtained as expected. Please refer to FIGS. 9A-C.

Construction of HVT-IBD #31

HVT-IBD #31 transfer plasmid (SEQ ID NO. 25) was chemically synthesized by GeneArt, ThermoFisher. 0.01 ug of linearized transfer plasmid (by digestion with EcoR1 and HindIII) was co-transfected with 2.5 ug of the HVT-gfp-A that was digested with SbfI into secondary CEF cells using PEI (Polyethylenimine) transfection reagent in 6-well plate. 4 days post transfection, 1 non-green foci were seen while no foci were seen with HVT-gfp-A digested with SbfI alone. After passage, 2 non-green foci were purified 3 times by limiting dilution method using 96-well plate. The purified virus was expanded using CEF cells and frozen stock made. It was designated as "HVT-IBD #31".

Figure 10A:
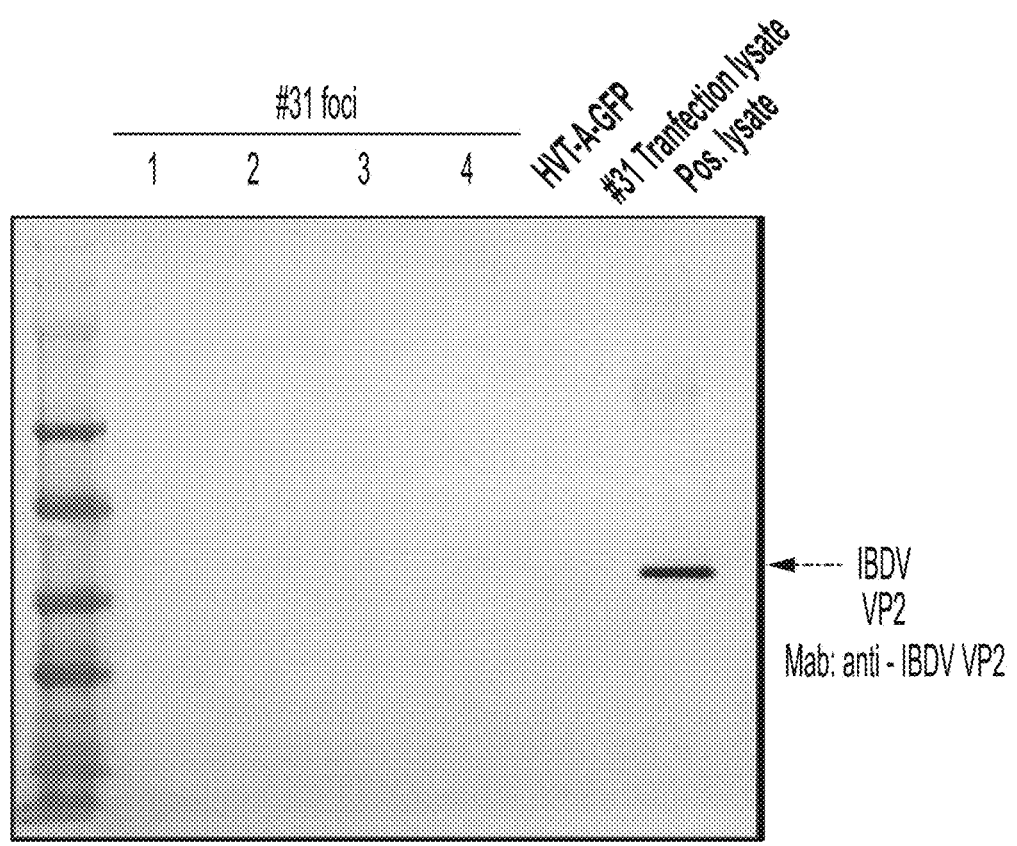
FIGS. 10A and 10B are representations of Western blot analysis of transfected/infected cell lysates using a monoclonal antibody against IBDVR63 for HVT IBD 31.
Figure 10B:
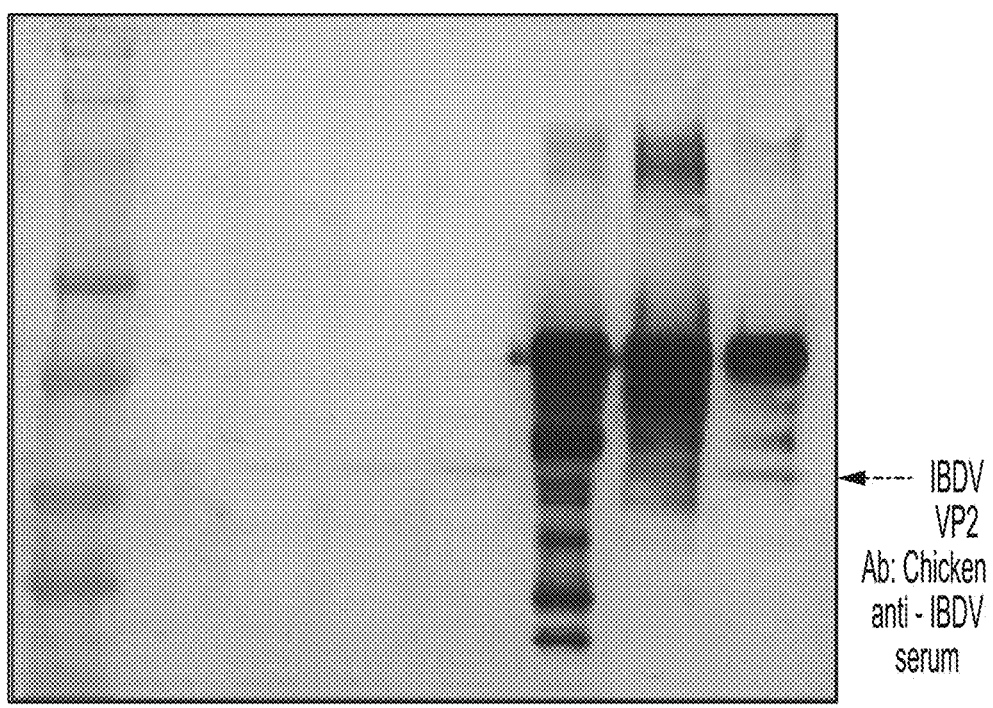

Infected cell lysate was prepared, and Western Blot analysis was performed using monoclonal antibody against IBDV R63. A protein band of about 50 KD was seen in all lanes with anti-IBDV chicken serum as probe only, not with mAb for IBDV R63. Please see FIGS. 10A and B.

Figure 11A:
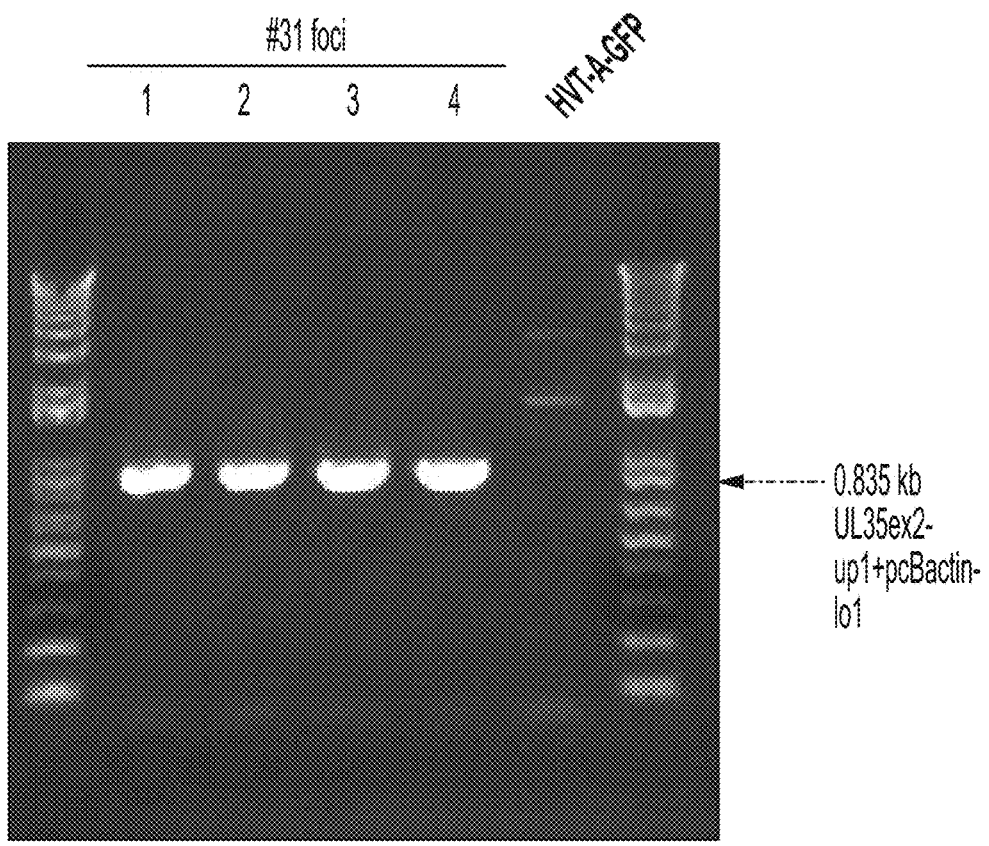
FIGS. 11A and B are representations of PCR reactions demonstrating correct VP2 gene integration at the UL35/36 integration site in the HVT genome for HVT IBD 31.
Figure 11B:
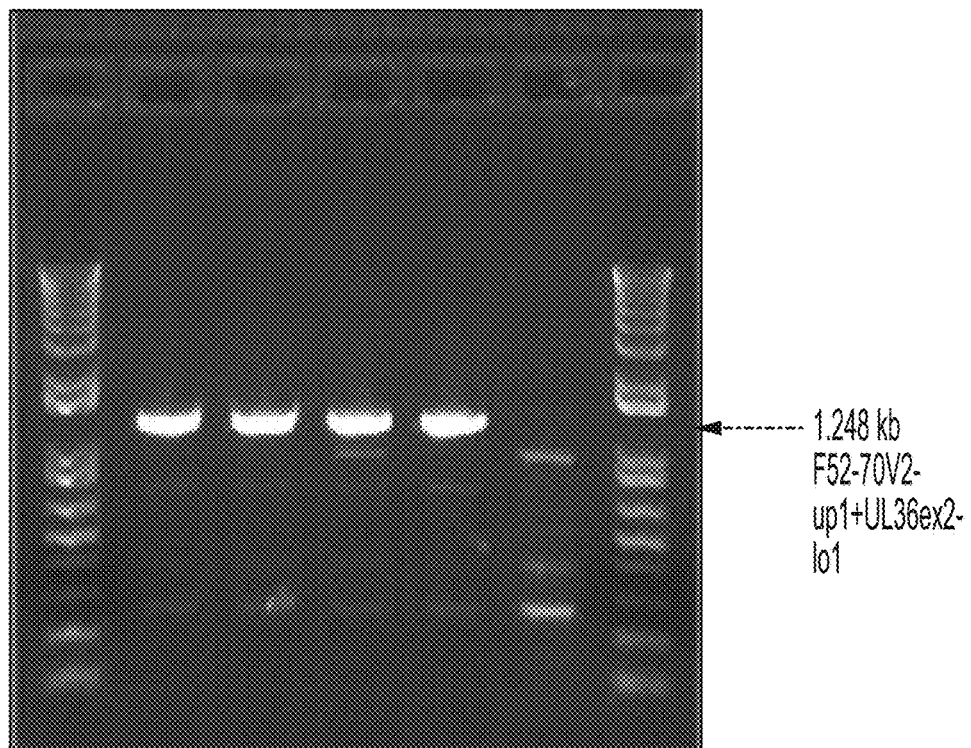

PCR analysis of the clones using 2 sets of primers to confirm the correct integration. The first primer set targeting upstream integration site: upper primer SEQ ID NO. 72 that localized upstream of UL35-UL36 integration site; lower primer SEQ ID NO. 73 that localized within the chicken beta-actin promoter. This set of primers gave a PCR band of 0.835 kb as expected. The second primer set targeting the downstream integration site: upper primer SEQ ID NO.76 that localized within the IBDV VP2 coding region; lower primer SEQ ID NO.77 that localized downstream of the UL35-UL36 insertion site. A PCR band of 1.248 kb was obtained as expected. Please refer to FIGS. 11 A and B.

Construction of HVT-IBD #34

HVT-IBD #34 transfer plasmid (SEQ ID NO. 28) was chemically synthesized by GeneArt, ThermoFisher. 2.5 ug of the plasmid was transfected into secondary CEF cells using LTX transfection reagent (Invitrogen) in 6-well plate. About 4-6 hours later, the transfected cells were infected with HVT-gfp-B at 0.05 moi. Three days later, the cells were passaged 1:15 to T75 with fresh CEF ($1\times10^7$ cells/T75). The infected cells were plated onto 10×96 well plates, grown for 3 days, then passage into replicate 96 well plates. One replicate was fixed and stained with anti-IBDV chicken serum and 3 wells containing foci which stained positive for IBDV were identified. The corresponding wells from the live replicate plate were purified by 3 rounds of limiting dilution cloning using 96 well plates. One of the purified viruses was expanded using CEF cells and frozen stock made. It was designated as "HVT-IBD #34".

PCR analysis of 3 different clones using primers for upstream region of integration site of Gene3-UL55 (upper primer: SEQ ID NO.78; lower primer: SEQ ID NO.79 that localized within chicken beta-actin promoter, panel A) gave a band of 0.815 kb as expected. The correct integration was further confirmed by using primers surrounding the downstream junction of the insertion (upper primer SEQ ID NO.80 that localized within IBDV VP2 coding region; lower primer SEQ ID NO.81 that localized downstream of Gene3-UL55 insertion site, panel B). A PCR band of 1.296 kb was obtained as expected. The correct construct was further confirmed by using primers outside of the expression cassette (upper primer SEQ ID NO.82; lower primer SEQ ID NO.83 (panel C). A PCR band of 3.001 kb was obtained as expected. Please refer to FIGS. 12 A-C.

Construction of HVT-ND #38

HVT-IBD #38 transfer plasmid (SEQ ID NO.29) was chemically synthesized by BioBasic, Inc. HindIII and ApoI digested transfer plasmid for HVT-ND #38 was co-transfected with SbfI digested HVT-gfp-A DNA using PEI (Polyethylenimine, 7.5 uL) in 6-well plate with secondary CEF cells. 6 days post transfection, the transfected cells were plated onto 96-well plate and live stained with NDV chicken serum. Seven wells containing the foci with positive staining were purified 3 times by limiting dilution. One of the purified viruses was expanded using CEF cells and frozen stock made. It was designated as "HVT-ND #38".

Figure 15A:
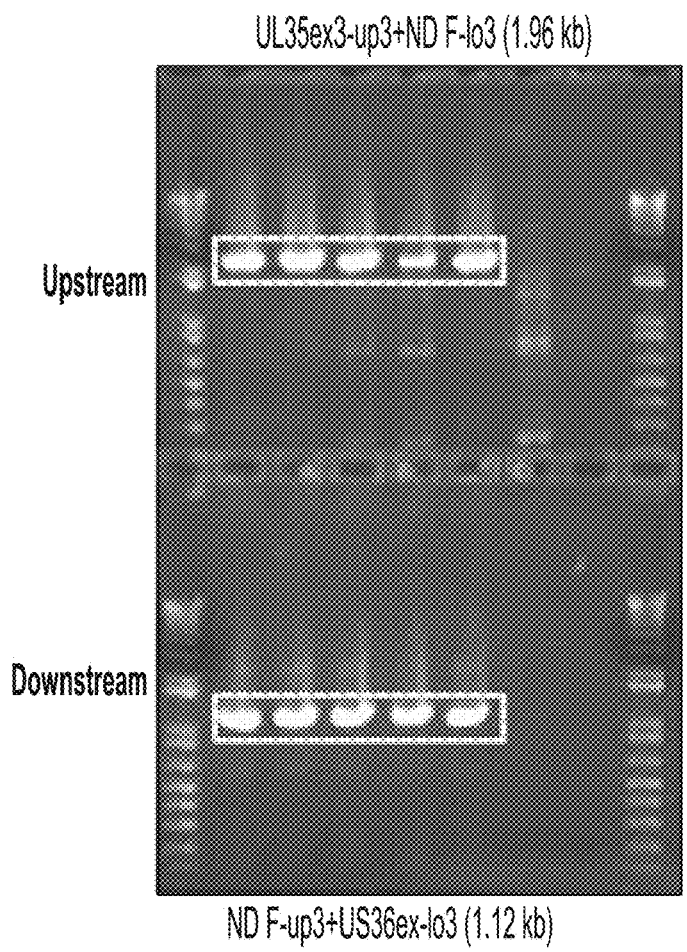
FIGS. 15A and 15B are representations of PCR reactions demonstration correct orientation of the NDVF insert for HVT ND #38.
Figure 15B:
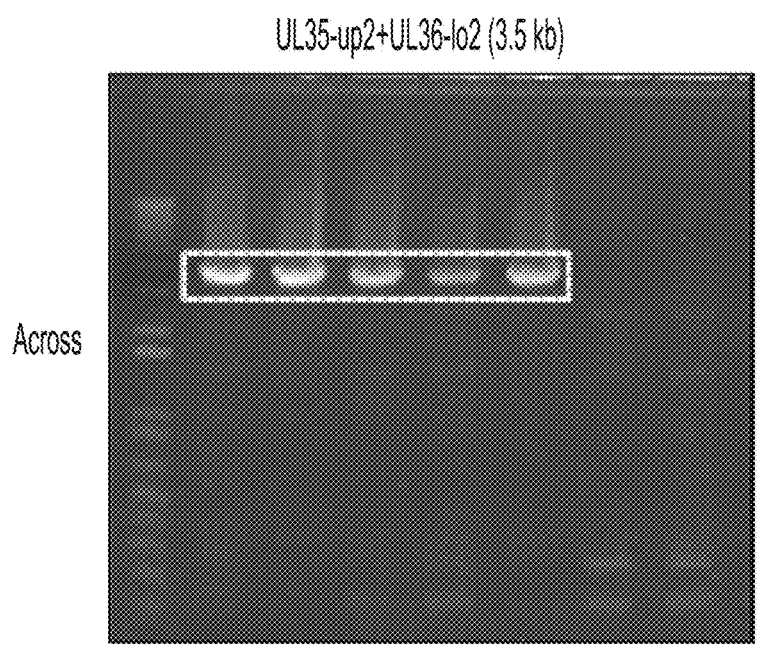

PCR analysis of 5 different clones using primers for upstream region of integration site of UL35-UL36 (upper primer: SEQ ID NO. 84; lower primer: SEQ ID NO.85 that localized within NDV F coding region, panel A) gave a band of 2.122 kb. The correct integration was further confirmed by using primers surrounding the 3' junction of the insertion (upper primer SEQ ID NO.86 that localized within NDV F coding region; lower primer SEQ ID NO.87 that localized downstream of UL35-UL36 insertion site, panel B). A PCR band of 1.127 kb was obtained as expected. The correct construct was further confirmed by using primers outside of the expression cassette (upper primer SEQ ID NO. 88; lower primer SEQ ID NO.89 (panel C). A PCR band of 3.657 kb was obtained as expected. Please refer to FIGS. 15A and B.

Construction of HVT-ND #39

Figure 16A:
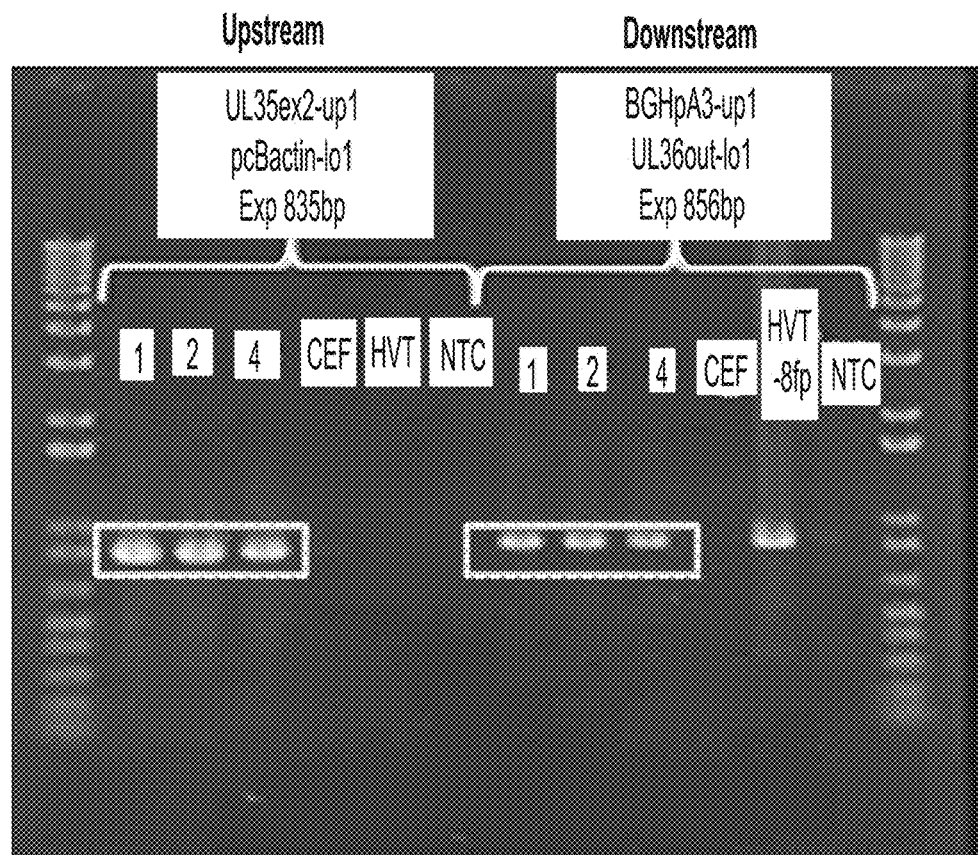
FIGS. 16A and 16B are representations of PCR reactions demonstration correct orientation for the NDVF insert for HVT ND #39.
Figure 16B:
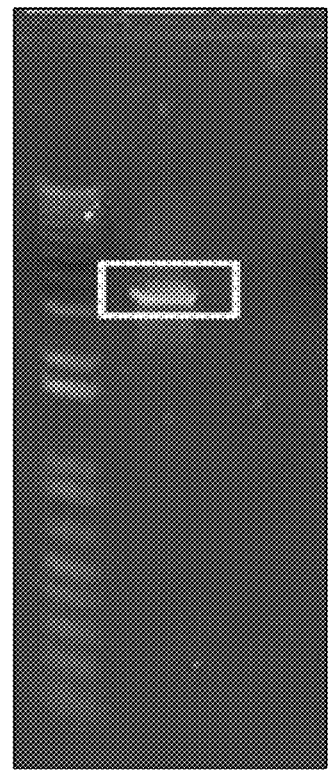
Figures 17A, 17B, 17C:
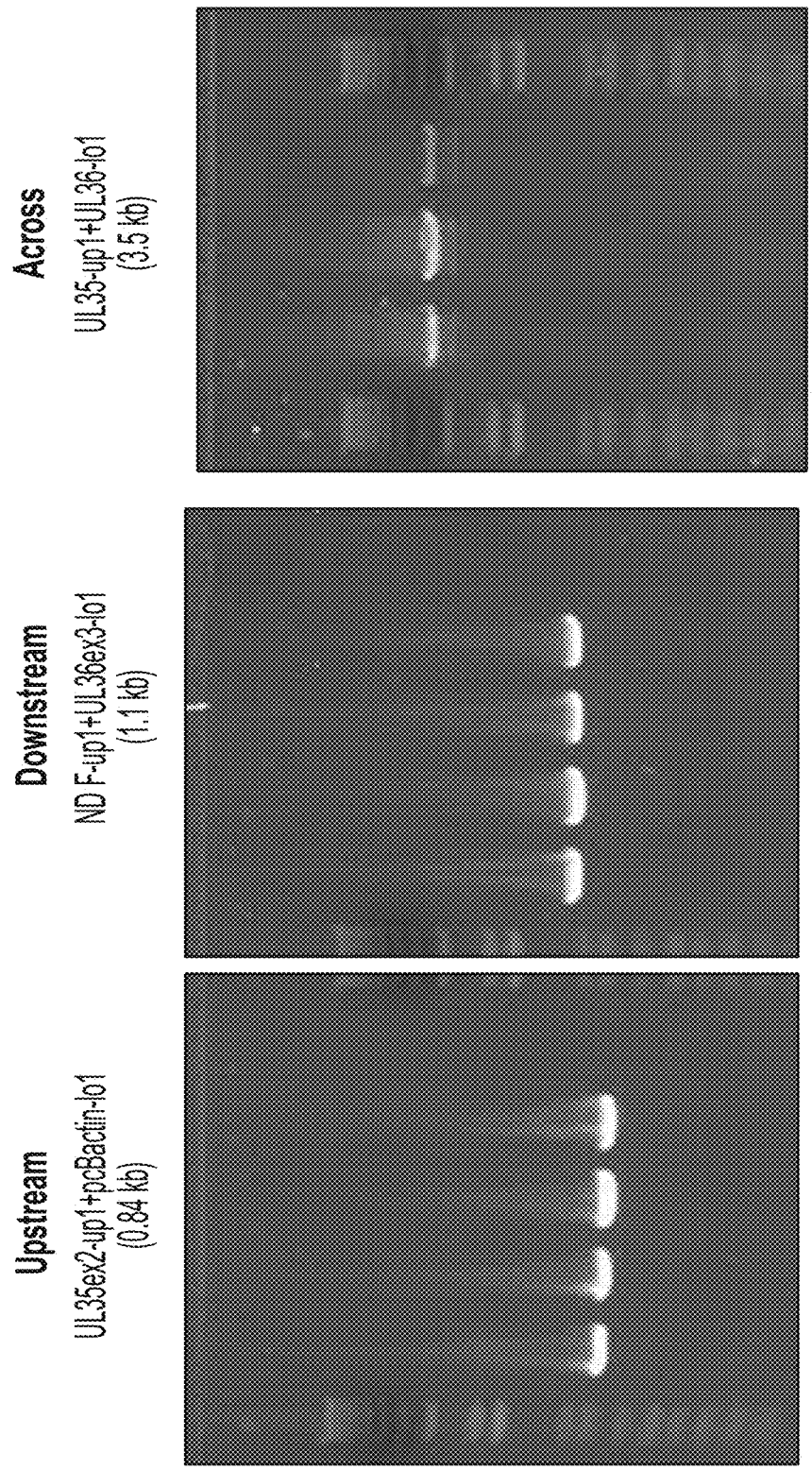
FIGS. 17A, 17B, 17C are representations of PCR reactions demonstrating correct orientation for the NDV F insert for HVT ND #40.
Figure 18:
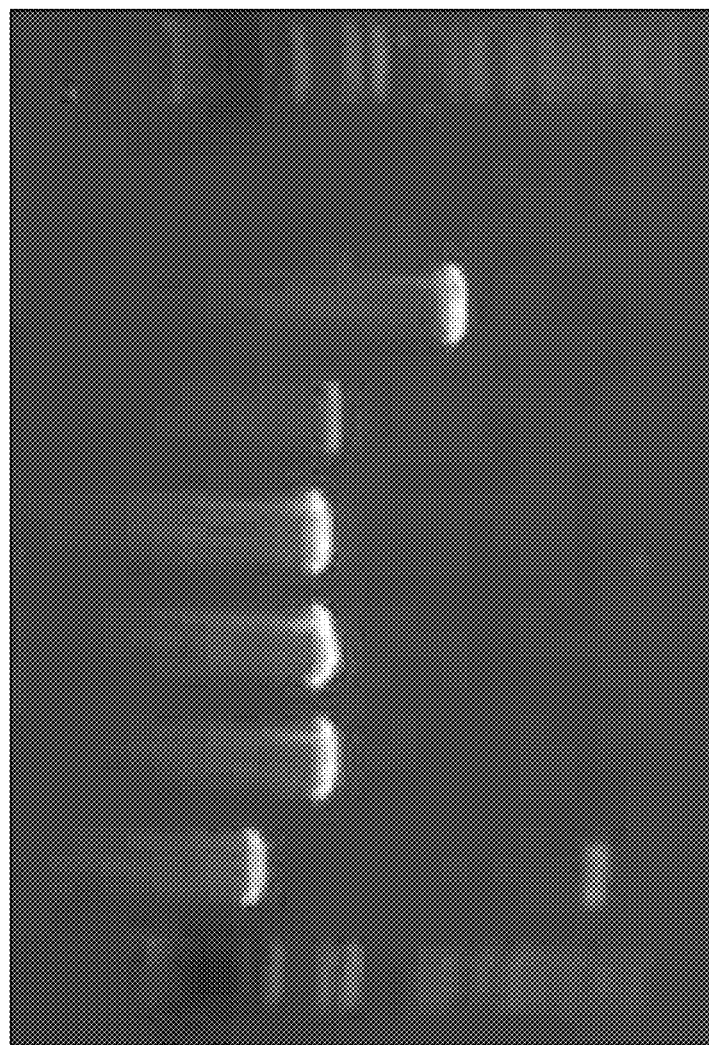
FIG. 18 is a representation of multiple PCR reactions demonstration correct orientation for the NDVF insert for HVT NDV 42.

HVT-IBD #39 transfer plasmid SEQ ID NO. 30) was chemically synthesized by BioBasic, Inc. Secondary CEF cells were co-transfected with 0.01 ug of the plasmid and 2.5 ug of HVT using PEI (Polyethylenimine) transfection reagent in a 6-well plate. Six days later, the cells were passaged 1:24 onto fresh CEF cells. Three days post passage, foci expressing NDV F protein were visualized by staining unfixed cultures with anti NDV specific chicken polyclonal serum, and these foci marked with the aid of a fluorescent microscope. A total of 4 positive foci were passaged onto fresh CEF cells via trypsinization using cloning cylinders to segregate the foci from non-F protein expressing foci. Four of these cultures were cloned three times following the same procedure before being amplified on primary CEFs in roller bottles. A frozen stock of cells (clone 2 in the figures) was put down and it was designated as "HVT-ND #39". PCR analysis of 3 different clones using primers for upstream region of integration site of UL35-UL36 (upper primer: SEQ ID NO 90; lower primer: SEQ ID NO. 91 that localized within chicken beta-actin promoter, panel A) gave a band of 0.835 kb. The correct integration was further confirmed by using primers surrounding the downstream junction of the insertion (upper primer SEQ ID NO.92 that localized within poly A region; lower primer SEQ ID NO.93 that localized downstream of UL35-UL36 insertion site, panel B). A PCR band of 0.856 kb was obtained as expected. The correct construct was further confirmed by using primers outside of the expression cassette (upper primer SEQ ID NO. 94; lower primer SEQ ID NO. 95 (panel C). A PCR band of 3.449 kb was obtained as expected. Please refer to FIGS. 16A and B.

Construction of HVT-ND #40

Figure 19:
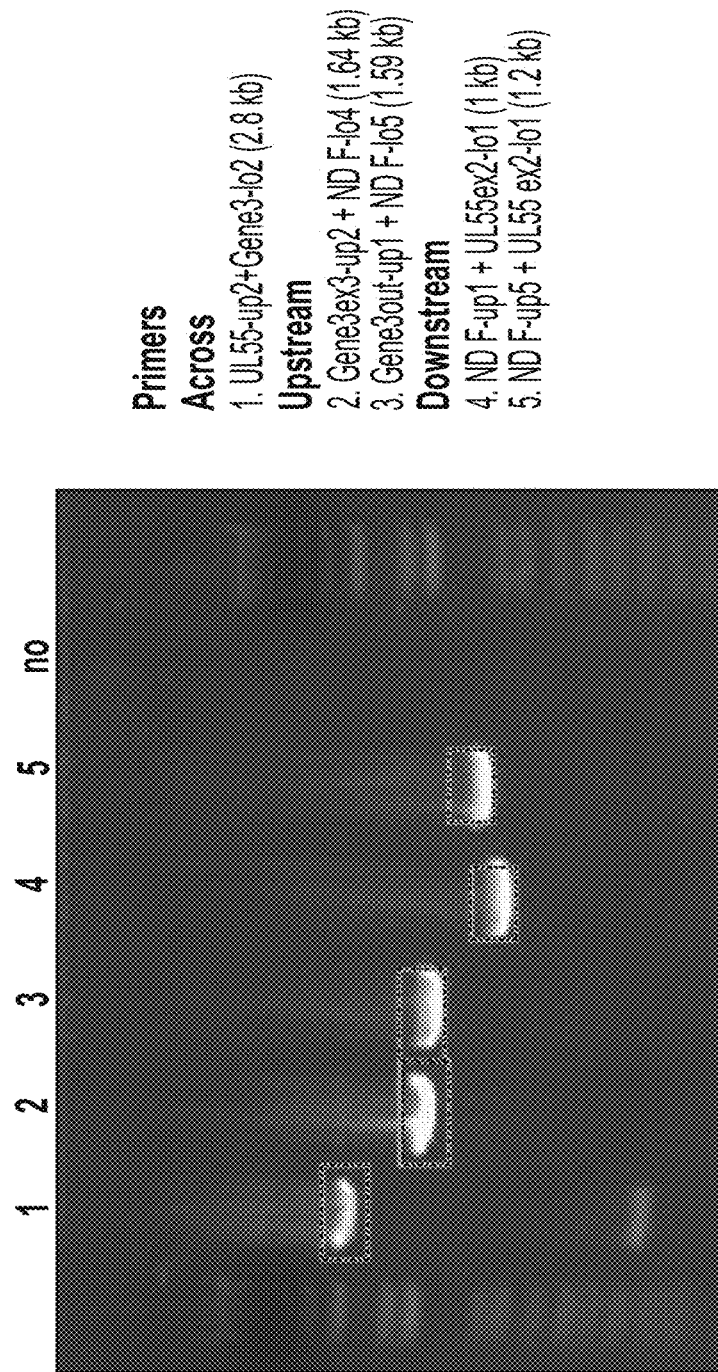
FIG. 19 is a representation of PCR reactions demonstrating the correct orientation of the NDVF insert for HVT NDV 45.
Figure 21:
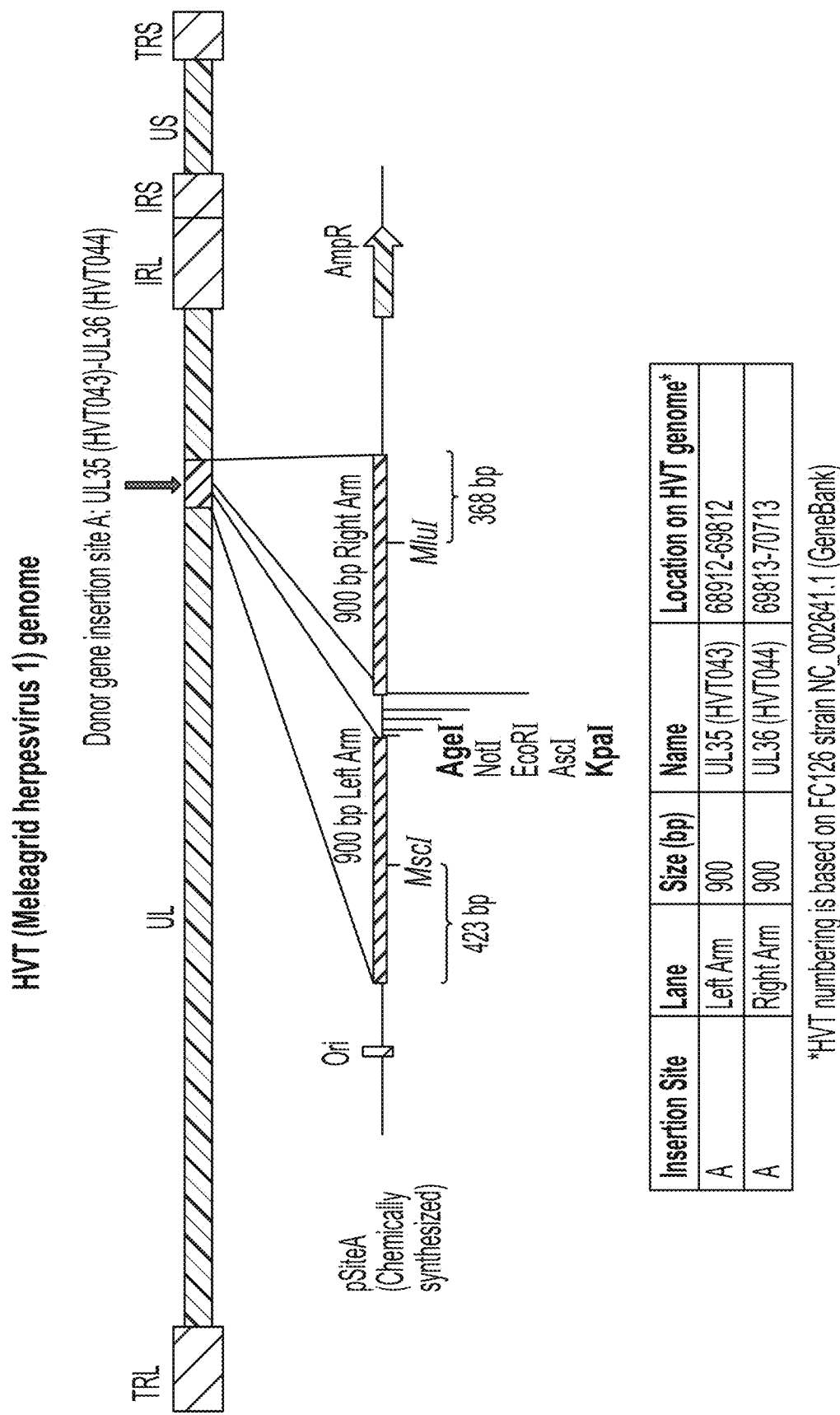
Figure 22:
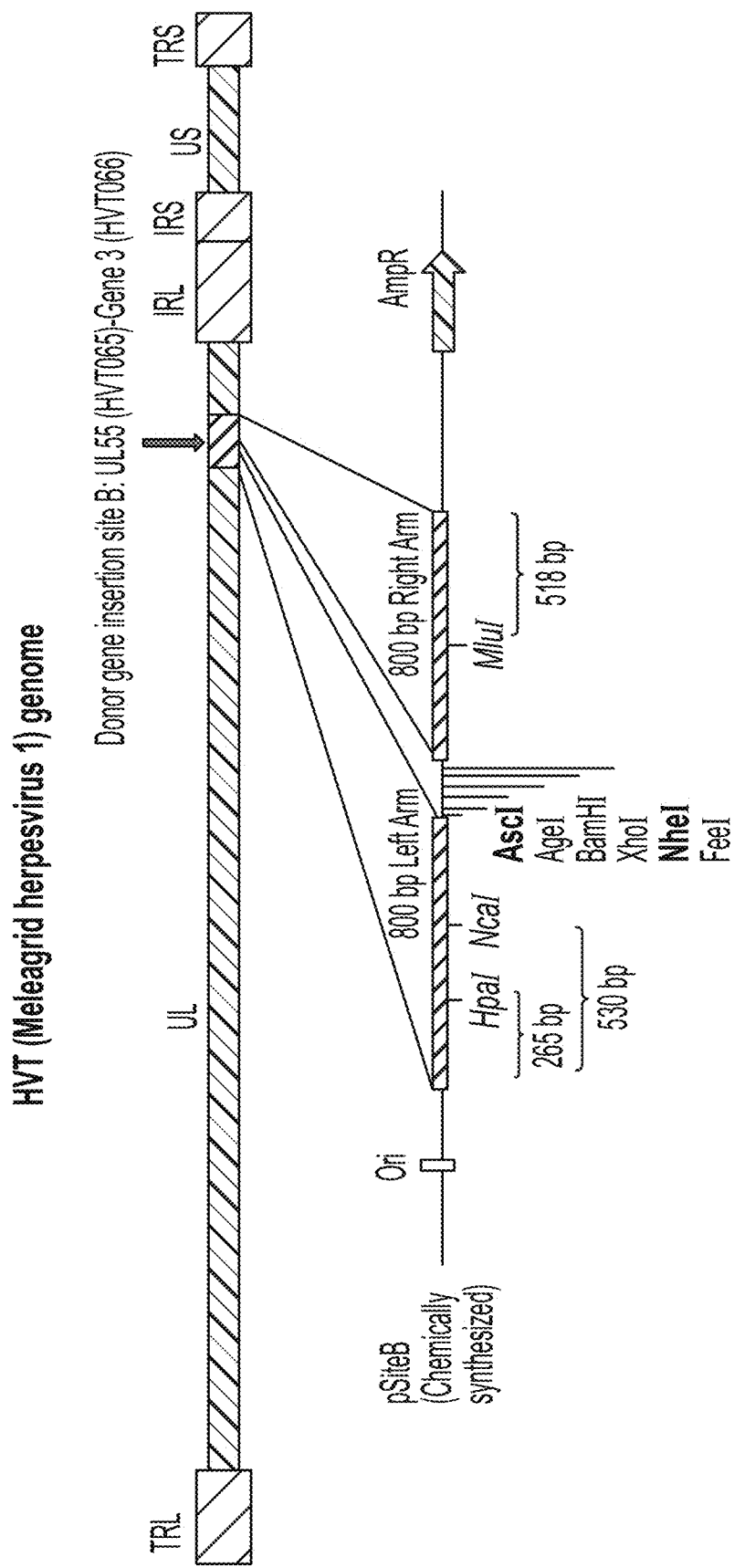
Figure 24:
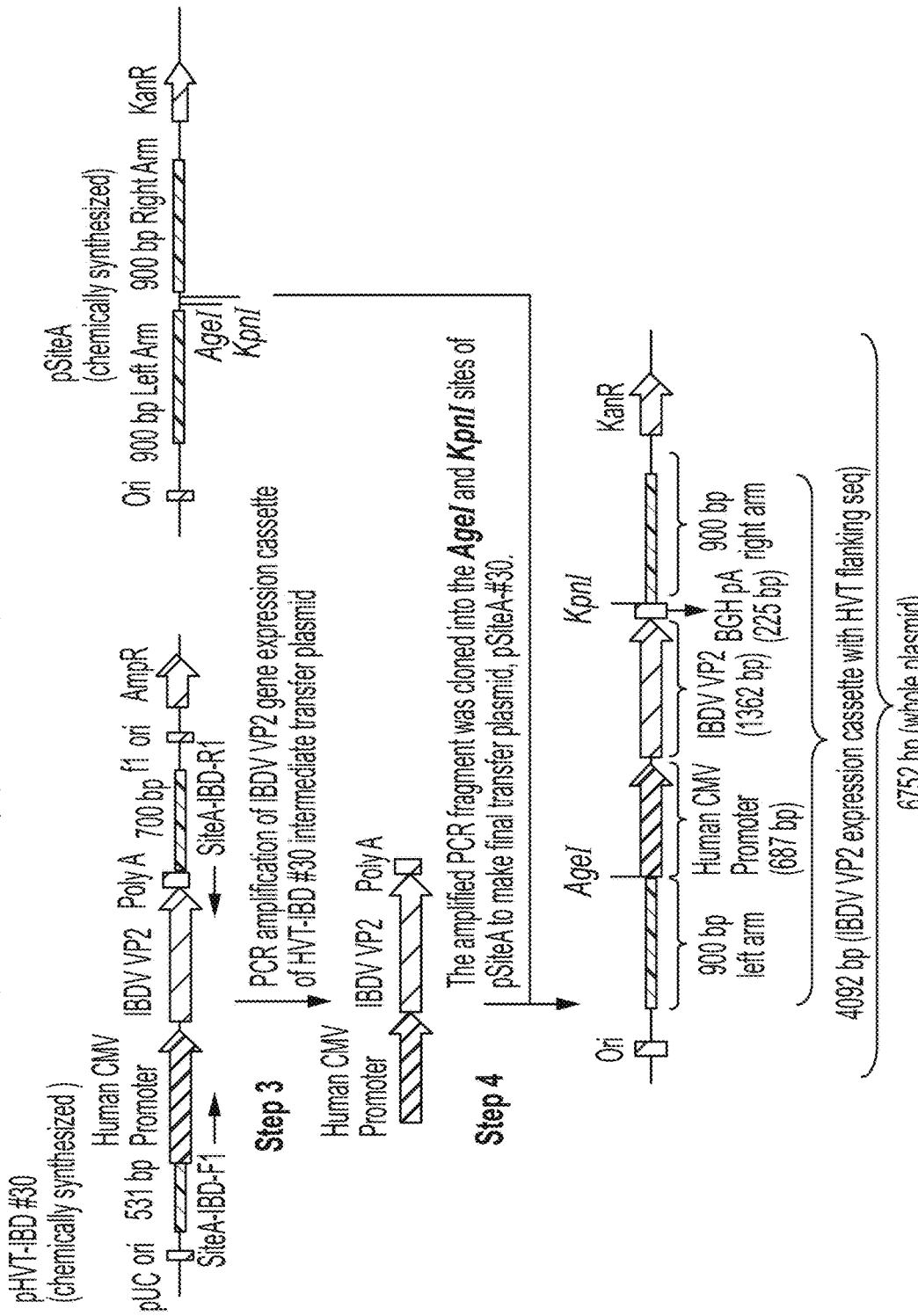
Figure 25:
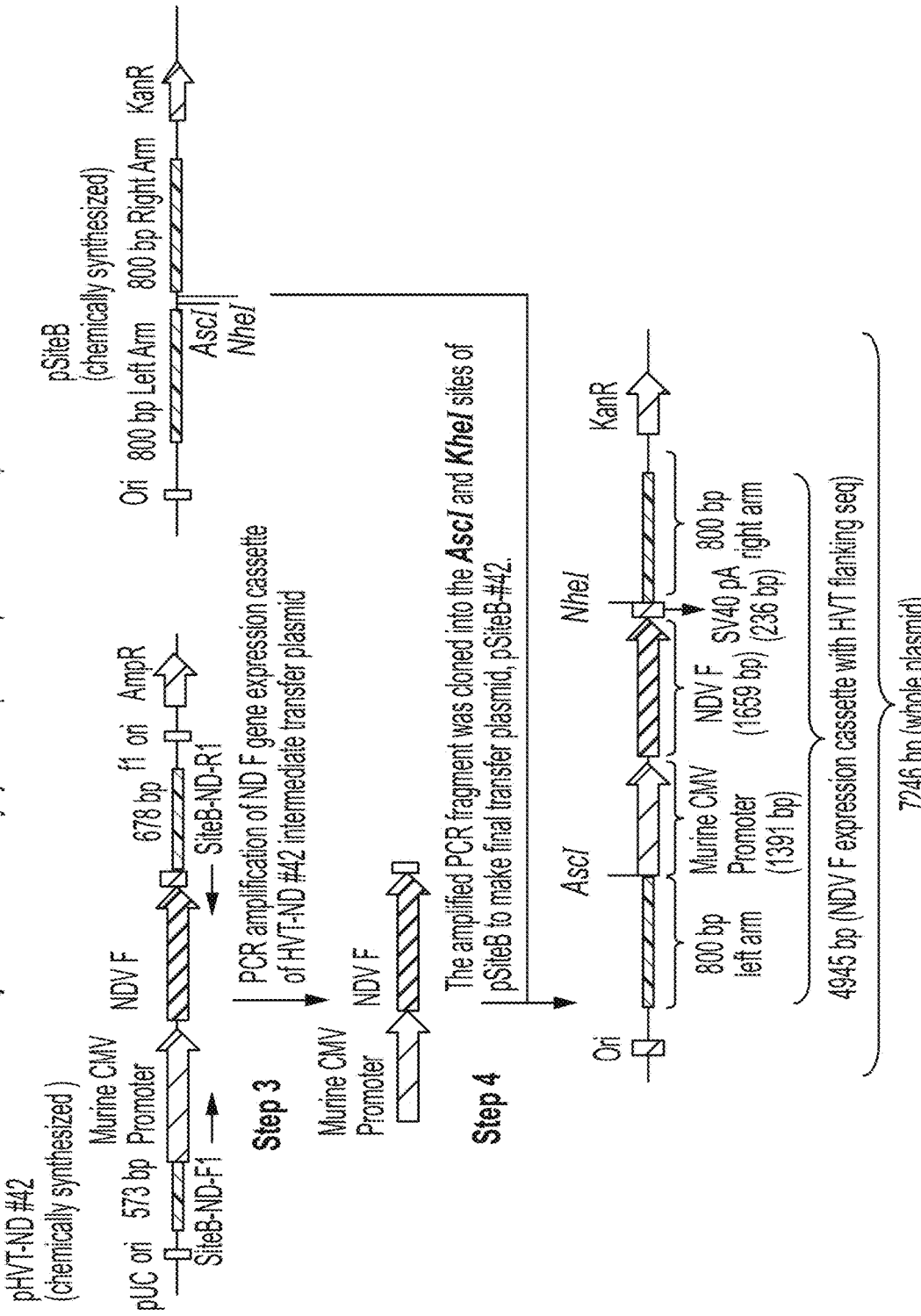
Figure 26:
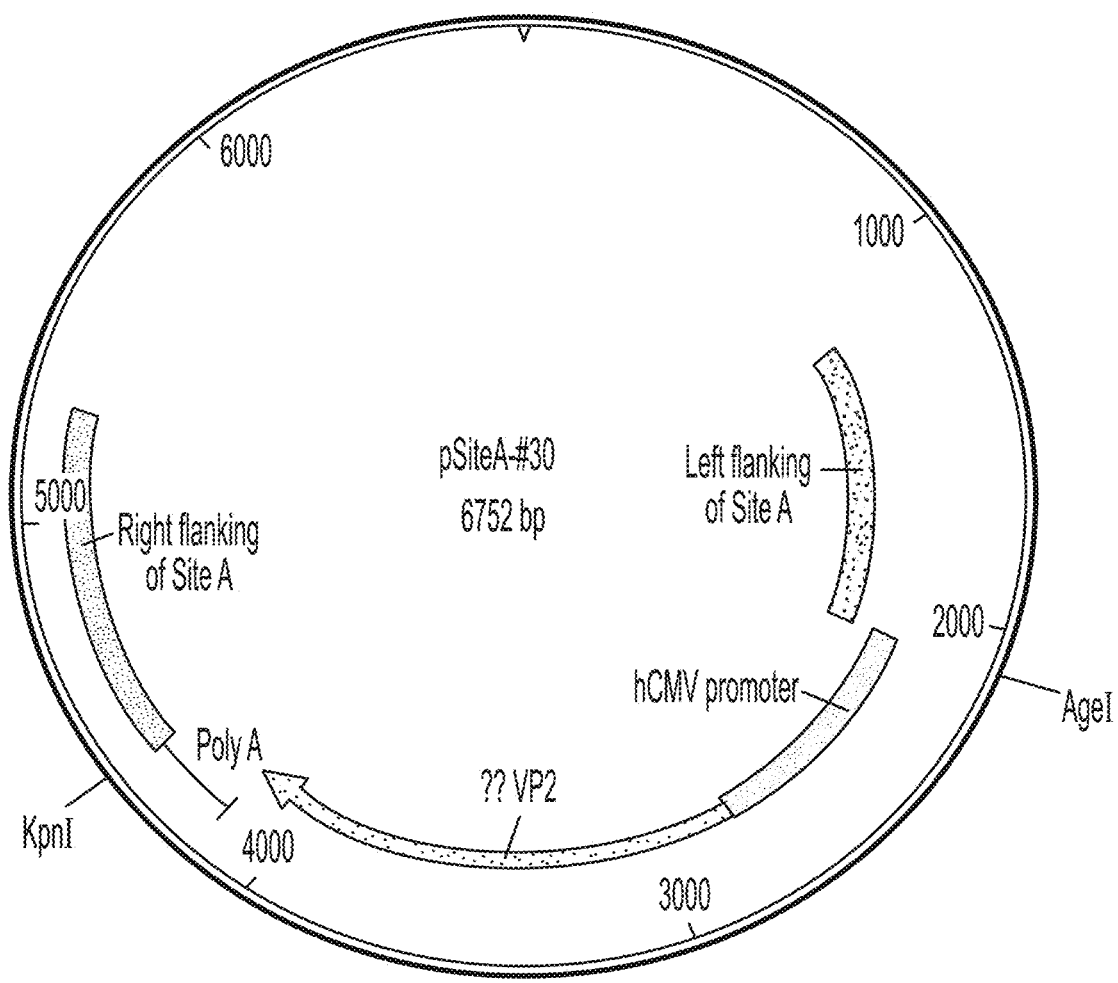
Figure 27:
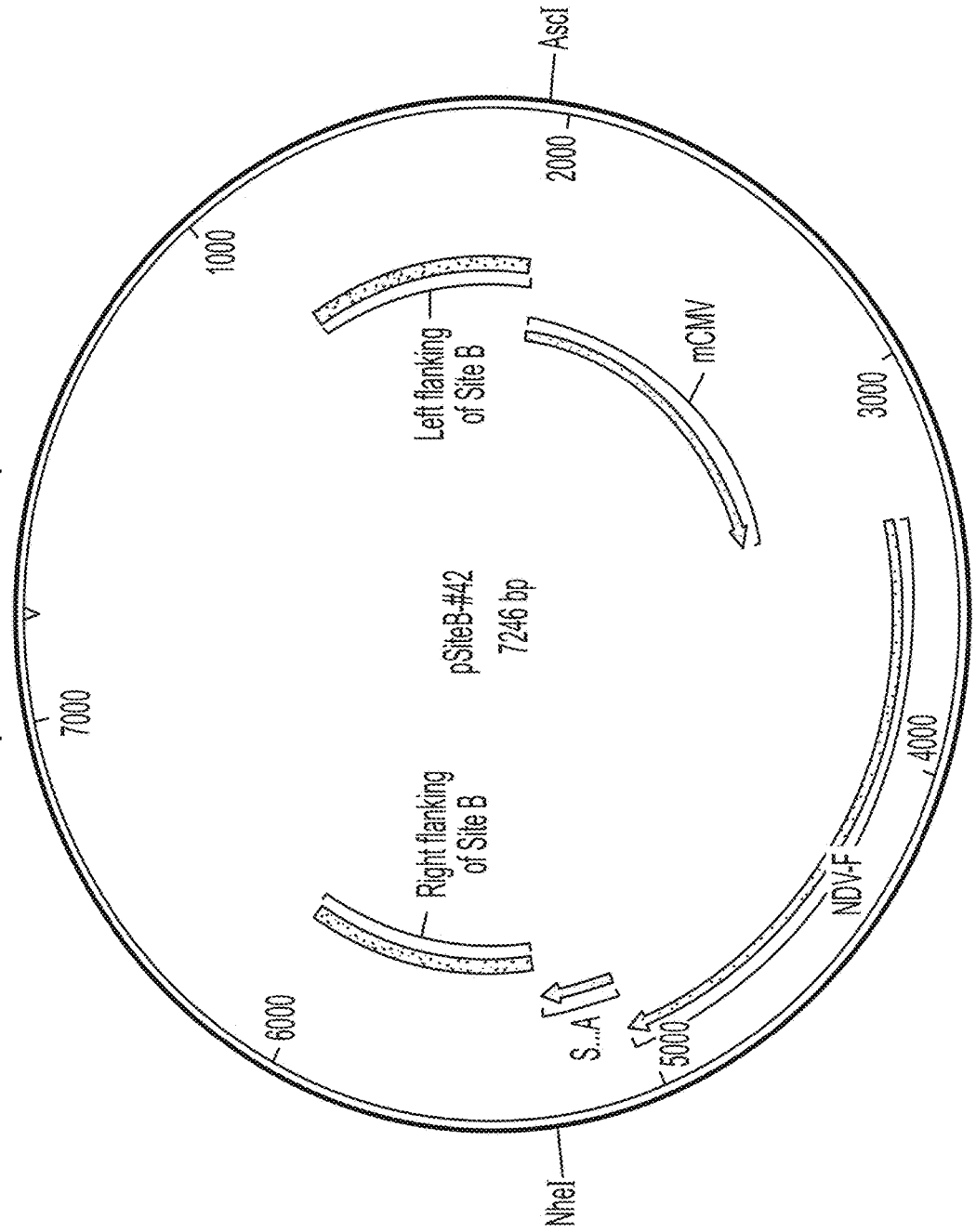
Figure 32:
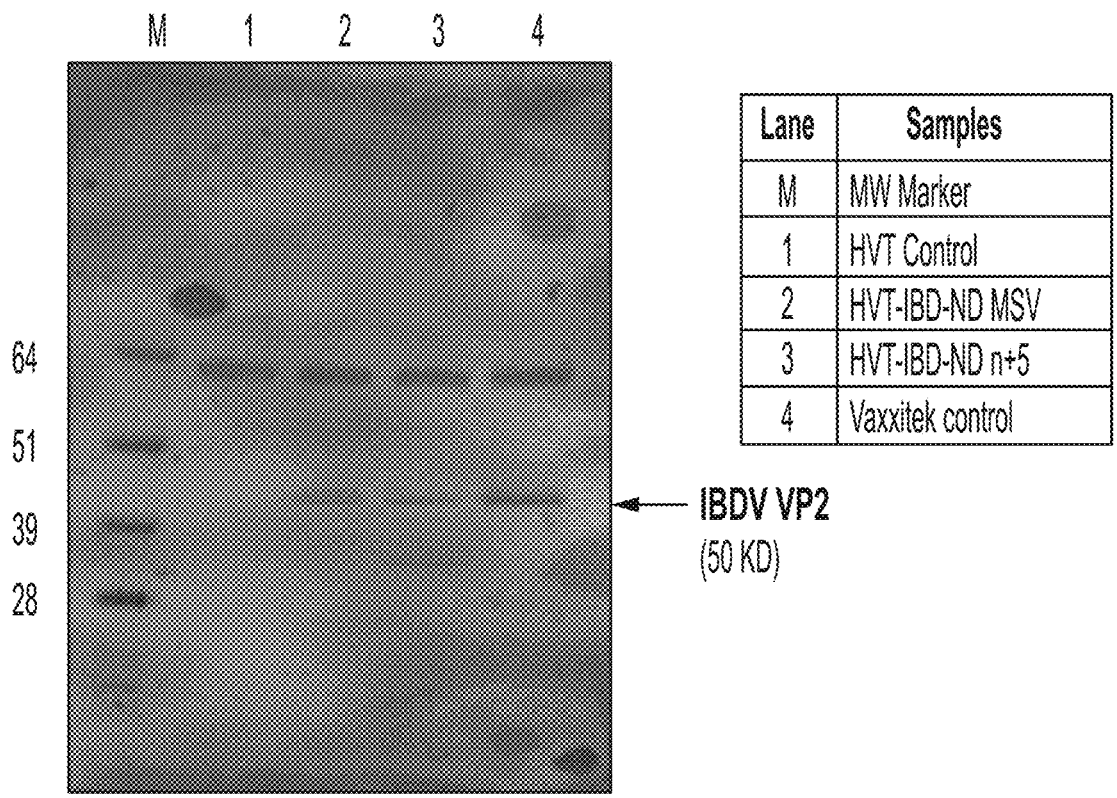

HVT-IBD #40 transfer plasmid (SEQ ID NO.31) was chemically synthesized by BioBasic, Inc. HindIII digested transfer plasmid for HVT-ND #40 was co-transfected with SbfI digested HVT-gfp-A DNA using PEI (Polyethylenimine, 7.5 uL) in 6-well plate with secondary CEF cells. 7 days post-transfection, the transfected cells were plated onto 24-well plates and live stained with NDV chicken serum Four wells containing the foci with positive staining were purified 3 times by limiting dilution. One of the purified viruses was expanded using CEF cells and frozen stock made. It was designated as "HVT-ND #40".

PCR analysis of 4 different clones using primers for upstream region of integration site of UL35-UL36 (upper primer: SEQ ID NO.96; lower primer: SEQ ID NO.97 that localized within chicken beta-actin promoter, panel A) gave a band of 0.835 kb. The correct integration was further confirmed by using primers surrounding the downstream junction of the insertion (upper primer SEQ ID NO.98 that localized within NDV F coding region; lower primer SEQ ID NO. 99 that localized downstream of UL35-UL36 insertion site, panel B). A PCR band of 0.856 kb was obtained as expected. The correct construct was further confirmed by using primers outside of the expression cassette (upper primer SEQ ID NO.100; lower primer SEQ ID NO.101 (panel C). A PCR band of 3.449 kb was obtained as expected. Please refer to FIGS. 17 A-C.

Construction of HVT-ND #42

Initial transfer plasmid HVT-ND #42 (SEQ ID NO. 33) was chemically synthesized by BioBasic, Inc. Cloning plasmid was chemically synthesized by DNA2.0.PCR amplification of NDV F gene expression cassette of HVT-ND #42 transfer plasmid by using the following primers: upper primer, SEQ ID NO.102; lower primer, 5'—SEQ ID NO. 103. The amplified PCR fragment was cloned into the AscI and NheI sites UL55/gene3 to make final transfer plasmid, HVT ND #42 (SEQ ID NO.35)

Transfer plasmid was transfected into CEF cells that was infected with HVT, using Lipofectamine LTX in 6-well plate. 3 days post transfection, the transfected/infected cells were plated onto duplicate 6 well plate and then 96-well plate for screening ND expressing foci by staining with NDV antiserum. Wells corresponding to containing the ND expression foci were purified 3 times by limiting dilution. One of the purified viruses was expanded using CEF cells and frozen stock made. It was designated as "HVT-ND #42".

PCR analysis of one final clone using primers outside of the expression cassette (primer set 1: upper primer SEQ ID NO. 104; lower primer SEQ ID NO. 105) gave a band of 3.597 kb as expected. Four sets of primers for upstream integration region of UL55-Gene 3 with all upper primers located upstream and outside of the expression cassette, all lower primers located within ND F coding region. The primer set 2: upper primer: SEQ ID NO. 106, lower primer: SEQ ID NO. 107 that gave a band of 2.243 kb; The primer set 3: upper primer: SEQ ID NO.108; lower primer: SEQ ID NO. 109 that gave a PCR band of 2.356 kb. The primer set 4: upper primer: SEQ ID NO. 110; lower primer: SEQ ID NO. 111 that gave a PCR band of 2.424 kb. The primer set 5: upper primer: SEQ ID NO. 112; lower primer: SEQ ID NO. 113 that gave a PCR band of 2.170 kb. The correct integration was further confirmed by using primers surrounding the downstream junction of the insertion (primer set 6: upper primer SEQ ID NO. 114 that localized within NDV F gene coding sequence; lower primer SEQ ID NO. 115 that localized downstream of UL55-Gene3 insertion site, panel C). A PCR band of 0.971 kb was obtained as expected. Please refer to FIG. 18.

Construction of HVT-ND #44

HVT-IBD #44 transfer plasmid (SEQ ID NO.36) was chemically synthesized by BioBasic, Inc. Transfer plasmid number 44 was digested with restriction enzymes EcoRI and HindIII to release the insert from plasmid sequences and the resultant digested DNA (10 ng) was used along with 2.5 μg of HVT-gfpB DNA to co-transfect secondary cells in using PEI (polyethylenimine) Four days post transfection the transfected cells were passed 1:6 with fresh secondary cells and live stained with chicken anti NDV polyclonal serum to identify NDV expressing foci three to four days post passage. Three positively staining foci were harvested via trypsinization using cloning. The harvested cells were serially diluted and plated on fresh secondary CEF cells. This process was repeated every three to four days until the NDV staining showed homogeneity, and then four subsequent clonings were performed. The cloned culture was then amplified, and frozen stock prepared. The frozen stock was designated as "HVT-ND #44".

PCR analysis of 1 final clone using primers for upstream region of integration site of UL55-Gene 3 (upper primer: SEQ ID NO. 116 that localized upstream of UL55; lower primer: SEQ ID NO. 117 that localized within chicken beta-actin promoter, panel A) gave a band of 0.71 kb; A similarly localized primer pair: upper primer: SEQ ID NO. 118 lower primer: SEQ ID NO. 119 (Panel B that gave a PCR band of 0.965 kb The correct integration was further confirmed by using primers surrounding the downstream junction of the insertion (upper primer SEQ ID NO. 120 that localized within NDV F gene coding sequence; lower primer SEQ ID NO. 121 that localized downstream of UL55-Gene3 insertion site, panel C). A PCR band of 0.971 kb was obtained as expected. The correct construct was further confirmed by using primers outside of the expression cassette (upper primer SEQ ID NO.122; lower primer SEQ ID NO.123 (panel D). A PCR band of 3.438 kb was obtained as expected.

Construction of HVT-ND #45

HVT-IBD #45 transfer plasmid (SEQ ID) was chemically synthesized by BioBasic, Inc. This plasmid was transfected into CEF cells that was infected with HVT-GFP-B, using Lipofectamine LTX in 6-well plate. 3 days post transfection, the transfected/infected cells were plated onto 96-well plate for screening of GFP negative foci. Wells containing the GFP negative foci were purified 3 times by limiting dilution. The purified viruses were IFA stained with chicken NDV serum to confirm the NDV F gene expression. One of the purified viruses was expanded using CEF cells and frozen stock made. It was designated as "HVT-ND #45".

PCR analysis of 1 final clone using primers outside of the expression cassette (primer set 1: upper primer SEQ ID NO.124; lower primer SEQ ID NO.125) gave a band of 2.830 kb as expected. Two sets of primers for upstream integration region of Gene 3-UL55 with both upper primers located upstream and outside of the expression cassette, both lower primers located within ND F coding region. The primer set 2: upper primer: SEQ ID NO.126, lower primer: SEQ ID NO. 127 that gave a band of 1.635 kb; The primer set 3: upper primer SEQ ID NO.128; lower primer: SEQ ID NO. 129 that gave a PCR band of 1.588 kb. The correct integration was further confirmed by using 2 sets of primers surrounding the downstream junction of the insertion: primer set 4: upper primer SEQ ID NO. 130 that localized within NDV F gene coding sequence; lower primer SEQ ID NO. 131 that localized downstream of Gene3-UL55 insertion site. A PCR band of 0.993 kb was obtained as expected. Primer set 5: upper primer: SEQ ID NO.132, lower primer:

SEQ ID NO.133, a PCR band of 1.137 kb was obtained as expected. Please refer to FIG. 19.

Construction of HVT-ND #46

HVT-ND #46 transfer plasmid (SEQ ID NO.38) was chemically synthesized by BioBasic, Inc. This plasmid was transfected together with HVT-GFP-B viral DNA into CEF cells using PEI (Polyethylenimine, 7.5 uL) in 6-well plate. 4 days post transfection, the transfected cells were plated onto 96-well plate for screening of GFP negative foci. Wells containing the GFP negative foci were purified 3 times by limiting dilution. The purified viruses were IFA stained with chicken NDV serum to confirm the NDV F gene expression. One of the purified viruses was expanded using CEF cells and frozen stock made. It was designated as "HVT-ND #46".

PCR analysis of 1 final clone using primers outside of the expression cassette (upper primer SEQ ID NO. 134; lower primer SEQ ID NO. 135) gave a band of 3.597 kb as expected. One sets of primers for upstream integration region of Gene 3-UL55 with upper primers located upstream and outside of the expression cassette (SEQ ID NO. 136), lower primers located within the murine CMV promoter (upper primer SEQ ID NO. 137) that gave a PCR band of 1.107 kb as expected. The correct integration was further confirmed by using 4 sets of primers surrounding the downstream junction of the insertion: P1: upper primer SEQ ID NO. 138 that localized within NDV F gene coding sequence; lower primer SEQ ID NO. 139 that localized downstream and outside of expression cassette. A PCR band of 1.003 kb was obtained as expected. P2: upper primer: SEQ ID NO. 140, lower primer: SEQ ID NO. 141, a PCR band of 1.147 kb was obtained as expected. P3: upper primer: SEQ ID NO. 142, lower primer: SEQ ID NO. 143, a PCR band of 1.019 kb was obtained as expected. P4: upper primer: SEQ ID NO. 144, lower primer: SEQ ID NO. 145, a PCR band of 1.018 kb was obtained as expected. Please refer to FIGS. 20 A-C.

Construction of HVT-ND #48

Linearized transfer plasmid for HVT-ND #48 (SEQ ID NO.39) was co-transfected with HVT-gfp-B DNA using PEI (Polyethylenimine, 7.5 uL) in 6-well plate with secondary CEF cells. 4 days post transfection, the transfected cells were plated onto 96-well plate and live stained with NDV chicken serum. Four non-green foci were found and 2 were stained positive with positive using NDV chicken serum. Please refer to FIGS. 33 A and B. The two clones were purified 3 times by limiting dilution. The purified virus was expanded using CEF cells and frozen stock made. It was designated as "HVT-ND #48".

HVT-IBD #48 transfer plasmid was chemically synthesized by BioBasic, Inc. The transfer plasmid was digested with EcoRI and HindIII to release the insert from plasmid sequences and the resultant digested DNA (10 ng) was used along with 2.5 μg of HVT-gfp-B DNA to co-transfect secondary cells in using PEI (polyethylenimine) Three days post transfection the transfected cells were passed 1:6 with fresh secondary cells and live stained with NDV chicken polyclonal serum to identify NDV expressing foci four days post passage. Three positively staining foci were harvested via trypsinization using cloning cylinders. The harvested cells were serially diluted and plated on fresh secondary CEF cells. This process was repeated every three to four days until the NDV staining showed homogeneity, and then four subsequent cloning were performed. The cloned culture was then amplified from six well plate to 75 cm2 flask, to 225 cm2 flask before a final amplification in an 850 cm2 roller bottle using primary CEF cells. The final culture was harvested and designated "HVT-ND #48".

PCR analysis of 1 final clone using primers for upstream region of integration site of Gene 3-UL55 (upper primer: SEQ ID NO.146; lower primer: SEQ ID NO.147 that localized within chicken beta-actin promoter, panel A) gave a band of 0.815 kb as expected; The correct integration was further confirmed by using primers surrounding the downstream junction of the insertion (upper primer SEQ ID NO. 148 that localized within NDV F coding region; lower primer SEQ ID NO.149 that localized downstream of Gene 3-UL55 insertion site, panel B). A PCR band of 1.003 kb was obtained as expected. Another similarly localized primers: upper primer: SEQ ID NO.150; lower primer: SEQ ID NO. 151 (Panel C) that gave a PCR band of 1.147 kb band as expected. The correct construct was further confirmed by using primers outside of the expression cassette (upper primer SEQ ID NO. 152; lower primer SEQ ID NO.153 (panel D). A PCR band of 3.430 kb was obtained as expected.

Example 3

In Vivo IBDV Efficacy Test of HVT-IBD #9, #34 of SFP Birds

Two HVT-IBD recombinants, HVT-IBD #9, #34 were tested for their in vivo efficacy against virulent IBDV challenge (STD strain, provided by USDA) in SPF birds. A positive control of a commercial vaccine Vaxxitek (Merial) was used in this study. 1500 pfu of each recombinant virus was injected in ovo at E18. The back-titer of each vaccine virus was also determined for each recombinant after vaccination. While 100% of HVT-IBD #9 express IBDV VP2 antigen, we found only 96% of HVT-IBD #34 express the antigen. IBDV STD challenge was carried out at Day 28 per USDA instruction. All birds were necropsied at 5 days post challenge. We observed 100% protection for HVT-IBD #9, and 90% protection for HVT-IBD #34, while our positive control Vaxxitek gave 97% protection.

TABLE 1

IBDV Efficacy Test in SPF Birds

| Group | Treatment | Dose (Pfu) Target/ Backtiter | Route | #Edema/ #challenged | Prevented Fraction (PF) |
|---|---|---|---|---|---|
| T01 | None | — | — | 0/29 (0%) | — |
| T02 | None | — | — | 22/22 (100%) | — |
| T03 | Vaxxitek | 1500/1053 | In ovo | 1/30 (3%) | 97% |
| T04 | HVT-IBD #9 | 1500/1322 | In ovo | 0/30 (0%) | 100% |
| T06 | HVT-IBD #34 | 1500/1353* | In ovo | 3/29 (10%) | 90% |

Example 4

In Vivo IBDV Efficacy Test of HVT-IBD #1, #5, #6a, #9, #30, #34 of SFP Birds Six HVT-IBD recombinants, HVT-IBD #1, #5, #6a, #9, #30, #34 were tested for their in vivo efficacy against virulent IBDV challenge (STD strain, provided by USDA) in SPF birds. A positive control of a commercial vaccine Vaxxitek (Merial) was used in this study. 1500 pfu of each recombinant virus was injected in ovo at E18. The back-titer of each vaccine virus was also determined for each recombinant after vaccination. All recombinants were found to have 100% expression for IBDV VP2 antigen. IBDV STD challenge was carried out at Day 28 per USDA instruction. All birds were necropsied at 5 days post challenge. We observed 100% protection for HVT-IBD #9, and 96% protection for HVT-IBD #1, #30, #34, and 92% protection for HVT-IBD #6a, while our positive control Vaxxitek gave 92% protection.

TABLE 2

IBDV Efficacy Test in SPF Birds

| Treatment Description | | | Necropsy results | | % susceptible (lesions + mortality) | Prevented Fraction (PF) |
|---|---|---|---|---|---|---|
| Trt | Vaccine | Dose (pfu) target/ backtiter | % Normal (#) | % Edema (#) | | |
| T01 | None | NA | 100.0 (24/24) | 0 | 0 | |
| T02 | None | NA | 0 | 100.0 (16/16) | 100.0 (24/24) | 0 |
| T03 | Vaxxitek | 1500/1459 | 95.7 (22/23) | 4.3 (1/23) | 8.3 (2/24) | 92 |
| T04 | HVT-IBD #9 | 1500/1519 | 100.0 (24/24) | 0 | 0 | 100 |
| T06 | HVT-IBD #1 | 1500/1319 | 100.0 (23/23) | 0 | 4.2 (1/24) | 96 |
| T07 | HVT-IBD #5 | 1500/1537 | 72.7 (16/22) | 27.3 (6/22) | 33.3 (8/24) | 67 |
| T08 | HVT-IBD #6a | 1500/1105 | 91.7 (22/24) | 8.3 (2/24) | 8.3 (2/24) | 92 |
| T09 | HVT-IBD #30 | 1500/1324 | 100.0 (23/23) | 0 | 4.2 (1/24) | 96 |
| T10 | HVT-IBD #31 | 1500/1255 | 95.8 (23/24) | 4.2 (1/24) | 4.2 (1/24) | 96 |

Example 5

IBDV Serology Responses of HVT-IBD #1, #5, #9, #15 of Commercial Broiler Birds

Figure 13:
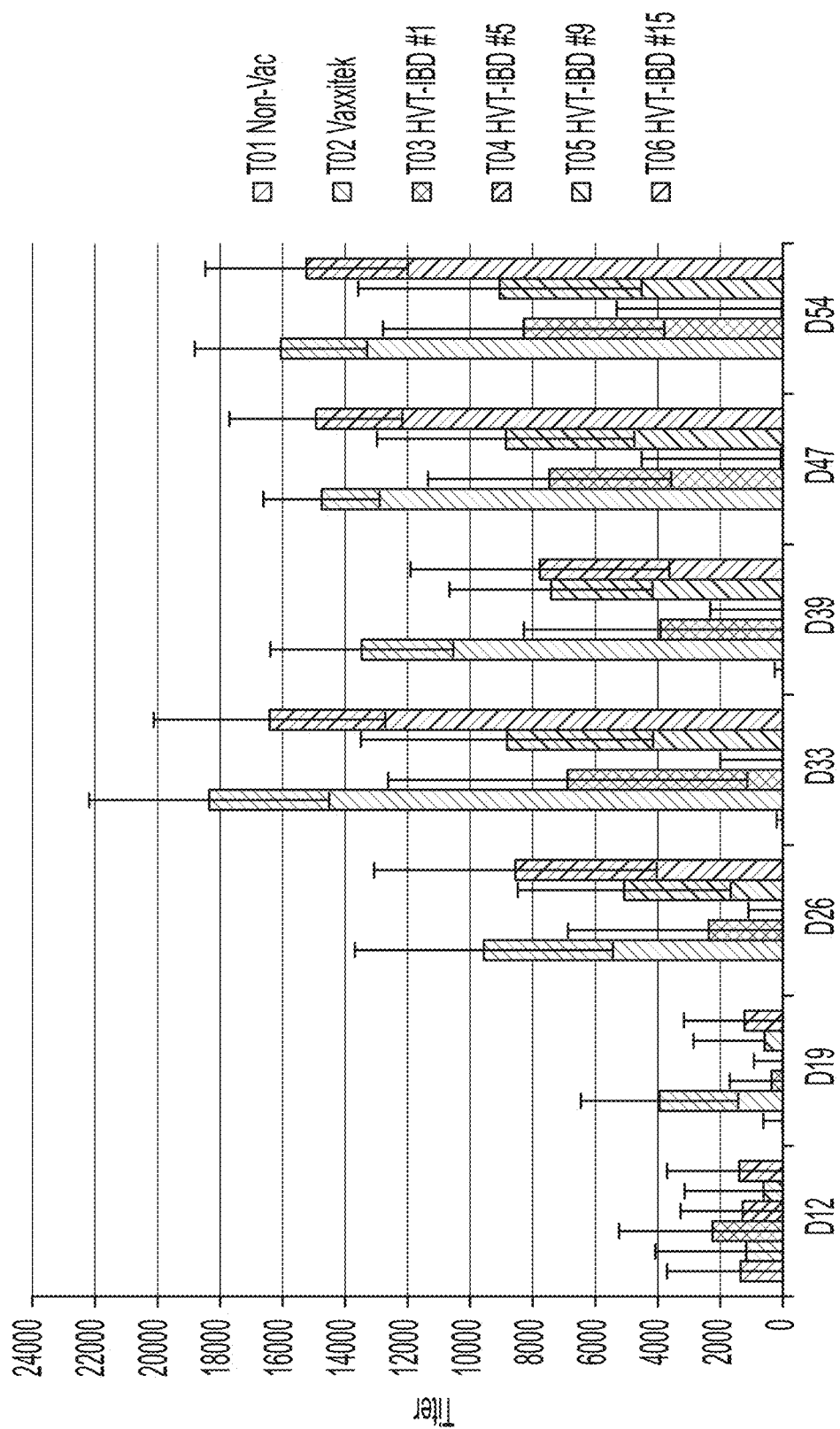
FIG. 13 is a graphical representation of the IBDV serology responses of HVT-IBD 1, 5, 9 and 15.

The serology responses against IBDV antigen was measured by using a commercial Elisa kit ProFlok ND plus. 1500 pfu (0.2 mL) of each recombinant (HVT-IBD #1, #5, #9, #15 were injected Subcutaneously (SC) for 1-day old chicks. Serum samples were isolated on days 12, 19, 26, 33, 39, 47 and 54 and can be seen in Table 3 below. The percentage of positive sample for each construct during the time course are shown in FIG. 13.

TABLE 3

| | | IBDV Titers (% Pos.) | | | | | | | |
|---|---|---|---|---|---|---|---|---|---|
| Trt | Vaccines | D 0 | D 12 | D 19 | D 26 | D 33 | D 39 | D 47 | D 54 |
| T01 | Control | | 90 | 20 | 0 | 3 | 3 | 0 | 0 |
| T03 | HVT-IBD #1 | | 95 | 78 | 90 | 95 | 90 | 95 | 95 |
| T04 | HVT-IBD #5 | | 90 | 35 | 8 | 20 | 43 | 50 | 43 |
| T05 | HVT-IBD #9 | | 80 | 80 | 95 | 95 | 95 | 95 | 95 |
| T06 | HVT-IBD #15 | | 90 | 90 | 95 | 95 | 97 | 100 | 100 |

Example 6

IBDV Serology Responses of HVT-IBD #6a, #30, #31 of Commercial Broiler Birds

Figure 14:
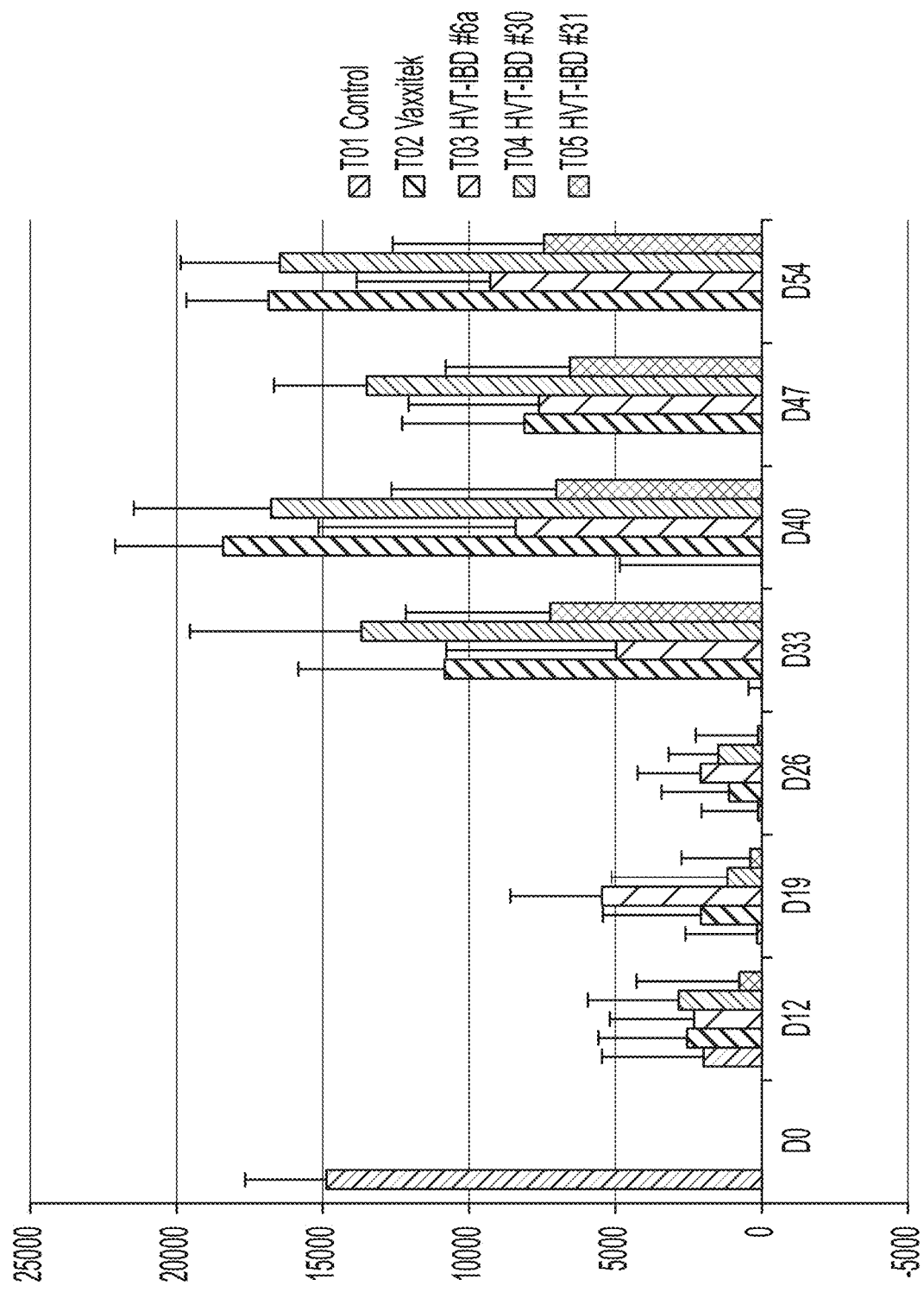
FIG. 14 is a graphical representation of the IBDV serology responses of HVT IBD 6a, 30, 31.

The serology responses against IBDV antigen was measured by using a commercial ELISA kit ProFlok IBD plus. 1500 pfu (0.2 mL) of each recombinant (HVT-IBD #61, #30, #31) were injected Subcutaneously (SC) for 1-day old chicks. Serum samples were isolated on days 12, 19, 26, 33, 39, 47 and 54 are shown in Table 4 below. The percentage of positive samples for each construct during the time course are shown in FIG. 14.

TABLE 4

| B1583 | | IBDV Titers (Geomean) | | | | | | | |
|---|---|---|---|---|---|---|---|---|---|
| Results | Vaccines | D 0 | D 12 | D 19 | D 26 | D 33 | D 40 | D 47 | D 54 |
| T01 | Control | 14883 | 1984 | 162 | 125 | 2 | 3 | 0 | 0 |
| T03 | HVT-IBD #6a | | 2305 | 5457 | 2083 | 4970 | 8414 | 7616 | 9281 |
| T04 | HVT-IBD #30 | | 2828 | 1171 | 1471 | 13686 | 16773 | 13505 | 16476 |
| T05 | HVT-IBD #31 | | 766 | 388 | 122 | 7227 | 7027 | 6553 | 7439 |

Example 7

In Vivo Efficacy Test of HVT-ND #38, #39, #44, #48 in SFP Birds

Four HVT-ND recombinants, HVT-IBD #38, #39, #44, #48 were tested for their in vivo efficacy against virulent NDV challenge (Texas GB strain, provided by USDA) in SPF birds. A positive control of a commercial vaccine Vectormune ND (Ceva) was used in this study. 1500 pfu of each recombinant virus was injected in ovo at E18. The back-titer of vaccine virus was also determined for each recombinant after vaccination. While 100% of HVT-ND #38 & #48 express NDV F antigen, we found only 95-96% of HVT-IBD #39 & #44 express the antigen. NDV Texas GB challenge was carried out at Day 28 per USDA instruction. All birds were observed for 2 weeks post challenge. We observed 90% protection for HVT-ND #38 and #48, and 50% protection for HVT-ND #39 and 60% protection for HVT-ND #44, while our positive control Vectormune ND gave 90% protection. Please refer to Table 5 below.

TABLE 5

NDV Efficacy Test in SPF Birds

| Trt | Description | Dose (pfu) Target/ back-titer | % Protected (alive) | % Affected (mortality) | Stability IFA by Titration |
|---|---|---|---|---|---|
| T01 | Negative | — | NA | NA | NA |
| T02 | Challenge control | — | 0 | 100 (20/20) | NA |
| T03 | Vectormune ND | 1500/1427 | 90 | 10 (2/20) | 100% |
| T06 | HVT-ND #38 | 1500/1215 | 90 | 10 (2/20) | 100% |
| T07 | HVT-ND #39 | 1500/1637 | 50 | 50 (10/20) | 95% |
| T08 | HVT-ND #44 | 1500/1377 | 60 | 40 (8/20) | 96% |
| T09 | HVT-ND #48 | 1500/1328 | 90 | 10 (2/20) | 100% |

The antibody response to various HVT-ND vaccine candidates were assayed by using ProFlok ND plus kit (Zoetis LLC). All titers were included without using the cut-off value (345) recommended by the kit. The percentage of birds with positive ND titer is shown in Table 6 below.

TABLE 6

| | | % Pos NDV ELISA Titer (GMT) | | | |
|---|---|---|---|---|---|
| Trt | Description | D 11 | D 14 | D 21 | D 27 |
| T01 | Negative | 0 (0.4) | 0 (0) | 0 (0) | 0 (0) |
| T02 | Challenge control | 0 (0) | 0 (0) | 0 (0) | 0 (0) |
| T06 | HVT-ND #38 | 0 (0) | 44 (6) | 72 (21) | 65 (22) |
| T07 | HVT-ND #39 | 0 (0) | 13 (0.5) | 30 (2) | 33 (3) |
| T08 | HVT-ND #44 | 0 (0) | 31 (2) | 41 (8) | 45 (11) |
| T09 | HVT-ND #48 | 33 (4) | 42 (5) | 80 (51) | 91 (104) |

Example 8

In Vivo NDV Efficacy Test of HVT-ND #40, #42, #45, #46 in SFP Birds

Four HVT-ND recombinants, HVT-IBD #40, #42, #45, #46 were tested for their in vivo efficacy against virulent NDV challenge (Texas GB strain, provided by USDA) in SPF birds. A positive control of a commercial vaccine Vectormune ND (Ceva) was used in this study. 1500 pfu of each recombinant virus was injected in ovo at El 8. The back-titer of vaccine virus was determined for each recombinant after vaccination. While 100% of HVT-ND #42, #45, #46 express NDV F antigen, we found only 94-99% of HVT-IBD #40 express the antigen. NDV Texas GB challenge was carried out at Day 28 per USDA instruction. All birds were observed for 2 weeks post challenge. We observed 95% protection for HVT-ND #42 and #45, and 80% protection for HVT-ND #46, 55% protection for HVT-ND #40, while the positive control Vectormune ND gave 90% protection. Please see Table 7 below.

TABLE 7

NDV Efficacy in SPF Birds

| Trt | Description | Dose (pfu) Target/ Backtiter | % Protected | % Affected (Mortality) | Stability IFA by Titration |
|---|---|---|---|---|---|
| T01 | Negative | — | NA | 0 (0/20) | |
| T02 | Challenge control | — | 0 | 100 (20/20) | |
| T03 | Vectormune ND | 1500/1220 | 90 | 10 (2/20) | |
| T08 | HVT-ND #40 | 1500/1230 | 55 | 45 (9/20) | 94-99% ND |
| T09 | HVT-ND #42 | 1500/1870 | 95 | 5 (1/20) | 100% ND |
| T10 | HVT-ND #45 | 1500/1230 | 95 | 5 (1/20) | 100% ND |
| T11 | HVT-ND #46 | 1500/1820 | 80 | 20 (4/20) | 100% ND |

The antibody response to various HVT-ND vaccine candidates were assayed by using ProFlok ND plus kit (Zoetis LLC). All titers were included without using the cut-off value (345) recommended by the kit. The percentage of birds with positive ND titers is shown in the Table 8 below.

TABLE 8

| | | % Pos NDV ELISA Titer (GMT) | | | |
|---|---|---|---|---|---|
| | | D 10 | D 13 | D 21 | D 27 |
| T01 | Negative | — | — | — | — |
| T02 | Challenge control | 0 (0) | 0 (0) | 0 (0) | 2 (0.1) |
| T08 | HVT-ND #40 | 0 (0) | 15 (0.9) | 26 (4) | 31 (4) |
| T09 | HVT-ND #42 | 0 (0) | 17 (1.4) | 81 (108) | 80 (128) |
| T10 | HVT-ND #45 | 0 (0) | 0 (0) | 42 (5) | 79 (50) |
| T11 | HVT-ND #46 | 0 (0) | 31 (4) | 80 (493) | 75 (68) |

Example 9

In Vivo MDV Efficacy Test of HVT-ND #38, #42, #45 in SFP Birds

Three HVT-ND recombinants, HVT-IBD #38, #42, #45 were tested for their in vivo efficacy against virulent MDV challenge (GA22) in SPF birds. A positive control of a commercial vaccine Vectormune ND (Ceva) was used in this study. 1500 pfu of each recombinant virus was injected in ovo at E18. The back-titer of vaccine virus was determined for each recombinant after vaccination. MDV GA22 challenge was carried out at Day 5" per USDA instruction. All birds were observed for 54 days post challenge. We observed 69% protection for HVT-ND #42 and #45, and 46% protection for HVT-ND #38, while the positive control Vectormune ND gave 62% protection. Please see Table 9 below.

TABLE 9

MDV Efficacy in SPF Birds

| Groups | Vaccine | PFU/dose (Target/ Back-titer) | # MD positive/ # challenged | Prevented Fraction (PF %) |
|---|---|---|---|---|
| T01 | Control | — | 1/15 (7%) | |
| T02 | Challenge control | — | 13/15 (87%) | 0 |
| T03 | Vetormune ND | 1500/2024 | 5/15 (33%) | 62 |
| T04 | HVT-ND #38 | 1500/1540 | 7/15 (47%) | 46 |
| T05 | HVT-ND #42 | 1500/1689 | 4/15 (27%) | 69 |
| T06 | HVT-ND #45 | 1500/1435 | 4/15 (27%) | 69 |

Example 10

In Vivo ND Efficacy Test of HVT-ND #38, #42, #45 in Broiler Birds

Three HVT-ND recombinants, HVT-IBD #38, #42, #45 were tested for their in vivo efficacy against virulent NDV challenge (Texas GB strain, provided by USDA) in broiler birds. A positive control of a commercial vaccine Vectormune ND (Ceva) was used in this study. 4000 pfu of each recombinant virus were injected in ovo at E1 8. The back-titer of vaccine virus was determined for each recombinant after vaccination. NDV Texas GB challenge was carried out at Day 28 per USDA instruction. All birds were observed for 2 weeks post challenge. We observed 100% protection for HVT-ND #42 and #45, and 37% protection for HVT-ND #38, while our positive control Vectormune ND gave 50% protection. The back-titer of Vectormune ND was 0.

TABLE 10

NDV Efficacy in Broiler Birds

| Trt | Description | Dose (pfu) Target/ Backtiter | % Mortality | PF (%) | ND Elisa Titer (% Pos. w/o cut-off) | | | | |
|---|---|---|---|---|---|---|---|---|---|
| | | | | | D 0 | D 10 | D 17 | D 25 | D 32 |
| T01 | Negative | — | NA | NA | 100 | 100 | 50 | 14 | 25 |
| T02 | Challenge control | — | 92 (11/12) | 0 | | 100 | 42 | 21 | 21 |
| T03 | Vectormune ND | 4000/0* | 46 (5/11) | 50 | | 100 | 68 | 65 | 81 |
| T04 | HVT-ND #38 | 4000/6907 | 58 (7/12) | 37 | | 100 | 79 | 43 | 18 |
| T05 | HVT-ND #42 | 4000/5350 | 0 (0/12) | 100 | | 100 | 71 | 82 | 86 |
| T06 | HVT-ND #45 | 4000/5057 | 0 (0/12) | 100 | | 100 | 68 | 71 | 93 |

The antibody response to various HVT-ND vaccine candidates were assayed by using ProFlok ND plus kit (Zoetis LLC). All titers were included without using the cut-off value (345) recommended by the kit.

Example 11

In Vivo NDV Efficacy Test of HVT-ND #38, #42, #45 in SPF Birds with Day 20 Challenge Three HVT-ND recombinants, HVT-IBD #38, #42, #45 were tested for their in vivo efficacy against virulent NDV challenge (Texas GB strain, provided by USDA) in SPF birds with Day 20 challenge. A positive control of commercial vaccine Vectormune ND (Ceva) was used in this study. 2000 pfu of each recombinant virus were injected in ovo at E18. The back-titer of vaccine virus was determined for each recombinant after vaccination. NDV Texas GB challenge was carried out at Day 20 per USDA instruction. All birds were observed for 2 weeks post challenge. We observed 87.5% protection for HVT-ND #42, and 70% protection for HVT-ND #45, 65% protection for HVT-ND #38, while our positive control Vectormune ND gave 87.5% protection. Please see Table 11 below.

TABLE 11

NDV Efficacy in SPF Birds with D20 Challenge

| Trt | Description | Dose (pfu) Target/ Backtiter | % Affected (Mortality) | PF (Prevented Fraction) |
| --- | --- | --- | --- | --- |
| T01 | Negative | — | NA | NA |
| T02 | Challenge control | — | 100% (40/40) | 0 |
| T03 | Vectormune ND | 2000/2880 | 12.5% (5/40) | 87.5 |
| T04 | HVT-ND #38 | 2000/1069 | 35% (14/40) | 65 |
| T05 | HVT-ND #42 | 2000/3032 | 12.5% (5/40) | 87.5 |
| T06 | HVT-ND #45 | 2000/2371 | 30% (12/40) | 70 |

Example 12

In Vivo NDV Efficacy Test of HVT-ND (#42, MSV+5) in SPF Birds with Day 17, 18 and 19 Challenge Three HVT-ND recombinant, HVT-ND (#42, MSV+5) was tested for its in vivo efficacy against virulent NDV challenge (Texas GB strain) in SPF birds with Day 17, 18 and 19 challenge. All birds were observed for 2 weeks post challenge. We observed 100% (40/40), 88% (35/40), 98% (39/40) of protection were observed for NDV challenges at Day 17, 18, 19, respectively, for in ovo vaccination. 75% (30/40), 88% (35/40), 93% (37/40) of protection were observed for subcutaneous vaccination on day of hatch. Please see Table 12 below.

TABLE 12

| | | | Challenge | % NDV Efficacy | | |
| --- | --- | --- | --- | --- | --- | --- |
| Trt | Vaccine | Route | (D 17, D 18, D 19) | D 31 (D 17) | D 32 (D 18) | D 33 (D 19) |
| T01 | Non-vaccinated | — | No | NA (40/40) | NA (40/40) | NA (40/40) |
| T02 | Chall control | — | Yes | 0 (0/40) | 0 (0/40) | 0 (0/40) |
| T03 | HVT-ND | Subcutaneous | Yes | 75 (30/40) | 88 (35/40) | 93 (37/40) |
| T04 | | In ovo | Yes | 100 (40/40) | 88 (35/40) | 98 (39/40) |

Example 13

In Vivo NDV Efficacy Test of HVT-ND (#42, MSV+5) in SPF Birds with Day 16 and 19 Challenge Three HVT-ND recombinant, HVT-ND (#42, MSV+5) was tested for its in vivo efficacy against virulent NDV challenge (Texas GB strain) in SPF birds with Day 16 and 19 challenge. All birds were observed for 2 weeks post challenge. We observed 85% (37/40) and 93% (37/40) of protection were observed for Day 16 and Day 19 NDV challenge for in ovo vaccination. 70% (28/40) and 95% (38/40) of protection were observed for subcutaneous vaccination on day of hatch. Please see Table 13 below.

TABLE 13

| Trt | Vaccine | Route | Challenge (D 16, D 19) | % NDV Efficacy D 30 (D 16) | D 33 (D 19) |
|---|---|---|---|---|---|
| T01 | Non-vaccinated | — | Yes | 0 (0/40) | 0 (0/40) |
| T02 | HVT-ND | Subcutaneous | Yes | 70 (28/40) | 95 (38/40) |
| T03 | | In ovo | Yes | 85 (34/40) | 93 (37/40) |

Example 14

Duration of Immunity Test of HVT-ND (#42, MSV+5) in SPF Birds by Day 63 Challenge Three HVT-ND recombinant, HVT-ND (#42, MSV+5) was tested for duration of immunity against virulent NDV challenge (Texas GB strain) in SPF birds with Day 63 challenge. All birds were observed for 2 weeks post challenge. We observed 100% (30/30) of protection for both in ovo vaccination or subcutaneous vaccination on day of hatch. Please see Table 14 below.

TABLE 14

| | | | NDV | % NDV Efficacy | | |
|---|---|---|---|---|---|---|
| Trt | Vaccine | Route | Challenge (D 63) | % Clinical Signs | % Mortality | % Protection |
| T01 | Non-vaccinated | — | No | 0 (0/30) | 0 (0/30) | NA (30/30) |
| T02 | Chall control | — | Yes | 80 (24/30) | 100 (30/30) | 0 (0/30) |
| T03 | HVT-ND | Sub-cutaneous | Yes | 0 (0/30) | 0 (0/30) | 100 (30/30) |
| T04 | | In ovo | Yes | 0 (0/30) | 0 (0/30) | 100 (30/30) |

Example 15

ND Immunogenicity Test of HVT-ND (#42, MSV+5) in SPF Birds

Three HVT-ND recombinant, HVT-ND (#42 MSV+5) was tested for immunogenicity against virulent NDV challenge (Texas GB strain, provided by USDA) on day 28 in SPF birds. All birds were observed for 2 weeks post challenge. We observed 100% (30/30) of protection for both in ovo vaccination or subcutaneous vaccination on day of hatch. Please see Table 15 below.

TABLE 15

| Trt | Description | Route | % Susceptible | % Protection | Route | % Susceptible | % Protection |
|---|---|---|---|---|---|---|---|
| T01 | Poulvac Diluent | SC | 0 (0/40) | 100 | In ovo | 0 (0/40) | 100 |
| T02 | HVT Placebo (CEF) | | 100 (40/40) | 0 | | 100 (40/40) | 0 |
| T04 | HVT-ND | | 0 (0/40) | 100 | | 7.5 (3/40) | 92.5 |

Example 16

MD Immunogenicity Test of HVT-ND (#42, MSV+5) in SPF Birds

Three HVT-ND recombinant, HVT-ND (#42, MSV+5) was tested for immunogenicity against virulent MDV challenge (GA22 strain) on day 5 in SPF birds. All birds were observed for 54 days post challenge. We observed 100% (30/30) of protection for both in ovo vaccination or subcutaneous vaccination on day of hatch. Please see Table 16 below.

TABLE 16

| Trt | Description | Route | % MD lesions | % Protection | Route | % MD lesions | % Protection |
|---|---|---|---|---|---|---|---|
| T01 | Poulvac Diluent | In ovo | 0 (0/30) | 100 | SC | 0 (0/30) | 100 |
| T02 | HVT Placebo (CEF) | | 90 (27/30) | 10 | | 100 (30/30) | 0 |
| T03 | HVT-ND X+5 | | 17 (5/30) | 83 | | 20 (6/30) | 80 |

Example 17

In Vitro Growth Experiment

In vitro growth experiment was carried out for HVT-ND #38, #42, #45. Roller bottles of 490 cm$^2$ were seeded with 5×108 primary CEF cells. HVT-ND #38, #42, #45 were inoculated into each roller bottle at three different MOI: 0.001, 0.003, 0.008. Infected cells were harvested at 48-hour post infection and titrated on CEF cells. Both HVT-ND #42 and #45 grow well and has titer of 2.86×106 and 2.97×106 pfu/mL, respectively. HVT-ND #38 had titer of 1.67×106 pfu/mL. Please see Table 17 below.

TABLE 17

Growth Experiment for HVT-ND preMS viruses

| Treatment | Virus | Cells/ 490RB | MOI | Virus/ 490RB (PFU) | Reps/Trt (490 RB) | Total Cells/ Trt | Total Virus/ Trt | Total Virus mL/ Candidate | Pfu/mL | Pfu/mL (Ave) |
|---|---|---|---|---|---|---|---|---|---|---|
| T01 | HVT- | 5.00E+08 | 0.001 | 5.00E+05 | 2 | 1.00E+09 | 1.00E+06 | 10.00 | 2.17E+05 | 1.67E+06 |
| T02 | ND #38 | 5.00E+08 | 0.003 | 1.50E+06 | 2 | 1.00E+09 | 3.00E+06 |  | 1.13E+06 |  |
| T03 |  | 5.00E+08 | 0.008 | 4.00E+06 | 2 | 1.00E+09 | 8.00E+06 |  | 1.71E+06 |  |
| T04 | HVT- | 5.00E+08 | 0.001 | 5.00E+05 | 2 | 1.00E+09 | 1.00E+06 | 1.36 | 1.37E+06 | 2.86E+06 |
| T05 | ND #42 | 5.00E+08 | 0.003 | 1.50E+06 | 2 | 1.00E+09 | 3.00E+06 |  | 2.88E+06 |  |
| T06 |  | 5.00E+08 | 0.008 | 4.00E+06 | 2 | 1.00E+09 | 8.00E+06 |  | 4.32E+06 |  |
| T07 | HVT- | 5.00E+08 | 0.001 | 5.00E+05 | 2 | 1.00E+09 | 1.00E+06 | 1.35 | 1.05E+06 | 2.97E+06 |
| T08 | ND #45 | 5.00E+08 | 0.003 | 1.50E+06 | 2 | 1.00E+09 | 3.00E+06 |  | 3.15E+06 |  |
| T09 |  | 5.00E+08 | 0.008 | 4.00E+06 | 2 | 1.00E+09 | 8.00E+06 |  | 4.70E+06 |  |

Example 18

Construction of HVT-IBD-ND #42-#30 LP C2

Generation of Transfer Plasmid-#42:

Initial transfer plasmid HVT-ND #42 was chemically synthesized by BioBasic, Inc. Cloning plasmid UL55/gene 3 was chemically synthesized by DNA2.0 as described above. PCR amplification of NDV F gene expression cassette of HVT-ND #42 transfer plasmid by using the following primers: upper primer SEQ ID NO. 154; lower primer SEQ ID NO. 155.

The amplified PCR product was cloned into the AscI and NheI sites of UL55/gene3 to make final transfer plasmid #42. This plasmid was used for transfection/infection to make HVT-ND #42.

Generation of Transfer Plasmid-#30:

Initial transfer plasmid HVT-IBD #30 was chemically synthesized by BioBasic, Inc. Cloning plasmid was chemically synthesized by DNA2.0. PCR amplification of IBD gene expression cassette of plasmid #30 plasmid by using the following primers: upper primer SEQ ID NO. 156, lower primer and SEQ ID NO. 157. The amplified PCR product was cloned into the AgeI and KpnI sites of UL35/36 to make final transfer plasmid #30. This plasmid was used for transfection/infection to make HVT-IBD-ND #42-#30 LP C2.

Construction of HVT-ND #42:

Co-infection/transfection: Seed CEF cell in 6 well plate, next day perform HVT working seed infection (140 ul)+ plasmid-#42 (linearized by SpeI+SbfI digestion) transfection using Lipofectamine™ LTX Reagent (ThermoFisher). Harvested the transfected cells on day 2 post-transfection. Screened positive foci in 6 well plate by IFA with chicken anti-NDV polyclonal antibody (live stain, ~1:250 dilution), then further purified one time (by live stain) in 96 well plate by limited dilution to obtain the single clones. The purified clone was passed two times in 6 well plate in duplicate and the purity of the clone was confirmed by IFA (by fix and stain). The 6 well harvest was used for construction of HVT-IBD-ND #42-#30.

Construction of HVT-IBD-ND #42-#30:

Co-infection/transfection: Seed CEF cell in 6 well plate, next day perform HVT-ND #42 infection+plasmid #30 (linearized by SbfI digestion) transfection using Lipofectamine™ LTX Reagent (ThermoFisher). Harvested the transfected cells on day 3 post-transfection. Screened positive foci in 6 well plate by IFA with chicken anti-IBD polyclonal antibody (live stain, ~1:250 dilution), then further purified one time in 96 well plate (by live stain) by limited dilution to obtain the single clones. Two purified clones were picked and passed in 6 well plate in duplicate and the purity of the clones were confirmed by IFA (by fix and stain). The clones were scaled up sequentially in T-75 flask, T-150 flask, T-225 flask, 850 ml roller bottle. The recombinant virus was harvested and aliquoted 1 ml/vial, froze at −80 C overnight then transferred into LN tank.

Example 19

In Vivo NDV Efficacy Test of HVT-IBD-ND #42-#30, #42-#32, #104 in SFP Birds

Seven HVT-IBD-ND recombinants, HVT-IBD-ND #42-#30 (3 clones), #42-#32 (2 clones), #104 (2 clones), were tested for their in vivo efficacy against virulent NDV challenge in SPF birds. NDV Texas GB challenge was carried out at Day 28. About 1500 PFU of each recombinant virus was injected in ovo at E18. All birds were observed for 2 weeks post challenge. Please see Table 18 below.

TABLE 18

|  |  | % ND Efficacy | |
|---|---|---|---|
| Trt | Description | D 14 | D 21 |
| T01 | Negative | — (20/20) | — (20/20) |
| T02 | Challenge control | 0 (0/20) | 0 (0/20) |
| T05 | HVT-IBD-ND #42-#30 LP C1 p17 | 70 (14/20) | 100 (20/20) |
| T06 | HVT-IBD-ND #42-#30 LP C2 p17 | 75 (15/20) | 95 (19/20) |
| T07 | HVT-IBD-ND #42-#32 LP C1 p17 | 70 (14/20) | 100 (20/20) |

TABLE 18-continued

|  |  | % ND Efficacy | |
|---|---|---|---|
| Trt | Description | D 14 | D 21 |
| T08 | HVT-IBD-ND #42-#32 LP C2 p17 | 65 (13/20) | 100 (20/20) |
| T09 | HVT-IBD-ND #104 C1 | 70 (14/20) | 100 (20/20) |
| T10 | HVT-IBD-ND #104 C7 | 80 (16/20) | 100 (20/20) |
| T11 | HVT-IBD-ND #42-#32 preMSV p36 | 35 (7/20) | — [90 (36/40), B1943] |

Example 20

In Vivo IBD Efficacy Test of HVT-IBD-ND #42-#30, #42-#32, #104 in SFP Birds

Seven HVT-IBD-ND recombinants, HVT-IBD-ND #42-#30 (3 clones), #42-#32 (2 clones), #104 (2 clones), were tested for their in vivo efficacy against virulent IBDV challenge in SPF birds on Day 14 and Day 21, respectively. About 2000 PFU of each recombinant virus was injected in ovo at E18. All birds were necropsied at 5 days post challenge. Please see Table 19 below.

TABLE 19

|  |  | % IBD Efficacy | |
|---|---|---|---|
| Trt | Description | D 14 | D 21 |
| T01 | Negative | — (20/20) | — (20/20) |
| T02 | Challenge control | 0 (0/20) | 5 (1/20) |
| T05 | HVT-IBD-ND #42-#30 LP C1 p17 | 85 (17/20) | 95 (19/20) |
| T06 | HVT-IBD-ND #42-#30 LP C2 p17 | 90 (18/20) | 90 (18/20) |
| T07 | HVT-IBD-ND #42-#32 LP C1 p17 | 85 (17/20) | 100 (20/20) |
| T08 | HVT-IBD-ND #42-#32 LP C2 p17 | 75 (15/20) | 85 (17/20) |
| T09 | HVT-IBD-ND #104 C1 | 60 (12/20) | 100 (20/20) |
| T10 | HVT-IBD-ND #104 C7 | 70 (14/20) | 100 (20/20) |
| T11 | HVT-IBD-ND #42-#32 preMSV | 75 (15/20) | 95 (19/20) |

Example 21

In Vivo MDV Efficacy Test of HVT-IBD-ND #42-#30 (4 Clones) in SFP Birds

Three HVT-IBD-ND recombinants #42-#30 (4 clones) were tested for their in vivo efficacy against virulent MDV challenge (GA22) in SPF birds. About 1500 PFU of each recombinant virus was injected in ovo at E18. MDV GA22 challenge was carried out at Day 5. All birds were observed for 54 days post challenge. Please see Table 20 below.

TABLE 20

|  |  | MD Efficacy | |
|---|---|---|---|
| Groups | Vaccine | % Pos. (#) | % Protection |
| T01 | Negative | 0 (0/30) | 100 |
| T02 | Challenge control | 93 (28/30) | 7 |
| T04 | HVT-IBD-ND #42-#30 preMSV p33 | 30 (9/29) | 69 |
| T05 | HVT-IBD-ND #42-#30 LP C1 p17 | 30 (9/29) | 69 |
| T06 | HVT-IBD-ND #42-#30 LP C2 p17 | 13 (4/30) | 87 |
| T07 | HVT-IBD-ND #46-#30a preMSV p26 | 30 (9/30) | 70 |

Example 22

In Vivo vvIBD Efficacy Test of HVT-IBD-ND #42-#30, #42-#32, #104 in SPF Birds

Three HVT-IBD-ND recombinants, #42-#30 (2 clones), #42-#32 (2 clones), #104 were tested for their in vivo efficacy against very virulent IBDV challenge in SPF birds. About 1500 PFU of each recombinant virus were injected in ovo at E18. vvIBDV challenge was carried out at Day 14 and Day 21. All birds were observed for 10 days post challenge. Histology examination of bursa was conducted for each bird at end of study. Please see Table 21 below.

TABLE 21

|  |  | Day 14 vvIBD Efficacy | | | Day 21 vvIBD Efficacy | | |
|---|---|---|---|---|---|---|---|
| Trt | Description | % Mortality | Mean BF score | % Protection | % Mortality | Mean BF score | % Protection |
| T01 | Negative | 0 (0/19) | 0.42 | — (19/19) | 0 (0/20) | 0.11 | — (20/20) |
| T02 | Challenge control | 95 (19/20) | 5.00 | 0 (0/20) | 100 (19/19) | 0.00 | 0 (0/19) |
| T06 | HVT-IBD-ND #42-#30 LP C1 | 0 (0/20) | 2.35 | 65 (13/20) | 0 (0/20) | 1.20 | 85 (17/20) |
| T07 | HVT-IBD-ND #42-#30 LP C2 | 0 (0/20) | 2.80 | 60 (12/20) | 5 (1/20) | 0.90 | 85 (17/20) |
| T08 | HVT-IBD-ND #42-#32 LP C1 | 0 (0/19) | 2.89 | 53 (10/19) | 0 (0/20) | 0.90 | 85 (17/20) |
| T09 | HVT-IBD-ND #42-#32 LP C2 | 5 (1/20) | 2.58 | 50 (10/20) | 5 (1/20) | 0.68 | 95 (19/20) |
| T10 | HVT-IBD-ND #104 C7 | 0 (0/20) | 3.00 | 50 (10/20) | 10 (2/20) | 1.94 | 55 (11/20) |

Example 23

IBD Duration of Immunity Test of HVT-IBD-ND (#42-#30, X+5) in SPF Birds by Day 63 Challenge The HVT-IBD-ND recombinant, #42-#30 (MSV+5) was tested for duration of immunity against virulent classic IBDV challenge in SPF birds with Day 63 challenge. All birds were observed for four days post challenge and followed by necropsy. Please see Table 22

TABLE 22

| Trt | Vaccine | Route | % Post-chall Mortality | % IBD Protection |
|---|---|---|---|---|
| T01 | Diluent | In ovo | 0 (0/30) | NA (30/30) |
| T02 | Placebo | In ovo | 7 (2/30) | 7 (2/30) |
| T03 | HVT-IBD-ND | SC | 0 (0/30) | 100 (30/30) |
| T04 | HVT-IBD-ND | In ovo | 0 (0/30) | 100 (30/30) |

Example 24

ND Immunogenicity Test of HVT-IBD-ND (#42-#30, MSV+5) in SPF Birds

The HVT-IBD-ND recombinant, #42-#30 (MSV+5) was tested for immunogenicity against virulent NDV challenge (Texas GB strain) on day 28 in SPF birds. All birds were observed for 2 weeks post challenge. Please see Table 23.

TABLE 23

| Trt | Description | Route | % Susceptible | % Protection | Route | % Susceptible | % Protection |
|---|---|---|---|---|---|---|---|
| T01 | Diluent | SC | 0 (0/40) | NA | In ovo | 0 (0/40) | NA |
| T02 | Placebo (CEF) | | 100 (40/40) | 0 | | 100 (40/40) | 0 |
| T03 | HVT-IBD-ND X+5 | | 0 (0/40) | 100 | | 5 (2/40) | 95 |

Example 25

IBD Immunogenicity Test of HVT-IBD-ND (#42-#30, MSV+5) in SPF Birds

The HVT-IBD-ND recombinant, #42-#30 (MSV+5) was tested for immunogenicity against virulent IBDV challenge on day 34 in SPF birds. All birds were observed for 4 days post challenge and followed by necropsy for bursal lesions. Please see Table 24 below.

TABLE 24

| Trt | Description | Route | % Mortality | % IBD Lesions | % Protection | Route | % Mortality | % IBD Lesions | % Protection |
|---|---|---|---|---|---|---|---|---|---|
| T01 | Diluent | SC | 0 (0/30) | 0 (0/30) | NA | In ovo | 0 (0/30) | 0 (0/30) | NA |
| T02 | Placebo (CEF) | | 100 (30/30) | 100 (30/30) | 0 | | 43 (13/30) | 93 (28/30) | 7 |
| T03 | HVT-IBD-ND | | 0 (0/30) | 0 (0/30) | 100 | | 0 (0/30) | 0 (0/30) | 100 |

Example 26

MD Immunogenicity Test of HVT-IBD-ND (#42-#30, MSV+5) in SPF Birds

Three HVT-IBD-ND recombinant, #42-#30 (MSV+5) was tested for immunogenicity against virulent MDV challenge (GA22 strain) on day 5 in SPF birds. All birds were observed for 54 days post challenge. Please see Table 25 below.

TABLE 25

| Trt | Description | Route | % Mortality | % MD lesions | % MD Protection |
|---|---|---|---|---|---|
| T01 | Poulvac Diluent | SC | 0 (0/30) | 0 (0/30) | NA |
| T02 | Placebo (CEF) | | 40 (12/30) | 83 (25/30) | 17 |
| T04 | HVT-ND-IBD X+5 | | 3 (1/30) | 17 (5/30) | 83 |

Example 27

ND Immunogenicity Test of HVT-IBD-ND (#42-#30, MSV+5) in SPF Birds Against an EU Challenge Strain The HVT-IBD-ND recombinant, #42-#30 (MSV+5) was tested for immunogenicity against a virulent NDV Europe challenge (Herts Weybridge 33/56) on day 21 in SPF birds. All birds were observed for 2 weeks post challenge. Please see Table 26 below.

TABLE 26

| Trt | Description | Route | % Mortality | % Protection |
|---|---|---|---|---|
| T01 | Control | — | 100 (15/15) | NA |
| T03 | HVT-IBD-ND | SC | 4 (1/26) | 96 |
| T04 | HVT-IBD-ND | In ovo | 4 (1/26) | 96 |

Example 28

Compatibility of HVT-ND with Bursaplex

IBDV Efficacy

BURSAPLEX™ (Zoetis, U.S. Pat. No. 5,871,748, herein incorporated by reference) is a vaccine against Infectious Bursal Disease (IBD) that comprises a vaccine conjugate consisting of a live, attenuated IBD strain 2512 and neutralizing antibody, BDA, bound to the virus. Bursaplex produces active immunity against IBD in poultry, particularly chickens. On E18 eggs were in ovo injected with either control or test vaccine (HVT-ND with Bursaplex at 1:1 ratio) and transferred to an allotted hatcher as designated by Biometrics along with eggs which were not injected. On the day of hatch, T04 birds were subcutaneously vaccinated. Blood samples were collected on Days 5, 12, 19, 26 and 33 for IBDV serology. On Day 34, designated birds were challenged with classic virulent IBDV and on Day 38 all birds were necropsied for presence of bursal lesions. No chicken in T01 negative group developed grossly observable lesions and 100 percent of the chickens in T02 challenge control group developed grossly observable lesions. T03 (HVT-ND+Bursaplex, in ovo) and T04 (HVT-ND+Bursaplex, SC) were both protected at 100%. It can be concluded that Poulvac Procerta HVT-ND and Poulvac Bursaplex are compatible when administered together and remain efficacious against an IBDV challenge when administered either in ovo or subcutaneously.

NDV Efficacy

On E18 eggs were in ovo injected with either control or test vaccine (HVT-ND with Bursaplex at 1:1 ratio) and transferred to an allotted hatcher as designated by Biometrics along with eggs which were not injected. On the day of hatch, T04 birds were subcutaneously vaccinated. Blood samples were collected on Days 6, 13, 20 and 27 for NDV serology. On Day 28, designated birds were challenged with a velogenic NDV and on Day 42 all surviving birds were terminated. No chicken in T01 negative group developed clinical signs and 100 percent of the chickens in T02 challenge control group developed clinical signs of Newcastle disease, including mortality. T03 (HVT-ND+Bursaplex, in ovo) and T04 (HVT-ND+Bursaplex, SC) were protected at 92.5% and 95%, respectively. It can be concluded that Poulvac Procerta HVT-ND and Poulvac Bursaplex are compatible when administered together and remain efficacious against an NDV challenge when administered either in ovo or subcutaneously.

Example 29

Compatibility of HVT-ND with Magniplex

IBD Efficacy

MAGNIPLEX™ (Zoetis) is a vaccine against Infectious Bursal Disease (IBD) that comprises a vaccine conjugate consisting of a live, attenuated IBD strain V877 and neutralizing antibody, BDA, bound to the virus. Bursaplex produces active immunity against IBD in poultry, particularly chickens. On E18 eggs were in ovo injected with either control or test vaccine (HVT-ND Pre-license serial with Magniplex at 1:1 ratio) and transferred to an allotted hatcher as designated by Biometrics along with eggs which were not injected. On the day of hatch, T04 birds were subcutaneously vaccinated. Blood samples were collected on Days 5, 12, 19, 26 and 33 for IBDV serology. On Day 34, designated birds were challenged with classic virulent IBDV and on Day 38 all birds were necropsied for presence of bursal lesions. No chicken in T01 negative group developed grossly observable lesions and 100 percent of the chickens in T02 challenge control group developed grossly observable lesions. T03 (HVT-ND+Magniplex, in ovo) and T04 (HVT-ND+Magniplex, SC) were both protected at 100%. It can be concluded that Poulvac Procerta HVT-ND and Poulvac Magniplex are compatible when administered together and remain efficacious against an IBDV challenge when administered either in ovo or subcutaneously.

TABLE 27

| | | | | % IBD Efficacy | | |
| --- | --- | --- | --- | --- | --- | --- |
| Trt. | Vaccine | Route | Challenge (D 34) | % Neg Bursal Lesions | % Neg Mortality | % Protection |
| T01 | Diluent | In ovo | No | 100 (30/30) | 100 (30/30) | NA (30/30) |
| T02 | CEF cells | In ovo | Yes | 0 (0/30) | 70 (21/30) | 0 (0/30) |
| T03 | HVT-ND + | In ovo | Yes | 100 (30/30) | 100 (30/30) | 100 (30/30) |
| T04 | Magniplex | SC | Yes | 100 (30/30) | 100 (30/30) | 100 (30/30) |

TABLE 28

| | | | % Positive - IBDV ELISA | | | | IBDV ELISA GMT (sdev) | | | |
| --- | --- | --- | --- | --- | --- | --- | --- | --- | --- | --- |
| | | Route | D 6 | D 13 | D 20 | D 27 | D 6 | D 13 | D 20 | D 27 |
| T01 | Diluent | In ovo | 0 | 0 | 0 | 0 | 0 | 0 (0) | 0 (0) | 0 (0) |
| T02 | CEF cells | In ovo | 0 | 0 | 0 | 0 | 0 | 0 (0) | 0 (0) | 0 (0) |
| T03 | HVT-ND + | In ovo | 0 | 61 | 100 | 100 | 0 | 84 (739) | 5790 (2295) | 9510 (3453) |
| T04 | Magniplex | SC | 0 | 33 | 100 | 100 | 0 | 11 (1109) | 5813 (2246) | 11531 (2090) |

ND Efficacy

On E18 eggs were in ovo injected with either control or test vaccine (HVT-ND with Magniplex at 1:1 ratio) and transferred to an allotted hatcher as designated by Biometrics along with eggs which were not injected. On the day of hatch, T04 birds were subcutaneously vaccinated. Blood samples were collected on Days 6, 13, 20 and 27 for NDV serology. On Day 28, designated birds were challenged with a velogenic NDV and on Day 42 all surviving birds were terminated. No chicken in T01 negative group developed clinical signs and 100 percent of the chickens in T02 challenge control group developed clinical signs of Newcastle disease, including mortality. T03 (HVT-ND+ Magniplex, in ovo) and T04 (HVT-ND+Magniplex, SC) were protected at 92.5% and 95%, respectively. It can be concluded that Poulvac Procerta HVT-ND and Poulvac Magniplex are compatible when administered together and remain efficacious against an NDV challenge when administered either in ovo or subcutaneously.

TABLE 29

| | | | | % ND Efficacy | | |
|---|---|---|---|---|---|---|
| Trt. | Vaccines | Route | Challenge (D 28) | % Clinical Signs | % Live Birds | % Protection |
| T01 | Diluent | In ovo | No | 0 (0/40) | 100 (40/40) | NA (40/40) |
| T02 | CEF cells | In ovo | Yes | 75 (30/40) | 0 (0/40) | 0 (0/40) |
| T03 | HVT-ND + | In ovo | Yes | 0 (0/40) | 98 (1/40) | 98 (39/40) |
| T04 | Magniplex | SC | Yes | 0 (0/40) | 100 (40/40) | 100 (40/40) |

TABLE 30

| | | | % Signal Positive - NDV ELISA | | | | NDV ELISA GMT (sdev) | | | |
|---|---|---|---|---|---|---|---|---|---|---|
| Trt. | Vaccines | Route | D 6 | D 13 | D 20 | D 27 | D 6 | D 13 | D 20 | D 27 |
| T01 | Diluent | In ovo | 0 | 0 | 0 | 0 | 0 (0) | 0 (0) | 0 (0) | 0 (0) |
| T02 | CEF cells | In ovo | 0 | 0 | 0 | 0 | 0 (0) | 0 (0) | 0 (0) | 0 (0) |
| T03 | HVT-ND + | In ovo | 0 | 0 | 3 | 47 | 0 (0) | 0 (0) | 0.2 (86) | 18 (300) |
| T04 | Magniplex | SC | 0 | 0 | 14 | 47 | 0 (0) | 0 (0) | 1.3 (150) | 22 (451) |

What is claimed is:

1. A recombinant Herpesvirus of turkey (HVT) genome comprising one or more nucleotide sequence(s) coding for one or more heterologous antigen(s) inserted into the intergenic loci UL 35/UL 36 in the unique long (UL) region of the HVT genome.

2. A recombinant Herpesvirus of Turkey (HVT) genome comprising one or more nucleotide sequence(s) coding for one or more heterologous antigen(s) inserted into the intergenic loci UL 35/UL 36 in the unique long region of the HVT genome and one or more nucleotide sequence(s) coding for one or more heterologous antigens inserted at the UL55/Gene 3 site in the unique long region (UL) of the HVT genome.

3. The recombinant HVT of either claim 1 or claim 2 wherein the one or more heterologous antigen(s) are protective against avian pathogen(s) selected from the group consisting of: Infectious Bursal Disease Virus (IBDV); Newcastle disease virus (NDV); Infectious Bronchitis Virus (IBV); Infectious Laryngotracheitis Virus (ILTV); Chicken Anemia Virus (CAV); and Avian Influenza Virus (AIV).

4. The recombinant HVT of either claim 1 or claim 2, wherein the one or more heterologous antigens are selected from the group consisting of:
 a) the VP2, VP3 or VP4 proteins of the Infectious Bursal Disease Virus (IBDV):
 b) the VP1 or VP2 proteins of the Chicken Anemia Virus (CAV);
 c) the F/HN chimera protein or the F, NP, P, M, HN, or L proteins of the Newcastle Disease Virus (NDV);
 d) the S1, S2 or M proteins of Infectious Bronchitis Virus (IBV);
 e) the gB, gC, gD, gE, gH, gI or gL proteins of the Infectious Laryngotracheitis Virus (ILTV); and
 f) any of the HA, NA, NP or M proteins of the Avian Influenza Virus (AIV).

5. The recombinant HVT of claim 1 wherein the one or more heterologous antigen is protective against IBDV.

6. The recombinant HVT of claim 1, wherein the one or more heterologous antigen or antigens is protective against Newcastle Disease Virus (NDV).

7. The recombinant HVT of claim 2 wherein the one or more heterologous antigens are protective against NDV and IBDV.

8. The recombinant HVT of either claim 1 or claim 2 comprises a genome comprising one or more expression cassettes comprising one or more nucleotide sequences that encode one or more heterologous antigens.

9. The recombinant HVT genome of claim 8 wherein the expression cassette comprises one or more promoters.

10. The recombinant HVT of claim 9 wherein the one or more promoters are selected from the group consisting of: immediate early cytomegalovirus human (hCMV) promoter: guinea pig immediate early CMV promoter; murine immediate early CMV promoter; Pec promoter; β-chicken actin promoter; SV40 promoter; Pseudorabies Virus promoters of glycoprotein X promoter; Herpes Simplex Virus-1 alpha 4 promoter; Marek's Disease Virus promoters of glycoproteins gA, gC, gB, gE, or gl promoter; Infectious Laryngotracheitis Virus promoters of glycoprotein gB, gE, gl, gD promoter; and Bovine Herpesvirus 1/1 VP8 promoter.

11. The recombinant HVT of claim 10 further comprising a nucleotide sequence encoding a poly A signal.

12. An isolated DNA encoding the recombinant HVT genome of either claim 1 or claim 2.

13. An immunogenic composition comprising the recombinant HVT of either claim 1 or claim 2 further comprising a pharmaceutically acceptable carrier, excipient or adjuvant.

14. A vaccine composition comprising the recombinant HVT of either claim 1 or claim 2 further comprising a pharmaceutically acceptable carrier, excipient or adjuvant.

15. The vaccine composition of claim 14 wherein said vaccine prevents or treats one or more avian diseases selected from the group consisting of: Infectious Bursal Disease Virus (IBDV); Newcastle disease virus (NDV); Infectious Bronchitis Virus (IBV); Infectious Laryngotracheitis Virus (ILTV); Chicken Anemia Virus (CAV); and Avian Influenza Virus (AIV).

16. A method of vaccinating an avian to treat or prevent Marek's disease and one or more avian diseases caused by one or more avian pathogens comprises the step of administering an effective amount of the vaccine composition of claim 14.

17. The method of claim 16, wherein the one or more avian pathogens are selected from a group consisting of Infectious Bursal Disease Virus (IBDV); Newcastle disease virus (NDV); Infectious Bronchitis Virus (IBV); Infectious Laryngotracheitis Virus (ILTV); Chicken Anemia Virus (CAV); and Avian Influenza Virus (AIV).

18. The method of claim 17, wherein the administration is performed by spray administration, in ovo administration, subcutaneous administration, intramuscular administration, oral administration or nasal administration.

19. The method of claim 18, wherein the administration route comprises in ovo administration.

20. The method of claim 18 wherein the administration route comprises in ovo administration followed by spray administration.

21. The method of claim 18 wherein the administration route comprises spray administration.

\* \* \* \* \*